(12) United States Patent
Denardo et al.

(10) Patent No.: US 9,884,070 B2
(45) Date of Patent: *Feb. 6, 2018

(54) SELECTIVE HIGH-AFFINITY POLYDENTATE LIGANDS AND METHODS OF MAKING SUCH

(75) Inventors: Sally J. Denardo, El Macero, CA (US); Gerald L. Denardo, El Macero, CA (US); Rodney L. Balhorn, Livermore, CA (US)

(73) Assignees: Lawrence Livermore National Security, LLC, Livermore, CA (US); The Regents of the University of California, Oakland, CA (US)

( * ) Notice: Subject to any disclaimer, the term of this patent is extended or adjusted under 35 U.S.C. 154(b) by 351 days.

This patent is subject to a terminal disclaimer.

(21) Appl. No.: 12/988,801

(22) PCT Filed: Apr. 21, 2009

(86) PCT No.: PCT/US2009/041276
§ 371 (c)(1),
(2), (4) Date: Feb. 3, 2011

(87) PCT Pub. No.: WO2009/132020
PCT Pub. Date: Oct. 29, 2009

(65) Prior Publication Data
US 2011/0144065 A1 Jun. 16, 2011

Related U.S. Application Data

(60) Provisional application No. 61/046,712, filed on Apr. 21, 2008.

(51) Int. Cl.
A61K 31/675 (2006.01)
A61K 47/48 (2006.01)

(52) U.S. Cl.
CPC .......... *A61K 31/675* (2013.01); *A61K 47/481* (2013.01); *A61K 47/48315* (2013.01)

(58) Field of Classification Search
None
See application file for complete search history.

(56) References Cited

U.S. PATENT DOCUMENTS

| | | | |
|---|---|---|---|
| 4,331,647 A | 5/1982 | Goldenberg | |
| 4,361,544 A | 11/1982 | Goldenberg | |

(Continued)

FOREIGN PATENT DOCUMENTS

| | | |
|---|---|---|
| JP | 2005-518344 A | 6/2005 |
| WO | WO-99/53953 A2 | 10/1999 |
| WO | WO-2005/077065 A2 | 8/2005 |

OTHER PUBLICATIONS

Hok, et al., "Synethesis and Radiolabeling of Selective High-Affinity Ligands Designed to Target Non-Hodgkin's Lymphoma and Leukemia", Bioconjugate Chemistry 2007, vol. 18, No. 3, pp. 912-921 (May 2007).

(Continued)

*Primary Examiner* — Marcos Sznaidman
*Assistant Examiner* — Rayna B Rodriguez
(74) *Attorney, Agent, or Firm* — Foley & Lardner LLP

(57) ABSTRACT

This invention provides novel polydentate selective high affinity ligands (SHALs) that can be used in a variety of applications in a manner analogous to the use of antibodies. SHALs typically comprise a multiplicity of ligands that each bind different region son the target molecule. The ligands are joined directly or through a linker thereby forming a polydentate moiety that typically binds the target molecule with high selectivity and avidity.

11 Claims, 32 Drawing Sheets

(56) References Cited

U.S. PATENT DOCUMENTS

| | | | |
|---|---|---|---|
| 4,444,744 | A | 4/1984 | Goldenberg |
| 4,921,690 | A | 5/1990 | Beatty et al. |
| 5,034,223 | A | 7/1991 | Abrams et al. |
| 5,595,721 | A | 1/1997 | Kaminski et al. |
| 5,601,819 | A | 2/1997 | Wong et al. |
| 5,959,084 | A | 9/1999 | Ring et al. |
| 5,985,276 | A | 11/1999 | Lindhofer et al. |
| 6,010,902 | A | 1/2000 | Ledbetter et al. |
| 6,060,285 | A | 5/2000 | Lenz et al. |
| 6,106,833 | A | 8/2000 | Ring et al. |
| 6,210,668 | B1 | 4/2001 | Lindhofer et al. |
| 6,217,871 | B1 | 4/2001 | Rose et al. |
| 8,536,133 | B2 | 9/2013 | Denardo et al. |
| 2001/0001310 | A1 | 5/2001 | Weiner et al. |
| 2002/0155109 | A1 | 10/2002 | Lynch |
| 2003/0077282 | A1 | 4/2003 | Bigler et al. |
| 2003/0176662 | A1 | 9/2003 | Bolognesi et al. |
| 2004/0242851 | A1 | 12/2004 | Zhu |
| 2005/0079184 | A1 | 4/2005 | Hsing-Chang et al. |
| 2005/0136050 | A1 | 6/2005 | Kufer et al. |
| 2006/0018897 | A1 | 1/2006 | Lee et al. |
| 2006/0084115 | A1 | 4/2006 | DeNardo et al. |

OTHER PUBLICATIONS

DeNardo, et al., "Nanomolecular HLA-DR10 Antibody Mimics: A Potent System for Molecular Targeted Therapy and Imaging", Cancer Biotherapy & Radiopharmaceuticals, vol. 23, No. 6, pp. 783-795 (2008).

DeNardo, et al., "Pharmacokinetic Characterization in Xenografted Mice of a Series of First-Generation Mimics for HLA-DR Antibody, Lym-1, as Carrier Molecules to Image and Treat Lymphoma", The Journal of Nuclear Medicine, vol. 48, No. 8, pp. 1338-1347 (Aug. 2007).

DeNardo, et al., "Molecular Specific and Cell Selective Cytotoxicity Induced by a Novel Synthetic HLA-DR Antibody Mimic for Lymphoma and Leukemia", International Journal of Oncology 34:, pp. 511-516 (2009).

DeNardo, G.L. et al. (2007) "Characteristics of dimeric (bis) bidentate selective high affinity ligands as HLA-DR10 beta antibody mimics targeting non-Hodgkin's lymphoma," International Journal of Oncology 31:729-740.

Balhorn, R. et al. (2007) "Selective High-Affinity Ligand Antibody Mimics for Cancer Diagnosis and Therapy: Initial Application to Lymphoma/Leukemia," Clin Cancer Res. 13(18 Suppl):5621s-5628s.

Balhorn, R. et al. (2009) "Hexa-arginine enhanced uptake and residualization of selective high affinity ligands by Raji lymphoma cells," Molecular Cancer 8:25.

Cirino, N. M. et al. (1999) "Disruption of Anthrax Toxin Binding with the Use of Human Antibodies and Competitive Inhibitors," Infect Immun. 67(6):2957-2963.

Cosman, M. et al. (2002) "Identification of Novel Small Molecules That Bind to Two Different Sites on the Surface of Tetanus Toxin C Fragment," Chem. Res. Toxicol. 15(10):1218-1228.

Denardo, G.L. et al. (1998) "Comparison of 1,4,7,10-tetraazacyclododecane-N,N',N'',N'''-tetraacetic acid (DOTA)-peptide-ChL6, a novel immunoconjugate with catabolizable linker, to 2-iminothiolane-2-[p-(bromoacetamido)benzyl]-DOTA-ChL6 in breast cancer xenografts," Clinical Cancer Research 4(10):2483-2490.

Denardo, G.L. et al. (2008) "Systemic Radiotherapy Can Cure Lymphoma a Paradigm for Other Malignancies?" Cancer Biotherapy & Radiopharmaceuticals 23(4):383-397.

Denardo, S.J. et al. (1997) "Yttrium-90/indium-111-DOTA-peptide-chimeric L6: pharmacokinetics, dosimetry and initial results in patients with incurable breast cancer," Anticancer Res. 17(3B):17351744.

Fan, E. et al. (2000) "AB(5) toxins: structures and inhibitor design," Current Opinion in Structural Biology 10(6):680-686.

Final Office Action in U.S. Appl. No. 11/055,181, dated Dec. 31, 2008.

Final Office Action in U.S. Appl. No. 12/642,684, dated Jan. 3, 2013.

Henrichsen, D. et al. (1999) "Bioaffinity NMR Spectroscopy: Identification of an E-Selectin Antagonist in a Substance Mixture by Transfer NOE," Angew Chem Int Edit. 38:98-102.

International Search Report and Written Opinion (ISA/US) in International Application No. PCT/US2005/004134, dated Nov. 3, 2005.

International Search Report and Written Opinion (ISA/US) in International Application No. PCT/US2009/041276, dated Nov. 13, 2009.

Kostelny, S.A. et al. (2001) "Humanization and characterization of the anti-HLA-DR antibody 1D10," Int J Cancer 93(4):556-565.

Kramer, R.H. et al. (1998) "Spanning binding sites on allosteric proteins with polymer-linked ligand dimers," Nature 395(6703):710-713.

Lehnert, N.M. et al. (2001) "Structure-based design of a bispecific receptor mimic that inhibits T cell responses to a superantigen," Biochemistry 40(14):4222-4228.

Mammen, M. et al. (1998) "Polyvalent Interactions in Biological Systems: Implications for Design and Use of Multivalent Ligands and Inhibitors," Angew Chem Int Edit. 37:2755-2794.

Non-Final Office Action in U.S. Appl. No. 11/055,181, dated Apr. 30, 2008.

Non-Final Office Action in U.S. Appl. No. 12/642,684, dated Jul. 18, 2012.

Notice of Allowance in U.S. Appl. No. 11/055,181, dated Sep. 21, 2009.

Notice of Allowance in U.S. Appl. No. 12/642,684, dated May 21, 2013.

Restriction Requirement in U.S. Appl. No. 11/055,181, dated Oct. 1, 2007.

Restriction Requirement in U.S. Appl. No. 12/642,684, dated Apr. 13, 2012.

Shoichet, B.K. et al. (2002) "Lead discovery using molecular docking," Curr Opin Chem Biol. 6(4):439-446.

Shuker, S.B. et al. (1996) "Discovering high-affinity ligands for proteins: SAR by NMR," Science 274(5292):1531-1534.

West, J. et al. (2006) "Direct Antilymphoma Activity of Novel, First-Generation "Antibody Mimics" that Bind HLA-DR10-Positive Non-Hodgkin's Lymphoma Cells," Cancer Biotherapy and Radiopharmaceuticals 21(6):645-654.

Tissue Arrays: the Technique

Antigen retrieval with microwave in citrate buffer

Hybridization with biotin labeled SHAL or mouse scFv

Detection with anti-mouse and/or standard ABC streptavidin horseradish peroxidase Image acquistion with the ScanScope (Scanscope Inc.)

Analysis and histopatholgical interpretation by two pathologists

```
                                                            * **    . ****:***:*** * *
hla_dr10 ------------------------------GDTRPRFLEEVKFECHFFNGTERVRLLERR
 1aqd_B  ------------------------------GDTRPRFLWQLKFECHFFNGTERVRLLERC
 1d5m_B  ------------------------------GDTRPRFLEQVKHECHFFNGTERVRFLDRY
 1bx2_B  -------------------------------TRPRFLWQPKRECHFFNGTERVRFLDRY
 1a6a_B  ---------------------------------PRFLEYSTSECHFFNGTERVRYLDRY
 1i3r_B  RDSRGKKVITAFNEGLKGGGGSLVGGGSGGGGSRPWELEYCKSECHFYNGTQRVRLLVRY .:: ** *:****:********  ::: *. . *** : :.*
hla_dr10 VHNQEEYARYDSDVGEYRAVTELGRPDAEYWNSQKDLLERRRAAVDTYCRHNTGVGESFT
 1aqd_B  IYNQEESVRFDSDVGEYRAVTELGRPDAEYWNSQKDLIEQRRAAVDTYCRHNYGVGESFT
 1d5m_B  FYHQEEYVRFDSDVGEYRAVTELGRPDAEYWNSQKDLLEQKRAAVDTYCRHNYGVGESFT
 1bx2_B  FYNQEESVRFDSDVGEFRAVTELGRPDAEYWNSQKDIIEQARAAVDTYCRHNYGVVESFT
 1a6a_B  FHNQEENVRFDSDVGEFRAVTELGRPDAEYWNSQKDLIEQKRGRVDNYCRHNYGVVESFT
 1i3r_B  TYNLEENLRFDSDVGEFRAVTELGRPDAENWNSQPEFIEQKRAEVDTVCRHNYEIFDNFL

* *** * *****:*****:********..****.****** **:***:*:*****;:*
hla_dr10 VQRRVQPKVTVYPSKTQPLQHHNLLVCSVNGFYPGSIEVRWFRNGQEEKYGVVSTGLIQN
 1aqd_B  VQRRVEPKVTVYPSKTQPLQHHNLLVCSVSGFYPGSIEVRWFRNGQEERAGVVSTGLIQN
 1d5m_B  VQRRVYPRVTVYPAKTQPLQHHNLLVCSVNGFYPGSIEVRWFRNGQEEKTGVVSTGLIQN
 1bx2_B  VQRRVQPKVTVYPSKTQPLQHHNLLVCSVSGFYPGSIEVRWFLNGQEEKAGMVSTGLIQN
 1a6a_B  VQRRVHPKVTVYPSKTQPLQHHNLLVCSVSGFYPGSIEVRWFRNGQEEKTGVVSTGLIHN
 1i3r_B  VPRRVEPLVTVYPTKTQPLEHHNLLVCSVDFYPGNIEVRWFRNGKEEKTGIVSTGLVRN

*****************:************; .*:****:*:
hla_dr10 GDWTFQTLVMLETVPQSGEVYTCQVEHPSVMSPLTVEWRARSESAQSKMLSGVGGFVLGL
 1aqd_B  GDWTFQTLVMLETVPRSGEVYTCQVEHPSVTSPLTVEWRARSESAQSK------------
 1d5m_B  GDWTFQTLVMLETVPRSGEVYTCQVEHPSVTSPLTVEWRARS------------------
 1bx2_B  GDWTFQTLVMLETVPRSGEVYTCQVEHPSVTSPLTVEWRARSE-----------------
 1a6a_B  GDWTFQTLVMLETVPRSGEVYTCQVEHPSVTSPLTVEWRAR-------------------
 1i3r_B  GDWTFQTLVMLETVPQSGEVYTCQVEHPSLTDPVTVEWKAQSTSAQNK------------ hla_dr10 LFLGAGLFIYFRNQKGHSGLPPTGFLS    237
 1aqd_B  ---------------------------    198
 1d5m_B  ---------------------------    192
 1bx2_B  ---------------------------    191
 1a6a_B  ---------------------------    187
 1i3r_B  ---------------------------    228
```

*Fig. 8*

JP459
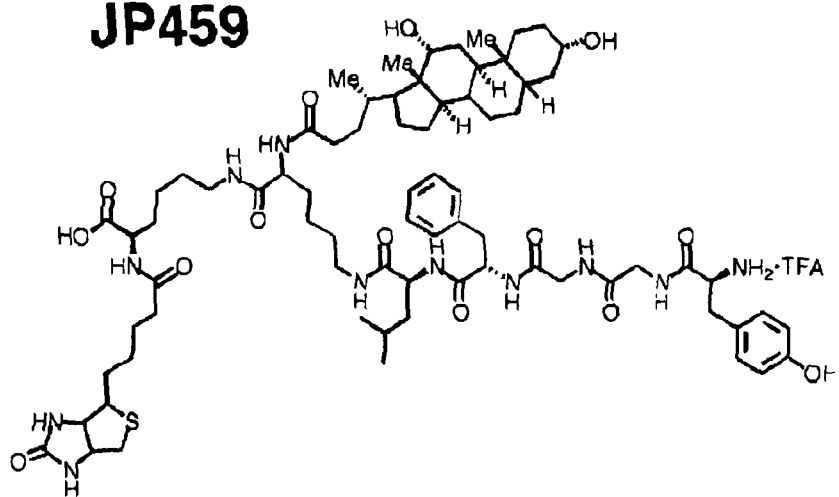
JP459B
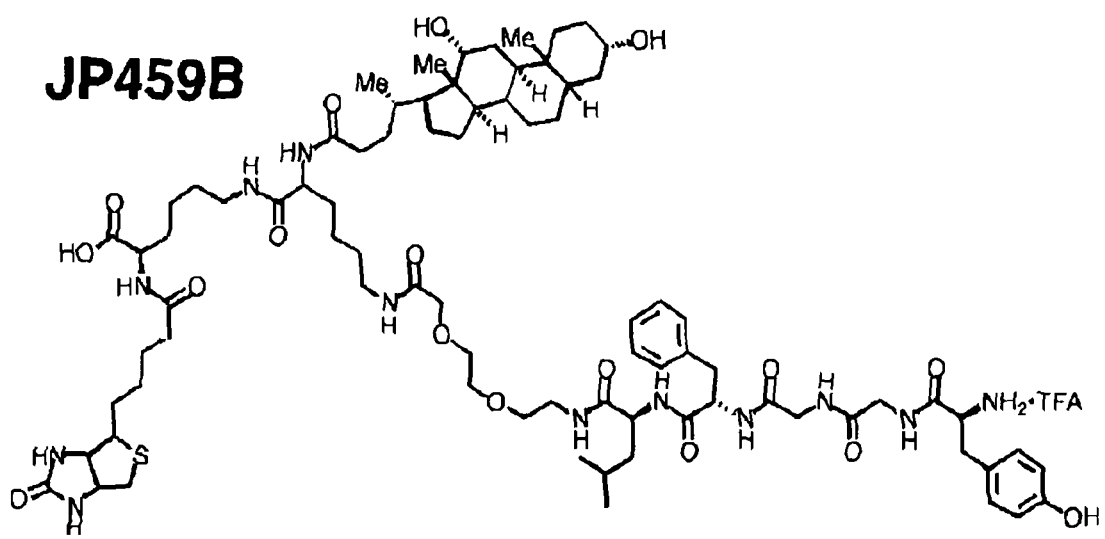
*Fig. 13B*

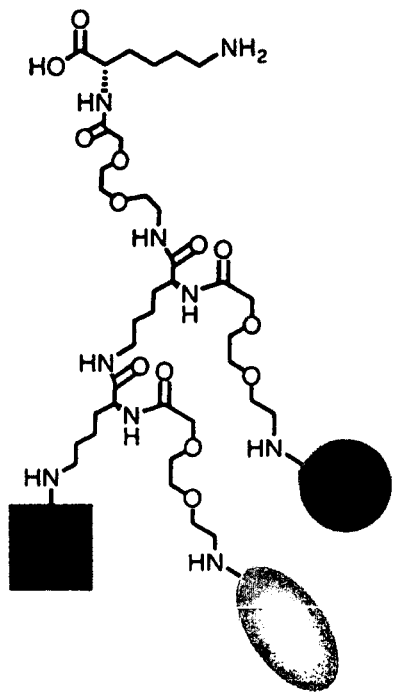
Free amine
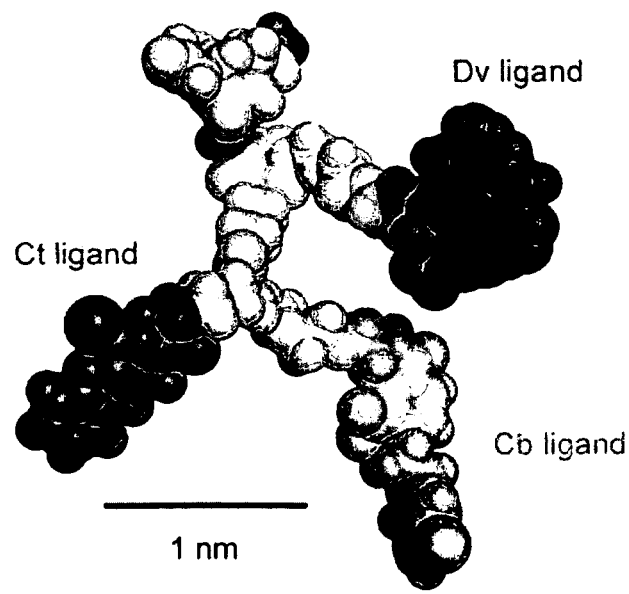
Fig. 28

SELECTIVE HIGH-AFFINITY POLYDENTATE LIGANDS AND METHODS OF MAKING SUCH

CROSS-REFERENCE TO RELATED APPLICATIONS

This application is a national stage application under 35 U.S.C. § 371 of International Application No. PCT/US2009/041276, filed Apr. 21, 2009, which in turn claims priority under 35 U.S.C. § 119(e) to and benefit of U.S. Application Ser. No. 61/046,712, filed on Apr. 21, 2008, the content of which is incorporated herein by reference in its entirety for all purposes.

STATEMENT AS TO RIGHTS TO INVENTIONS MADE UNDER FEDERALLY SPONSORED RESEARCH AND DEVELOPMENT

This work was supported in part by grant No: CA047829 from the National Institutes of Health, National Cancer Institute. In addition, pursuant to Contract No: DE-AC52-07NA27344 between the United States Department of Energy and Lawrence Livermore National Security LLC for the operation of Lawrence Livermore National Laboratory, the Government of the United States of America has certain rights in this invention.

FIELD OF THE INVENTION

This invention pertains to the development of targeting molecules. More particularly this invention pertains to the development of polydentate selective high affinity ligands (SHALs) that can be used in a manner analogous to antibodies and/or peptide ligands as affinity reagents or for the diagnosis and treatment of various diseases (e.g., cancer).

BACKGROUND OF THE INVENTION

In general, it has been found that cancericidal drugs, such as chemotherapeutics, are also toxic to cells of normal tissues. Consequently, the side effects of such drugs can be almost as devastating to the patient as the malignant disease itself. The advent of monoclonal antibodies and peptide ligands provided a new means for improving drug specificity/selectivity. By conjugating, e.g., a cytotoxic agent to an antibody or peptide ligand directed against antigens present on malignant cells, but not present on normal cells, selective killing of malignant cells has been achieved. Many different immunoconjugates comprising an antibody attached to a cytotoxic agent have been created directed against a variety of cell-surface antigens.

Cytotoxic agents used in such immunoconjugates include radioisotopes, various plant and bacterial toxins (e.g., *Pseudomonas exotoxin*, diphtheria toxin, ricin, abrin, etc.), various growth factors, and more recently, agents such as caspases. Although there have been some successes, notably in lymphoma and leukemias, antibody-based therapy whether using antibodies alone or immunoconjugates, has generally not fulfilled the expected potential.

Although significant advances have been made in the treatment of malignant disease, curative regimens for most patients have not yet been developed or are associated with toxicities unattractive for the patient. Therefore, new strategies for the treatment of most malignant diseases are needed. These strategies should have as their goal, the maximization of therapeutic effect, coupled with the minimization of toxicity. One approach has involved the use of ligands specific for cell surface receptors or antibodies specific for malignant cell associated antigens as a means of targeting drugs or radioisotopes to the malignant cells. The approach is attractive for many malignant diseases because the malignant cells display a variety of tumor-restricted or upregulated antigens and/or receptors on their cell surfaces which would be available for targeting. Thus far, antibody/antigen systems have been found to be better than ligand receptor systems because they are more restricted than receptors and in greater abundance on the malignant cell.

Despite these advantages, antibodies have not fulfilled their potential for many reasons. Among the reasons, antibodies are macromolecules (large molecules) that often do not effectively access and penetrate the malignant tumor. In addition, antibodies are often large immunogenic molecules and can induce an immune response in the patient directed against the therapeutic agent. In addition, antibodies often do not show sufficient specificity for the target (e.g., cancer) tissue and thus are useful in only limited therapeutic regimen.

SUMMARY OF THE INVENTION

The present disclosure provides a selective high affinity ligand (SHAL) that specifically binds to a cancer cell, said SHAL comprising a first ligand that binds to a first site on a marker for said cancer cell, said first ligand linked to a second ligand that binds a second site on the same marker or a different marker for said cancer cell wherein said first site and said second site are different sites; and wherein at least said first ligand is a ligand selected from the group consisting of BOC-4-aminomethyl-L-Phe, 4[[5-(Trifluoromethyl)pyridin-2-yl]oxy]phenyl]N-phenylcarbamate, (R)-2-[4-(5-chloro-3-fluoro-2-pyridyloxy)phenoxy]propionic acid, 2-(((3-chloro-5(trifluoromethyl)pyridin-2-yloxy)phenoxy)methyl)acrylates, 2-(((3-chloro-5(trifluoromethyl)pyridin-2-yloxy)phenyl)methyl)acrylates, 2-(((3-chloro-5(trifluoromethyl)pyridin-2-yloxy)phenyl)methyl)acrylonitriles, 3-(3-chloro-4-{[5-(trifluoromethyl)-2-pyridinyl]oxy}anilino)-3-oxopropanoic acid, Sethoxydim, Clethodim, 5-(Tetradecyloxy)-2-furoic acid, 2-[(2,6-Dichlorophenyl)amino]benzeneacetic acid, 2-[4-(4-Chlorophenoxy)phenoxy]propanoic acid, (RS)-2-{4-[3-chloro-5-(trifluoromethyl)-2-pyridinyl]oxy]phenoxy}propanoic acid, (RS)-2-[4-(6-chloro-1,3-benzoxazol-2-yloxy)phenoxy]propanoic acid, (RS)-2-[4-(2,4-dichlorophenoxy)phenoxy]propanoic acid, (RS)-2-{4-[5-(trifluoromethyl)-2-pyridyloxy]phenoxy}propanoic acid, (RS)-2-[4-(6-chloroquinoxalin-2-yloxy)phenoxy]propanoic acid, (RS)-2-[4-($\alpha,\alpha,\alpha$-trifluoro-p-tolyloxy)phenoxy]propanoic acid, 5-([4,6-Dichlorotriazin-2-yl]amino)fluorescein hydrochloride, 3-[N-(4-acetylphenyl)carbomoyl]pyridine-2-Carboxylic acid, 3-(2-{[3-chloro-5-(trifluoromethyl)-2-pyridinyl]oxy}anilino)-3-oxopropanoic acid, L-ornithine-beta-alanine, 2-Methyl-1-(3-morpholinopropyl)-5-phenyl-1H-pyrrole-3-carboxylic acid, Hippuric acid, Hippuryl-D-lysine, and hippuryl-L-phenylalanine.

In one embodiment, said first ligand binds a site that is different than the site bound by the second ligand. In another embodiment, said first site is a pocket on said marker. In yet another embodiment, said second site is a pocket on said marker.

In one embodiment, said marker is an HLA-DR cell surface antigen. In another embodiment, said first ligand and said second ligand bind sites within an epitope recognized by the Lym-1 antibody.

In any of the above embodiments, said first ligand is a small organic molecule. In any of the above embodiments, said second ligand is a small organic molecule.

Suitable second ligand can be selected from Tables 1, 5, 6, 7, or 8.

In one embodiment, the SHAL is tridentate further comprising a third ligand. Suitable second and third ligands can be independently selected from the group of ligands found in Tables 1, 5, 6, 7, or 8.

In one embodiment of SHAL, said third ligand is 4-(Dimethylamino)azobenzene-4'-sulfonyl-L-valine (Dv); said second ligand is 4-[4-(4-chlorobenzyl)piperazino]-3-nitrobenzenecarboxylic acid (Cb); and said first ligand is selected from the group consisting of 4[[5-(Trifluoromethyl)pyridin-2-yl]oxy]phenyl]N-phenylcarbamate, (R)-2-[4-(5-chloro-3-fluoro-2-pyridyloxy)phenoxy]propionic acid, 2-(((3-chloro-5(trifluoromethyl)pyridin-2-yloxy)phenoxy)methyl)acrylates, 2-(((3-chloro-5(trifluoromethyl)pyridin-2-yloxy)phenyl)methyl)acrylates, 2-(((3-chloro-5(trifluoromethyl)pyridin-2-yloxy)phenyl)methyl)acrylonitriles, 3-(3-chloro-4-{[5-(trifluoromethyl)-2-pyridinyl]oxy}anilino)-3-oxopropanoic acid, Sethoxydim, Clethodim, 5-(Tetradecyloxy)-2-furoic acid, 2-[(2,6-Dichlorophenyl)amino]benzeneacetic acid, 2-[4-(4-Chlorophenoxy)phenoxy]propanoic acid, (RS)-2-{4-[3-chloro-5-(trifluoromethyl)-2-pyridinyl]oxy]phenoxy}propanoic acid, (RS)-2-[4-(6-chloro-1,3-benzoxazol-2-yloxy)phenoxy]propanoic acid, (RS)-2-[4-(2,4-dichlorophenoxy)phenoxy]propanoic acid, (RS)-2-{4-[5-(trifluoromethyl)-2-pyridyloxy]phenoxy}propanoic acid, (RS)-2-[4-(6-chloroquinoxalin-2-yloxy)phenoxy]propanoic acid, and (RS)-2-[4-(α,α,α-trifluoro-p-tolyloxy)phenoxy]propanoic acid.

Other examples of SHAL are further provided in Table 2.

For any SHAL of the above embodiments that have two ligands, said first ligand is joined to said second ligand by a linker selected from the group consisting of a PEG type linker, a peptide or peptide analog linker, an avidin/biotin linker, a straight chain carbon linker, a heterocyclic linker, a branched carbon linker, a dendrimer, a nucleic acid linker, a sugar or carbohydrate linker, a thiol linker, an ester linker, a linker comprising an amine, and a linker comprising a carboxyl. In one embodiment, said linker comprises polyethyleneglycol. In another embodiment, said linker comprises polyethyleneglycol and/or a lysine.

For any SHAL of the above embodiments that have three ligands, said second ligand and said third ligand are joined to each other by a linker comprising a moiety selected from the group consisting of a PEG type linker, a peptide linker, an avidin/biotin linker, a straight chain carbon linker, a heterocyclic linker, a branched carbon linker, a dendrimer, a nucleic acid linker, a sugar or carbohydrate linker, a thiol linker, an ester linker, a linker comprising an amine, and a linker comprising a carboxyl. In one embodiment, said linker comprises polyethyleneglycol. In another embodiment, said linker comprises polyethyleneglycol and/or a lysine.

Another embodiment of the present disclosure provides a selective high affinity ligand (SHAL) that specifically binds to a cancer cell, said SHAL comprising: three ligands attached to each other, wherein said first ligand is 4-(Dimethylamino)azobenzene-4'-sulfonyl-L-valine (Dv); said second ligand is 4-[4-(4-chlorobenzyl)piperazino]-3-nitrobenzenecarboxylic acid (Cb); and said third ligand is selected from the group consisting of 3-(2-([3-chloro-5-(trifluoromethyl)-2-pyridinyl]oxy)-anilino)-3-oxopropanoic acid (Ct), or an analogue thereof.

In one embodiment, said first ligand, said second ligand and said third ligand are joined to each other by a linker comprising a moiety selected from the group consisting of a PEG type linker, a peptide linker, an avidin/biotin linker, a straight chain carbon linker, a heterocyclic linker, a branched carbon linker, a dendrimer, a nucleic acid linker, a sugar or carbohydrate linker, a thiol linker, an ester linker, a linker comprising an amine, and a linker comprising a carboxyl. In one aspect, said linker comprises polyethyleneglycol. In another aspect, said linker comprises polyethyleneglycol and/or a lysine.

Another embodiment of the present disclosure provides a SHAL comprising the structure:

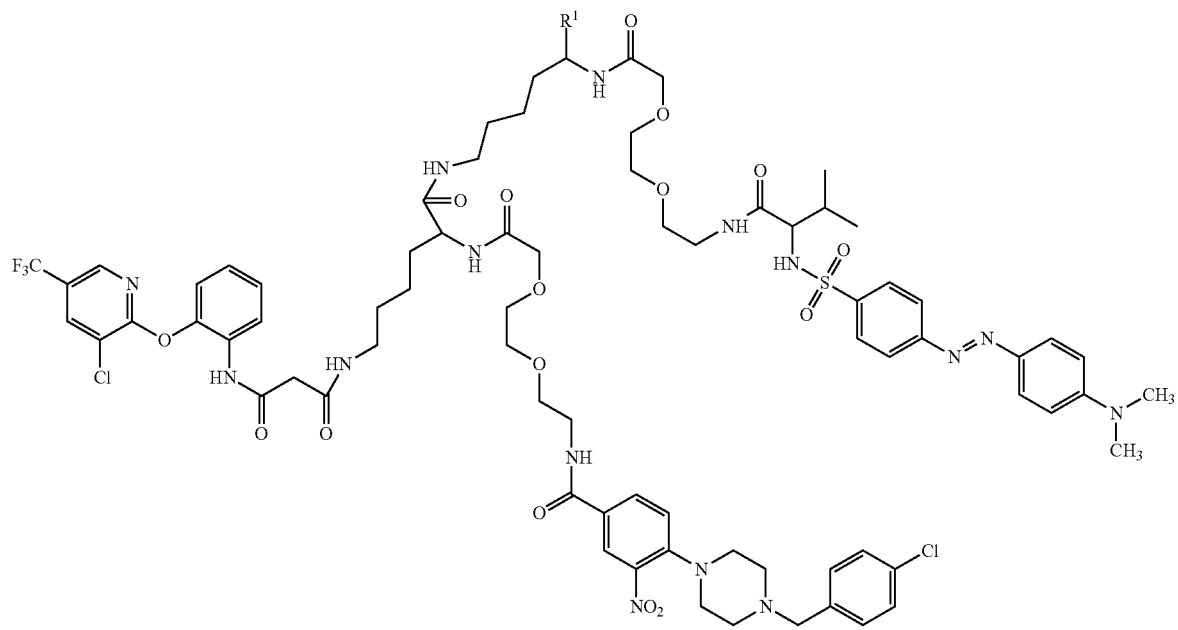

wherein R¹ is selected from the group consisting of COOH, a linker, an effector, and a linker attached to an effector.

Yet another embodiment of the present disclosure provides a SHAL comprising the structure:

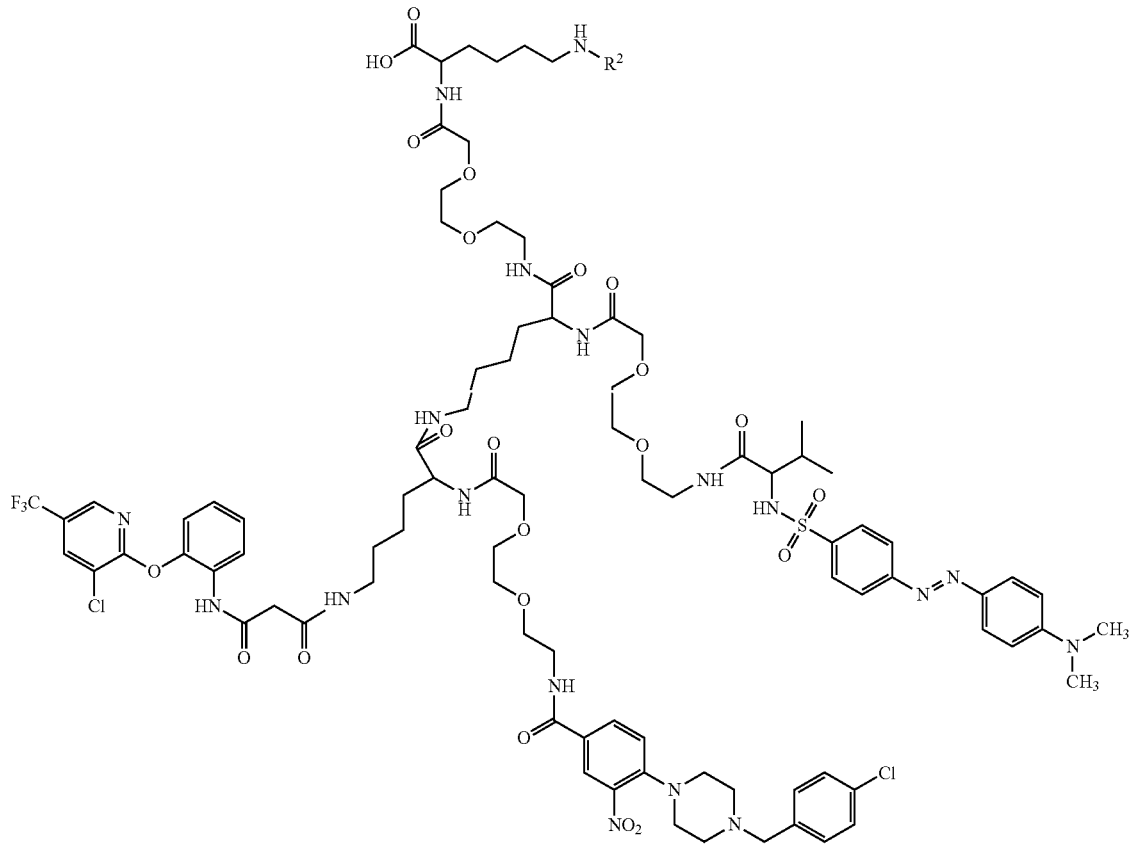

wherein R² comprises an effector.

In any of the above embodiments, a SHAL can be bivalent.

In some embodiments, said SHAL is attached to a transduction peptide. In one embodiment, said transduction peptide is selected from the group consisting of nuclear localization signal of SV40, the protein transduction domain of HIV Tat protein, the integrin-binding peptide (RGD peptide), the heparin-binding domain of vitronectin (VN peptide), antennapedia protein of *Drosophila*, VP22, oligoarginine, lactosylated poly-L-lysine or other oligocation, S-G-E-H-T-N-G-P-S-K-T-S-V-R-W-V-W-D, S-M-T-T-M-E-F-G-H-S-M-I-T-P-Y-K-I-D, Q-D-G-G-T-W-H-L-V-A-Y-C-A-K-S-H-R-Y, M-S-D-P-N-M-N-P-G-T-L-G-S-S-H-I-L-W, S-P-G-N-Q-S-T-G-V-I-G-T-P-S-F-S-N-H, S-S-G-A-N-Y-F-F-N-A-I-Y-D-F-L-S-N-F, and G-T-S-R-A-N-S-Y-D-N-L-L-S-E-T-L-T-Q. In another embodiment, said transduction peptide is hexa-arginine.

In any of the above embodiments, said SHAL is attached to an effector. In one embodiment, said effector is selected from the group consisting of an epitope tag, an antibody, a second SHAL, a label, a cytotoxin, a liposome, a radionuclide, a drug, a prodrug, an enzyme inhibitor, a viral particle, a cytokine, and a chelate. In another embodiment, said effector is an epitope tag selected from the group consisting of an avidin, and a biotin. In yet another embodiment, said effector is a cytotoxin selected from the group consisting of a Diphtheria toxin, a *Pseudomonas* exotoxin, a ricin, an abrin, and a thymidine kinase. In still another embodiment, said effector is a chelate comprising a metal isotope selected from the group consisting of $^{99}$Tc, $^{203}$Pb, $^{67}$Ga, $^{68}$Ga, $^{72}$As, $^{111}$In, $^{113m}$In, $^{97}$Ru, $^{62}$Cu, $^{64}$Cu, $^{52}$Fe, $^{52m}$Mn, $^{51}$Cr, $^{186}$Re, $^{188}$Re, $^{77}$As, $^{90}$Y, $^{67}$Cu, $^{169}$Er, $^{121}$Sn, $^{127}$Te, $^{142}$Pr, $^{143}$Pr, $^{198}$Au, $^{199}$Au, $^{161}$Tb, $^{109}$Pd, $^{165}$Dy, $^{149}$Pm, $^{151}$Pm, $^{153}$Sm, $^{157}$Gd, $^{159}$Gd, $^{166}$Ho, $^{172}$Tm, $^{169}$Yb, $^{175}$Yb, $^{177}$Lu, $^{105}$Rh, and $^{111}$Ag. Further in another embodiment, said effector is a chelate comprising an alpha emitter. In one aspect, said alpha emitter is bismuth 213. In another embodiment, said effector is a chelate comprising DOTA. In another embodiment, said effector is a lipid or a liposome. In a particular embodiment, said effector is selected from the group consisting of 3-(2-([3-chloro-5-(trifluoromethyl)-2-pyridinyl]oxy)-anilino)-3-oxopropanoic acid (Ct), 4[[5-(Trifluoromethyl)pyridin-2-yl]oxy]phenyl]N-phenylcarbamate, (R)-2-[4-(5-chloro-3-fluoro-2-pyridyloxy)phenoxy]propionic acid, 2-(((3-chloro-5(trifluoromethyl)pyridin-2-yloxy)phenoxy)methyl)acrylates, 2-(((3-chloro-5(trifluoromethyl)pyridin-2-yloxy)phenyl)methyl)acrylates, 2-(((3-chloro-5(trifluoromethyl)pyridin-2-yloxy)phenyl)methyl)acrylonitriles, 3-(3-chloro-4-{[5-(trifluoromethyl)-2-pyridinyl]oxy}anilino)-3-oxopropanoic acid, Sethoxydim, Clethodim, 5-(Tetradecyloxy)-2-furoic acid, 2[(2,6-Dichlorophenyl)amino]benzeneacetic acid, 2-[4-(4-Chlorophenoxy)phenoxy]propanoic acid, (RS)-2-{4-[3-chloro-5-(trifluoromethyl)-2-pyridinyl]oxy]phenoxy}propanoic acid, (RS)-2-[4-(6-chloro-1,3-benzoxazol-2-yloxy)phenoxy]propanoic acid, (RS)-2-[4-(2,4-dichlorophenoxy)phenoxy]propanoic acid, (RS)-2-{4-[5-(trifluoromethyl)-2-pyridyloxy]phenoxy}propanoic acid, (RS)-2-[4-(6-chloroquinoxalin-2-yloxy)phenoxy]propanoic acid, and (RS)-2-[4-(α,α,α-trifluoro-p-tolyloxy)phenoxy]propanoic acid.

One embodiment of the present disclosure provides a method of inhibiting the growth or proliferation of a cancer cell that expresses an HLA-DR10 marker, said method comprising: contacting said cancer with a selective high-affinity polydentate ligand (SHAL) of any of the above embodiments.

In one aspect, said cell is a metastatic cell. In another aspect, said cell is a solid tumor cell. In yet another aspect, said cancer cell is a malignant B lymphocyte. In a particular aspect, said cancer cell is associated with non-Hodgkins lymphoma or leukemia or other B-cell derived malignancies.

Still in another embodiment, the present disclosure provides a pharmaceutical formulation said formulation comprising: a pharmaceutically acceptable excipient and a SHAL of any of the above embodiments. In one aspect, said formulation is a unit dosage formulation.

Further provided, in one embodiment, is a method of detecting a cancer cell, said method comprising: contacting said cancer cell with a chimeric molecule comprising an SHAL of any of the above embodiments attached to a detectable label; and detecting the presence or absence of said detectable label. In one aspect, said detectable label is a selected from the group consisting of a gamma-emitter, a positron-emitter, an x-ray emitter, an alpha emitter, and a fluorescence-emitter.

Still further provided, in one embodiment, is a method of detecting a cancer cell, said method comprising: contacting a cancer cell with a chimeric molecule comprising chimeric molecule comprising a SHAL of any of the above embodiments attached to an epitope tag; contacting said chimeric molecule with a chelate comprising a detectable moiety whereby said chelate binds to said epitope tag thereby associating said detectable moiety with said chelate; and detecting said detectable moiety.

In one aspect, said detectable moiety is a radionuclide. In another aspect, said detectable moiety is selected from the group consisting of a gamma-emitter, a positron-emitter, an alpha emitter, an x-ray emitter, and a fluorescence-emitter. In one aspect, said detecting comprises external imaging. In another aspect, said detecting comprises internal imaging. In a particular aspect, said detectable moiety comprises a metal isotope selected from the group consisting of $^{99}$Tc, $^{203}$Pb, $^{67}$Ga, $^{68}$Ga, $^{72}$As, $^{111}$In, $^{113m}$In, $^{97}$Ru, $^{62}$Cu, $^{64}$Cu, $^{52}$Fe, $^{52m}$Mn, $^{51}$Cr, $^{186}$Re, $^{188}$Re, $^{77}$As, $^{90}$Y, $^{67}$Cu, $^{169}$Er, $^{121}$Sn, $^{127}$Te, $^{142}$Pr, $^{143}$Pr, $^{198}$Au, $^{199}$Au, $^{161}$Tb, $^{109}$Pd, $^{165}$Dy, $^{149}$Pm, $^{151}$Pm, $^{153}$Sm, $^{157}$Gd, $^{159}$Gd, $^{166}$Ho, $^{172}$Tm, $^{169}$Yb, $^{175}$Yb, $^{177}$Lu, $^{105}$Rh, and $^{111}$Ag. In another aspect, said chelate comprises DOTA. In yet another aspect, said epitope tag is an avidin, a biotin, or an enzyme.

In certain embodiments this invention provides novel polydentate selective high affinity ligands (SHALs) that can function to specifically bind particular target molecules in a manner analogous to antibody binding. Methods for the design and generation of SHALs as affinity reagents for basic or applied research or for diagnosis and treatment of infectious and/or malignant diseases and their administration to patients with infectious and/or malignant diseases are described.

The SHALs typically comprise two or more ligands (binding moieties) that each bind different regions on the intended target attached to each other directly or through a linker. Where the SHAL is directed to a marker on a cancer cell, the SHAL associates in greater density (abundance) or accessibility on the target cell as compared to normal cells. The SHAL thus provides selectivity appropriate for diagnosis or treatment of the target cells. Different SHALs can be readily generated for different malignant cells and malignant diseases. The SHAL represents a core building block (e.g., a targeting moiety) that can be incorporated into larger e.g., chimeric molecules to affect specific delivery of an effector to the target.

Thus, in one embodiment, this invention provides a method of making a selective high-affinity polydentate ligand (SHAL) that specifically binds a target molecule. In certain embodiments, the method typically involves screening a first ligand library to identify a first ligand that binds to the target molecule; screening a second ligand library to identify a second ligand that binds to the target molecule where the second ligand is different than the first ligand; linking the first ligand to the second ligand to form a SHAL; and screening the SHAL for the ability to specifically bind to the target molecule. In certain embodiments the target molecule is a protein. In certain embodiments the target molecule is a cancer marker (e.g., Lym-1 epitope, Muc-1, C-myc, p53, Ki67, Her2, Her4, BRCA1, BRCA2, Lewis Y, CA 15-3, G250, HLA-DR cell surface antigen, CEA, CD20, CD22, integrin, cea, 16, EGFr, AR, PSA, and other growth factor receptors, etc.). The method can optionally further involve screening the SHAL to identify a SHAL that binds to the target with an avidity and/or specificity higher than either ligand comprising the SHAL. The first ligand library and the second ligand library can be the same library or can be different libraries. In certain embodiments the first and/or second ligand library is a library of small organic molecules. In certain embodiments screening the first ligand library and/or screening the second ligand library comprises virtual in silico screening. The virtual in silico screening can comprise screening a compound database (e.g., MDL® Available Chemicals Directory, ChemSpider, GNU-Darwin) using one or more algorithms as utilized in the DOCK program. The virtual in silico screening can comprise screening a compound database using the DOCK program. The virtual in silico screening can involve screening for a first ligand and/or multiple ligands that bind a pocket on a protein. In certain embodiments the pocket is identified using an algorithm utilized by the SPHGEN program. In certain embodiments the pocket is identified using the SPHGEN program. The virtual in silico screening can involve screening for a second or third ligand that binds different regions of the target than the ligands identified when screening the first ligand library.

In certain embodiments screening a first ligand library and/or screening a second ligand library additionally comprises screening one or more ligands identified in the virtual in silico screening in a physical assay for the ability to bind to the target. Suitable physical assays include, but are not limited to a BIAcore assay, saturation transfer difference nuclear magnetic resonance spectroscopy, and transfer NOE (trNOE) nuclear magnetic resonance spectroscopy, ELISA, competitive assay, tissue binding assay, a live cell binding assay, a cellular extract assay, and the like.

Linking of the ligands can involve directly linking two or more ligands or linking two or more ligands with a linker (e.g., a PEG type linker, a peptide linker, an avidin/biotin linker, a straight chain carbon linker, a heterocyclic linker, a branched carbon linker, a dendrimer, a nucleic acid linker, a thiol linker, an ester linker, a linker comprising an amine, a linker comprising a carboxyl, etc.). The linking can optionally comprise linking two or more ligands with linkers of different lengths to produce a library of SHALs having different length linkers; and, optionally, screening the library of SHALs having different length linkers to identify members of the library that have the highest avidity and/or specificity for the target. In certain embodiments the method further involves comprising screening the SHAL(s) to identify a SHAL that binds to the target with an avidity and/or specificity higher than either ligand comprising the SHAL. The screening of individual ligands and/or bivalent or polyvalent SHAL(s) can be by any of a variety of methods including, but not limited to a BIAcore assay, saturation transfer difference nuclear magnetic resonance spectroscopy, and transfer NOE (trNOE) nuclear magnetic resonance spectroscopy, ELISA, competitive assay, tissue binding assay, live cell binding assay, a cellular extract assay, and the like. In certain embodiments the target molecule is a protein and/or a cancer marker (e.g., a Lym1 epitope, Muc-1, C-myc, p53, Ki67, Her2, Her4, BRCA1, BRCA2, Lewis Y, CA 15-3, G250, HLA-DR cell surface antigen, etc.).

Also provided is a method of synthesizing an inhibitor for an enzyme or other binding protein or receptor. In certain embodiments the method typically involves identifying a first pocket (or bump) and a second or third pocket (or bump) in the enzyme or other binding protein or receptor where the first, second and third pockets flank opposite sides of the active site or binding site of the enzyme or other binding protein or receptor; screening a first ligand library to identify a first ligand that binds to the first pocket (or bump); screening a second ligand library to identify a second ligand that binds to the second pocket (or bump); screening a third ligand library to identify a third ligand that binds to a third pocket or bump; linking the first ligand to the second and third ligands to form a polydentate selective high affinity ligand (SHAL); and screening the SHAL for the ability to specifically bind to and inhibit the enzyme or other binding protein. In certain embodiments the pockets or "bumps" need not be located on opposite sides of the active site or binding site of the enzyme or binding protein or receptor, but are simply located so that binding of the SHAL blocks binding of the native cognate ligand to that site. In certain embodiments the target molecule comprises a molecule selected from the group consisting of a protein, an enzyme, a nucleic acid, a nucleic acid binding protein, and a carbohydrate. In certain embodiments the method further involves screening the SHAL to identify a SHAL that binds to the target with an avidity and/or specificity higher than either ligand comprising the SHAL. The first, second and third ligand libraries can be the same library or can be different libraries. In certain embodiments the first and/or second and/or third ligand library is a library of small organic molecules. In certain embodiments screening the first, second and/or third ligand library comprises virtual in silico screening. The virtual in silico screening can comprise screening a compound database (e.g., MDL® Available Chemicals Directory) using one or more algorithms as utilized in the DOCK program. The virtual in silico screening can comprise screening a compound database using the DOCK program. The virtual in silico screening can involve screening for a first, second and/or third ligand that binds a pocket on a protein. In certain embodiments the pocket is identified using an algorithm utilized by the SPHGEN program. In certain embodiments the pocket is identified using the SPHGEN program. The virtual in silico screening can involve screening for a second ligand that binds different region of the target than the ligands identified when screening the first ligand library.

In certain embodiments screening a first, second or third ligand library and/or screening a second ligand library additionally comprises screening one or more ligands identified in the virtual in silico screening in a physical assay for the ability to bind to the target. Suitable physical assays include, but are not limited to a BIAcore assay, saturation transfer difference nuclear magnetic resonance spectroscopy, and transfer NOE (trNOE) nuclear magnetic resonance spectroscopy, ELISA, competitive assay, tissue binding assay, a live cell binding assay, a cellular extract assay, and the like.

Linking of the ligands can involve directly linking two or more ligands or linking two or more ligands with a linker (e.g., a PEG type linker, a peptide linker, an avidin/biotin linker, a straight chain carbon linker, a heterocyclic linker, a branched carbon linker, a dendrimer, a nucleic acid linker, a thiol linker, an ester linker, a linker comprising an amine, a linker comprising a carboxyl, etc.). The linking can optionally comprise linking the ligands with linkers of different lengths to produce a library of SHALs having different length linkers; and, optionally, screening the library of SHALs having different length linkers to identify members of the library that have the highest avidity and/or specificity for the target.

This invention also provides a polydentate selective high affinity ligand (SHAL) that specifically binds to a desired target (e.g., a cancer cell). Where the target is a cancer cell, the SHAL typically comprises a first ligand that binds to a first site on a marker for the cancer cell linked (directly or through a linker) to a second or third ligand that binds to a second or third site on same marker or on a different marker for the cancer cell where the first site, the second site and the third site are different sites (e.g., all three ligands are capable of simultaneously binding to the target(s)). In certain embodiments the first site, second site and/or the third site is a pocket (or "bump") on the marker(s). Suitable markers include, but are not limited to a Lym-1 epitope, Muc-1, C-myc, p53, Ki67, Her2, Her4, BRCA1, BRCA2, Lewis Y, CA 15-3, G250, HLA-DR cell surface antigen, CEA, CD20, CD22, integrin, CEA, 16, EGFr, AR, PSA, other growth factor receptors, and the like.

In certain preferred embodiments, the marker is an HLA-DR cell surface antigen. In certain embodiments the three ligands bind sites within an epitope recognized by the Lym-1 or other HLA-DR specific antibodies. In certain embodiments the three ligands are each small organic molecules. In certain embodimens, the first ligand is a ligand selected from Table 1, and the second and third ligand, when present, are independently selected from the ligands in Tables 1, 5, 6, 7, or 8. In certain embodiments the SHAL comprises a first, second and/or third ligand selected from Tables 2, 3, or 4. In certain embodiments the SHAL comprises a first, second and/or third ligand selected from Table 4. The three ligands can be joined directly together or the first ligand can be attached to the second and/or third ligand by a linker (e.g., a PEG type linker, a peptide linker, an avidin/biotin linker, a straight chain carbon linker, a heterocyclic linker, a branched carbon linker, a dendrimer, a nucleic acid linker, a thiol linker, an ester linker, a linker comprising an amine, a linker comprising a carboxyl, etc.). In certain embodiments the SHAL has an avidity for the marker greater than about $10^{-6}$ M while the individual ligands comprising the SHAL each have a binding affinity for the marker less than about $10^{-6}$ M. In certain embodiments the SHAL has a formula as shown herein and in the Figures or is an analogue thereof.

This invention also provides chimeric molecules comprising a SHAL as described herein attached to an effector (e.g., an epitope tag, a second SHAL, an antibody, a label, a cytotoxin, a liposome, a radionuclide, a drug, a prodrug, a viral particle, a cytokine, and a chelate. In certain embodiments the effector is an epitope tag selected from the group consisting of an avidin, and a biotin. In certain embodiments the effector is a cytotoxin selected from the group consisting of a Diphtheria toxin, a *Pseudomonas* exotoxin, a ricin, an abrin, and a thymidine kinase. In certain embodiments the effector is a chelate comprising a metal isotope selected from the group consisting of $^{99}$Tc, $^{203}$Pb, $^{67}$Ga, $^{68}$Ga, $^{72}$As, $^{111}$In, $^{113m}$In, $^{97}$Ru, $^{62}$Cu, $^{64}$Cu, $^{52}$Fe, $^{52m}$Mn, $^{51}$Cr, $^{186}$Re, $^{188}$Re, $^{77}$As, $^{90}$Y, $^{67}$Cu, $^{169}$Er, $^{121}$Sn, $^{127}$Te, $^{142}$Pr, $^{143}$Pr, $^{198}$Au, $^{199}$Au, $^{161}$Tb, $^{109}$Pd, $^{165}$Dy, $^{149}$Pm, $^{151}$Pm, $^{153}$Sm, $^{157}$Gd, $^{159}$Gd, $^{166}$Ho, $^{172}$Tm, $^{169}$Yb, $^{175}$Yb, $^{177}$Lu, $^{105}$Rh, and $^{111}$Ag. In certain embodiments effector is a chelate comprising an alpha emitter (e.g., bismuth 213). In certain embodiments the effector is a chelate comprising DOTA. In certain embodiments the effector is a lipid or a liposome (e.g., a liposome containing a drug).

In still another embodiment, this invention provides a pharmaceutical formulation the formulation comprising a polydentate selective high affinity ligand (SHAL) that specifically binds to a cancer cell as described herein and a pharmaceutically acceptable excipient. In certain embodiments the formulation can be provided as a unit dosage formulation. In certain embodiments the formulation can be provided as a time-release formulation.

This invention also provides a pharmaceutical formulation the formulation comprising a pharmaceutically acceptable excipient and a chimeric molecule comprising a SHAL as described herein. In certain embodiments the formulation can be provided as a unit dosage formulation. In certain embodiments the formulation can be provided as a time-release formulation.

Methods are provided for inhibiting the growth or proliferation of a cancer cell. The methods typically involves contacting the cancer cell (e.g., metastatic cell, tumor cell, etc.) with a polydentate selective high affinity ligand (SHAL) that specifically binds to a cancer cell and/or with a chimeric molecule comprising a polydentate selective high affinity ligand (SHAL) that specifically binds to a cancer cell attached to an effector (e.g., drug, liposome, cytotoxin, radionuclide, or chelator).

In certain embodiments, this invention provides SHALS that specifically bind to a desired target. The target can be any target for which it is desired to create a binding moiety. The SHAL typically comprises two or more ligands joined directly or through a linker where a first ligand that binds to a first site on the target and the second and/or third ligand binds to second and/or third site on the target on same target marker where the first, second and/or third sites are different sites (e.g., all three ligands are capable of simultaneously binding to the target(s)). In certain embodiments the first, second and/or third site is a pocket (or "bump") on the target(s). In certain embodiments the first, second and/or third sites are on the same target molecule.

This invention also provides various detection methods. In certain embodiments this invention provides a method of detecting a cancer cell. The method typically involves contacting the cancer cell with a chimeric molecule comprising a SHAL that specifically binds to a cancer cell (e.g., to a cancer marker) attached to a detectable label (e.g., gamma-emitter, a positron-emitter, an x-ray emitter, an alpha emitter, a fluorescence-emitter, etc.) and detecting the presence or absence of the detectable label. In certain embodiments the method typically involves contacting a cancer cell with a chimeric molecule comprising chimeric molecule comprising SHAL that specifically binds to a cancer cell (e.g., to a cancer marker) attached to an epitope tag; contacting the chimeric molecule with a chelate comprising a detectable moiety whereby the chelate binds to the epitope tag thereby associating the detectable moiety with the chelate; and detecting the detectable moiety. In certain embodiments the detectable moiety is a radionuclide (e.g., a gamma-emitter, a positron-emitter, an alpha emitter, an x-ray emitter, etc.). In certain embodiments the detecting comprises external imaging and/or internal imaging. In certain embodiments the detectable moiety comprises a metal isotope selected from the group consisting of $^{99}$Tc, $^{203}$Pb, $^{67}$Ga, $^{68}$Ga, $^{72}$As, $^{111}$In, $^{113m}$In, $^{97}$Ru, $^{62}$Cu, $^{64}$Cu, $^{52}$Fe, $^{52m}$Mn, $^{51}$Cr, $^{186}$Re, $^{188}$Re, $^{77}$As, $^{90}$Y, $^{67}$Cu, $^{169}$Er, $^{121}$Sn, $^{127}$Te, $^{142}$Pr, $^{143}$Pr, $^{198}$Au, $^{199}$Au, $^{161}$Tb, $^{109}$Pd, $^{165}$Dy, $^{149}$Pm, $^{151}$Pm, $^{153}$Sm, $^{157}$Gd, $^{159}$Gd, $^{166}$Ho, $^{172}$Tm, $^{169}$Yb, $^{175}$Yb, $^{177}$Lu, $^{105}$Rh, and $^{111}$Ag. In certain embodiments the chelate comprises DOTA. In certain embodiments the epitope tag is an avidin or a biotin.

This invention also contemplates kits for creating and/or using SHALs of this invention and/or chimeric molecules comprising SHALs of this invention. In certain embodiments the kit comprises a container containing a SHAL as described herein and/or containers containing ligands for assembly into a SHAL as described herein. The like can optionally further include one or more linkers, one or more effectors (chelates, radionuclides, etc.), and the like. In certain embodiments the SHAL is in a pharmacologically acceptable excipient.

In certain embodiments, this invention expressly excludes SHALs where the binding moieties comprising the SHAL are antibodies, single chain antibodies, and the like. In certain embodiments the SHALs are not polyvalent antibodies or polyvalent single chain antibodies. In certain embodiments the ligands comprising the SHALs are not proteins. In certain embodiments, this invention expressly excludes SHALS where the binding moieties comprising the SHAL preferentially and/or specifically bind nucleic acids. In certain embodiments the ligands comprising the SHALs are small organic molecules.

Definitions

The terms "specific binding" or "preferential binding" refer to that binding which occurs between such paired species as enzyme/substrate, receptor/agonist, antibody/antigen, and lectin/carbohydrate which may be mediated by covalent and/or non-covalent interactions. When the interaction of the two species typically produces a non-covalently bound complex, the binding which occurs is typically electrostatic, and/or hydrogen-bonding, and/or the result of lipophilic interactions. Accordingly, "specific binding" occurs between pairs of species where there is interaction between the two that produces a bound complex. In particular, the specific binding is characterized by the preferential binding of one member of a pair to a particular species as compared to the binding of that member of the pair to other species within the family of compounds to which that species belongs. Thus, for example, a ligand may show an affinity for a particular pocket on a HLA-DR10 molecule that is at least two-fold preferably at least 10 fold, more preferably at least 100 fold, at least 1000 fold, or at least 10000 fold greater than its affinity for a different pocket on the same or related proteins.

The terms "ligand" or "binding moiety", as used herein, refers generally to a molecule that binds to a a particular target molecule and forms a bound complex as described above. The binding can be highly specific binding, however, in certain embodiments, the binding of an individual ligand to the target molecule can be with relatively low affinity and/or specificity. The ligand and its corresponding target molecule form a specific binding pair. Examples include, but are not limited to small organic molecules, sugars, lectins, nucleic acids, proteins, antibodies, cytokines, receptor proteins, growth factors, nucleic acid binding proteins and the like which specifically bind desired target molecules, target collections of molecules, target receptors, target cells, and the like.

The term "small organic molecule" refers to a molecule of a size comparable to those organic molecules generally used in pharmaceuticals. The term excludes natural biological macromolecules (e.g., proteins, nucleic acids, etc.). Preferred small organic molecules range in size up to about 5000 Da, more preferably up to 2000 Da, and most preferably up to about 1000 Da.

The term "ligand library" refers to a collection (e.g., to a plurality) of ligands or potential ligands. The ligand library can be an actual physical library of ligands and/or a database (e.g., a compound database comprising descriptions of a plurality of potential ligands such as the MDL® Available Chemicals Directory, ChemSpider, and the like).

The term "SHAL" refers to a molecule comprising a plurality of ligands that each bind to a different region of the target molecule to which the SHAL is directed. The ligands are joined together either directly or through a linker to form a polydentate moiety that typically shows high avidity for the target molecule. In certain embodiments, the SHAL comprises two or more ligands that bind their target with low affinity (e.g., $<10^{-6}$M and/or dissociates within seconds or less) that, when coupled together, form a SHAL that binds the target with high affinity (e.g., $>10^{-6}$M, or $>10^{-7}$ M, or $>10^{-8}$ M and/or dissociates slowly, e.g., hours to days).

The term "polydentate" when used with respect to a SHAL indicates that the SHAL comprises two or more ligands. The ligands typically bind to different parts of the target to which the SHAL is directed.

The terms "bidentate", "tridentate", and so forth when used with respect to a SHAL refer to SHALs consisting of two ligands, SHALs consisting of three ligands, and so forth.

The term "polyvalent SHAL" refers to a molecule in which two or more SHALs (e.g., two or more bidentate SHALs) are joined together. Thus, for example a bivalent SHAL refers to a molecule in which two SHALs are joined together. A trivalent SHAL refers to a molecule in which three SHALs are joined together, and so forth. A bivalent version of the bidentate SHAL JP459B is illustrated in FIG. 14).

A "polyspecific SHAL" is 2 or more SHALs joined together where each SHAL is polydentate and either or both can be polyvalent synthesized (or otherwise generated) so that they have 2 or more targets for each SHAL (set of poly ligands). For example, a SHAL can be synthesized with two or more ligands for the cavities of HLA-DR and cavities on a CDXX, eg CD20 or CD22, or all 3, etc. Another example involves joining a MUC-1 SHAL and an antilyphoma SHAL because some lymphomas overexpress traditional HLA-DR and CD receptors and MUC-1 (upregulated). SHAL synthesized with 2 or more ligands for the cavities of HLA-DR and cavities for a chelate, e.g DOTA, etc. where in the univalent or bivalent SHAL targets the malignant cell and the univalent or bivalent 2nd module catches a subsequently delivered agent, eg DOTA chelated radiometal or a prodrug intended to activate the drug transported to the malignant cell by the 1st SHAL.

The term "virtual in silico" when used, e.g., with respect to screening methods refers to methods that are performed without actual physical screening of the subject moieties. Typically virtual in silico screening is accomplished computationally, e.g., utilizing models of the particular molecules of interest. In certain embodiments, the virtual methods can be performed using physical models of the subject molecules and/or by simple visual inspection and manipulation.

The phrase "target for a SHAL" refers to the moiety that is to be specifically bound by the bidentate or polydentate SHAL.

The phrase "an algorithm found in . . . ", e.g., "an algorithm found in SPHGEN" refers to an algorithm that is implemented by (found in) the referenced software. The algorithm, however, can be manually, or by a program other than the referenced software and still represent a use of an algorithm found in the referenced software.

The term "pocket" when referring to a pocket in a protein refers to a cavity, indentation or depression in the surface of the protein molecule that is created as a result of the folding of the peptide chain into the 3-dimensional structure that makes the protein functional. A pocket can readily be recognized by inspection of the protein structure and/or by using commercially available modeling software (e.g., DOCK).

The term "cancer markers" refers to biomolecules such as proteins that are useful in the diagnosis and prognosis of cancer. As used herein, "cancer markers" include but are not limited to: PSA, human chorionic gonadotropin, alpha-fetoprotein, carcinoembryonic antigen, cancer antigen (CA) 125, CA 15-3, CD20, CDH13, CD 31, CD34, CD105, CD146, D16S422HER-2, phospatidylinositol 3-kinase (PI 3-kinase), trypsin, trypsin-1 complexed with alpha(1)-antitrypsin, estrogen receptor, progesterone receptor, c-erbB-2, bcl-2, S-phase fraction (SPF), p185erbB-2, low-affinity insulin like growth factor-binding protein, urinary tissue factor, vascular endothelial growth factor, epidermal growth factor, epidermal growth factor receptor, apoptosis proteins (p53, Ki67), factor VIII, adhesion proteins (CD-44, sialyl-TN, blood group A, bacterial lacZ, human placental alkaline phosphatase (ALP), alpha-difluoromethylornithine (DFMO), thymidine phosphorylase (dTHdPase), thrombomodulin, laminin receptor, fibronectin, anticyclins, anti-cyclin A, B, or E, proliferation associated nuclear antigen, lectin UEA-1, CEA, 16, and von Willebrand's factor.

The terms "polypeptide", "peptide" and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers. The term also includes variants on the traditional peptide linkage joining the amino acids making up the polypeptide.

The terms "nucleic acid" or "oligonucleotide" or grammatical equivalents herein refer to at least two nucleotides covalently linked together. A nucleic acid of the present invention is preferably single-stranded or double stranded and will generally contain phosphodiester bonds, although in some cases, as outlined below, nucleic acid analogs are included that may have alternate backbones, comprising, for example, phosphoramide (Beaucage et al. (1993) *Tetrahedron* 49(10):1925) and references therein; Letsinger (1970) *J. Org. Chem.* 35:3800; Sprinzl et al. (1977) *Eur. J. Biochem.* 81: 579; Letsinger et al. (1986) *Nucl. Acids Res.* 14: 3487; Sawai et al. (1984) *Chem. Lett.* 805, Letsinger et al. (1988)

*J. Am. Chem. Soc.* 110: 4470; and Pauwels et al. (1986) *Chemica Scripta* 26: 1419), phosphorothioate (Mag et al. (1991) *Nucleic Acids Res.* 19:1437; and U.S. Pat. No. 5,644,048), phosphorodithioate (Briu et al. (1989) *J. Am. Chem. Soc.* 111:2321, O-methylphosphoroamidite linkages (see Eckstein, *Oligonucleotides and Analogues: A Practical Approach*, Oxford University Press), and peptide nucleic acid backbones and linkages (see Egholm (1992) *J. Am. Chem. Soc.* 114:1895; Meier et al. (1992) *Chem. Int. Ed. Engl.* 31: 1008; Nielsen (1993) *Nature*, 365: 566; Carlsson et al. (1996) *Nature* 380: 207). Other analog nucleic acids include those with positive backbones (Denpcy et al. (1995) *Proc. Natl. Acad. Sci. USA* 92: 6097; non-ionic backbones (U.S. Pat. Nos. 5,386,023, 5,637,684, 5,602,240, 5,216,141 and 4,469,863; Angew. (1991) *Chem. Intl. Ed. English* 30: 423; Letsinger et al. (1988) *J. Am. Chem. Soc.* 110:4470; Letsinger et al. (1994) *Nucleoside & Nucleotide* 13:1597; Chapters 2 and 3, ASC Symposium Series 580, "Carbohydrate Modifications in Antisense Research", Ed. Y. S. Sanghui and P. Dan Cook; Mesmaeker et al. (1994), *Bioorganic & Medicinal Chem. Lett.* 4: 395; Jeffs et al. (1994) *J. Biomolecular NMR* 34:17; *Tetrahedron Lett.* 37:743 (1996)) and non-ribose backbones, including those described in U.S. Pat. Nos. 5,235,033 and 5,034,506, and Chapters 6 and 7, ASC Symposium Series 580, Carbohydrate Modifications in Antisense Research, Ed. Y. S. Sanghui and P. Dan Cook. Nucleic acids containing one or more carbocyclic sugars are also included within the definition of nucleic acids (see Jenkins et al. (1995), *Chem. Soc. Rev. pp* 169-176). Several nucleic acid analogs are described in Rawls, C & E News Jun. 2, 1997 page 35. These modifications of the ribose-phosphate backbone may be done to facilitate the addition of additional moieties such as labels, or to increase the stability and half-life of such molecules in physiological environments.

The term "biotin" refers to biotin and modified biotins or biotin analogues that are capable of binding avidin or various avidin analogues. "Biotin", can be, inter alfa, modified by the addition of one or more addends, usually through its free carboxyl residue. Useful biotin derivatives include, but are not limited to, active esters, amines, hydrazides and thiol groups that are coupled with a complimentary reactive group such as an amine, an acyl or alkyl group, a carbonyl group, an alkyl halide or a Michael-type acceptor on the appended compound or polymer.

Avidin, typically found in egg whites, has a very high binding affinity for biotin, which is a B-complex vitamin (Wilcheck et al. (1988) *Anal. Biochem,* 171:1). Streptavidin, derived from *Streptomyces avidinii*, is similar to avidin, but has lower non-specific tissue binding, and therefore often is used in place of avidin. As used herein "avidin" includes all of its biological forms either in their natural states or in their modified forms. Modified forms of avidin which have been treated to remove the protein's carbohydrate residues ("deglycosylated avidin"), and/or its highly basic charge ("neutral avidin"), for example, also are useful in the invention.

The term "residue" as used herein refers to natural, synthetic, or modified amino acids.

As used herein, an "antibody" refers to a protein consisting of one or more polypeptides substantially encoded by immunoglobulin genes or fragments of immunoglobulin genes. The recognized immunoglobulin genes include the kappa, lambda, alpha, gamma, delta, epsilon and mu constant region genes, as well as myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

A typical immunoglobulin (antibody) structural unit is known to comprise a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

Antibodies exist as intact immunoglobulins or as a number of well characterized fragments produced by digestion with various peptidases. Thus, for example, pepsin digests an antibody below the disulfide linkages in the hinge region to produce F(ab)'$_2$, a dimer of Fab which itself is a light chain joined to $V_H$-$C_H$1 by a disulfide bond. The F(ab)'$_2$ may be reduced under mild conditions to break the disulfide linkage in the hinge region thereby converting the (Fab')$_2$ dimer into a Fab' monomer. The Fab' monomer is essentially a Fab with part of the hinge region (see, *Fundamental Immunology*, W. E. Paul, ed., Raven Press, N.Y. (1993), for a more detailed description of other antibody fragments). While various antibody fragments are defined in terms of the digestion of an intact antibody, one of skill will appreciate that such Fab' fragments may be synthesized de novo either chemically or by utilizing recombinant DNA methodology. Thus, the term antibody, as used herein also includes antibody fragments either produced by the modification of whole antibodies or synthesized de novo using recombinant DNA methodologies. Preferred antibodies include single chain antibodies (antibodies that exist as a single polypeptide chain), more preferably single chain Fv antibodies (sFv or scFv) in which a variable heavy and a variable light chain are joined together (directly or through a peptide linker) to form a continuous polypeptide. The single chain Fv antibody is a covalently linked $V_H$-$V_L$ heterodimer which may be expressed from a nucleic acid including $V_H$- and $V_L$-encoding sequences either joined directly or joined by a peptide-encoding linker. Huston, et al. (1988) *Proc. Nat. Acad. Sci. USA*, 85: 5879-5883. While the $V_H$ and $V_L$ are connected to each as a single polypeptide chain, the $V_H$ and $V_L$ domains associate non-covalently. The first functional antibody molecules to be expressed on the surface of filamentous phage were single-chain Fv's (scFv), however, alternative expression strategies have also been successful. For example Fab molecules can be displayed on phage if one of the chains (heavy or light) is fused to g3 capsid protein and the complementary chain exported to the periplasm as a soluble molecule. The two chains can be encoded on the same or on different replicons; the important point is that the two antibody chains in each Fab molecule assemble post-translationally and the dimer is incorporated into the phage particle via linkage of one of the chains to, e.g., g3p (see, e.g., U.S. Pat. No. 5,733,743). The scFv antibodies and a number of other structures converting the naturally aggregated, but chemically separated light and heavy polypeptide chains from an antibody V region into a molecule that folds into a three dimensional structure substantially similar to the structure of an antigen-binding site are known to those of skill in the art (see e.g., U.S. Pat. Nos. 5,091,513, 5,132,405, and 4,956,778). Particularly preferred antibodies should include all that have been displayed on phage or yeast (e.g., scFv, Fv, Fab and disulfide linked Fv (Reiter et al. (1995) *Protein Eng.* 8: 1323-1331).

The term "specifically binds", as used herein, when referring to a SHAL or to a biomolecule (e.g., protein, nucleic acid, antibody, etc.), refers to a binding reaction that is determinative of the presence of the SHAL or biomolecule in a heterogeneous population of molecules (e.g., proteins and other biologics). Thus, under designated conditions (e.g., binding assay conditions in the case of a SHAL or stringent hybridization conditions in the case of a nucleic acid), the specified ligand or SHAL preferentially binds to its particular "target" molecule and preferentially does not bind in a significant amount to other molecules present in the sample.

An "effector" refers to any molecule or combination of molecules whose activity it is desired to deliver/into and/or localize at a target (e.g., at a cell displaying a characteristic marker). Effectors include, but are not limited to labels, cytotoxins, enzymes, growth factors, transcription factors, drugs, lipids, liposomes, etc.

A "reporter" is an effector that provides a detectable signal (e.g., is a detectable label). In certain embodiments, the reporter need not provide the detectable signal itself, but can simply provide a moiety that subsequently can bind to a detectable label.

The term "conservative substitution" is used in reference to proteins or peptides to reflect amino acid substitutions that do not substantially alter the activity (specificity or binding affinity) of the molecule. Typically, conservative amino acid substitutions involve substitution of one amino acid for another amino acid with similar chemical properties (e.g., charge or hydrophobicity). The following six groups each contain amino acids that are typical conservative substitutions for one another: 1) Alanine (A), Serine (S), Threonine (T); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); and 6) Phenylalanine (F), Tyrosine (Y), Tryptophan (W).

The terms "epitope tag" or "affinity tag" are used interchangeably herein, and usually refers to a molecule or domain of a molecule that is specifically recognized by an antibody or other binding partner. The term also refers to the binding partner complex as well. Thus, for example, biotin or a biotin/avidin complex are both regarded as an affinity tag. In addition to epitopes recognized in epitope/antibody interactions, affinity tags also comprise "epitopes" recognized by other binding molecules (e.g., ligands bound by receptors), ligands bound by other ligands to form heterodimers or homodimers, $His_6$ bound by Ni-NTA, biotin bound by avidin, streptavidin, or anti-biotin antibodies, and the like.

Epitope tags are well known to those of skill in the art. Moreover, antibodies specific to a wide variety of epitope tags are commercially available. These include but are not limited to antibodies against the DYKDDDDK (SEQ ID NO:1) epitope, c-myc antibodies (available from Sigma, St. Louis), the HNK-1 carbohydrate epitope, the HA epitope, the HSV epitope, the $His_4$, $His_5$, and $His_6$ epitopes that are recognized by the His epitope specific antibodies (see, e.g., Qiagen), and the like. In addition, vectors for epitope tagging proteins are commercially available. Thus, for example, the pCMV-Tagl vector is an epitope tagging vector designed for gene expression in mammalian cells. A target gene inserted into the pCMV-Tagl vector can be tagged with the FLAG® epitope (N-terminal, C-terminal or internal tagging), the c-myc epitope (C-terminal) or both the FLAG (N-terminal) and c-myc (C-terminal) epitopes.

A PEG type linker refers to a linker comprising a polyethylene glycol (PEG).

BRIEF DESCRIPTION OF THE DRAWINGS

FIG. 8 illustrates the amino acid sequence alignment of HLA-DR molecules with known crystal structures. PDB codes identify the HLA-DR1(1aqd), HLA-DR2(1bx2), HLA-DR3(1a6a) and HLA-DR4 molecules (1dm5) sequences. 1i3r is a homologous MHC fusion protein. Hla_DR10: (SEQ ID NO:3), 1aqd_B: (SEQ ID NO:4), 1d5 m_B (SEQ ID NO:5), 1bx2_B: (SEQ ID NO:6), 1a6a_B: (SEQ ID NO:7), 1i3r_B: (SEQ ID NO:8).

FIGS. 13A and 13B illustrate bidentate SHALs synthesized by combining the appropriate pairs of the individual ligands identified to bind to HLA-DR10. FIG. 13A illustrates the three molecules. FIG. 13B illustrates two SHALs, synthesized by linking together deoxycholate and 5-leu-enkephalin, that have been shown to bind to isolated HLA-DR10 with nM affinities. The red part is one ligand (deoxycholate), the green is the other ligand (e.g., 5-leu-enkephalin), the blue is a lysine used to make the shortest linker, and the black is a combination of things: the PEG molecules used to make the linker between the two ligands longer, and a biotin molecule attached to the SHALs for testing purposes.

FIG. 17A illustrates increased binding of SHAL JP459B and Lym-1 MAb on large cell lymphoma compared to small cell lymphoma (panels A-D) and selective binding of live Raji cells (crystal violet stained) but not other cell types on plates coated with streptavidin horse radish peroxidase (SHRP) and biotinylated SHAL (panels E-H). (panels A-D) The SHAL was preincubated with SAHRP and detected by DAB reagent. Lym-1 binding was detected with a biotinylated anti-mouse MAb, followed by SAHRP and DAB. Panel A) SHAL on large cell lymphoma Panel B) SHAL on small cell lymphoma Panel C) Lym-1 MAb on large cell lymphoma and Panel D) Lym-1 MAb on small cell lymphoma. (Panels E-H) Images show selective binding of SHAL JP459B to live Raji cells (Panel E), but not to non-lymphoma LnCAP (Panel F), 22RV (Panel G) or DU145 (Panel H) cell lines. FIG. 17B shows that SHAL JP459B binds only to live-cultured tumor cells containing HLA-DR10, the plates are coated with steptavidin over night, they are washed and then the SHAL is added and incubated for 2 hrs and then the plates are washed again to remove unbound SHAL. Then the cells are added. The cells were washed and stained by Cresyl Violet.

FIG. 28. Structure of the tridentate SHAL containing the Ct ligand shown as a 2-D schematic (upper) and as a 3-D space-filling molecular structure (lower). The ligands used to produce this SHAL were dabsyl-L-valine (Dv), 4-[4-(4-chlorobenzyl)piperazino]-3-nitrobenzenecarboxylic acid (Cb) and (3-(2-([3-chloro-5-trifluoromethyl)-2-pyridinyl]oxy)-anilino)-3-oxopropanionic acid) (Ct). The 1st lysine residue provided a free amine for covalent binding of moieties such as metal binding macrocycles and biotin. Additional lysine residues were used to create branch points in the linker and PEG monomers were used to provide the appropriate distance between the ligands. The three ligands were identified by docking to cavities in the β subunit of HLA-DR10, flanking the amino acid arginine 70 shown critical for Lym-1 binding and cytotoxicity. Functional molecules can be incorporated at specific positions along the linker by inserting additional lysine residues, and attaching them to the free epsilon amine of the primary lysine.

DETAILED DESCRIPTION

Figure 1:
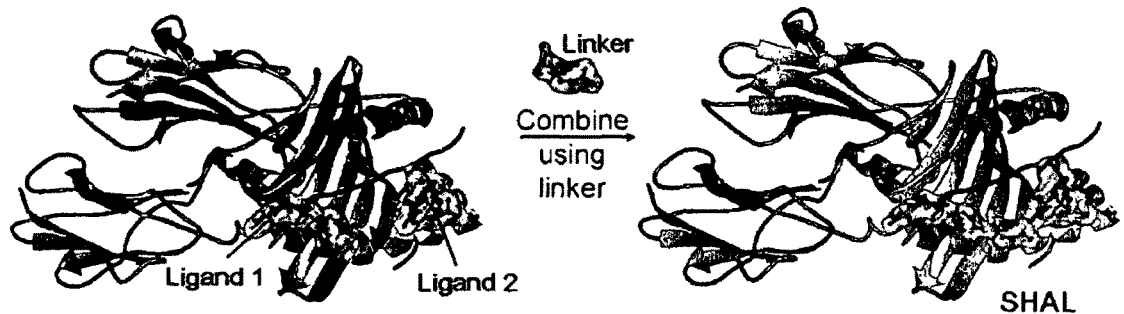
FIG. 1 illustrates a method of creating SHALs by identifying individual ligands (blue) that bind to two unique sites on the surface of a target (e.g., HLA-DR10 encompassing the Lym-1 epitope (red, green, yellow amino acids)) and linking them together synthetically to produce a molecule that binds to both sites.

This invention pertains to the development of a new class of binding molecules that can be used to specifically bind just about any target molecule(s). This class of binding molecules are referred to herein as Selective High Affinity Ligands or "SHALs". The SHALs can be used in a manner analogous to antibodies in a wide variety of contexts that include, but are not limited to capture reagents in affinity columns for purification of biological or other materials, binding agents in bio sensors, agents for the assembly of nanoparticles or nanomachines, diagnostics, and therapeutics.

SHALs can also be used to detect molecular signatures that can distinguish between various pathogen types or strains. SHALs also have use in biodefense applications for the detection of unique protein signatures present in toxins and on the surfaces of pathogenic organisms and to distinguish these biothreat agents from naturally occurring non-hazardous materials. Because the SHALs can be relatively stable when exposed to the environment, they are particular well suited for use in biosensors for biodefense, diagnostic, and other applications.

In certain preferred embodiments, the SHALs are used in the diagnosis and/or treatment of cancers. In such embodiments, the SHALs are directed to unique and/or specific sites (e.g., cancer-specific markers) on the surfaces of cancers (e.g., various malignant cells).

In certain embodiments, the SHALs can have a therapeutic effect when administered per se (e.g., in a manner analogous to the antibody therapeutic Herceptin™). A SHAL, like an antibody, can have a direct effect on a malignant cell that leads to cell death because the SHAL serves as an agonist against a normal pathway, thereby initiating or blocking critical cell functions and leading to malignant cell death. A SHAL can also act as a vaccine because it provides malignant cell identification either because it represents an aberrant cell surface marker or enhances a usual malignant cell marker.

In addition, or alternatively, the SHAL(s) can be used as targets (when bound to the targeted cell), or as carriers (targeting moieties) for other effectors that include, but are not limited to agents such as cytotoxic agents, markers for identification by the immune system, detectable labels (for imaging), and the like.

Radioisotopes are attractive examples of cytotoxic effectors that can be attached to the carrier SHAL to selectively deliver radiotherapy to the malignant cell(s). This therapy can be administered as single agent therapy, or in combination with marrow reconstitution in order to achieve greater dose intensity, or other drugs that may enhance the radiation effects on the malignant disease. Although there are many different drugs, chemotherapeutic, biological and otherwise, that can be combined with the SHAL, taxanes are one attractive example.

Examples of cytotoxic agents include radioisotopes, immunotoxins, chemotherapeutics, enzyme inhibitors, biologicals, etc. Interesting examples include apoptotic signals and enzymes such as the caspases. Radioisotopes represent interesting cytotoxic agents that have been shown to be effective in conjunction with antibody antigen and ligand-receptor systems. For treatment purposes, according to the present invention, it is considered that, in some embodiments, labeling with a particle emitter such as beta–, beta+ (positron) are preferable. In some cases, labeling with an alpha emitter or Auger-electron emitter is appropriate. There are many examples of therapeutic radioisotopes including yttrium-90 or iodine-131 that are of considerable current interest.

For certain imaging purposes, according to the present invention, it is considered that technetium-99, indium-111, iodine-123, or iodine-131 are attractive for single photon imaging and that beta+ (positron) emitters such as copper-64, yttrium-86, gallium-68, etc. are particularly likely to be very attractive when attached to a SHAL for diagnostic purposes A SHAL consists of two or more ligands (also referred to as binding moieties) linked together directly or through a linker to generate a core "polydentate" molecule (SHAL) that has been designed to specifically bind to essentially any desired target (e.g., unique or specific sites (pockets) on an intended target malignant cell surface molecule). The ligands (binding moieties) comprising the SHAL can include essentially any moiety capable of binding a site on the target. Such binding moieties can include, but are not limited to various chemicals (e.g., small organic molecules), proteins, sugars, carbohydrates, lectins, lipids, metals, nucleic acids, peptide and nucleic acid analogues, and the like.

Although not required, the individual ligands comprising the SHAL often have relatively low affinity (e.g., less than about $10^{-6}$ M) for the target. In contrast, the polydentate SHAL (comprising a plurality of ligands) typically shows relatively high avidity (e.g., greater than about $10^{-6}$ M, preferably greater than about $10^{-8}$ or $10^{-9}$ or $10^{-10}$ M, still greater than about $10^{-11}$ M, and most preferably greater than about $10^{-12}$ M).

In certain embodiments, where the target to which the SHAL is to be directed is a protein, the ligands comprising the SHAL can be selected to bind certain non-functional sites on the protein. A protein often has a number (few to >50) of "pockets" or cavities distributed across its surface.

These cavities are produced as the protein chain is folded into a three dimensional structure to make the protein functional. This observation makes it possible to consider designing SHALs that exhibit much greater binding specificity for a given protein than previously possible. By linking together two moieties that bind to unique pockets on the surface of a protein with only micromolar affinities, it is possible to design polydentate molecules (SHALs) that bind with nanomolar to picomolar affinities and are highly selective and do not cross react with other functionally related molecules. For proteins with a known or predicted structure, computational methods can be used to generate a three-dimensional map of the molecular surface and identify suitable sized pockets that are structurally unique for that protein as described herein.

Databases containing the structures of known small molecules can be screened for their ability to bind into pockets on the target protein using a "docking" program. The top candidates can then be tested using a variety of experimental techniques as described herein to identify the molecules that actually bind to the protein as well as those that bind to the correct site. Pairs or triplets of the ligands (e.g., one from each set) can then be attached to opposite ends of an appropriate length linker using solid or solution phase chemistry to generate bidentate SHALs (FIG. 1) or tridentate SHALs. The highest affinity and most selective SHALs can then be identified by conducting conventional binding studies.

It was a surprising discovery that linking together two or more, small ligands that bind weakly to target (e.g., a protein) and exhibit little or insufficient selectivity can result in the production of a molecule that binds to its intended target (e.g., target protein) three to six or more orders of magnitude more tightly and with high selectivity.

Without being bound to a particular theory, it is believed that while the presence of two or more ligands in the SHAL would be expected to increase the odds that the molecule might bind to a wider variety of proteins, we have observed that this non-specific binding is weak (approximately the same as the free ligand) and those molecules attached to non-target proteins via only one of the ligands will not remain bound long. The enhanced affinity and selectivity observed when both ligands in a bidentate SHAL or all the ligands comprising a polydentate SHAL bind to their respective targets (e.g., pockets on a target protein) is derived from three factors that relate to the nature of the SHAL-target interaction: First, the presence of the linker prevents the individual ligands comprising the SHAL that dissociate from their target from diffusing away from the target surface, increasing significantly the rate at which the free ligand rebinds. Second, the reduced off rate of release of the bidentate or polydentate SHAL is dictated by the fact that the probability that both (or all) ligands comprising the SHAL will simultaneously release from their target is substantially lower than the probability that either one will release/The spacing between the ligands comprising the SHAL which is determined by the attachment chemistry (e.g., the linker), allows the ligands comprising the SHAL to bind simultaneously to their target only if the ligands are separated by the correct distance. If either ligand in the SHAL binds independently to another target, its low affinity (1-10 micromolar affinity is typical for the ligands we identify) would result in the ligand falling off rapidly (the off-rate would be high). Thus the only situation in which the bidentate or polydentate SHAL would bind tightly to the intended target (nanomolar affinity or higher) would be when both ligands comprising the SHAL bind simultaneously to the target molecule (e.g., target protein). Once both or all ligands are bound, the off-rate of the entire molecule (the SHAL) would be reduced dramatically. If the ligand binding sites are selected properly (e.g., by targeting regions that vary in amino acid sequence or structure in the case of a protein target), it becomes highly improbable that identical sites will be found on another target separated by the same distance. If this extremely unlikely event were to occur, an additional ligand binding site (e.g., a third binding site adjacent to Site 1 and -2) can be identified, and an additional ligand can be incorporated into the SHAL (e.g., to create a tridentate, quadridentate, etc. SHAL).

SHALs have certain advantages over antibodies, particularly in therapeutic and/or diagnostic applications. Typically SHALs are considerably smaller than antibodies. They are consequently able to achieve greater tumor penetration. In certain embodiments, they are also able to cross the blood brain barrier, e.g., for the treatment of brain tumors. It is believed that the SHALS are also often less immunogenic than antibodies, and are often cleared from the circulation less rapidly.

In certain embodiments SHALs described herein are typically polydentate, i.e., the SHAL comprises two or more ligands, that are joined together directly or through one or more linkers. In certain embodiments the ligands bind to different parts of the target (e.g., different epitopes on a single protein) to which the SHAL is directed. In certain embodiments the ligands bind to different molecules, e.g., different cancer markers on a cancer cell, different proteins comprising a receptor, and the like. In certain embodiments polyspecific SHALS can be used for crosslinking the same or different antigens on the same cell thereby enhancing the signal transduction, or for pretargeting, e.g., where one SHAL is designed to target malignant cells and is attached to other SHALs designed to "catch" a subsequently administered carrier of a cytotoxic agent (e.g, chelated radiometal, etc), to recruit an immunologically active cell (e.g., macrophage, T-cell, etc.) to the site, to activate a prodrug on the targeted SHAL, and so forth.

In certain embodiments this "multiple specificity" is achieved by the use of polyvalent SHALs. Polyvalent SHALs are molecules in which two or more SHALs (e.g., two or more bidentate SHALs) are joined together. The different SHALs comprising the polyvalent SHAL can be directed to the same or different targets, e.g., as described above.

I. Construction of SHALs.

SHALs of this invention are created by identifying ligands (binding moieties) that bind, and in some embodiments, that specifically (or preferentially) bind, different regions of the target molecule or molecules. Ligands binding different regions of the target molecules are then joined directly or through a linker to produce a bidentate SHAL comprising two different binding moieties or a polydentate SHAL comprising two or more different biding moieties. The SHAL can then be screened for its ability to bind the intended target.

The initial identification of ligands that bind different regions of the target can be accomplished using virtual in silico methods (e.g., computational methods) and/or empirical methods, e.g., as described herein.

Once two or more suitable ligands (binding moieties) are identified they can, optionally be screened (validated) for the ability to bind the target at different sites. Suitable binding ligands can then be coupled together directly or through a linker to form a bidentate or polydentate SHAL that can then, optionally, be screened for the ability to bind the target.

A) Target Selection.

Figure 21:
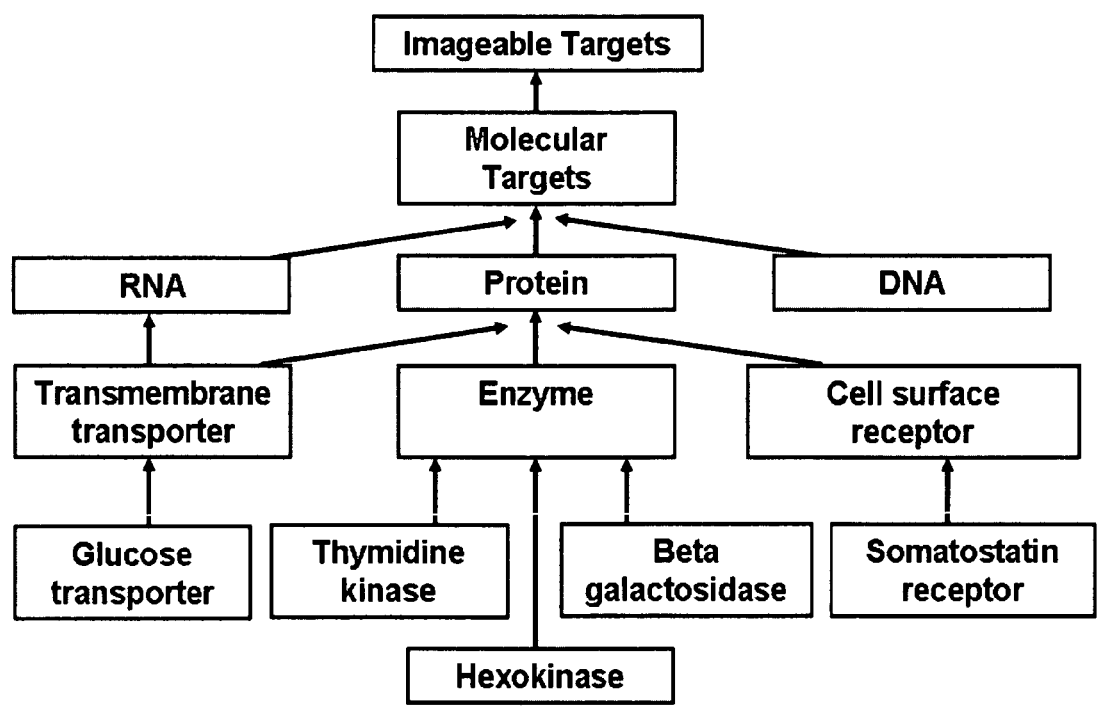
FIG. 21 illustrates various classes of SHAL targets.

Virtually any molecule, receptor, combination of molecules can serve as a target for a SHAL (see, e.g., FIG. 21). Target selection is determined by the application for which the SHAL is intended. Thus, for example, where the SHAL is to be incorporated into an affinity column (e.g., to purify a protein or nucleic acid) the target is the molecule (e.g., protein, nucleic acid, etc.) that is to be purified using the affinity column comprising the SHAL.

Where the SHAL is to be used in the treatment and/or diagnosis of a cancer, the target is typically a molecule, collection of molecules, receptor, enzyme, or other structure that is characteristic of the cancer (e.g., that permits the SHAL to preferentially bind to the cancer cell as compared to a normal healthy cell).

A number of cancer-specific markers are known to those of skill in the art. Such markers include, but are not limited to Lym-1 epitope, Muc-1, C-myc, p53, Ki67, erbB-2, Her2, Her4, BRCA1, BRCA2, Lewis Y, CA 15-3, G250, HLA-DR cell surface antigen, CD2, CD3, CD7, CD19, CD20, CD22, integrin, EGFr, AR, PSA, carcinoembryonic antigen (CEA), the L6 cell surface antigen (see, e.g., Tuscano et al. (2003) *Neoplasia,* 3641-3647; Howell et al. (1995) *Int. J Biol Markers* 10:126-135; Marken et al. (1992) *Proc. Natl. Acad. Sci. U.S.A.* 89: 3503-3507, 1992), growth factor receptors, and/or various intracellular targets (e.g., receptors, nucleic acids, phosphokinases, etc.) and the like.

In certain embodiments, SHALs can be generated for cell surface membrane target proteins that influence intracellular functions, thereby promoting these functions (agonist) or inhibiting these functions (antagonist) by blocking other molecular binding or causing an inhibitory or enhanced intracellular signal, e.g, phosphokinase signaling. SHALs can be generated for cell surface membrane target proteins such as antigens and antibodies that can be internalized into the cell. In common with antibodies that target internalizing antigens and peptide ligands that target internalizing receptors, these SHALs will be internalized and in the cell where they can have agonist or antagonist effects on critical cell functions such as protooncogenes, phosphokinases, lysosomes and DNA/RNA/mRNA because of their agonist or antagonist functions or because they deliver a toxin or radioisotope payload. There are several advantages of SHALs over antibodies and peptide ligands. They include small size and the range of charge that can be used to permit free movement into and within the cell when an intracellular molecule is the primary target.

SHALS can be used to preferentially select specific cells by their membrane targets and, upon dissociation from the targeted cell surface membrane may freely move across the cell surface membrane to access the inside of the cell. The SHAL can be made multi-specific so that when it is internalized, or when it dissociates and penetrates the cell surface membrane, the second specificity can permit targeting of internal cell molecules such as phosphokinases, lysosomal enzymes, hormone receptors, gene and proto oncogene protein products, DNA/RNA/mRNA, and the like. In certain embodiments, uni-specific but multivalent SHALs can be generated that both target call surface molecules and cross-link these molecules leading to enhanced biologic effects that have been described for cross-linked antibody-antigen systems.

In contrast to antibodies and peptide ligands that typically cannot directly and readily penetrate cell surface membranes, because of the small size of SHALs, and the ability to select the hydrophobic or hydrophilic character of the SHAL, SHALs can be produced that are capable of penetrating the cell membrane and various intracellular compartments. This makes it possible to generate SHALs specifically for the purpose of targeting intracellular molecules of importance to cell function, such as proto oncogenes, phosphokinases, lysosomal and other enzymes, DNA/RNA/mRNA, etc. This capability makes it possible to target entire classes of intracellular molecules of critical importance to cell function, a capability not previously achievable by specific targeting molecules. In addition to direct effects of these SHALs, they can be used as carriers of payloads, as described herein.

Proto oncogene products provide an example of a class of intracellular targets that can be targeted by SHALs and create a useful effect in cancer treatment. It is noted that Ras proteins, encoded by proto oncogenes, have been targeted in vitro by antibodies injected into the cells and this blockage has resulted in cells that no longer divide. Mutation have been related to impaired control activity of these products.

Many signaling pathways are susceptible to interference by the one (directly intra cellular) or two step (membrane targeting followed by internalization) SHAL targeting of intracellular molecules. These include, but are not limited to such key pathways as "G" protein signaling and tyrosine specific protein kinase activity e.g., EGFR, Neu, etc. Multiple hormone receptor interventions can also be targeted by SHALs to create a change in cell function and/or in cell growth. Hormone or enzyme targets can be bound and the function blocked. Hormone receptor blocks that can be useful include the use of SHALs to block the binding of estrogen like molecules to the ER (estrogen receptor) and similar effects to AR (androgen receptor). This would in turn interfere with DNA binding of the complex, with the resulting interference in hormone sensitive tumor cell growth and viability.

This invention also contemplates the use of SHALS to treat infectious diseases (e.g., AIDs, influenza, etc.) by either primary binding of the infectious agent and/or by blocking cell invasion, and/or by blocking metabolic pathways critical to propagation of the infectious agent (e.g., by blocking CCR5 to prevent HIV infection of cells).

Where the target to which the SHAL is to be directed comprises a protein, in certain embodiments, at least one of the ligands (binding moieties) comprising the SHAL bind to a pocket in the protein. In certain embodiments, where at least two of the binding moieties comprising the SHAL bind to pockets of the protein and those two ligands bind to different pockets. In certain embodiments, all of the ligands comprising the SHAL bind to pockets in the target protein. This is not to suggest that all ligands comprising the SHAL must bind to protein pockets. Certain embodiments are contemplated wherein one ligand binds to a pocket and another ligand binds to a region that is not a pocket or where none of the ligands bind to a pocket.

When structural information is not available for a particular target (e.g., a cancer marker or a domain or epitope within a cancer marker) then the target or domain within the target can be modeled to identify ligand binding sites for the design of a SHAL for this specific target. If the target has been structurally characterized, then the crystal or NMR structure of related molecules can be used in this manner. In the event that information is not available, a less usual circumstance, then empirical approaches can be used to identify suitable ligands for the construction of a SHAL as described herein.

The empirical approaches described herein can also be used to accelerate the process of SHAL development. IN this circumstance, modeling and other analytical steps can be performed after empirical development of a SHAL as desired for better understanding the SHAL and/or to guide subsequent generations of SHAL development.

Although the examples illustrate one preferred embodiment where the SHAL is intended as a carrier for an imaging and therapeutic radioisotopes, such as indium-111 and yttrium-90, for diagnosis and treatment, and the intended target is the HLA-DR cell surface molecule found on malignant, and normal, B lymphocytes, and therefore useful in most lymphomas and leukemias, it should be emphasized that this is only one of many embodiments even in B cell lymphoma and leukemias. For example, antibodies are known to identify a number of other cell surface antigens known to be attractive for antibody targeting of B cell lymphoma and leukemias. These could also be used for the same purposes and in the same manner as those for HLA-DR. Of additional interest, the region targeted by SHALs designed for HLA-DR targeting, is in the area of the pit known for peptide presentation of importance to immune identification and rejection. Of even greater importance, antigens and epitopes have been characterized and shown to be important for antibody targeting of adenocarcinomas of all types, including, breast, prostate, and colon malignant diseases. The aberrant mucins of the adenocarcinomas and the CEA found abundantly on many adenocarcinomas also provide attractive targets that have been rather well characterized.

Figure 4A:
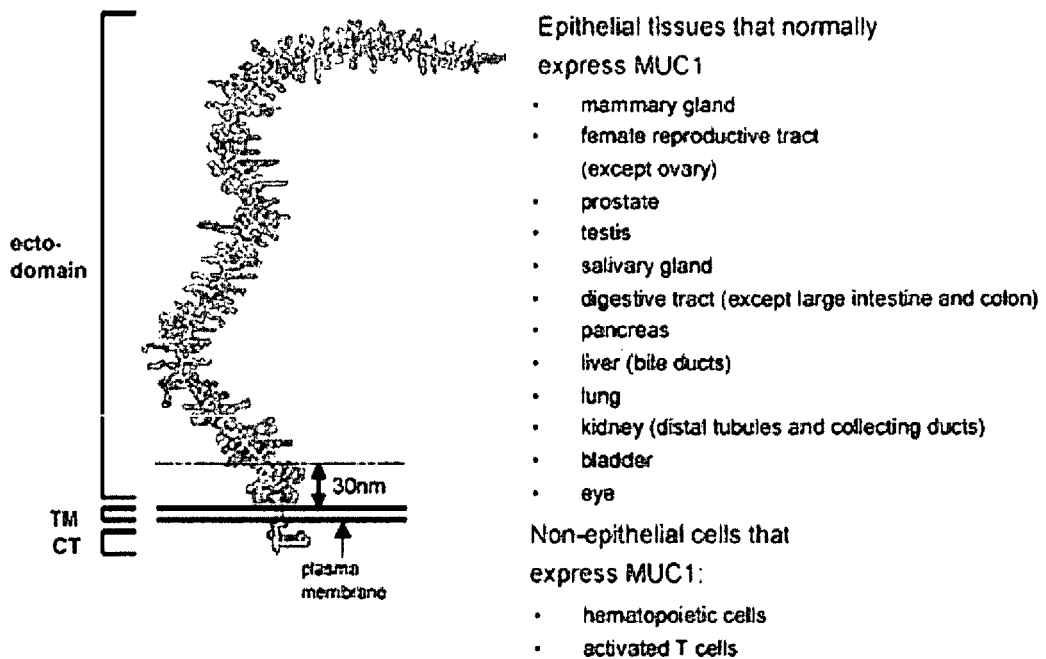
FIG. 4A illustrates the organization of normal MUC-1. Abnormal MUC1, also a good target, is less glycosylated, has an exposed VNTR, and a tandem repeat unit: 20 aa GVTSAPDTRPAPGSTAPPAH (SEQ ID NO:2).
Figure 4B:
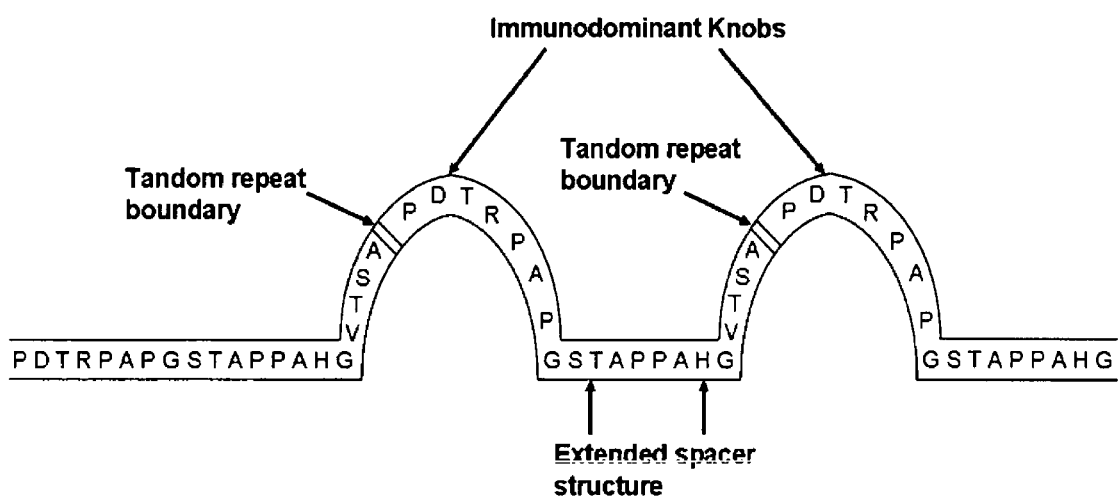
FIG. 4B illustrates the conserved structural features of the tandem repeat domain of MUC-1. These features include repeating and protruding knob-like structures consisting of sequential reverse turns that span tandem repeat interfaces (residues 17-27, 37-47), an extended region consisting of polyproline II and β-strand structure (residues 10-15, 30-35, 50-55). The N- and C-terminal 2-3 residues are unordered due to the absence of adjoining tandem repeats.
Figure 5:
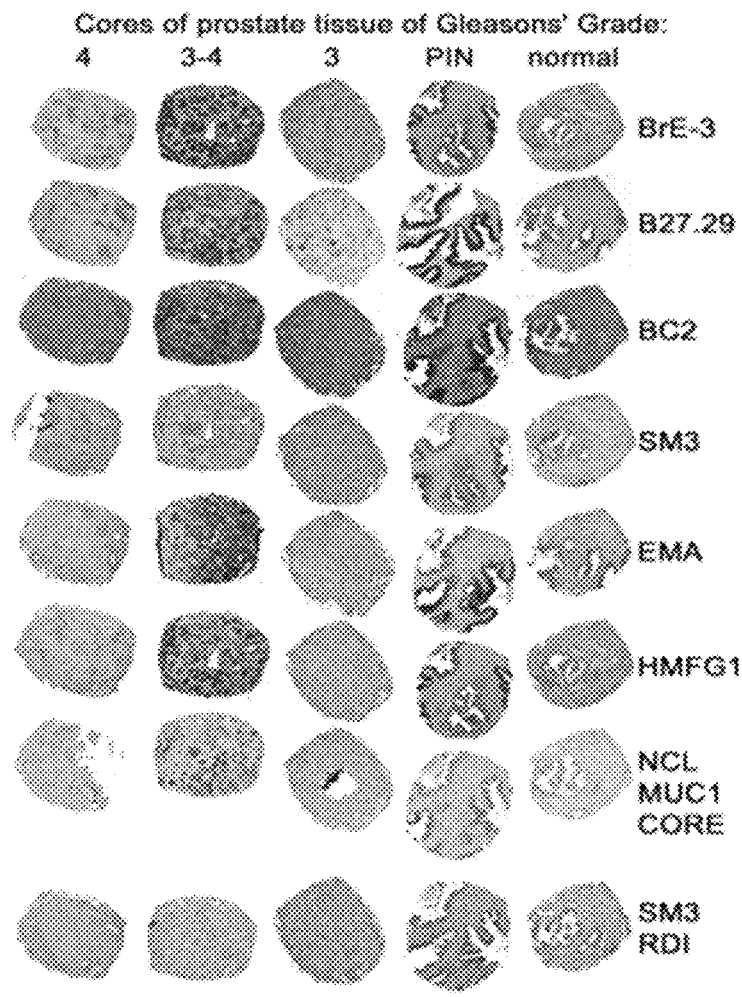
FIG. 5 illustrates a prostate cancer tissue array stained by anti-muc1 monoclonal antibodies.
Figure 6:
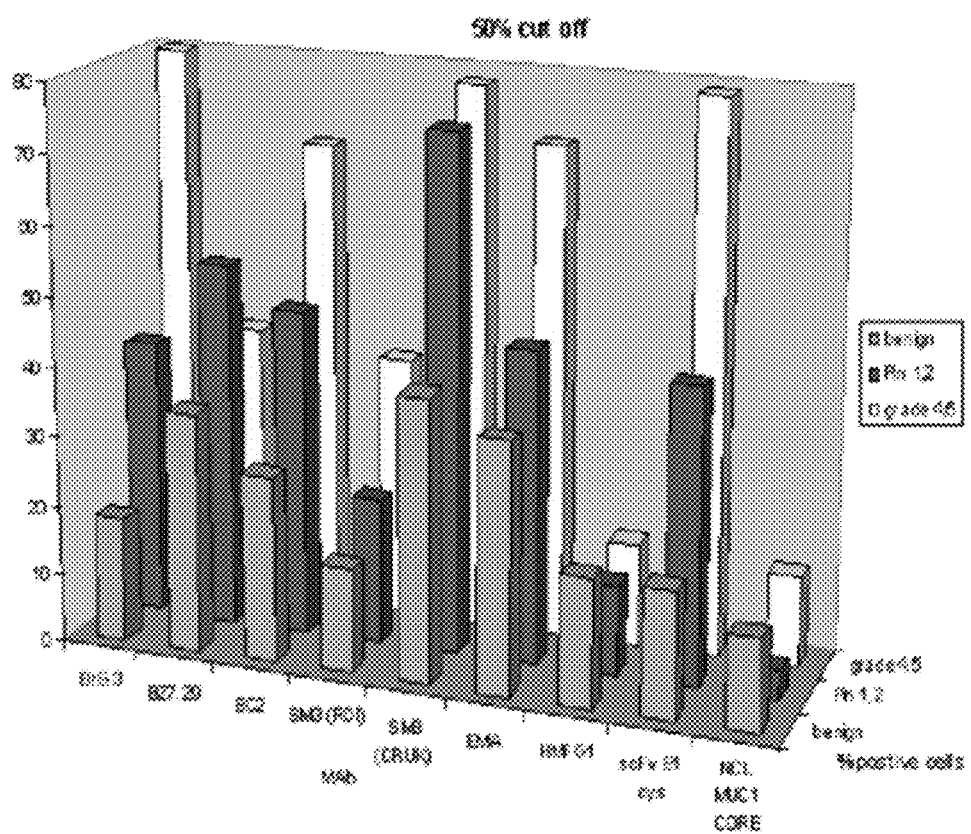
FIG. 6 shows that prostate cancer had increased MUC-1 peptide staining associated with grade and stage.
Figure 7:
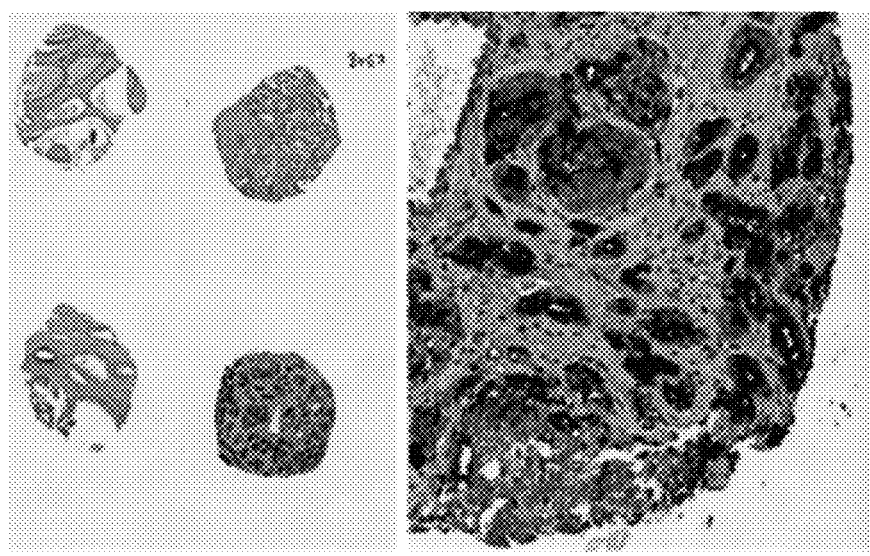
FIG. 7 shows anti MUC1 peptide core MoAb BrE-3 demonstrating target epitope in grade 4 prostate cancer. The knobs on MUC-1 differ in different grades of prostate cancer. Consequently, SHALS can be designed that bind to knobs and that can be used to grade malignant tissue.

In certain embodiments, it is believed the core tandem repeat protein of mucin (MUC1) (see, e.g., FIG. 4) provides a good target for cancer-directed SHALs. MUC-1 has been shown to be upregulated and readily available on epithelial cancers, such as prostate, breast, colon and ovarian cancers (see, e.g., FIGS. 5, 6, and 7).

Radioimmunotherapy (RIT), using Y-90 on a variety of monoclonal antibodies (mAbs), including those against MUC-1, has shown promise in preclinical studies and trials in patients. These studies have shown that epithelial cancers can be targeted effectively using radiolabeled mAbs, and that MUC-1 is one of the more attractive targets. Whole antibodies, however, are not readily concentrated in and typically do not penetrate through solid cancers. Consequently the therapeutic index for such moieties has proven to be relatively low.

However, MUC1-directed SHALs made, e.g., according to the methods described herein, directed against the protein core tandem repeat of MUC-1, an epitope shown in preclinical studies and RIT trials in patients to be a unique antigenic epitope upregulated on epithelial cancers are expected to be highly effective. SHALs (selective high affinity ligands) are quite small (~2000 Daltons) relative to whole antibodies (~150,000 D), or even single chain variable fragments (~25,000 D), so that SHALs readily penetrate and concentrate in malignant tumors, or are rapidly cleared or excreted by the kidneys.

In certain embodiments, additional ligand(s) beyond one or two chosen for docking sites in the epitopic region of interest are chosen for docking sites outside the region of interest on the target. This provides greater selectivity and "effective" affinity. In the case of a multimeric target, for example, HLA-DR, additional ligands can be directed to the same or to a different subunit of the target. Specifically, in the case of HLA-DR, one or two ligands can be directed to known docking sites in the epitopic region defined for Lym-1 monoclonal antibody reactivity and additional ligands can be chosen for docking sites in the same or a different multimer, for example, the beta subunit or the alpha subunit of HLA-DR.

Other examples are SHALs with ligands chosen to react with the tandem repeats of mucins, such MUC-1 as described above. In this instance, the core protein is repetitive at ten mer intervals so that SHALs of similar or identical nature can be joined to provide multivalent linkage to identical or similar but different repeats of known (or unknown) distance. Alternatively, the SHAL can have a third ligand that is identical to one of the initial ligands but linked at a distance to docking sites at a remote region of the core tandem repeat of MUC-1.

Also, docking sites can be protrusions in addition to cavities, although the latter are likely to confer greater (affinity) by virtue of the potential for more contact interactions.

B) Compounds (Putative Ligands/Binding Moieties) to be Screened.

Virtually any agent can be screened for its ability to bind a target and thereby for its suitability for incorporation into a SHAL according to the methods of this invention. Such agents include, but are not limited to nucleic acids, proteins/peptides, nucleic acid or peptide analogs, metals, sugars, polysaccharides, glycoproteins, lipids, lectins, large and small organic molecules, antibody CDRs, and the like.

In one preferred embodiment, high throughput screening methods involve providing a combinatorial chemical library containing a large number of potential ligands (binding moieties). Such "combinatorial chemical libraries" are then screened in one or more assays, as described herein to identify those library members (particular chemical species or subclasses) that display the desired binding activity. The compounds thus identified can serve as a component of a SHAL.

A combinatorial chemical library is a collection of diverse chemical compounds generated by either chemical synthesis or biological synthesis by combining a number of chemical "building blocks" such as reagents. For example, a linear combinatorial chemical library such as a polypeptide (e.g., mutein) library is formed by combining a set of chemical building blocks called amino acids in every possible way for a given compound length (i.e., the number of amino acids in a polypeptide compound). Millions of chemical compounds can be synthesized through such combinatorial mixing of chemical building blocks. For example, one commentator has observed that the systematic, combinatorial mixing of 100 interchangeable chemical building blocks results in the theoretical synthesis of 100 million tetrameric compounds or 10 billion pentameric compounds (Gallop et al. (1994) *J. Med. Chem.*, 37(9): 1233-1250).

Preparation of combinatorial chemical libraries is well known to those of skill in the art. Such combinatorial chemical libraries include, but are not limited to, peptide libraries (see, e.g., U.S. Pat. No. 5,010,175; Furka (1991) *Int. J. Pept. Prot. Res.*, 37: 487-493; Houghton et al. (1991) *Nature*, 354: 84-88). Peptide synthesis is by no means the only approach envisioned and intended for use with the present invention. Other chemistries for generating chemical diversity libraries can also be used. Such chemistries include, but are not limited to: peptoids (PCT Publication No WO 91/19735), encoded peptides (PCT Publication WO 93/20242), random bio-oligomers (PCT Publication WO 92/00091), benzodiazepines (U.S. Pat. No. 5,288,514), diversomers such as hydantoins, benzodiazepines and dipeptides (Hobbs et al., (1993) *Proc. Nat. Acad. Sci. USA* 90: 6909-6913), vinylogous polypeptides (Hagihara et al. (1992) *J. Amer. Chem. Soc.* 114: 6568), nonpeptidal peptidomimetics with a beta-D-glucose scaffolding (Hirschmann et al., (1992) *J. Amer. Chem. Soc.* 114: 9217-

9218), analogous organic syntheses of small compound libraries (Chen et al. (1994) *J. Amer. Chem. Soc.* 116: 2661), oligocarbamates (Cho, et al., (1993) *Science* 261:1303), and/or peptidyl phosphonates (Campbell et al., (1994) *J. Org. Chem.* 59: 658). See, generally, Gordon et al., (1994) *J. Med. Chem.* 37:1385, nucleic acid libraries (see, e.g., Strategene, Corp.), peptide nucleic acid libraries (see, e.g., U.S. Pat. No. 5,539,083) antibody libraries (see, e.g., Vaughn et al. (1996) *Nature Biotechnology,* 14(3): 309-314), and PCT/US96/10287), carbohydrate libraries (see, e.g., Liang et al. (1996) *Science,* 274: 1520-1522, and U.S. Pat. No. 5,593,853), and small organic molecule libraries (see, e.g., benzodiazepines, Baum (1993) C&EN, January 18, page 33, isoprenoids U.S. Pat. No. 5,569,588, thiazolidinones and metathiazanones U.S. Pat. No. 5,549,974, pyrrolidines U.S. Pat. Nos. 5,525,735 and 5,519,134, morpholino compounds U.S. Pat. No. 5,506,337, benzodiazepines U.S. Pat. No. 5,288,514, and the like).

Devices for the preparation of combinatorial libraries are commercially available (see, e.g., 357 MPS, 390 MPS, Advanced Chem Tech, Louisville Ky., Symphony, Rainin, Woburn, Mass., 433A Applied Biosystems, Foster City, Calif., 9050 Plus, Millipore, Bedford, Mass.).

In certain embodiments, the initial screen for ligands (binding moieties) with which to build the SHAL can be performed as a virtual in silico screening method and, in this case, it is not necessary to have the physical compounds in hand. In such instances chemical structure databases provide a wide range of moieties that can be screened for their suitability for inclusion in a SHAL as described herein.

Chemical structure databases are well known to those of skill in the art. For example, the MDL® Available Chemicals Directory (MDL ACD) is presently the largest structure-searchable database of commercially available chemicals in the world and is available from MDL Information Systems, Inc., San Leandro, Calif. This database is merely illustrative and not intended to be limiting. Other chemical structure databases (e.g. ChemSpider, ZINC, etc.) are well known to those of skill in the art and include, but are not limited to various organic molecule, peptide, carbohydrate or nucleic acid structural databases.

C) Computational Identification of Ligands that Bind the Target.

Using a virtual in silico approach, computational methods can be used to characterize (e.g., model) the target (e.g., target protein) and to identify molecules (binding moieties) that are expected to specifically bind to certain regions of the target. The use of computational methods to identify molecules that specifically bind to a particular target is often referred to as "DOCKING".

Docking methods are well known to those of skill in the art. Two approaches to docking are "rigid molecule docking" in which the molecules involved are treated as rigid objects that cannot change their spatial shape during the docking process, and soft (flexible) docking where the molecules are (computationally) allowed to change shape as they dock.

There are several physical and chemical forces that interact between the two molecules. These forces are used to define various docking scores that measure quality of each solution. These scores take into account the strength of these forces and the plausibility of the docking solution. The most significant forces typically considered in docking algorithms include electrical forces, van der Walls forces, and hydrogen bonds.

The docking problem is often formally stated as follows: Let A,B be two rigid molecules (e.g., the target and the potential ligand that is to bind the target) with their geometric representation in R3. We would like to find a rigid transformation T:R3→R3 such that the contact surface between T·A and B is maximal. The contact surface is typically defined as the surface where the distance between the molecules is smaller than a given threshold. Typically docking algorithms try to achieve a contact surface which is "large enough" instead of "maximal" and that we try to maximize not the size of the contact surface but a score measuring the quality of the proposed docking solutions. These two parameters are correlated but are not equivalent.

1. Rigid Docking.

One approach to the rigid docking algorithm was described by Kuntz et al. (1982) *J. Mol. Biol.*, 161: 269-288. The Kuntz et al. algorithm is primarily used in solving ligand-protein docking while trying to focus on 'interesting' sites on the surface of the molecules. The basic stages of the algorithm involve first computing the molecular surface using Connolly's method (see, e.g., Connolly (1983) *J. Appl. Crystallography,* 16: 548-558; Connolly (1983) *Science,* 221: 709-713)). This produces a set of points on the "smoothed" molecular surface with their normals. Then a "sphere generator" (e.g., SPHGEN) is used to create a new representation of the molecular surface of the target (e.g., protein) and the ligand using "pseudo-atoms" and then uses this representation to find plausible docking sites on the molecular surface—these docking sites that SPHGEN is looking for are cavities in the surface of the receptor.

SPHGEN typically consists of the following five stages: First, for each pair on Connolly points $p_i$, $p_j$ a sphere passing through this pair is placed such that its center is on one of the points normal. The algorithm then defines $S_{norm}(i)$ ={Spheres whose center is on the normal of $p_i$}. Assuming that there n Connolly points, then for each $1<=i<=n$ and $p_i$ is on the surface of the target, we throw away all the spheres in $S_{norm}(i)$ and leave only the one with the smallest radius. This throws all the spheres that penetrate the surface of the target. The algorithm then typically only leaves the spheres where Theta (e.g., the angle between the pi normal and the radius from $p_j$ to the center of the sphere)<90°. Otherwise the points that define the sphere, pi and pj, are too close to each other and therefore are not located in a cavity on the target's surface. Then the algorithm typically for each atom leaves only the sphere with the maximal radius. This step leaves only the spheres that 'touch' the surface of the atom. Finally, if the points that define the sphere, $p_i$ and $p_j$, belong to two different atoms, and the distance between these atoms on the molecular sequence is less than 4—the sphere is discarded. This is done because the length of a curve on an Alpha-helix is 3.6 and these sites are typically not to be treated as possible docking sites.

The remaining spheres are called pseudo-atoms. The next stage looks for clusters of intersecting pseudo-atoms. The existence of this kind of cluster indicates the existence of a cavity in the molecular surface, which is considered to be a good docking site.

After all this is performed on the target the same is done on the ligand, but this time we take the points and the vectors opposite to their normals, in order to create the spheres inside the surface instead of outside the surface. The result of SPHGEN on the target is sometimes called the 'negative image' and on the ligand it's called the 'positive image'. In certain embodiments, the vectors with respect to the ligand and the target can be reversed (e.g., to find elements of the target that dock within cavities in the ligand).

"Matching" is then typically performed. In this operation, for each docking site, the algorithm tries to find a transformation T that gives a good correspondence between the centers of the pseudo-atoms of the target to those of the ligand (in some cases, the centers of the real atoms of the ligand are used, instead of the centers of its pseudo-atoms). In some versions of DOCK, clusters of pseudo-atoms are separated into sub-clusters in order to improve the complexity of this stage. One way of doing this is to discard the largest sphere in the cluster, which sometimes causes the cluster to be divided into two sub-clusters.

In the matching problem of rigid docking a search is performed to to find a translation and rotation of one molecule, such that good matching between the interesting points in both molecules is formed. In certain embodiments, the distances between the point used instead of the points locations: For each molecule, the target (T) and the ligand (L), an appropriate distance matrix is defined—$d^T_{i,j}$ and $d^L_{i,j}$, respectively. A search is then performed to try to find two subsets in T and L such that their distances are the same, with some tolerance of error. These two subsets define two subgraphs with almost similar distances between their vertices. This can be done using a method similar to the interpretation tree by Grimson and Lozano-Perez.

Another way of solving the matching problem is to find a "large enough" clique in a matching graph. If there are n points in the target and m points in the ligand, the matching graph has n*m vertices where each vertex represents a point from the target and a point from the ligand. Let G=(V,E) be the matching graph and let u,v be vertices in V where u represents $u_L$ and $u_T$ (points in the ligand and the target, respectively) and v represents $v_L$ and $v_T$. An edge e=(u,v) will be added to E only when ABS $[d^L(u_L,v_L)-d^T(u_T,v_T)]$ <tolerance. Therefore, a clique in the matching graph defines subsets of points in the ligand and the receptor with similar distances.

In order to evaluate the quality of the match a score is calculated. The score preferably takes into account the size of the contact surface between the molecules and typically does not allow one molecule to penetrate the other. The DOCK algorithm uses a cubic grid that fills the binding site and every cell in this grid has a score according to its distance from the centers of the receptor's atoms: 1 if the distance is 2.8 Å-4.5 Å, −127 if the distance is less than 2.8 Å, and 0 if the distance is more than 4.5 Å. (In some cases the distance 2.8 Å is replaced by 2.4 Å). For each proposed transformation, the position of the ligand's points (i.e. the centers of its atoms or pseudo-atoms) in the grid are calculated and the score is calculated as the sum of scores of these points. Additional or alternative scores can be used various versions of the algorithm. For example, in one version a van der Waals energy score can be calculated for the transformations that have good matching scores.

Construction of a computer model of HLA-DR 10. Using the crystal structures that have been determined for four closely related human HLA-DR molecules (HLA-DR 1-4), the identification of unique "pockets" on surface of the protein, the identification of ligands that bind certain unique pockets and the construction of a SHAL using these ligands is illustrated herein in the examples.

The foregoing description is intended to be illustrative of one approach to rigid docking and is not intended to be limiting. Other approaches are known to those of skill in the art. It is noted that the SPHGEN and DOCK programs are commercially available (e.g., directly from the University of California and various commercial manufacturers of software).

2. Soft (Flexible) Docking.

Soft docking algorithms are also well known to those of skill in the art (see, e.g., Jiang and Kim (1991) *J. Mol. Biol.*, 219: 79-102; Katchalski-Katzir et al. (1992) *Proc. Natl. Acad. Sci. U.S.A.*, 89(6): 2195-2199, etc.).

In the method described by Jiang and Kim, supra, an enumeration on the 6-dimensional space of rigid transformation is performed and these transformations are given scores according to their energetic value. Both molecules are placed on a grid and the matching is evaluated using the distances between grid cells, the number of penetrations and the directions of the points' normals. The algorithm works on the output of Connolly's algorithm and works on the entire molecular surface (i.e. no cavities are looked for—as opposed to the DOCK algorithm). In order to decrease the enumeration, the algorithm typically uses two resolutions—low and fine. The low resolution uses ~0.3 points per square angstrom, and the fine resolution uses ~1 point per square angstrom.

Each cell in the grid is marked as "surface" (if it contains at least one Connolly point) or "volume" (if it doesn't contain any Connolly point). Usually, each surface cell contains 2-3 Connolly points.

An enumeration on the rotations of one of the molecules (usually smaller one) is performed. For each rotation the following is performed: The surface and volume cell of the molecule is calculated. Assuming that there's at least one pair of surface cells (one from each molecule) that are matched by the transformation, an enumeration on all of these pairs is performed. For each pair the transformation is calculated and it is evaluated by checking the directions of the normals, the number of surface-to-surface matches and the number of penetrations. The good transformations are those who have a small number of penetrations and a lot of surface-to-surface matches. This is done first in low resolution and the best results are calculated again in fine resolution with the addition of an approximated energetic score. The approximated energetic score is calculated according to the number of "favorable" and "unfavorable" interactions. There are several categories for the atoms of each molecule and combinations of these categories are marked as "favorable" if they have a good contribution to the energetic plausibilty of the match, or "unfavorable" otherwise.

For example, it is unfavorable that an atom with positive charge is placed near another atom with positive charge, but it is favorable if two atoms are adjacent if one of them is an H-donor and the other is an H-acceptor.

The approach of Katchalski-Katzir et al., supra, is to enumerate on the possible translations, while using FFT to calculate the matching score efficiently. Similar to the previous algorithm, both molecules are placed on a 3-dimensional grid, but here 3 types of grid cells are defined—"volume", "surface" and "intermediate". If the molecules are A and B, the matrices $A_{l,m,n}$ and $B_{l,m,n}$ are defined as follows (l,m,n are the grid coordiantes): $A_{l,m,n}=\{1$—if (l,m,n) is a "surface" cell, q—if (l,m,n) is an "intermediate" cell, 0—otherwise$\}$, and $B_{l,m,n}=\{1$—if (l,m,n) is a "surface" cell, r—if (l,m,n) is an "intermediate" cell, 0—otherwise$\}$.

In certain embodiments, parameters are chosen such that q<0 and r>0 while |q| is large and |r| is small. The scalar product of these matrices can be efficiently calculated using FFT thus improving the algorithm's performance considerably.

Again, it is noted that the foregoing description is intended to be illustrative of one approach to rigid docking and is not intended to be limiting. Other approaches are known to those of skill in the art. For example, additional approaches/programs include, but are not limited to: FlexX from Tripos (http://www.biosolveit.de/FlexX/) which is commonly used for high-throughput screening. It uses an empirical scoring function. It allows for flexible docking by rotating around torsional bonds. It is sold as a module of the Sybyl program (distributed by Tripos, Inc., St. Louis). GOLD from CCDC (http://www.ccdc.cam.ac.uk/prods/gold/) which uses a genetic algorithm to generate conformers for a ligand. It also enables customization of the torsional energy within smaller fragments of the molecule and can accommodate local protein flexibility. Autodock UCSD (http://www.scripps.edu/pub/olson-web/doc/autodock/) uses a Lamarckian genetic algorithm to generate conformers for a ligand. AutoDock is best used when there are only a few ligands and the binding energies need to be more accurate. Some good reviews on Docking include Lyne (2002) *Drug Discovery Today.* 7 (20): 1047, and Taylor et al. (2002) *J. Computer-Aided Mol. Design.*, 16: 151.

D) Empirical Approaches and Verification of Ligand Binding.

The use of computational methods to identify ligands for use in the construction of a SHAL requires at least some information regarding the structure of the target molecule(s). This invention also contemplates the use of methods that require no knowledge regarding the structure of the target to which the SHAL is to be directed.

In certain "empirical" embodiments, individual ligands or libraries of ligands are screened against the target molecule(s) and/or cells, bacteria, viruses, etc. displaying the target molecule(s) to identify ligands that bind the desired target (at least low affinity). Ligands are identified that bind to different regions of the target molecule(s). In certain embodiments, ligands are identified that bind to different regions of the target molecules and that do not exclude each other from such binding.

Ligands that can simultaneously bind to the target without excluding each other can then be joined together, directly or through a linker, to create a polydentate SHAL which can, optionally, be subsequently screened for the ability to bind to the target molecule(s), e.g., at high affinity.

In addition to use in empirical approaches for ligand identification, physical screening methods are also desirable for validating binding of ligands identified using the virtual in silico approaches discussed above. In addition, it can be desirable to additionally determine the binding orientation of two or more ligands, e.g., to confirm that the ligands bind to different sites on the target and/or to estimate spacing when the ligands are incorporated into a SHAL.

Assays for detecting the binding of one or more ligands to a target are well known to those of skill in the art. For example, in one simple embodiment, the ligands can be labeled with a detectable label and contacted with the target molecule(s) which are immobilized on a substrate. After a wash, detection of the labels in association with the immobilized target molecule(s) indicates that the ligands bind to the target. In certain embodiments, different ligands can be labeled with different labels (e.g., different color fluorescent labels), and the simultaneous binding of multiple ligands can be visualized.

Alternatively, competitive binding assays can be performed. In such assays the target molecule(s) are contacted with one ligand known to bind the target. The target is also contacted with the "test" ligand and the ability of the test ligand to bind to the target in the presence of the first ligand is evaluated.

Fluid phase assays can also be performed. For example, the ligand(s) and the targets can be labeled with different labels. The ligands can be contacted to the target molecule(s) and binding of the two can readily be evaluated, e.g., using a flow cytometer. Flow cytometry methods are well known to those of skill in the art (see, e.g., Omerod (1994) *Flow Cytometry: A Practical Approach*. IRL Press, Oxford.; Shapiro Practical Flow Cytometry. 3rd Edition. Alan R Liss, Inc.; Givan (1992) *Flow Cytometry. First Principles*. Wiley-Liss, New York; Robinson (1993) *Handbook of Flow Cytometry Methods*, Wiley-Liss, New York, and the like).

Determination of ligand binding and orientation can also be determined using a number of different methods. These include, but are not limited to Saturation Transfer Difference nuclear magnetic resonance (Mayer and Meyer (1999) *Angew Chem Int Edit,* 38:1784-1788) and Transfer NOE (trNOE) nuclear magnetic resonance (NMR) spectroscopy (Henrichsen et al. (1999) *Angew Chem Int Edit.*, 38:98-102; Cosman et al. (2002) *Chem Res Toxicol* 15: 1218-1228). These methods can be used to screen the ligands in mixtures of several to several hundred per experiment to determine which ligands bind to the target molecule(s) e.g., under biologically relevant conditions and to determine which ligands bind to the same (or different) sites. Diffusion experiments (Lin et al. (1997) *J. Organic Chem.*, 62: 8930-8931) can also be performed with those ligands that have been determined to bind in order to assess the relative binding affinity of each compound.

Other approaches to detecting binding of the ligands to the target molecule(s) include, but are not limited to surface plasmon resonance (BIAcore assay), saturation transfer difference nuclear magnetic resonance spectroscopy, other nuclear magnetic resonance spectroscopy measurements, mass spectrometry, capture microarrays, bead-based library assays, and other physical binding assays.

The foregoing assays are intended to be illustrative and not limiting. Using the teaching provided herein numerous other assays for detecting ligand binding to the target molecule(s) will be known to those of skill in the art.

Following the identification of a set of ligands that bind to the target molecule(s) (e.g., HLA-DR10), competition experiments can be performed, e.g., by NMR to determine if they bind to one of the pockets comprising the target molecule(s) (e.g., in the case of HLA-DR10, to one of the pockets encompassing the Lym-1 epitope.

As indicated above, this can readily be accomplished by preparing a complex between the target and a known binding ligand and determining if a second ligand can bind the complex. Thus, for example, the case of HLA-DR10 target, a Lym-1:HLA-DR10 complex can be prepared and the set of ligands that bind to HLA-DR10 can be re-tested to determine if they will still bind to the protein when the Lym-1 antibody is bound.

Those ligands that no longer bind to the Lym-1:HLA-DR10 complex can be identified (these ligands bind to the unique sites that distinguish HLA-DR10 from the other HLA-DR molecules) and used in a second set of competition experiments to identify those molecules that bind to different sites within the Lym-1 epitope. In experiments conducted with pairs of ligands, transfer nuclear Overhauser effects (trNOE) that occur between the bound ligands and the HLA-DR10 protein (Cosman et al. (2002) *Chem Res Toxicol* 15: 1218-1228), in the absence of the Lym-1 antibody, can be used to identify those ligands that bind to the same and different sites. Bound ligands exhibit negative NOE signals, while unbound ligands have positive signals (Id.). If both ligands in the pair are observed to be bound to the protein at the same time, the results will indicate that the two ligands must bind to different sites. The screening thus can readily identify sets of ligands that bind to different sites within the target molecule(s) (e.g., to different sites (Site 1 and Site 2) within the Lym-1 epitope of HLA-DR10).

After sets of ligands have been identified that to bind to different sites on the target, the orientation of the ligands in the binding sites can, optionally, be further evaluated using classical molecular dynamics simulations. The methods of molecular dynamics simulations are clearly described in the Examples. For example, for each ligand, one to three orientations within the binding pocket can be simulated for 500 psec. This will help determine which functional groups on the ligands are likely to be in contact with the target and which functional groups are accessible by solvent. This information can be used to identify analogs with modified or different functional groups that can be tested for their ability to bind to the target and confirm that a particular functional group can be used as the site for linker attachment without disrupting the binding of the ligand to the target.

The use of these approaches to identify ligands that bind to specific sites on various targets is described in the literature. For example, these methods have been used to identify ligands that bind to specific sites on the targeting domain of tetanus neurotoxin (Cosman et al. (2002) *Chem Res Toxicol* 15: 1218-1228; Lightstone et al. (2000) *Chem. Res. Toxicol.*, 13: 356-362) as well as eleven ligands we've already identified that bind to HLA-DR10.

Our previous studies using a similar approach to identify ligands that bind to two sites on the targeting domain of tetanus neurotoxin (Id.) have required screening less than 30 ligands experimentally. Over half of the ligands predicted to bind to the protein were observed to bind experimentally. Thus we believe that screening a set of 30 ligands per site should provide a sufficient number of compounds that bind to initiate SHAL synthesis. However, if in some embodiments, a suitable number of ligands (e.g., 3-5) are not identified to bind in the first round of NMR screens, additional sets of ligands can be selected and screened until suitable ligands are found that bind to two different sites in the target.

In certain embodiments, the selection of the ligand pairs (or other multi-ligand combinations) to be linked together is based on the following criteria (in descending order of importance): 1) binding site (the two ligands that comprise a pair preferably bind to different sites); 2) reliability of information obtained on available functional groups that can be used to attach the molecules to the linker without disrupting binding (analogs with known derivatives that are confirmed to bind, indicating the modification of particular functional group does not affect binding, are given priority); 3) the ligand's expected ease of attachment to the linker (the ligands preferably have functional groups that facilitate asymmetric attachment chemistry to put a different ligand on opposite ends of the linker); 4) relative binding affinity, e.g., as determined from the NMR diffusion experiments (ligands exhibiting the strongest binding to the protein are typically selected first); 5) known information on their toxicity in animals or humans (priority is typically given to use of ligands that are known to be non-toxic or have already been approved for use in other pharmaceuticals); and 6) ligand cost.

Because it is likely that a number of the individual ligands (binding moieties) may bind weakly to other proteins, it will not be necessary (or meaningful) to prescreen the individual ligands to determine if they bind to other proteins that might be encountered in the circulation before they are used to create SHALs. The binding of any single ligand (half of the pair used to create a bidentate SHAL) to other proteins is expected to be weak (micromolar at best). Consequently, the off-rate of the molecule will be high and the SHAL that only binds through one ligand to other proteins will be quickly removed from the tissue and circulation. High affinities (and low off-rates) typically will only be obtained when both ligands in the pair bind simultaneously to sites separated by the proper distance, which is dictated by the length of the linker connecting them. These two criteria will only be met when the SHAL comes in contact with the intended target. Once bound, the off-rate is expected to be reduced 1000 to 1,000,000 fold (based on previous studies) over that observed for either ligand alone. For this reason, cross-reactivity is not expected to be a significant complication.

E) Combined Computational/Empirical Approaches.

The binding of a SHAL to the region(s) of its target is based upon fit and charge and is dependent on the 3D structure and constituents of the binding moieties. In the computational approach described above, generating SHALs can involve definition/identification of attractive region(s) on the target molecule. Thus, for example, proteins of all types, including antigens, receptors and signaling proteins, can be modeled to find docking sites and ligands. The ligands can subsequently be tested using empiric methods. These methods typically require knowledge of the constituent molecules to be included in the modeling.

The empirical methods described above, rely on screening of libraries (e.g., combinatorial libraries) of potential ligands to find suitable binders. In this approach, no foreknowledge is required beyond availability of a target (e.g., protein, cell, etc.) of interest. Libraries are experimentally culled for binders. This can be followed by competition with a molecule, such as an antibody, peptide or chemical (ligand) known to react with the molecule in the region chosen to be targeted. This approach permits the elimination of binding chemicals or peptides that are not of interest and definition of those that bind to the region of interest.

A third approach is intermediate in nature and uses foreknowledge of attractive target molecules and regions of these molecules for initial competitive screening and counter-screening. Thus, for example, initial targets or ligand-library constituents can be computationally predicated. The optimized target or target collection and/or optimized library can then be screened and counter-screened as described herein to identify optimal binders.

F) Bead-Based Library Screening.

One approach for screening for ligands that bind the target molecules involves producing a combinatorial library comprising a large number of potential ligands each attached to a different bead/solid support. The combinatorial library can be a "random" library, or can be synthesized to provide numbers of variant having, e.g., particular (e.g., optimized) core chemistry.

Combinatorial synthetic methods are well known and are used to rapidly make large "libraries" of distinct compounds. In various embodiments the starting material (e.g., an amino acid) is covalently anchored to solid support. This is followed by the stepwise addition of monomers (typically protected monomers) such as amino acids, nucleotides, small organic molecules, and the like. Millions of distinct molecules can be created by varying number of steps and number of reactants (e.g., in a split-mix synthesis approach), but typically each bead contains only one compound.

The compounds comprising the library can be screened while still bound to the beads. Colorimetric, fluorometric, radiographic methods or other methods can be used to visualize positive (binding) beads. These can be captured (e.g., with a pipette, with a metal bar if the beads are magnetic), and the compound can then be characterized.

Thus, for example, one can synthesize a library of peptide ligands that bind HLA-DR10 molecules. Peptide synthesis chemistry is well developed. However, to obtain peptide ligands that have a longer half-life in vivo, one might choose to produce a peptide ligand library where the peptides comprise D-amino acids. Such peptides are expected to be more resistant to proteolysis in vivo. Moreover, D-amino acids are generally considered non-toxic.

The Lym-1 epitope on HLA-DR10 is highly polar. Thus, in synthesizing the library of potential binders on can select polar D-amino acids for synthesis (e.g., Ser, Asp, etc.) Using Split/Mix synthesis (see, e.g., U.S. Pat. No. 5,574,656) a library of D-peptides bound to beads is created.

Then HRP-tagged HLA-DR10 is added to the bead mixture. The HRP color label is visualized and the positive beads are removed. The positive beads can then be tested against, e.g., HLA-DR10 positive cell lines. Beads that test positive in this assay can then be tested against, e.g., a tissue panel to ensure that binding is HLA-DR10 specific. The specific binders in this assay can then be characterized (e.g., sequenced using Edman degradation, mass spectrometry, etc.).

Alternatively, there are strategies for encoding the identity of each the compound during the synthesis of the library (see, e.g., U.S. Pat. Nos. 5,565,324; 5,723,598; 5,834,195; 6,060,596; 6,503,759; 6,507,945; 6,721,665; 6,714,875; and the like). Using such "tagging" strategies the identity of the positive binders can then readily be determined.

G) Linking the Ligands (Binding Moieties) to Produce a Polydentate SHAL.

Once two more ligands (binding moieties) are identified that bind to different sites on the target, the ligands are linked either directly or through a linker to produce a polydentate SHAL. Where only two ligands are joined the SHAL is bidentate. Where three ligands are joined the SHAL is tridentate, and so forth.

A number of chemistries for linking molecules directly or through a linker are well known to those of skill in the art. The specific chemistry employed for attaching the ligands (binding moieties) to each other to form a SHAL will depend on the chemical nature of the ligand(s) and the "interligand" spacing desired. Ligands typically contain a variety of functional groups e.g., carboxylic acid (COOH), free amine (—NH2) groups, that are available for reaction with a suitable functional group on a linker or on the other ligand to bind the ligand thereto.

Alternatively, the ligand(s) can be derivatized to expose or attach additional reactive functional groups. The derivatization may involve attachment of any of a number of linker molecules such as those available from Pierce Chemical Company, Rockford Ill.

A "linker", as used herein, is a molecule that is used to join two or more ligands (binding moieties) to form a polydentate SHAL. The linker is typically chosen to be capable of forming covalent bonds to all of the ligands comprising the SHAL. Suitable linkers are well known to those of skill in the art and include, but are not limited to, straight or branched-chain carbon linkers, heterocyclic carbon linkers, amino acids, nucleic acids, dendrimers, synthetic polymers, peptide linkers, peptide and nucleic acid analogs, carbohydrates, polyethylene glycol and the like. Where one or more of the ligands comprising the SHAL are polypeptides, the linkers can be joined to the constituent amino acids through their side groups (e.g., through a disulfide linkage to cysteine) or through the alpha carbon amino or carboxyl groups of the terminal amino acids.

In certain embodiments, a bifunctional linker having one functional group reactive with a group on a the first ligand and another group reactive with a functional group on a second ligand can be used to form the desired SHAL. Alternatively, derivatization may involve chemical treatment of the ligand(s), e.g., glycol cleavage of the sugar moiety of glycoprotein, carbohydrate or nucleic acid with periodate to generate free aldehyde groups. The free aldehyde groups can be reacted with free amine or hydrazine groups on a linker to bind the linker to the ligand (see, e.g., U.S. Pat. No. 4,671,958). Procedures for generation of free sulfhydryl groups on polypeptide, such as antibodies or antibody fragments, are also known (See U.S. Pat. No. 4,659,839).

Figure 13A:
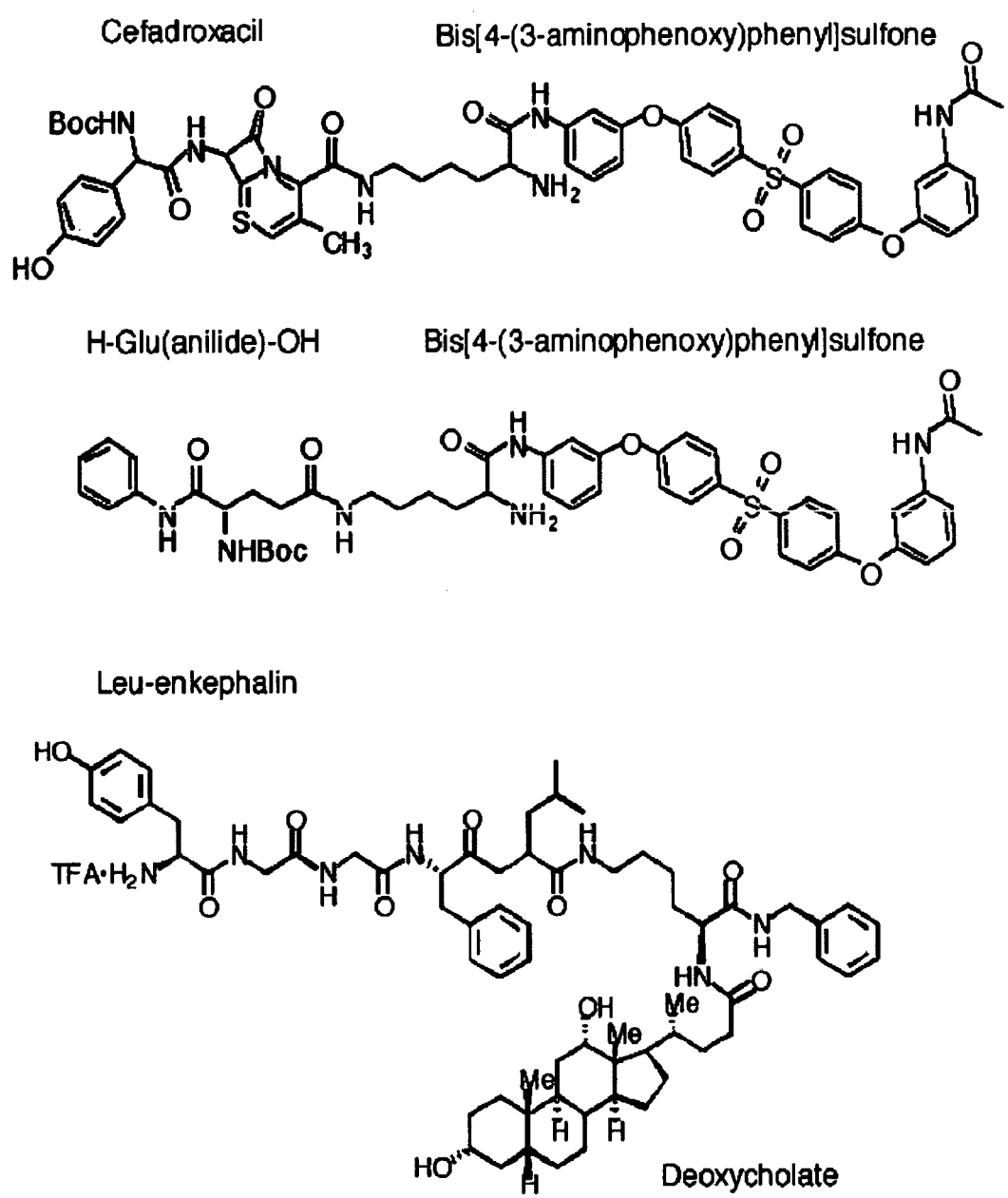

In certain embodiments, lysine, glutamic acid, and polyethylene glycol (PEG) based linkers different length are used to couple the ligands. A number of SHALs have been synthesized using a combination of lysine and PEG to create the linkers (see, e.g., Examples and FIG. 13). Chemistry of the conjugation of molecules to PEG is well known to those of skill in the art (see, e.g., Veronese (2001) *Biomaterials*, 22: 405-417; Zalipsky and Menon-Rudolph (1997) Pp. 318-341 In: Poly(ethyleneglycol) Chemistry and Biological Applications. J. M. Harris and X. Zalipsky (eds)., Am. Chem. Soc. Washington, D.C.; Delgado et al. (1992) *Drug Carrier Syst.*, 9: 249-304; Pedley et al. (1994) *Br. J. Cancer*, 70: 1126-113-0; Eyre and Farver (1991) Pp. 377-390 In: Textbook of Clinical Oncology, Holleb et al. (eds), Am. Cancer Soc., Atlanta Ga.; Lee et al. (1999) *Bioconjug. Chem.*, 10: 973-981; Nucci et al. (1991) *Adv. Drug Deliv.*, 6: 133-151; Francis et al. (1996) *J. Drug Targeting*, 3: 321-340).

One advantageous feature of the synthetic scheme used to create these SHALs is that the approach allows the attachment of almost any type of molecule to a third site on the linker. In the first round of SHAL synthesis, biotin has been attached at this site to facilitate the in vitro binding studies. The biotin tag makes it possible to quickly measure the binding to the isolated protein by surface plasmon resonance and examine the selectivity of the SHAL for binding to live cells and tissue sections.

Once the SHAL has been tested and confirmed to bind to the target (e.g., HLA-DR10), metal chelators such as DOTA (or other effectors) can be attached in the final round of synthesis to enable the delivery of radionuclides or other effectors to target bearing cells (e.g., tumor cells).

After retesting the effector-SHAL conjugates to reconfirm their ability to bind to the target, the conjugates exhibiting the best selectivity for their targets can, optionally be tested for their biodistribution in test organisms (e.g., mice). Other unique molecules can also be attached to this site in future studies so these same SHALs can also be used, for example, to test the utility of pre-targeting approaches for radioisotope delivery.

H) Stepwise Solid-Phase SHAL Synthesis.

In certain embodiments, SHAL synthesis proceeds by a stepwise-solid phase synthesis approach. In this approach each linker component or ligand is attached onto a growing molecule (SHAL) covalently attached to the surface of a resin. After each chemical reaction the resin can be extensively washed to remove the unreacted products.

In one approach, DOTA was attached to the linker at the beginning of the synthesis. After the excess DOTA was washed away, multiple additional chemical reactions that were carried out on the resin to add the various linkers and ligands, and after each reaction the unreacted products were again washed away. By the time the synthesis of the SHAL was completed, the amount of free DOTA present in the sample was undetectable when examined by HPLC and mass spectroscopy. The DOTA link is extremely stable, so it does not come off the SHAL once it's been attached.

I) Screening SHALs for Affinity and Selectivity.

In certain embodiments, a library of SHALS comprising different ligands (binding moieties) and/or comprising different length linkers is screened to identify those SHALS that have the best affinity and/or selectivity for the target. Such screening assays can be performed in a number of formats including, but not limited to screening for binding to isolated targets, screening for binding to cells in culture, screening for binding to cells in tissue arrays, and screening for in vivo binding to the desired target.

1. SHAL Binding to Isolated Targets (e.g., Proteins).

In certain embodiments, the binding affinities of the best SHALs can be estimated by mass spectrometry of the SHAL-target complexes, followed by a more accurate surface plasmon resonance (SPR) spectroscopy (Shuck (1997) *Annu Rev Biophys Biomol Struct.*, 26: 541-566; Van Regenmortal (2001) *Cell Mol Life Sci.*, 58: 794-800) measurement of the SHAL-target binding affinity using for example, the IASYS Plus or BiaCore instruments. In order to perform the SPR measurement, biotin can be added to the linker through a third functional group (as described above) and the SHAL can be bound to commercially available streptavidin coated chips. In certain preferred embodiments, only those SHALs exhibiting nM or higher binding affinities can be considered useful. The SHALs exhibiting the greatest affinity can then be tested for their selectivity. Experiments can be performed to test the selectivity of SHAL binding to targets in the presence of molecules related to the targets. Thus, for example, where the SHAL is directed to HLA-DR10, the SHAL can be evaluated for its ability to bind target molecules in the presence of Raji cell surface proteins extracted and separated by affinity chromatography. After treating the gel with the biotinylated SHAL and rinsing out excess unbound SHAL, the location of the bound SHAL can be detected by staining with Rhodamine tagged streptavidin. In certain embodiments, the SHALs that are considered to exhibit reasonable protein selectivity can be those molecules in which 95% or more of the fluorescence is associated with the HLA-DR10 monomer and multimer peaks.

2. SHAL Binding to Cells in Culture.

Where the SHAL target is a marker on a cell (e.g., a cancer cell marker) it may be desired to assess the specificity of binding of the SHAL to intact cells.

Cell binding studies can be conducted with the biotinylated (or otherwise labeled) SHALs, using for example the fluorescence of bound Rhodamine-tagged streptavidin to confirm the SHALs bind to target (e.g., Raji) cells. If the SHAL is observed to bind, SPR measurements can be conducted to determine the affinity of intact cells to the SHAL. In certain embodiments, those SHALs that exhibit at least a 2-fold, preferably at least a 5-fold, and more preferably at least a 10-fold difference in the staining intensity of target (e.g., tumor) cells over controls can be selected for further testing and development. Analogs of the most promising SHALs can be synthesized with a DOTA molecule attached to the linker, and binding experiments can be conducted using radionuclide-tagged SHALs to obtain more quantitative data and also attempt to determine if the SHAL is retained on the surface of the cell or is internalized using NanoSIMS or other methods. This information is useful in making decisions about the type of radioisotope that is to be loaded into the chelator. If the SHAL remains on the surface, the SHAL is typically utilized alone or with effectors that do not require internalization (e.g., alpha emitters such as $^{90}$Yttrium, various detectable labels, and the like). If evidence is obtained to suggest the SHAL is internalized upon binding to the target cells, it is possible to utilize the SHAL with effectors that are active when internalized.

3. Analysis of Cell Selectivity Using Tissue Arrays.

Figure 2:
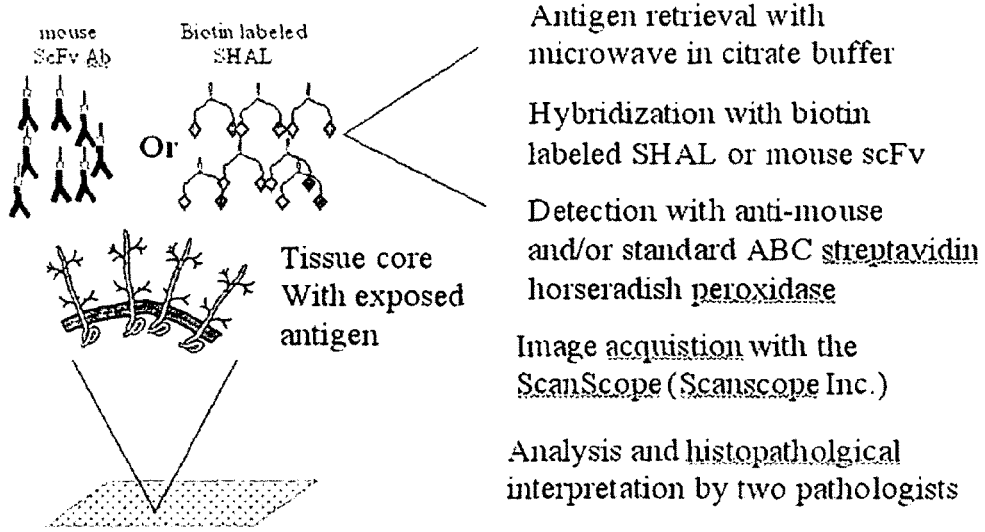
FIG. 2 illustrates the use of tissue microarrays that contain, for example, a large number of both normal tissues and lymphocytic neoplasms. These tissues can be treated with biotin-tagged SHALs, rinsed with rhodamine-tagged streptavidin, and the binding of the SHAL assessed by fluorescence microscopy.
Figure 3:
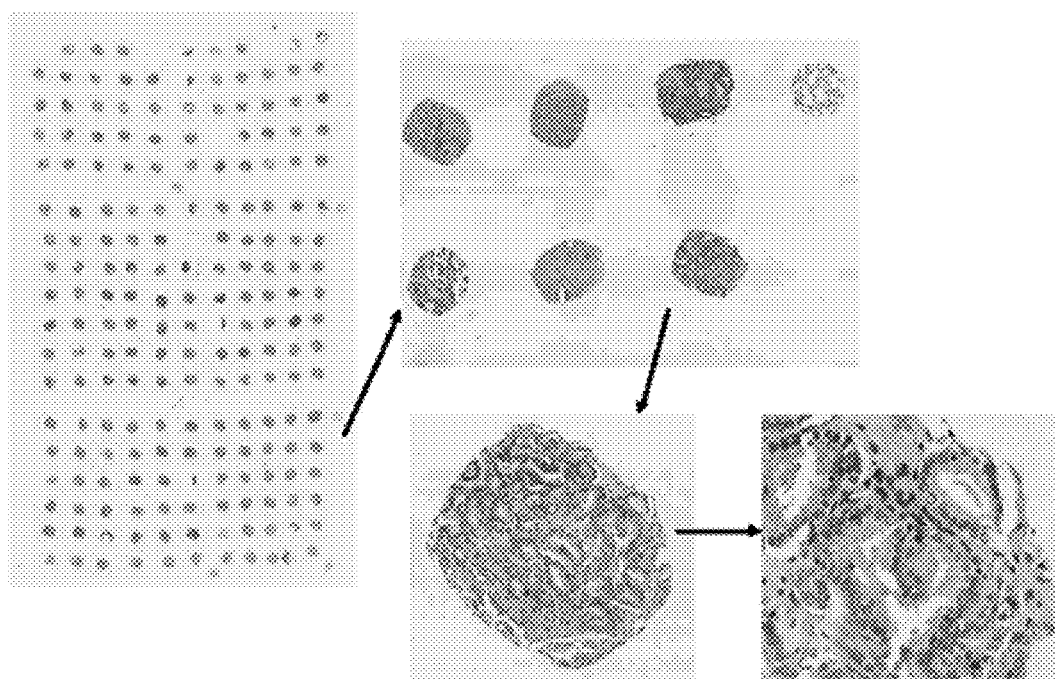
FIG. 3 illustrates a human tissue microarray comprising hematoxylin and eosin stained, formalin-fixed, paraffin embedded tissue cores. All four panels are derived from a single ScanScope digital image. This illustrates the high resolution of the archived image. Similar images can be captured for immunohistochemical or SHAL binding studies. In this way, investigators using the arrays have easy shared access for all studies applied to the arrays.

Tissue array technology can be used to screen SHALs to determine tissue specificity (e.g., malignant and normal tissue reactivity in the case of anti-tumor SHALs). Tissue arrays are well known to those of skill in the art (see, e.g., Kononen et al. (1998) *Nat. Med.*, 4:844-847; Torhorst et al. (2001) *Am J Pathol.*, 159: 2249-2256; Nocito et al. (2001) *Int J Cancer*, 94: 1-5, and the like). In its basic form, a tissue microarrays is formed by taking small cores of each individual tumor case/block and assembling these cores into a single block (Id.). By sectioning this new block, standard immunohistochemistry and in-situ hybridization techniques can be used. Therefore, one can assay hundreds of tissue samples in one experiment rather than having to perform hundreds of different experiments. FIGS. 2 and 3 outline how the tissue arrays can be used and show a diagram of illustrative tissue array.

In one embodiment, for the normal tissue array we have identified 80 unique tissues, which include oropharynx, heart, lung, stomach, spleen, liver, kidney, intestine, bone marrow, pancreas, bladder, muscle, adrenal, breast, brain, normal prostate and skin for placement on the tissue microarray. For a lymphocyte specific tissue array, we have included neoplastic lymphocytic lines, xenografts, and patient material collected from the Human Biological Specimen Repository at UC Davis. Using these or similar tissue arrays, one can determine the non-specific binding of the SHALs to normal tissue and specific binding to lymphocytic and prostatic neoplasms. The hybridization of the SHALs to the tissue arrays is straightforward. Using biotinylated SHALS as described herein, labeled streptavidin (e.g., Rhodamine-tagged streptavidin) can readily be used to identify those cells that bind the SHALs. When required, the tissue microarray results can be verified by conventional histology and immunohistology.

In one illustrative approach, 2-4 tissue cylinders, with a diameter of 0.6-mm, can be punched from the selected areas of each "donor" tissue block and brought into a recipient paraffin block in order to assemble the tissue microarray, using a Tissue Microarrayer (e.g., Beecher Instruments, Silver Spring, Md.) and the techniques described by Kononen et al. (1998) *Nat. Med.*, 4:844-847. Tissue microarray slides containing, for example, 200-400 cores can then be sectioned at a thickness of 4 µm. Routine Hematoxylin & Eosin staining can be performed in order to verify that each core represents its selected histopathology. For immunohistochemistry, microwave in a citrate buffer can be used for antigen retrieval. The images of the slides can be captured by confocal scanner (ScanScope, Mountain View, Calif.) and visualized with MrSid Viewer 2.0 (LizardTech, Inc.) as described below. The ability to view the tissue array images on a computer rather than a microscope dramatically increases the efficiency of analysis.

The major obstacle to digital pathology has been the representation of glass slides in a digital format. Unlike radiology, which begins with a digital representation of a patient rendered by CT, MRI, or now "digital plain film", pathology requires that all tissue samples be processed and made into stained tissue sections mounted on glass slides for interpretation. The new technology produces images of the entire glass slide, thereby producing a true digital representation of the entire histopathologic specimen (Whole Slide Imaging). Most of the current instruments use a microscope equipped with a digital camera and a robotic stage to capture thousands of individual images. Each image is focused by the content expert. Once acquired, these images are typically be stitched (or tiled) together to form the final representation of the slide. This process is both very time consuming and, due to the high number of images involved, the images are often misaligned.

ScanScope, (Aperio® Technology) is a new type of digital slide scanner that scans a microscope slide in 3 to 5 minutes, capturing 8 to 12 gigabyte images at 50,000 dpi. The images are then compressed, processed and stored for presentation (see below). MrSid® by Lizardtech® compresses the large, 8 to 12 gigabyte images using a proprietary multi-layer wavelet Jpeg format with compression ratios reaching 20:1 without significant image degradation. The images can then be either viewed locally or served from a web server. Unlike standard web-based still images, which are typically downloaded to be viewed within a browser, the MrSid processed images are viewed from the web, and the browser application never downloads the entire image. Because the images are acquired at their maximal resolution, "lower" magnification views of an image are constructed by the server. Using the combination of ScanScope and Zoomify browser, entire slides (12 gigabytes) can be captured and processed in less than 20 minutes.

4. In Vivo Analysis of Selectivity.

Of course in vivo selectivity of a SHAL can also readily be determined. This can be accomplished by administering the SHAL to a test animal (e.g., a laboratory rat) comprising a cell or tissue that displays the target to which the SHAL is directed. After sufficient time, the animal can be sacrificed and the target tissue(s) and normal tissues examined (e.g., histologically) to evaluate the specificity and amount of SHAL delivery. In certain embodiments, the SHAL can be coupled to an imaging reagent that permits non-invasive imaging and thereby permit the evaluation of real time pharmacodynamics.

By way of illustration, pharmacokinetic and radiation dosimetric mouse studies can be performed, e.g., on the SHALs illustrated in the Examples, to generate data upon which to select one for clinical trials of pharmacokinetics and radiation dosimetry in patients, using established methods. Pharmacokinetics can be performed in female nude mice bearing Raji human lymphoma xenografts of defined size using established methods (DeNardo et al. (1998) *Clin. Cancer Res.*, 4: 2483-2490; Kukis et al. (1995) *Cancer Res.*, 55: 878-884). Mice can be injected with DOTA-tagged SHALs containing $^{111}$In $^{111}$In or $^{90}$Y and mice can be sacrificed, e.g., at each of at least 5 time points to provide samples for analysis.

Initial studies can be conducted at the extremes of early and late time points expected for these small molecules so that the intermediate time points can be determined. Data for peptides can be used to define the extreme time points. When using $^{111}$In or $^{90}$Y as a tracer, the longest time point would typically be about 5 days. Total body clearances can be determined using a sodium iodide detector system. Blood clearance can be monitored by taking periodic blood samples from the tail veins of the mice. At the time of sacrifice, the xenograft and normal tissues can be removed, weighed and counted in a gamma well counter to provide organ distribution data.

In order to assess SHAL dose (mass) effect, studies can be conducted at, e.g., 5 dose levels, once again beginning with small and large SHAL amounts to guide selection of the intermediate amounts to be studied. Because of the novelty of the SHALs, selection of study time points and dose levels will typically be guided by information available for antibody (e.g., Lym-1) studies in mice and for, e.g., somatostatin receptor peptide ligands.

In certain embodiments, the ideal pharmacokinetics and dosimetry to achieve with our SHALs are those that approach what has been accomplished using sodium iodide (NaI) in the treatment of thyroid tumors. The SHALs should be small enough to completely penetrate the malignancy and be readily excreted in the urine. Typically at least an order of magnitude better target recognition and binding affinity to lymphomas and leukemias than current antibodies will provide the desired tumor cell selectivity. While the rapid clearance of smaller molecules, such as the SHALs, from the circulation might be considered a disadvantage, the remarkable effectiveness of NaI in treating thyroid tumors has shown this "disadvantage" can be turned into an advantage if the reagent has the right combination of affinity and selectivity. If the SHALs are taken up well, target only a specific family of cells (e.g., B lymphocytes and their malignant relatives), bind tightly with low off-rates, and are cleared rapidly from the system, the dose received by normal tissue (relative to malignant) should be substantially lower than that obtained using existing targeting antibodies.

Using established methods (DeNardo et al. (2000) *J. Nucl. Med.*, 41: 952-958; DeNardo et al. (1999) *J. Nucl. Med.*, 40: 1317-1326; DeNardo et al. (1999) *J. Nucl. Med.*, 40: 302-310; Shen et al. (1994) *J. Nucl. Med.*, 35: 1381-1389; Siegel (1994) *J. Nucl. Med.*, 35: 1213-1216) as guidelines, protocols can readily be developed for conducting pharmacokinetic and radiation dosimetry studies in patients with lymphomatous diseases of the B cell type or other cancers. Projected SHAL dose (mass) levels can be determined using the data generated in mice and adjusted for the relative BSA of mice and patients using known methods (see, e.g., Freireich et al. (1996) *Cancer Chemother. Rep.*, 50: 219-244). In certain embodiments, a protocol is selected that provides the optimal dose level using information on the therapeutic indices for tumor to marrow for a nonmyeloablative strategy and tumor to dose-limiting non-marrow organ for a myeloablative strategy.

J) Optimization of SHAL Affinity, Selectivity and Metabolism by Varying the Linker Length and Linker and Ligand Structure.

SHAL affinity, selectivity and metabolism can be optimized by varying the linker length, and/or the linker and ligand structure, using computer modeling and experimental studies. Linker lengths can be reduced or increased to improve the SHAL's affinity for its target. Changes in the individual ligands used to create the SHAL or alterations in individual ligand structure can also be made to improve binding, target selectivity and optimize the clearance of unbound SHAL from the organism. Modifications in the structure of the linker itself can also be considered to facilitate SHAL clearance, if necessary, from normal tissues and peripheral blood through the incorporation of cleavable bonds (e.g., a peptide or other cleavable linker) that attach the chelator to the SHAL.

If a particular SHAL is observed to exhibit non-specific binding (e.g., to many proteins in the cell extracts or to both Raji and control cells), additional SHALs can be synthesized using different pairs of ligands until a suitably specific SHAL is identified.

1. Maximization of SHAL Binding Affinity for Target Molecule(s).

Binding affinity of multidentate reagents to protein or cell surface targets can be increased by one to several orders of magnitude by changing and optimizing the length of the linker separating the ligands. Without being bound to a particular theory, it is believed that this increase is related to achieving the optimal separation between the ligands to allow them to bind to their individual sites as well as to providing sufficient rotational flexibility within the linker itself to enable the optimal interaction of each ligand within its binding site (e.g., binding pocket).

In certain embodiments, the initial linker length that is chosen for use in the initial SHALs is identified by estimating the distance between the two (or more) bound ligands that are to be linked together. Once it has been determined that a particular combination of linked ligands actually binds to the target, additional modeling can be conducted to further refine the length of the linker and optimize the SHALs binding affinity.

For example, where the target is HLA-DR10, the structure of the HLA-DR10 beta subunit can modeled with both ligands bound in their respective pockets and various length PEG linkers interconnecting the ligands (see, e.g., the Examples herein). From molecular dynamics studies the orientations of the bound ligands can be evaluated to improve the linker design. Further molecular dynamics simulations can be performed to include the linkers and the ligands, thus simulating the polydentate ligands interacting with the target, e.g., as described herein.

Once the results of these modeling experiments are obtained, an additional set of SHALs can be synthesized with linkers spanning the range of sizes predicted to be optimal, and their binding affinities can be experimentally tested.

2. Optimization of Target Selectivity and Metabolism of SHAL.

Computational methods can also be sued to determine if changes in the structure of the individual ligands that are linked together to produce the SHAL improve target selectivity and optimize SHAL metabolism and its clearance from normal tissues and peripheral circulation. This can be accomplished, for example, by examining the types of functional groups present inside a targeted binding pocket and their location relative to the bound ligand.

Molecular dynamics studies can be conducted using different conformations of the ligand and selected ligand analogs to aid the identification of ligand derivatives that fit optimally into each binding site (e.g., pocket). Diffusion NMR experiments (Lin et al. (1997) *J. Organic Chem.*, 62: 8930-8931) can be conducted to compare and rank the affinities of a subset of the ligand analogs. The particular analogs chosen for analysis are typically selected based on the results provided by computer modeling and the analog's commercial availability or ease of synthesis. If higher affinity analogs are identified experimentally, a set of new SHALs can be synthesized and tested for their affinity, selectivity in binding to targets, and desirable metabolic properties (e.g., rapid clearance from peripheral circulation, liver and kidney).

In certain embodiments, the small size of the SHAL can result in its being cleared from the tissues too quickly to be effective in delivering a suitable amount of effector to the target cells. If this is observed, various approaches can be used to optimize the retention time of the SHAL in the target tissue. One involves using a biotin attachment site on the linker to add a third ligand that binds to another site on the target. This is expected to increase the affinity of the SHAL to subpicomolar levels and reduce the off-rate of the bound molecule dramatically. Alternatively, the effective size of the SHAL can be increased substantially by attaching it to larger, multi-arm PEG molecules and/or to other molecules.

K) Illustrative SHALs.

Using the teachings provided herein, a number of different SHALs that bind, for example cancer markers (e.g., HLA-DR10) can readily be prepared. In various embodiments the SHALS include, but are not limited to bidentate SHALS (comprising two binding ligands), tridentate SHALS (comprising three binding ligands), tetradenate SHALS (comprising four binding ligands), pentadentate SHALS (comprising five binding ligands), and so forth. In various embodiments can be multimeric (e.g., structures and/or complesxes comprising two, three, four, five, or more SHALs). The SHALs can be homomultimeric (comprising two, three, four, five, or more of the same type of SHAL), or heteromultimeric (comprising, for example, two, three, four, or five or more SHALS where at least two are different species of SHAL).

In certain embodiments the SHALS comprise one or more, preferably two or more, or three or more ligands described in any of Tables 1, 5, 6, 7, or 8 and/or analogues thereof. Certain preferred SHALS include, but are not limited to bidentate SHALS (see, e.g. FIGS. 22 and 23), tridentate SHALS (see, e.g., FIG. 24A), dimeric bidentate SHALS, bimeric (bis) tridentate SHALS (see, e.g., FIG. 24B), and the like. In certain embodiments, the SHALS comprise one or more of the ligands shown in Table 1.

TABLE 1

Illustrative ligands that can be included in SHALS as described herein. Some of these (marked with *) could be used in place of the Ct ligand or attached to the linker as a fourth component, functioning not to help the SHAL bind to the protein better but as an inhibitor once the SHAL gets inside the cell.

| | |
|---|---|
| 1 | BOC-4-aminomethyl-L-Phe |
| 2 | *4[[5-(Trifluoromethyl)pyridin-2-yl]oxy]phenyl]N-phenylcarbamate |
| 3 | *(R)-2-[4-(5-chloro-3-fluoro-2-pyridyloxy)phenoxy]propionic acid |
| 4 | *2-(((3-chloro-5(trifluoromethyl)pyridin-2-yloxy)phenoxy)methyl)acrylates |
| 5 | *2-(((3-chloro-5(trifluoromethyl)pyridin-2-yloxy)phenyl)methyl)acrylates |
| 6 | *2-(((3-chloro-5(trifluoromethyl)pyridin-2-yloxy)phenyl)methyl)acrylonitriles |
| 7 | *3-(3-chloro-4-{[5-(trifluoromethyl)-2-pyridinyl]oxy}anilino)-3-oxopropanoic acid |
| 8 | *Sethoxydim |
| 9 | *Clethodim |
| 10 | *5-(Tetradecyloxy)-2-furoic acid |
| 11 | *2-[(2,6-Dichlorophenyl)amino]benzeneacetic acid |
| 12 | *2-[4-(4-Chlorophenoxy)phenoxy]propanoic acid |

TABLE 1-continued Illustrative ligands that can be included in SHALS as described herein. Some of these (marked with *) could be used in place of the Ct ligand or attached to the linker as a fourth component, functioning not to help the SHAL bind to the protein better but as an inhibitor once the SHAL gets inside the cell.

13 *(RS)-2-{4-[3-chloro-5-(trifluoromethyl)-2-pyridinyl]oxy]phenoxy}propanoic acid
14 *(RS)-2-[4-(6-chloro-1,3-benzoxazol-2-yloxy)phenoxy]propanoic acid
15 *(RS)-2-[4-(2,4-dichlorophenoxy)phenoxy]propanoic acid
16 *(RS)-2-{4-[5-(trifluoromethyl)-2-pyridyloxy]phenoxy}propanoic acid
17 *(RS)-2-[4-(6-chloroquinoxalin-2-yloxy)phenoxy]propanoic acid
18 *(RS)-2-[4-(α,α,α-trifluoro-p-tolyloxy)phenoxy]propanoic acid
19 5-([4,6-Dichlorotriazin-2-yl]amino)fluorescein hydrochloride
20 3-[N-(4-acetylphenyl)carbomoyl]pyridine-2-Carboxylic acid
21 3-(2-{[3-chloro-5-(trifluoromethyl)-2-pyridinyl]oxy}anilino)-3-oxopropanoic acid
22 L-ornithine-beta-alanine
23 2-Methyl-1-(3-morpholinopropyl)-5-phenyl-1H-pyrrole-3-carboxylic acid
24 Hippuric acid
25 Hippuryl-D-lysine
26 Hippuryl-L-phenylalanine Certain illustrative SHALS are also shown in Table 2.

TABLE 2

List of illustrative multidentate and dimeric, multidentate SHALs and their molecular weight (MW in Daltons). DOTA on the SHAL contributes an additional 400 (or 244 for biotin) Daltons.

| Acronym | Identity | MW |
| --- | --- | --- |
| Multidentate | | |
| LeacPLD | acetylated 5-leuenkephalin PEG lysine deoxycholate | 1,505 |
| ItPLD | triiodothyronine PEG lysine deoxycholate | 1,559 |
| DvLPBaPL | dabsyl-L-valine lysine PEG N-benzoyl-L-arginyl-4-amino-benzoic acid PEG lysine | 1,317 |
| CtLPTPL | 3-(2-([3-chloro-5-trifluoromethyl)-2-pyridinyl]oxy)-anilino)-3-oxopropanionic acid lysine PEG L-thyronine PEG lysine | 1,163 |
| CtLPBaPL | 3-(2-([3-chloro-5-trifluoromethyl)-2-pyridinyl]oxy)-anilino)-3-oxopropanionic acid lysine PEG N-benzoyl-L-arginyl-4-amino-benzoic acid PEG lysine | 1,287 |
| DvPLLCtPCbL | dabsyl-L-valine PEG lysine lysine 3-(2-([3-chloro-5-trifluoromethyl)-2-pyridinyl]oxy)-anilino)-3-oxopropanionic acid PEG 4-[4-(4-chlorobenzyl)piperazino]-3-nitrobenzenecarboxylic acid lysine | 1,765 |
| Dimeric, Multidentate | | |
| (LeacPLD)$_2$LP | (acetylated 5-leuenkephalin PEG lysine deoxycholate)$_2$ lysine PEG | 3,006 |
| (ItPDP)$_2$LL | (triiodothyronine PEG deoxycholate PEG)$_2$ lysine lysine | 3,113 |
| (DvLPBaP)$_2$LL | (dabsyl-L-valine lysine PEG N-benzoyl-L-arginyl-4-aminobenzoic acid PEG)$_2$ lysine lysine | 2,626 |
| (DvLPBaPP)$_2$LL | (dabsyl-L-valine lysine PEG N-benzoyl-L-arginyl-4-aminobenzoic acid PEG PEG)$_2$ lysine lysine | 2,921 |
| (DvLPBaPPP)$_2$LL | (dabsyl-L-valine lysine PEG N-benzoyl-L-arginyl-4-aminobenzoic acid PEG PEG PEG)$_2$ lysine lysine | 3,210 |
| (DvLPBaPPPP)$_2$LL | (dabsyl-L-valine lysine PEG N-benzoyl-L-arginyl-4-aminobenzoic acid PEG PEG PEG PEG)$_2$ lysine lysine | 3,501 |
| (DvLCsPBaPPP)$_2$CsLL | (dabsyl-L-valine lysine cysteic acid PEG N-benzoyl-L-arginyl-4-aminobenzoic acid PEG PEG PEG)$_2$ cysteic acid lysine lysine | 3,666 |
| (DvPLLCtPCbPPP)$_2$LL | (dabsyl-L-valine PEG lysine lysine 3-(2-([3-chloro-5-trifluoromethyl)-2-pyridinyl]oxy)-anilino)-3-oxopropanionic acid PEG 4-[4-(4-chlorobenzyl)piperazino]-3-nitrobenzenecarboxylic acid PEG PEG PEG)$_2$ lysine lysine | 4,267 |

It was discovered that various SHALS described herein are effective alone to inhibit the growth and/or proliferation of a cancer cell and in certain instances kill the cancer cell. The SHALS can thus be used alone, or attached to one or more effectors, e.g., as described herein.

L) SHALS Attached to Transduction Peptides.

In certain embodiments the SHALs include (e.g., are attached to) one or more transduction peptides. A transduction peptide is a peptide that acts as a "transmembrane shuttle" facilitating entry of the peptide into a cell (e.g., facilitating penetration of the cell membrane). Transduction peptides are well known to those of skill in the art. Such peptides include, but are not limited to the nuclear localization signal (NLS) of simian virus 40 (SV40) T antigen ((Yoneda (1997) *J. Biochem.*, 121: 811-817), the protein transduction domain of HIV Tat protein (Tat peptide) (Vives et al. (1997) *J. Biol. Chem.* 272: 16010-16017; Schwarze et al. (1999) *Science* 285: 1569-1572; Torchilin et al. (2003) *Proc. Natl. Acad. Sci., USA,* 100: 1972-1977.), the integrin-binding peptide (RGD peptide) (Hart et al. (1994) *J. Biol. Chem.* 269: 12468-12474), the heparin-binding domain of vitronectin (VN peptide) (Vogel et al. (1993) *J. Cell Biol.* 121: 461-4-68), antennapedia protein of *Drosophila* (see, e.g., Joliot et al. (1991) *Proc. Natl. Acad. Sci., USA,* 88: 1864-1868), penetratin (Tseng et al. (2002) *Mol. Pharmacol.*, 62: 864-887), intact proteins that naturally pass through cell membranes (the herpes virus protein VP22 (Phelan et al. (1998) *Nat. Biotechnol.*, 16: 440-443), synthetic cationic peptide transporters such as oligoarginine (Tung and Weissleder (2003) *Adv. Drug Delivery Rev.*, 55: 281-294; Futaki (2005) *Adv. Drug Delivery Rev.*, 57: 547-558), lactosylated poly-L-lysine (Midoux et al. (1993) *Nucl Acids Res.*, 21: 871-878), short peptide sequences selected from phage display libraries (Kamada et al. (2007) *Biol Pharm Bull.* 30: 218-223; see also peptides 1-6 in Table 3) that exhibit sequence similarities to know peptide shuttles, and the like.

alone as therapeutics (e.g., to inhibit growth and/or proliferation of a cancer cell) and/or they can be coupled to an effector to provide efficient and specific delivery of the effector (e.g., an effector molecule such as a cytotoxin, a radiolabel, etc.) to various cancer cells (e.g., isolated cells, metastatic cells, solid tumor cells, etc.).

In certain preferred embodiments, the SHALs of this invention are utilized in a "pretargeting" strategy (resulting in formation of a chimeric moiety at the target site after administration of the effector moiety) or in a "targeting" strategy where the SHAL is coupled to an effector molecule prior to use to provide a chimeric molecule.

A chimeric molecule or chimeric composition or chimeric moiety refers to a molecule or composition wherein two or more molecules that exist separately in their native state are joined together to form a single molecule having the desired functionality of its constituent molecules. Typically, one of the constituent molecules of a chimeric molecule is a "targeting molecule" in this instance one or more SHALs. The targeting molecule acts to direct the chimeric molecule to its particular target, e.g., a cancer cell.

Another constituent of the chimeric molecule is an "effector". The effector molecule refers to a molecule or group of molecules that is to be specifically transported to the target cell (e.g., a cancer cell). It is noted that in this context, such specific transport need not be exclusively to or into a cancer

TABLE 3

Amino acid sequences of illustrative transduction peptides.

| Peptide | Sequence | Seq ID No. |
|---|---|---|
| 1 | S-G-E-H-T-N-G-P-S-K-T-S-V-R-W-V-W-D | 9 |
| 2 | S-M-T-T-M-E-F-G-H-S-M-I-T-P-Y-K-I-D | 10 |
| 3 | Q-D-G-G-T-W-H-L-V-A-Y-C-A-K-S-H-R-Y | 11 |
| 4 | M-S-D-P-N-M-N-P-G-T-L-G-S-S-H-I-L-W | 12 |
| 5 | S-P-G-N-Q-S-T-G-V-I-G-T-P-S-F-S-N-H | 13 |
| 6 | S-S-G-A-N-Y-F-F-N-A-I-Y-D-F-L-S-N-F | 14 |
| 8 | G-T-S-R-A-N-S-Y-D-N-L-L-S-E-T-L-T-Q | 15 |
| Tat13 | G-R-K-K-R-R-Q-R-R-R-P-P-Q | 16 |
| Antennapedia | R-Q-I-K-I-WF-Q-N-R-R-M-K-WK-K | 17 |
| VP22 | N-A-K-T-R-R-H-E-R-R-R-K-L-A-I-E-R | 18 |
| hexa-Arg | R-R-R-R-R-R | 19 |

The foregoing list of transduction peptides is intended to be illustrative and not limiting. Other transduction peptides will be known to and readily available to one of ordinary skill in the art and using the teaching provided herein can readily be incorporated into/attached to a SHAL. A review of illustrative transduction peptides is provided by Derossi et al. (1998) *Trends Cell Biol.* 8: 84-87.

II. Chimeric Moieties Comprising SHALs (e.g., Cancer Specific SHALs).

The SHALS of this invention are selected to specifically bind to particular targets. Where the targets are markers characteristic of a particular cell type (e.g., a tumor cell) the SHALS can be used to specifically deliver one or more effectors to the target cell.

In certain embodiments, the SHALs specifically bind to cancer cells. In these embodiments, the SHALs can be used cell, but merely need to provide preferential delivery of the effector to, or into, the cancer cell as compared to normal healthy cells.

The effector molecule typically has a characteristic activity that is to be delivered to the target cell. Effector molecules include, but are not limited to cytotoxins, labels, radionuclides, ligands, antibodies, drugs, liposomes, nanoparticles, viral particles, cytokines, and the like.

In certain embodiments, the effector is a detectable label, with preferred detectable labels including radionuclides. Among the radionuclides and labels useful in the radionuclide-chelator—(e.g., biotin) conjugates of the present invention, gamma-emitters, positron-emitters, x-ray emitters and fluorescence-emitters are suitable for localization, diagnosis and/or staging, and/or therapy, while beta and alpha-emitters and electron and neutron-capturing agents, such as boron and uranium, also can be used for therapy.

The detectable labels can be used in conjunction with an external detector and/or an internal detector and provide a means of effectively localizing and/or visualizing prostate cancer cells. Such detection/visualization can be useful in various contexts including, but not limited to pre-operative and intraoperative settings. Thus, in certain embodiment this invention relates to a method of intraoperatively detecting cancers in the body of a mammal. These methods typically involve administering to the mammal a composition comprising, in a quantity sufficient for detection by a detector (e.g., a gamma detecting probe), a cancer specific SHAL labeled with a detectable label (e.g., antibodies of this invention labeled with a radioisotope, e.g., $^{161}$Tb, $^{123}$I, $^{125}$I, and the like), and, after allowing the active substance to be taken up by the target tissue, and preferably after blood clearance of the label, subjecting the mammal to a radioimmunodetection technique in the relevant area of the body, e.g., by using a gamma detecting probe.

The label-bound SHAL can be used in the technique of radioguided surgery, wherein relevant tissues in the body of a subject can be detected and located intraoperatively by means of a detector, e.g., a gamma detecting probe. The surgeon can, intraoperatively, use this probe to find the tissues in which uptake of the compound labeled with a radioisotope, that is, e.g., a low-energy gamma photon emitter, has taken place.

In addition to detectable labels, preferred effectors include cytotoxins (e.g., *Pseudomonas* exotoxin, ricin, abrin, Diphtheria toxin, and the like), or cytotoxic drugs or prodrugs, in which case the chimeric molecule can act as a potent cell-killing agent specifically targeting the cytotoxin to cancer cells.

In still other embodiments, the effector can include a liposome encapsulating a drug (e.g., an anti-cancer drug such as doxirubicin, vinblastine, taxol, etc.), an antigen that stimulates recognition of the bound cell by components of the immune system, an antibody that specifically binds immune system components and directs them to the cancer, and the like.

A) Certain Preferred Effectors.

1) Imaging Compositions.

In certain embodiments, the chimeric molecules of this invention can be used to direct detectable labels to a tumor site. This can facilitate tumor detection and/or localization. In certain particularly preferred embodiments, the effector component of the chimeric molecule is a "radioopaque" label, e.g., a label that can be easily visualized using x-rays. Radioopaque materials are well known to those of skill in the art. The most common radiopaque materials include iodide, bromide or barium salts. Other radiopaque materials are also known and include, but are not limited to organic bismuth derivatives (see, e.g., U.S. Pat. No. 5,939,045), radiopaque polyurethanes (see U.S. Pat. No. 5,346,981, organobismuth composites (see, e.g., U.S. Pat. No. 5,256,334), radiopaque barium polymer complexes (see, e.g., U.S. Pat. No. 4,866,132), and the like.

The SHALs of this invention can be coupled directly to the radiopaque moiety or they can be attached to a "package" (e.g., a chelate, a liposome, a polymer microbead, etc.) carrying or containing the radiopaque material as described below.

In addition to radioopaque labels, other labels are also suitable for use in this invention. Detectable labels suitable for use as the effector molecule component of the chimeric molecules of this invention include any composition detectable by spectroscopic, photochemical, biochemical, immunochemical, electrical, optical or chemical means. Useful labels in the present invention include magnetic beads (e.g., Dynabeads™), fluorescent dyes (e.g., fluorescein isothiocyanate, texas red, rhodamine, green fluorescent protein, and the like), radiolabels (e.g., $^3$H, $^{125}$I, $^{35}$S, $^{14}$C, $^{32}$P, $^{18}$F, etc.) or other tags for imaging, enzymes (e.g., horse radish peroxidase, alkaline phosphatase and others commonly used in an ELISA), and colorimetric labels such as colloidal gold or colored glass or plastic (e.g., polystyrene, polypropylene, latex, etc.) beads.

Various preferred radiolabels include, but are not limited to $^{99}$Tc, $^{203}$Pb, $^{67}$Ga, $^{68}$Ga, $^{72}$As, $^{111}$In, $^{113m}$In, $^{97}$Ru, $^{62}$Cu, 641Cu, $^{52}$Fe, $^{52m}$Mn, $^{51}$Cr, $^{186}$Re, $^{188}$Re, $^{77}$As, $^{90}$Y, $^{67}$Cu, $^{169}$Er, $^{121}$Sn, $^{127}$Te, $^{142}$Pr, $^{143}$Pr, $^{198}$Au, $^{199}$Au, $^{161}$Tb, $^{109}$Pd, $^{165}$Dy, $^{149}$Pm, $^{151}$Pm, $^{153}$Sm, $^{157}$Gd, $^{159}$Gd, $^{166}$Ho, $^{172}$Tm, $^{169}$Yb, $^{175}$Yb, $^{177}$Lu, $^{105}$Rh, and $^{111}$Ag.

Means of detecting such labels are well known to those of skill in the art. Thus, for example, radiolabels may be detected using photographic film, scintillation detectors, and the like. Fluorescent markers may be detected using a photodetector to detect emitted illumination. Enzymatic labels are typically detected by providing the enzyme with a substrate and detecting the reaction product produced by the action of the enzyme on the substrate, and colorimetric labels are detected by simply visualizing the colored label.

2) Radiosensitizers.

In another embodiment, the effector can be a radiosensitizer that enhances the cytotoxic effect of ionizing radiation (e.g., such as might be produced by $^{60}$Co or an x-ray source) on a cell. Numerous radiosensitizing agents are known and include, but are not limited to benzoporphyrin derivative compounds (see, e.g., U.S. Pat. No. 5,945,439), 1,2,4-benzotriazine oxides (see, e.g., U.S. Pat. No. 5,849,738), compounds containing certain diamines (see, e.g., U.S. Pat. No. 5,700,825), BCNT (see, e.g., U.S. Pat. No. 5,872,107), radiosensitizing nitrobenzoic acid amide derivatives (see, e.g., U.S. Pat. No. 4,474,814), various heterocyclic derivatives (see, e.g., U.S. Pat. No. 5,064,849), platinum complexes (see, e.g., U.S. Pat. No. 4,921,963), and the like.

3) Radioisotopes.

In certain embodiments, the effector comprises one or more radioisotopes that when delivered to a target cell bring about radiation-induced cell death.

For medical purposes, the most important types of decay are gamma emission, beta decay, alpha decay, and electron capture. The gamma emitted by a radionuclide, such a $^{131}$I, exits the body, allowing the use of external scintigraphic imaging to determine the biodistribution of radiolabeled antibodies (the optimal energy range for immunoscintigraphy is 100-250 keV). In contrast, beta particles deposit most of their energy within a few millimeters of the point of decay. Beta emissions from radionuclides such as $^{131}$I or $^{90}$Y that have targeted antigen-positive tumor cells can kill nearby antigen-negative tumor cells through a "crossfire" effect.

Yttrium-90, a pure beta emitter, has several properties that make it an attractive choice for radioimmunotherapy: 1) a high beta energy ($E_{max}$=2.29 MeV; maximum range of particulate energy in tissue=11.9 mm) which enables it to kill adjacent tumor cells; 2) metal chemistry, which facilitates the synthesis of radioisotope-antibody conjugates and use of a pretargeting approach; and 3) a sufficiently long physical half-life (2.67 days) for use with intact SHALs, which may take 1-3 days to reach their peak concentration in tumors.

In certain embodiments, the effector can include an alpha emitter, i.e. a radioactive isotope that emits alpha particles and/or an auter-electron emitter. Alpha-emitters and auger-electron emitters have recently been shown to be effective in the treatment of cancer (see, e.g., Bodei et al. (2003) *Cancer Biotherapy and Radiopharmaceuticals*, 18:861). Suitable alpha emitters include, but are not limited $^{212}$Bi, $^{213}$Bi, $^{211}$At, and the like.

Figure 22:
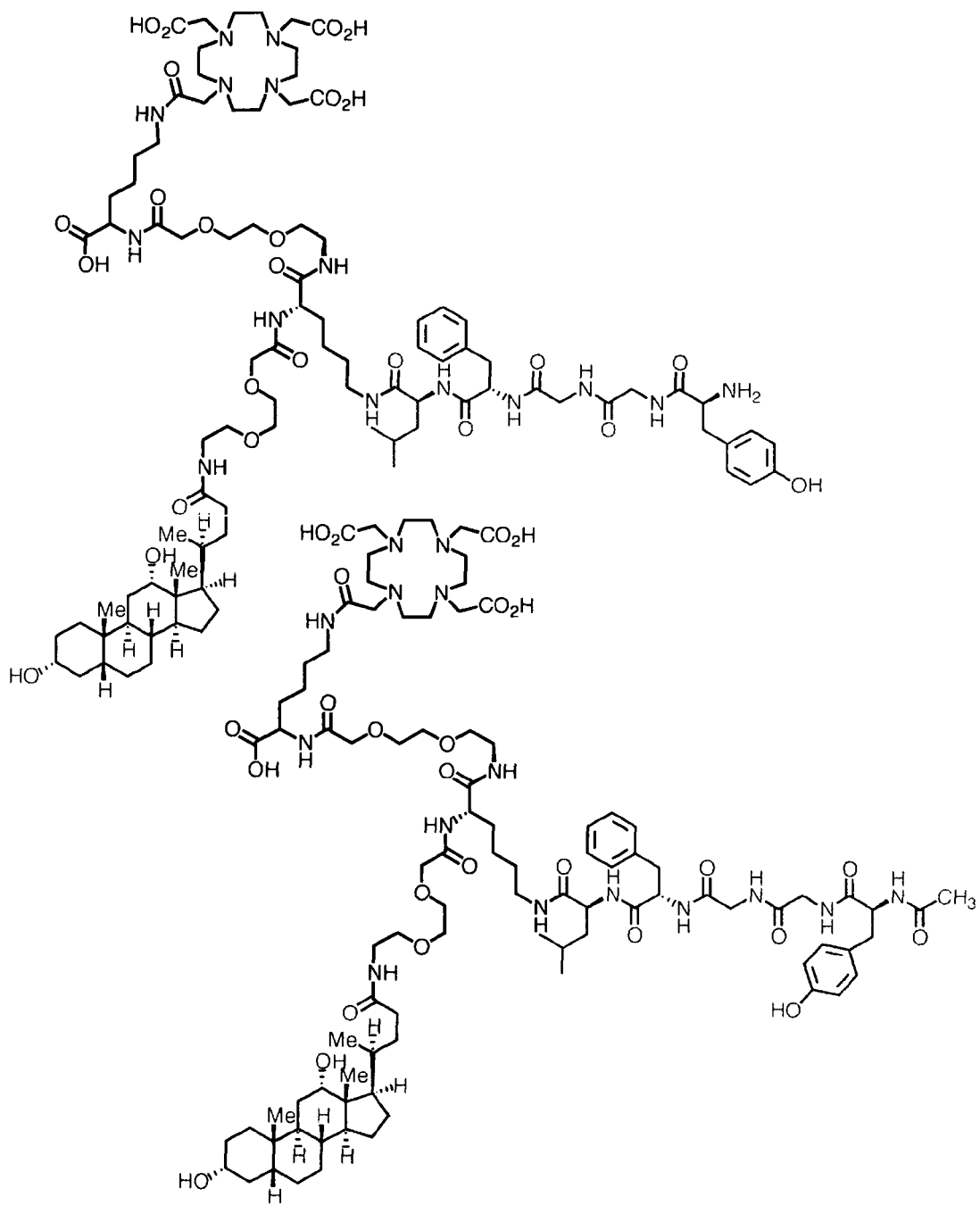
FIG. 22 illustrates SHALs attached to DOTA. The red part is one ligand (deoxycholate), the green is the other ligand (5-leu-enkephalin), the blue is a lysine used to make the shortest linker, and the black is a combination of things: the PEG molecules used to make the linker between the two ligands longer, a DOTA ring attached to the SHAL for binding the radioactive metal.
Figure 23:
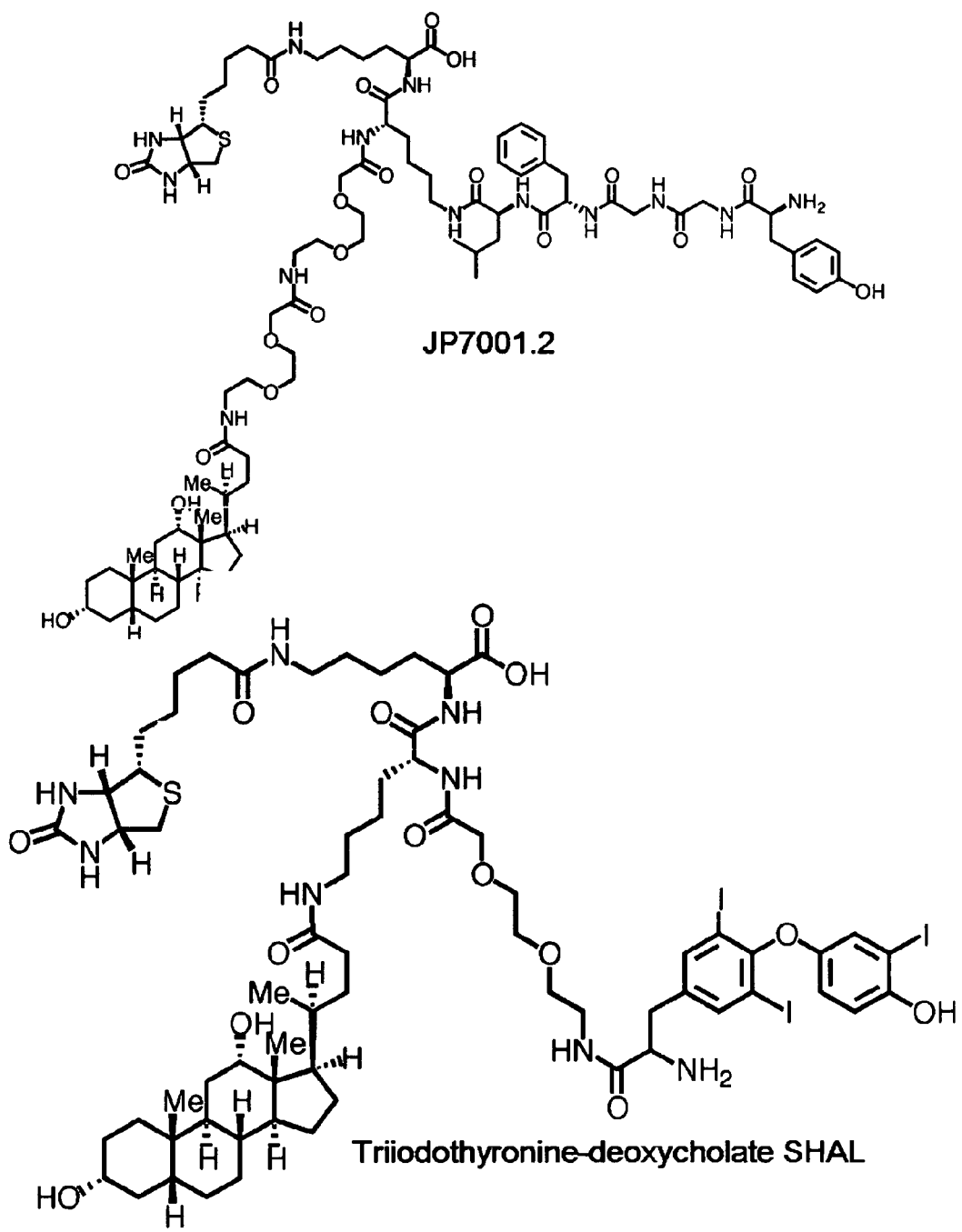
FIG. 23 shows formulas for JP7001.2 and triiodothyronine-deoxycholate SHALs.
Figure 24A:
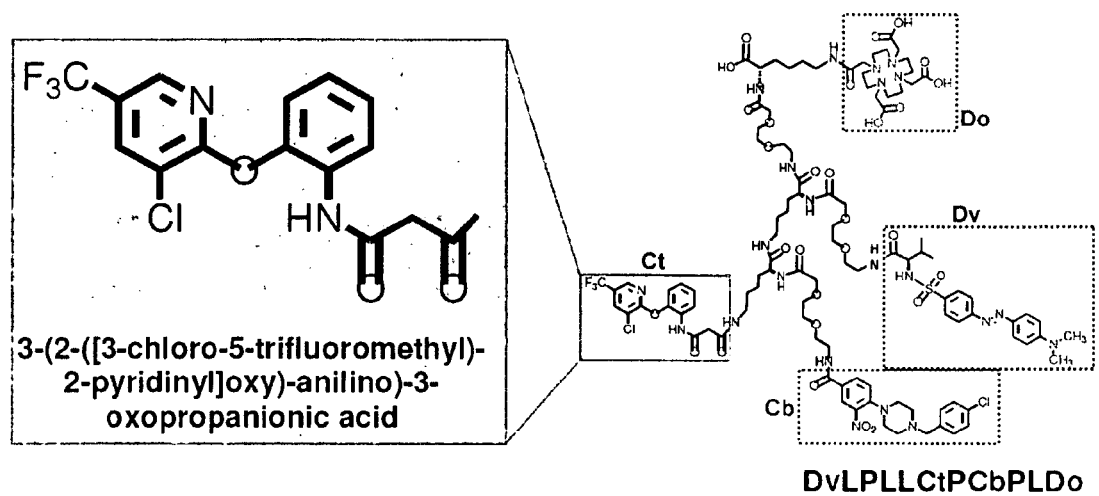
FIGS. 24A and 24B show chemical structures in 2 dimensions and acronyms for the tridentate SHAL (FIG. 24A) DvLPLLCtPCbPLDo; (dabsyl-L-valine PEG lysine lysine 3-(2-([3-chloro-5-trifluoromethyl)-2-pyridinyl]oxy)-anilino)-3-oxopropanionic acid PEG 4-[4-(4-chlorobenzyl) piperazino]-3-nitrobenzenecarboxylic acid lysine-DOTA having the Ct ligand (FIG. 24A insert); and the dimeric, tridentate SHAL (FIG. 24B) (DvLPLLCtPCbPPP)$_2$LLDo; ((dabsyl-L-valine PEG lysine lysine 3-(2-([3-chloro-5-trifluoromethyl)-2-pyridinyl]oxy)-anilino)-3-oxopropanionic acid PEG 4-[4-(4-chlorobenzyl)piperazino]-3-nitrobenzenecarboxylic acid PEG PEG PEG)$_2$ lysine lysine-DOTA. In various embodiments, analog biotinylated SHALs differ only with respect to substitution of biotin for the DOTA chelate, upper right of each SHAL.
Figure 24B:
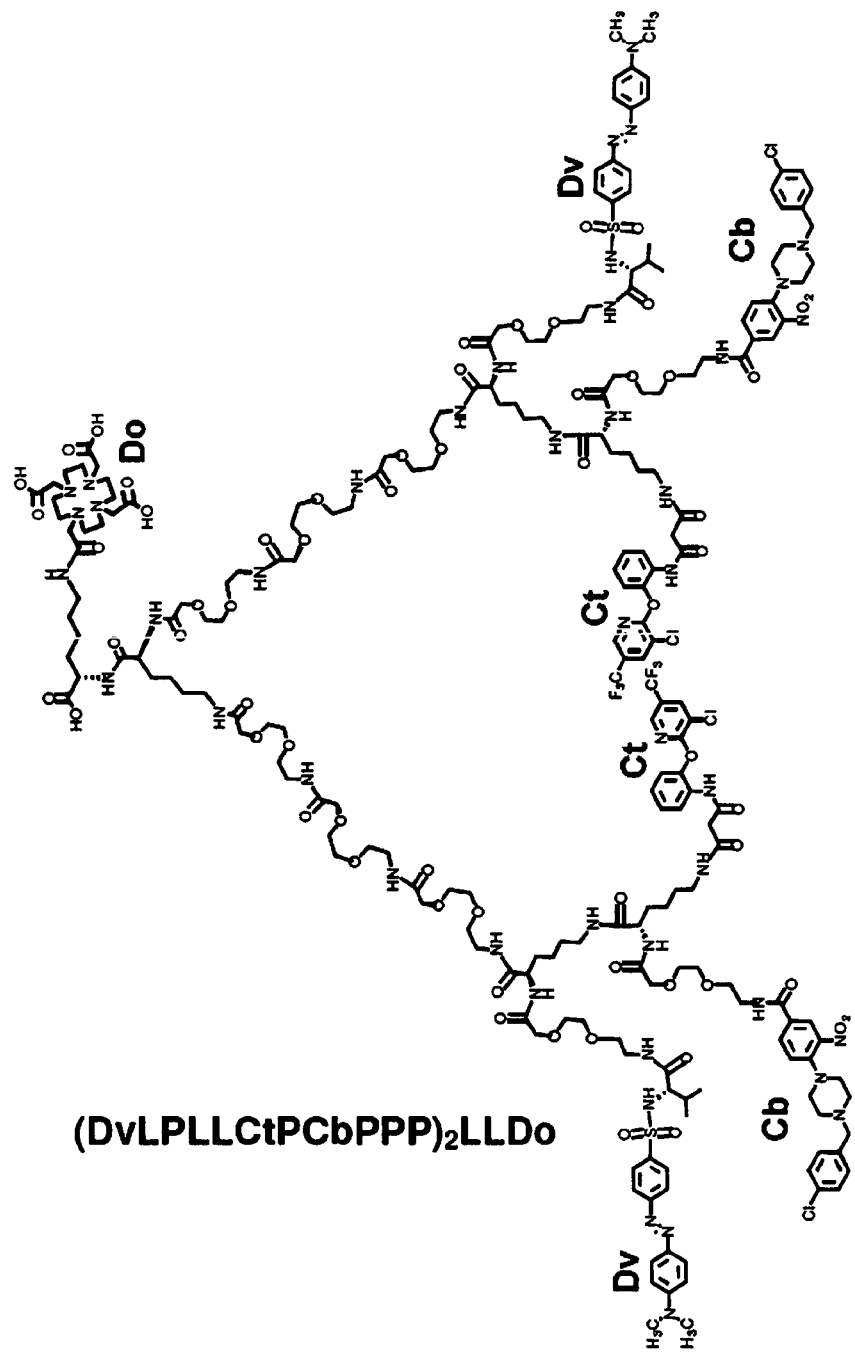

Table 4 illustrates some radionuclides suitable for radioimmunotherapy. This list is intended to be illustrative and not limiting.

droxybenzyl)-ethylenediamine-N,N'-diacetic acid (HBED), triethylene tetramine hexa-acetic acid (TTHA), 1,4,7,10-tetraazacyclododecane-N,N',N'',N'''-tetra-acetic acid (DOTA), hydroxyethyldiamine triacetic acid (HEDTA), 1,4,8,11-tetra-azacyclotetradecane-N,N',N'',N'''-tetra-acetic acid (TETA), substituted DTPA, substituted EDTA, and the like (see, e.g., FIG. 22).

Examples of certain preferred chelators include unsubstituted or, substituted 2-iminothiolanes and 2-iminothiacyclohexanes, in particular 2-imino-4-mercaptomethylthiolane.

TABLE 4

Illustrative radionuclides suitable for radioimmunotherapy.

| Radio-nuclide | Decay mode | Physical half life | Max. particulate energy (%) | Advantages | Disadvantages |
|---|---|---|---|---|---|
| I-131 | β, γ | 8 d | 807 keV (1)*<br>606 keV (86)*<br>336 keV(13)* | Iodine chemistry, inexpensive | Dehalogenation, radiation safety concerns |
| Cu-67 | β, γ | 62 h | 577 keV (20)*<br>484 keV (35)*<br>395 keV(45)* | Images, metal chemistry, long retention in tumor | Scarce |
| Lu-177 | β, γ | 6.7 d | 497 keV (90)*<br>384 keV (3)*<br>175 keV(7)* | Images | Scarce, bone seeker |
| Re-186 | β, γ electron capture | 91 h | 1.07 MeV (77)*<br>934 keV (23)* | $^{99m}$Tc chemistry | Scarce |
| Y-90 | β | 64 h | 2.29 MeV (100)* | Metal chemistry | Doesn't image, bone seeker |
| Re-188 | β | 17 h | 2.13 MeV (100)* | | Scarce, short ½ life |
| Bi-212 | α, β | 1 h | 6.09 MeV (27)<br>6.05 MeV (70)<br>5.77 MeV (2)<br>5.61 MeV (1) | | Doesn't image, short ½ life, unstable daughter product |
| At-211 | α, electron capture | 7 h | 5.87 MeV (100)** | High RBE, hypoxia lesss important, short range | Doesn't image, short ½ life, unstable daughter product |
| I-125 | Electron capture | 60 d | 35 keV (100) | Short range | Doesn't image, long ½ life |

*beta irradiation
**alpha irradiation
RBE, relative biologic effectiveness

4) Ligands.

In various embodiments the effector molecule can also be a ligand, an epitope tag, or an antibody. Particularly preferred ligand and antibodies are those that bind to surface markers on immune cells. Chimeric molecules utilizing such antibodies as effector molecules act as bifunctional linkers establishing an association between the immune cells bearing binding partner for the ligand or antibody and the prostate cancer cell(s).

5) Chelates

Many of the pharmaceuticals and/or radiolabels described herein are preferably provided as a chelate, particularly where a pre-targeting strategy is utilized. The chelating molecule is typically coupled to a molecule (e.g., biotin, avidin, streptavidin, etc.) that specifically binds an epitope tag attached to a prostate cancer specific antibody of this invention.

Chelating groups are well known to those of skill in the art. In certain embodiments, chelating groups are derived from ethylene diamine tetra-acetic acid (EDTA), diethylene triamine penta-acetic acid (DTPA), cyclohexyl 1,2-diamine tetra-acetic acid (CDTA), ethyleneglycol-O,O'-bis(2-aminoethyl)-N,N,N',N'-tetra-acetic acid (EGTA), N,N-bis(hy- One chelating agent, 1,4,7,10-tetraazacyclododecane-N, N,N'',N'''-tetraacetic acid (DOTA), is of particular interest because of its ability to chelate a number of diagnostically and therapeutically important metals, such as radionuclides and radiolabels.

Conjugates of DOTA and proteins such as antibodies have been described. For example, U.S. Pat. No. 5,428,156 teaches a method for conjugating DOTA to antibodies and antibody fragments. To make these conjugates, one carboxylic acid group of DOTA is converted to an active ester which can react with an amine or sulfhydryl group on the antibody or antibody fragment. Lewis et al. (1994) *Bioconjugate Chem.* 5: 565-576, describes a similar method wherein one carboxyl group of DOTA is converted to an active ester, and the activated DOTA is mixed with an antibody, linking the antibody to DOTA via the epsilon-amino group of a lysine residue of the antibody, thereby converting one carboxyl group of DOTA to an amide moiety.

Alternatively, the chelating agent can be coupled, directly or through a linker, to an epitope tag or to a moiety that binds an epitope tag. Conjugates of DOTA and biotin have been described (see, e.g., Su (1995) *J. Nucl. Med.*, 36 (5 Suppl): 154P, which discloses the linkage of DOTA to biotin via available amino side chain biotin derivatives such as DOTA-LC-biotin or DOTA-benzyl-4-(6-amino-caproamide)-biotin). Yau et al., WO 95/15335, disclose a method of producing nitro-benzyl-DOTA compounds that can be conjugated to biotin. The method comprises a cyclization reaction via transient projection of a hydroxy group; tosylation of an amine; deprotection of the transiently protected hydroxy group; tosylation of the deprotected hydroxy group; and intramolecular tosylate cyclization. Wu et al. (1992) *Nucl. Med. Biol.*, 19(2): 239-244 discloses a synthesis of macrocylic chelating agents for radiolabeling proteins with $^{111}$In and $^{90}$Y. Wu et al. makes a labeled DOTA-biotin conjugate to study the stability and biodistribution of conjugates with avidin, a model protein for studies. This conjugate was made using a biotin hydrazide which contained a free amino group to react with an in situ generated activated DOTA derivative.

It is noted that the macrocyclic chelating agent 1,4,7,10-tetraazacyclododecane-N,N',N",N'"-tetraacetic acid (DOTA) binds $^{90}$Y and $^{111}$In with extraordinary stability. Kinetic studies in selected buffers to estimate radiolabeling reaction times under prospective radiopharmacy labeling can be performed to determine optimal radiolabeling conditions to provide high product yields consistent with FDA requirements for a radiopharmaceutical. It is also noted that protocols for producing Yttrium-90-DOTA chelates are described in detail by Kukis et al. (1998) *J. Nucl. Med.*, 39(12): 2105-2110.

6) Cytotoxins.

The SHALs of this invention can be used to deliver a variety of cytotoxic drugs including therapeutic drugs, a compound emitting radiation, molecules of plants, fungal, or bacterial origin, biological proteins, and mixtures thereof. The cytotoxic drugs can be intracellularly acting cytotoxic drugs, such as short-range radiation emitters, including, for example, short-range, high-energy α-emitters as described above, or enzyme inhibitors.

Enzymatically active toxins and fragments, thereof are exemplified by diphtheria toxin A fragment, nonbinding active fragments of diphtheria toxin, exotoxin A (from *Pseudomonas aeruginosa*), ricin A chain, abrin A chain, modeccin A chain, .alpha.-sacrin, certain *Aleurites fordii* proteins, certain Dianthin proteins, *Phytolacca americana* proteins (PAP, PAPII and PAP-S), *Morodica charantia* inhibitor, curcin, crotin, *Saponaria officinalis* inhibitor, gelonin, mitogillin, restrictocin, phenomycin, and enomycin, for example.

Particularly preferred cytotoxins include *Pseudomonas* exotoxins, Diphtheria toxins, ricin, and abrin. *Pseudomonas* exotoxin A (PE) is an extremely active monomeric protein (molecular weight 66 kD), secreted by *Pseudomonas aeruginosa*, which inhibits protein synthesis in eukaryotic cells through the inactivation of elongation factor 2 (EF-2) by catalyzing its ADP-ribosylation (catalyzing the transfer of the ADP ribosyl moiety of oxidized NAD onto EF-2).

The toxin contains three structural domains that act in concert to cause cytotoxicity. Domain Ia (amino acids 1-252) mediates cell binding. Domain II (amino acids 253-364) is responsible for translocation into the cytosol and domain III (amino acids 400-613) mediates ADP ribosylation of elongation factor 2, which inactivates the protein and causes cell death. The function of domain Ib (amino acids 365-399) remains undefined, although a large part of it, amino acids 365-380, can be deleted without loss of cytotoxicity (see, e.g., Siegall et al. (1989) *J. Biol. Chem.* 264: 14256-14261).

Where the SHAL is attached to PE, one preferred PE molecule is one in which domain Ia (amino acids 1 through 252) is deleted and amino acids 365 to 380 have been deleted from domain Ib. However all of domain Ib and a portion of domain II (amino acids 350 to 394) can be deleted, particularly if the deleted sequences are replaced with a linking peptide such as GGGGS (SEQ ID NO:20).

In addition, the PE molecules can be further modified using site-directed mutagenesis or other techniques known in the art, to alter the molecule for a particular desired application. Means to alter the PE molecule in a manner that does not substantially affect the functional advantages provided by the PE molecules described here can also be used and such resulting molecules are intended to be covered herein.

For maximum cytotoxic properties of a preferred PE molecule, several modifications to the molecule are recommended. An appropriate carboxyl terminal sequence to the recombinant molecule is preferred to translocate the molecule into the cytosol of target cells. Amino acid sequences which have been found to be effective include, REDLK (SEQ ID NO:21) (as in native PE), REDL (SEQ ID NO:22), RDEL (SEQ ID NO:23), or KDEL (SEQ ID NO:24), repeats of those, or other sequences that function to maintain or recycle proteins into the endoplasmic reticulum, referred to here as "endoplasmic retention sequences". See, for example, Chaudhary et al. (1991) *Proc. Natl. Acad. Sci. USA* 87:308-312 and Seetharam et al, *J. Biol. Chem.* 266: 17376-17381. Preferred forms of PE comprise the PE molecule designated PE38QQR. (Debinski et al. *Bioconj. Chem.*, 5: 40 (1994)), and PE4E (see, e.g., Chaudhary et al. (1995) *J. Biol. Chem.*, 265: 16306).

Methods of cloning genes encoding PE and coupling such cytotoxins to targeting moieties are well known to those of skill in the art (see, e.g., Siegall et al. (1989) *FASEB J.*, 3: 2647-2652; and Chaudhary et al. (1987) *Proc. Natl. Acad. Sci. USA*, 84: 4538-4542, and references therein).

Like PE, diphtheria toxin (DT) kills cells by ADP-ribosylating elongation factor 2 thereby inhibiting protein synthesis. Diphtheria toxin, however, is divided into two chains, A and B, linked by a disulfide bridge. In contrast to PE, chain B of DT, which is on the carboxyl end, is responsible for receptor binding and chain A, which is present on the amino end, contains the enzymatic activity (Uchida et al. (1972) *Science*, 175: 901-903; Uchida et al. (1973) *J. Biol. Chem.*, 248: 3838-3844).

In a preferred embodiments, the SHAL-Diphtheria toxin chimeric molecules of this invention have the native receptor-binding domain removed by truncation of the Diphtheria toxin B chain. Particularly preferred is DT388, a DT in which the carboxyl terminal sequence beginning at residue 389 is removed. Chaudhary et al. (1991) *Bioch. Biophys. Res. Comm.*, 180: 545-551. Like the PE chimeric cytotoxins, the DT molecules can be chemically conjugated to the prostate cancer specific antibody, but, in certain preferred embodiments, the antibody will be fused to the Diphtheria toxin by recombinant means (see, e.g., Williams et al. (1990) *J. Biol. Chem.* 265: 11885-11889).

7) Viral Particles.

In certain embodiments, the effector comprises a viral particle. The SHAL can be conjugated to the viral particle e.g., via a protein expressed on the surface of the viral particle (e.g., a filamentous phage). The viral particle can additionally include a nucleic acid that is to be delivered to the target (prostate cancer) cell. The use of viral particles to deliver nucleic acids to cells is described in detail in WO 99/55720.

8) Other Therapeutic Moieties.

Other suitable effector molecules include pharmacological agents or encapsulation systems containing various pharmacological agents. Thus, the SHAL can be attached directly to a drug that is to be delivered directly to the tumor. Such drugs are well known to those of skill in the art and include, but are not limited to, doxorubicin, vinblastine, genistein, an antisense molecule, and the like.

Alternatively, the effector molecule can comprise an encapsulation system, such as a viral capsid, a liposome, or micelle that contains a therapeutic composition such as a drug, a nucleic acid (e.g., an antisense nucleic acid or another nucleic acid to be delivered to the cell), or another therapeutic moiety that is preferably shielded from direct exposure to the circulatory system. Means of preparing liposomes attached to antibodies are well known to those of skill in the art (see, for example, U.S. Pat. No. 4,957,735, Connor et al. (1985) *Pharm. Ther.*, 28: 341-365) and similar methods can be used for coupling SHALs.

B) Attachment of the SHAL to the Effector.

One of skill will appreciate that the SHALs of this invention and the effector molecule(s) can be joined together in any order. Thus, in various embodiments, the effector can be attached to any ligand comprising the SHAL and/or to the linker joining the various ligands comprising the SHAL.

The SHAL and the effector can be attached by any of a number of means well known to those of skill in the art. Typically the effector is conjugated, either directly or through a linker (spacer), to the SHAL.

In one embodiment, the SHAL is chemically conjugated to the effector molecule (e.g., a cytotoxin, a label, a ligand, or a drug or liposome, etc.). Means of chemically conjugating molecules are well known to those of skill.

The procedure for attaching an effector to a SHAL will vary according to the chemical structure of the effector and/or the SHAL. The ligands comprising the SHAL and/or the linker joining the ligands can contain a variety of functional groups; e.g., carboxylic acid (COOH), free amine (—NH$_2$), hydroxyl (—OH), thiol (—SH), and other groups, that are available for reaction with a suitable functional group on an effector molecule or on a linker attached to an effector molecule to effectively bind the effector to the SHAL.

Alternatively, the ligand(s) comprising the SHAL and/or the linker joining the ligands can be derivatized to expose or attach additional reactive functional groups. The derivatization can involve attachment of any of a number of linker molecules such as those described above for coupling the ligands to each other.

In some circumstances, it is desirable to free the effector from the SHAL when the chimeric molecule has reached its target site. Therefore, chimeric conjugates comprising linkages that are cleavable, e.g., in the vicinity of the target site can be used when the effector is to be released from the SHAL. Cleaving of the linkage to release the agent from the antibody may be prompted by enzymatic activity or conditions to which the conjugate is subjected, e.g., either inside the target cell or in the vicinity of the target site. When the target site is a tumor, a linker which is cleavable under conditions present at the tumor site (e.g., when exposed to tumor-associated enzymes or acidic pH) may be used.

In certain instances, the cleavable linker can be a peptide that can be subject to proteolysis. In certain embodiments, the cleavable linker comprises a peptide having a recognition site for a protease.

A number of different cleavable linkers are known to those of skill in the art. See U.S. Pat. Nos. 4,618,492; 4,542,225, and 4,625,014. The mechanisms for release of an agent from these linker groups include, for example, irradiation of a photolabile bond and acid-catalyzed hydrolysis. U.S. Pat. No. 4,671,958, for example, includes a description of immunoconjugates comprising linkers which are cleaved at the target site in vivo by the proteolytic enzymes of the patient=s complement system. In view of the large number of methods that have been reported for attaching a variety of radiodiagnostic compounds, radiotherapeutic compounds, drugs, toxins, and other agents to antibodies one skilled in the art will be able to determine a suitable method for attaching a given agent to an antibody or other polypeptide.

1) Conjugation of Chelates.

In certain preferred embodiments, the effector comprises a chelate that is attached to an antibody or to an epitope tag. The cancer specific SHAL bears a corresponding epitope tag or antibody so that simple contacting of the SHAL to the chelate results in attachment of the SHAL to the effector. The combining step can be performed before the moiety is used (targeting strategy) or the target tissue can be bound to the SHAL before the chelate is delivered. Methods of producing chelates suitable for coupling to various targeting moieties are well known to those of skill in the art (see, e.g., U.S. Pat. Nos. 6,190,923, 6,187,285, 6,183,721, 6,177,562, 6,159,445, 6,153,775, 6,149,890, 6,143,276, 6,143,274, 6,139,819, 6,132,764, 6,123,923, 6,123,921, 6,120,768, 6,120,751, 6,117,412, 6,106,866, 6,096,290, 6,093,382, 6,090,800, 6,090,408, 6,088,613, 6,077,499, 6,075,010, 6,071,494, 6,071,490, 6,060,040, 6,056,939, 6,051,207, 6,048,979, 6,045,821, 6,045,775, 6,030,840, 6,028,066, 6,022,966, 6,022,523, 6,022,522, 6,017,522, 6,015,897, 6,010,682, 6,010,681, 6,004,533, 6,001,329, and the like).

III. SHALs that Inhibit Receptors, Enzymes and Other Biomolecules.

In certain embodiments, this invention provides SHALs that inhibit the activity of enzymes, receptors, or the activity of other biomolecules. Typically such SHALS comprise ligands that bind to different sites around or near the active site or binding site of the enzyme or receptor. In certain embodiments, the ligands are selected to bind to a a first pocket and a second pocket in the enzyme, receptor, or other binding protein where the first and second pocket flank opposite sides of the active site or biding site of said enzyme, receptor, or other binding protein or the first pocket comprises or is located in active site and second pocket is located nearby/adjacent to the first pocket or either or both pockets are located in or sufficiently near the site used by the protein, enzyme, or receptor for binding to another molecule such that the binding of a ligand in either or both pockets disrupts or block the binding of the enzyme, receptor, or other biomolecule to is cognate ligand. When the SHAL is contacted with its target, it binds to the target effectively blocking the active site and/or binding site thereby in habiting the activity of the enzyme, receptor or other biomolecule.

IV. Pharmaceutical Compositions.

The SHALs, and/or chelates, and/or chimeric molecules of this invention (particularly those specific for cancer or other pathologic cells) are useful for parenteral, topical, oral, or local administration (e.g., injected into a tumor site), aerosol administration, or transdermal administration, for prophylactic, but principally for therapeutic treatment. The pharmaceutical compositions can be administered in a variety of unit dosage forms depending upon the method of administration. For example, unit dosage forms suitable for oral administration include powder, tablets, pills, capsules and lozenges. It is recognized pharmaceutical compositions of this invention, when administered orally, can be protected from digestion. This is typically accomplished either by complexing the active component (e.g., the SHAL, the chimeric molecule, etc.) with a composition to render it resistant to acidic and enzymatic hydrolysis or by packaging the active ingredient(s) in an appropriately resistant carrier such as a liposome. Means of protecting components from digestion are well known in the art.

The pharmaceutical compositions of this invention are particularly useful for parenteral administration, such as intravenous administration or administration into a body cavity or lumen of an organ. The compositions for administration will commonly comprise a solution of the SHAL and/or chimeric molecule dissolved in a pharmaceutically acceptable carrier, preferably an aqueous carrier. A variety of aqueous carriers can be used, e.g., buffered saline and the like. These solutions are sterile and generally free of undesirable matter. These compositions may be sterilized by conventional, well known sterilization techniques. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like. The concentration of chimeric molecule in these formulations can vary widely, and will be selected primarily based on fluid volumes, viscosities, body weight and the like in accordance with the particular mode of administration selected and the patient's needs.

Thus, a typical pharmaceutical composition for intravenous administration would be about 0.1 to 10 mg per patient per day. Dosages from 0.1 up to about 100 mg per patient per day may be used, particularly when the drug is administered to a secluded site and not into the blood stream, such as into a body cavity or into a lumen of an organ. Actual methods for preparing parenterally administrable compositions will be known or apparent to those skilled in the art and are described in more detail in such publications as *Remington's Pharmaceutical Science,* 15th ed., Mack Publishing Company, Easton, Pa. (1980).

The compositions containing the present SHALs and/or chimeric molecules or a cocktail thereof (i.e., with other therapeutics) can be administered for therapeutic treatments. In therapeutic applications, compositions are administered to a patient suffering from a disease, e.g., a cancer, in an amount sufficient to cure or at least partially arrest the disease and its complications. An amount adequate to accomplish this is defined as a "therapeutically effective dose." Amounts effective for this use will depend upon the severity of the disease and the general state of the patient's health.

Single or multiple administrations of the compositions may be administered depending on the dosage and frequency as required and tolerated by the patient. In any event, the composition should provide a sufficient quantity of the SHALs to effectively treat the patient.

It will be appreciated by one of skill in the art that there are some regions that are not heavily vascularized or that are protected by cells joined by tight junctions and/or active transport mechanisms which reduce or prevent the entry of macromolecules present in the blood stream.

One of skill in the art will appreciate that in these instances, the therapeutic compositions of this invention can be administered directly to the tumor site. Thus, for example, brain tumors can be treated by administering the therapeutic composition directly to the tumor site (e.g., through a surgically implanted catheter).

Alternatively, the therapeutic composition can be placed at the target site in a slow release formulation. Such formulations can include, for example, a biocompatible sponge or other inert or resorbable matrix material impregnated with the therapeutic composition, slow dissolving time release capsules or microcapsules, and the like.

Typically the catheter or time release formulation will be placed at the tumor site as part of a surgical procedure. Thus, for example, where major tumor mass is surgically removed, the perfusing catheter or time release formulation can be emplaced at the tumor site as an adjunct therapy. Of course, surgical removal of the tumor mass may be undesired, not required, or impossible, in which case, the delivery of the therapeutic compositions of this invention may comprise the primary therapeutic modality.

V. Kits.

Where a radioactive, or other, effector is used as a diagnostic and/or therapeutic agent, it is frequently impossible to put the ready-for-use composition at the disposal of the user, because of the often poor shelf life of the radiolabeled compound and/or the short half-life of the radionuclide used. In such cases the user can carry out the labeling reaction with the radionuclide in the clinical hospital, physician's office, or laboratory. For this purpose, or other purposes, the various reaction ingredients can then be offered to the user in the form of a so-called "kit". The kit is preferably designed so that the manipulations necessary to perform the desired reaction should be as simple as possible to enable the user to prepare from the kit the desired composition by using the facilities that are at his disposal. Therefore the invention also relates to a kit for preparing a composition according to this invention.

Such a kit according to the present invention preferably comprises a SHAL as described herein. The SHAL can be provided, if desired, with inert pharmaceutically acceptable carrier and/or formulating agents and/or adjuvants is/are added. In addition, the kit optionally includes a solution of a salt or chelate of a suitable radionuclide (or other active agent), and (iii) instructions for use with a prescription for administering and/or reacting the ingredients present in the kit.

The kit to be supplied to the user may also comprise the ingredient(s) defined above, together with instructions for use, whereas the solution of a salt or chelate of the radionuclide which can have a limited shelf life, can be put to the disposal of the user separately.

The kit can optionally, additionally comprise a reducing agent and/or, if desired, a chelator, and/or instructions for use of the composition and/or a prescription for reacting the ingredients of the kit to form the desired product(s). If desired, the ingredients of the kit may be combined, provided they are compatible.

In certain embodiments, the complex-forming reaction with the SHAL can simply be produced by combining the components in a neutral medium and causing them to react. For that purpose the effector may be presented to the SHAL in the form of a chelate.

When kit constituent(s) are used as component(s) for pharmaceutical administration (e.g., as an injection liquid) they are preferably sterile. When the constituent(s) are provided in a dry state, the user should preferably use a sterile physiological saline solution as a solvent. If desired, the constituent(s) can be stabilized in the conventional manner with suitable stabilizers, for example, ascorbic acid, gentisic acid or salts of these acids, or they may comprise other auxiliary agents, for example, fillers, such as glucose, lactose, mannitol, and the like.

While the instructional materials, when present, typically comprise written or printed materials they are not limited to such. Any medium capable of storing such instructions and communicating them to an end user is contemplated by this invention.

Such media include, but are not limited to electronic storage media (e.g., magnetic discs, tapes, cartridges, chips), optical media (e.g., CD ROM), and the like. Such media may include addresses to internet sites that provide such instructional materials.

EXAMPLES

The following examples are offered to illustrate, but not to limit the claimed invention.

Example 1

Creation of HLA-DR10 Specific SHALs

Preclinical and clinical studies have revealed that the epitopic region (unique region recognized by antibodies) on the beta subunit of HLA-DR 10, and related HLA-DR major histocompatibility cell surface proteins, are particularly attractive targets for systemic radioisotopic therapy for B-cell lymphomas and leukemias and provide other opportunities for cancer treatment and prevention. Although HLA-DR 10 has characteristics in common with other B-cell surface proteins, like CD20, that make it a suitable target, it has disparate characteristics that we believe provide great attractiveness.

In common with CD20 antigen, the HLA-DR 10 protein is located on the surface of B lymphocytes, persists through B-cell differentiation, but disappears during transformation of the lymphocyte to the plasma cell stage (Epstein et al. (1987) *Cancer Res.*, 47: 830-840). The discrete Lym-1 antigen epitope appears on committed B-cell precursors, but is not expressed earlier during B-cell development. In addition, it is not generally found on T cells or other normal cells. Expression of class 2 MHC molecules on B-cells is developmentally controlled. Early and pre-B-cells are class 2 mRNA negative and cannot be induced to express class 2 antigens. HLA-DR antigen is acquired during the late pre-B-cell stage. Because the basal level of class 2 expression on B-cells is about 100 times lower than that found on malignant B-cell lines (Rose et al. (1996) *Cancer Immunol Immunother.*, 43: 26-30.; Rose et al. (1999) *Mol. Immunol.*, 36: 789-797), this provides an explanation for the observation that only 5 mg of Lym-1 antibody is needed to target extravascular malignant lymphoma (DeNardo et al. (1998) *J Clin Oncol.*, 16: 3246-3256), whereas 50 mg of CD22 and hundreds of mg of CD20 antibodies are required due to the density of CD22 and CD20 antigens on normal lymphocytes (Press (1999) *Semin Oncol.*, 26: 58-65; Knox et al. (1996) *Clin Cancer Res.*, 2: 457-470). Treatment doses of iodine-131, copper-67, or yttrium-90 attached to small amounts of Lym-1 cures most mice with Raji xenografts (DeNardo et al. (1991) *Antibody Immunoconj Radiophar.*, 4: 777-785; DeNardo et al. (1997) *Clin Cancer Res.*, 3:71-79), the human Burkitt's malignant lymphoma cell line used as the immunogen to generate Lym-1 (Epstein et al. (1987) *Cancer Res.*, 47: 830-840). Similarly, these radiopharmaceuticals, in Phase I/II trials in patients with B-cell non-Hodgkin's lymphoma and a subset of patients with chronic lymphocytic leukemia, have induced a high and durable response rate, with frequent complete remissions and some long-term survivals when used as single agent therapy. HLA-DR provides cell identification, and antigenic peptides are displayed on HLA-DR. This may explain unusually long survivals in a subset of our patients with aggressive lymphoma in whom an idiotypic antibody cascade, including human polyclonal antibodies cytotoxic for Raji cells and Raji tumors, has been documented (DeNardo et al. (1998) *Cancer Biother Radiopharm.*, 13: 1-12; Lamborn et al. (1997) *Clin Cancer Res.*, 3: 1253-1260).

However, as well as these antibodies work, there is still a need to improve upon them. The antibody is a macromolecule that penetrates vascular barriers and the tumor poorly and interacts with a variety or receptors, which limits their selectivity as radioisotope carriers and adds to the adverse event profile. The immunogenicity of antibody-based reagents can be minimized, but not eliminated, using "humanized" antibodies (Brown et al. (2001) *Clin Lymphoma.*, 2: 188-90; Kostelny et al. (2001) *Int J Cancer*, 93: 556-65; Leonard et al. (2002) *Semin Oncol.*, 29: 81-6; Lundin et al. (2002) *Blood*, 100: 768-73; Ligibel and Winer (2002) *Semin Oncol.*, 29: 38-43). Immunogenicity may be avoided by creating non-protein based reagents. Whole antibodies also exhibit appreciable reactivity (e.g., Fc interactions) with non-target cells that reduces selectivity and increases adverse events. Even small improvements in the targeting agent's selectivity can be used to minimize collateral damage and enhance the drug's therapeutic index.

Lym-1 is a murine IgG-2a monoclonal antibody (MAb) that selectively binds a protein highly expressed on the surface of malignant human B-cells (Epstein et al. (1987) *Cancer Res.*, 47: 830-840). We have shown that a discrete epitope on HLA-DR 10 was the original antigen in Raji cells that generated the Lym-1 MAb, and this epitope is not shared by all HLA-DR subtypes (Rose et al. (1996) *Cancer Immunol Immunother.*, 43: 26-30; Rose et al. (1999) *Mol. Immunol.*, 36: 789-797). Our data suggest that the critical Lym-1 binding residues are contained in the 19 differences in amino acid sequence between the reactive HLA-DR 10 beta subunit and the unreactive, largely identical HLA-DR 3 and HLA-DR 52 beta subunits. This serves as the basis for the selectivity of the Lym-1 epitope or binding site among HLA-DR containing white blood cells, yet provides the basis for the existence of this protein in virtually all patients with malignant B-cells. Of the 19 residues comprising the critical Lym-1 binding region, only the amino acids Q70 or R70, followed by R71 were found in all Lym-1 reactive specimens and were absent in Lym-1 unreactive specimens. In many of the unreactive HLA-DR molecules, these two residues were often replaced by D70 and/or E71. The hypothesis that the subtypes containing the putative critical Lym-1 binding residues (Q/R70-R71) would be most reactive has been confirmed in a series of studies including extensive cytotoxicity assays conducted in lymphoblastoid cell lines of B and T cell type, incorporating 31 HLA-DR genotypes (Rose et al. (1999) *Mol. Immunol.*, 36: 789-797). All the strongly reactive cells expressed at least one Q/R70-R71-containing HLA-DR allele while none of the least reactive cell lines expressed that sequence at position 70-71 of the beta chain. Cytotoxicity assays also showed that the former were dramatically more affected than the latter (Id.). Although Lym-1 reacted with peripheral blood lymphocytes from healthy donors, the avidities were much lower, consistent with a lower HLA-DR protein density on normal lymphocytes and the hypothesis that univalent rather than bivalent binding may occur, further explaining the selectivity of Lym-1 for malignant cells in patients with lymphoma (Id.). Thus, it seems that both the critical Lym-1 glutamine/arginine residues and a threshold antigen density contribute to the selectivity of Lym-1 binding to malignant B-cells over normal lymphocytes. In any event, the data confirm that Lym-1 binds preferentially to lymphoblastoid cells over normal PBLs, thereby providing an attractive difference from other malignant B-cell targeting proteins (Id.).

Our experience with CMRIT has led us to appreciate the complexities of implementation and to realize that many patients with advanced NHL are ineligible for BMT because of their disease and insufficient marrow harvest. For these reasons and because of unique opportunities to dose intensify using novel approaches to develop targeting molecules that can dramatically improve the therapeutic index, we have developed high affinity ligands (SHALs) that mimic $^{131}$I-iodide in thyroid cancer. $^{131}$I-iodide in thyroid cancer, the prototype for radioisotopic molecular targeted systemic radiotherapy, has led to cure of otherwise incurable thyroid cancer because the $^{131}$I is rapidly trapped and retained by the cancer or excreted in the urine, providing a therapeutic index approaching infinity and the opportunity to administer almost unlimited radioisotope without significant toxicity.

We believe that small molecule SHALs can better fulfill the potential of "RIT", and represent a natural extension of our ongoing translational activities involving HLA-DR as a target for radioisotopic carrier molecules to deliver systemic radiotherapy. As described below, we have synthesized a number of bidentate SHALs and determined that at least one of these SHALs binds to isolated HLA-DR10.

A) Development of a Computer Model of the Molecular Structure of the HLA-DR 10 Beta Subunit Containing the Region Shown to be Critical for Lym-1 Antibody Binding to Malignant B Cells and Compare the Structure with Other HLA-DR Molecules.

Crystal structures for four different closely related HLA-DR molecules (HLA-DR 1-4) have been determined previously and deposited in the PDB structure database by others (Jardetzky et al. (1994) Nature, 368:711-718; Bolin et al. (2000) J. Med. Chem., 43:2135-2148; Smith et al. (1998) J. Exp. Med., 188:1511-1520; Ghosh et al. (1995) Nature, 378:457-462). Protein sequences for these four proteins, HLA-DR1, HLA-DR2, HLA-DR3 and HLA-DR4, were aligned with the HLA-DR10 sequence and compared to identify both the locations of the variable amino acids and those regions of the HLA-DR10 molecule containing the amino acid residues that had been identified as the critical epitope of the Lym-1 antibody (Rose et al. (1996) Cancer Immunol Immunother., 43: 26-30; Rose et al. (1999) Mol. Immunol., 36: 789-797). This alignment revealed that all five proteins exhibit such a high degree of sequence similarity (FIG. 8) that we were able to create a sufficiently accurate 3-D model of the HLA-DR10 beta subunit by homology modeling and use the coordinates of the model to screen for ligand binding using the program DOCK.

Two different approaches were used to create models of the HLA-DR10 beta subunit for use in ligand docking. The first approach used the coordinates of the entire structure of HLA-DR3 as the template for creating the homology model, and the nineteen amino acids that differed between HLA-DR3 and HLA-DR10 were mutated (changed) in the HLA-DR3 sequence. The coordinates of the amino-terminal four amino acids, which are present in HLA-DR10, HLA-DR1 and HLA-DR2 but absent in HLA-DR3, were obtained from the HLA-DR1 structure and used to complete the model. In the second approach, a hybrid model was generated using the atomic coordinates obtained from different segments of the HLA-DR 1, HLA-DR2 and HLA-DR4 crystal structures. The particular segments of the three HLA crystal structures used in the model were selected based on similarities in their secondary structural elements. Sequence-structure alignments were generated using the Smith-Waterman (Smith and Waterman (1981) J. Mol. Biol., 147:195-197), FASTA (Pearson (1991) Genomics, 11: 635-650), BLAST and PSI-BLAST (Altschul et al. (1997) Nucleic Acids Res., 25: 3389-3402) algorithms, and the backbone of the model was created automatically using the AS2TS system (see http://sb9.llnl.gov/adamz/LGA/AL2TS/as2ts.html website). The coordinates for the amino terminal four residues of the structure were taken from the 1seB crystal structure of HLA-DR1, residues 5-122 were obtained from the 1aqd structure of HLA-DR1, residues 123-170 were taken from the 1d5m HLA DR4 structure, and the remaining residues (aa171-193) were obtained from the 1bx2 structure of HLA-DR2. The construction of the terminal regions and loops, amino acid insertions and deletions, and template-model structure comparisons were performed using the LGA program developed at LLNL (see website http://predictioncenter.llnl.gov/local/lga/lga.html). The majority of the side chain atom's coordinates were incorporated from the four structural templates (listed above) due to their high level of homology. The side chains in selected regions of the protein model were built using the SCWRL program (Id.). Energy minimization was performed on both structures to eliminate inappropriate side chain contacts and the resulting structures were "optimized" using molecular dynamics.

Figure 9:
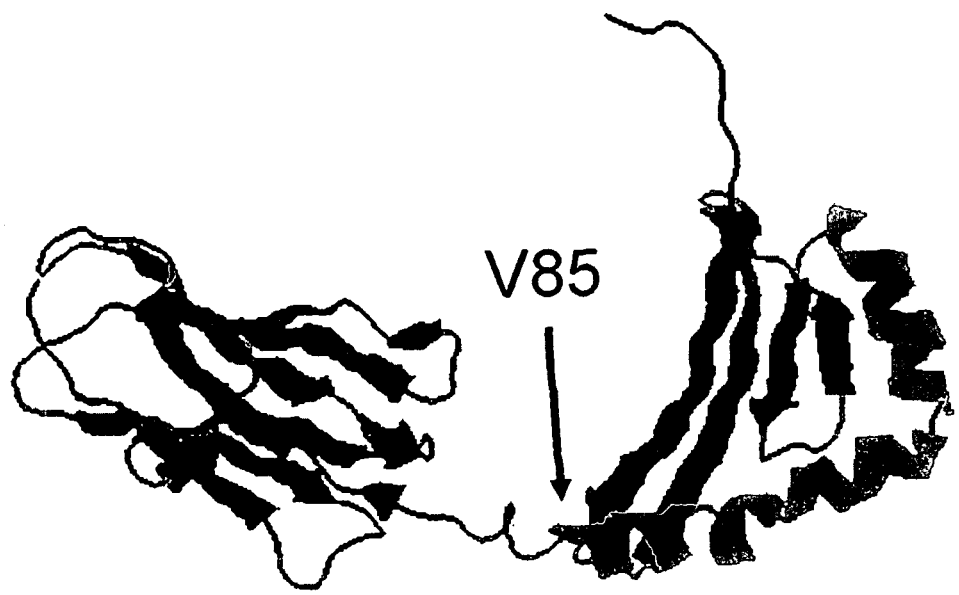
FIG. 9 Homology model of beta subunit of HLA-DR10 showing the two structural domains (See Appendix for color).

Analyses of the resulting models revealed the two approaches yielded structures that were remarkably similar. Extended molecular dynamics runs appeared to provide little additional improvements. The results of the modeling revealed that the structure of the HLA-DR10 molecule is comprised of two domains linked by a hinge with one of the Lym-1 reactive residues, V85, positioned directly adjacent to the hinge (FIG. 9).

Figure 10:
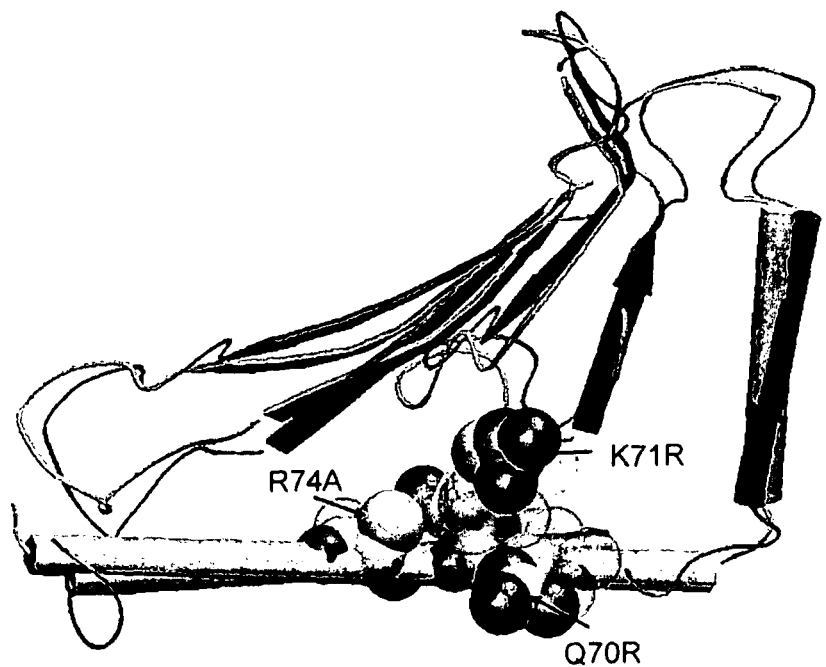
FIG. 10 shows superposition of HLA-DR3 crystal structure (light blue, transparent atoms) and homology model of HLA-DR10 (dark blue, solid atoms) showing the structural similarity in the region of the beta subunit that comprises the Lym-1 epitope. The amino acid residues critical for Lym-1 binding are shown as space filling atoms.

The majority of the core of the relaxed structure of HLA-DR10, when compared with the HLA-DR3 crystal structure, was found to be essentially identical (FIG. 10). The other three amino acids that were observed to play a role in Lym-1 binding, R70, R71 and A74 (A or E at this position appears important for Lym-1 binding), are all located on the exposed surface of a long alpha helix (FIGS. 9 and 10) located immediately adjacent to the hinge B) Identification of Unique Sites on the Surface of HLA-DR10 within the Lym-1 Epitope that can be Targeted for Ligand Binding.

Figure 11:
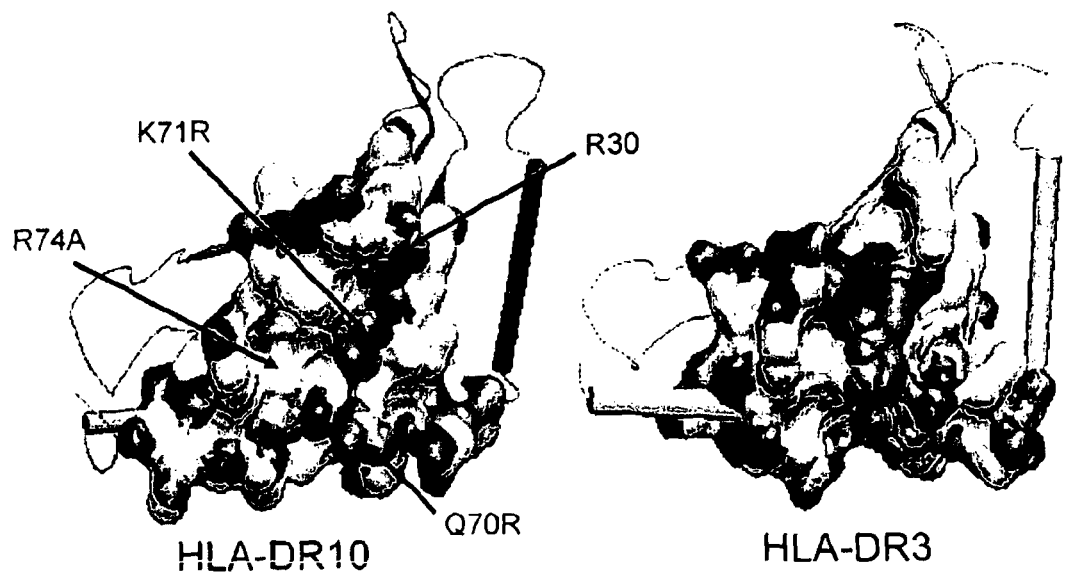
FIG. 11 shows surface plots of HLA-DR10 and HLA-DR3 beta subunits showing differences in the structure of the "pockets" in the region of the protein that comprises the Lym-1 epitope. Charge distribution is shown as dark blue (positive or basic), red (negative or acidic) and light blue (neutral or hydrophobic). The sulfur atom in cysteine is shown in yellow.

Solvent accessible surfaces of the HLA-DR10 protein and the crystal structure of HLA-DR3 were calculated using the atomic coordinates obtained for HLA-DR3 from the Protein Data Bank and our HLA-DR10 model. The site surrounding the three key amino acids in the Lym-1 epitope (within 6 Å) were examined and compared. As shown in FIG. 11, these three amino acid changes in the HLA-DR10 sequence (Q70R, K71R, and R74A) change both the charge distribution and topography of the protein's exposed surface in this region.

A program developed to identify "pockets" on the surface of the protein (SPHGEN) was used to identify potential cavities that could be targeted for ligand binding. Details of the programs used are described in Example 2. Two adjacent pockets (cavities) in the modeled HLA-DR10 surface were selected as appropriate sites for ligand binding (FIG. 12), based on their proximity to each other, the three Lym-1 reactive residues, and the uniqueness of the amino acids lining the pocket. An examination of the crystal structures of the other four HLA-DR molecules also showed that pockets exist at or in the near vicinity of these sites in each HLA-DR molecule, but as expected (based on the amino acid sequence differences in the peptide chains in this region of the HLA-DR structure) the pockets present on each HLA-DR differ in size, shape, and distance separating them. Since the amino acid "landscape" surrounding these two sites differs significantly in HLA-DR3 and HLA-DR10, docking runs performed at both sites would be expected to identify ligands that bind selectively to the pockets on HLA-DR10 but not to HLA-DR3. These sites, identified as Site 1 and Site 2 and shown filled with red and blue spheres in FIG. 12, flank both sides of the most important amino acid in the Lym-1 epitope, R70. A third unique site, which can be targeted as a backup if suitable ligands cannot be identified that bind to Site 1 or Site 2, has also been located and characterized.

C) Computationally Screening a "Virtual" Ligand Library to Identify Small Molecules that May Bind to Specific Pockets on HLA-DR10 Encompassing the Lym-1 Epitope.

Figure 12:
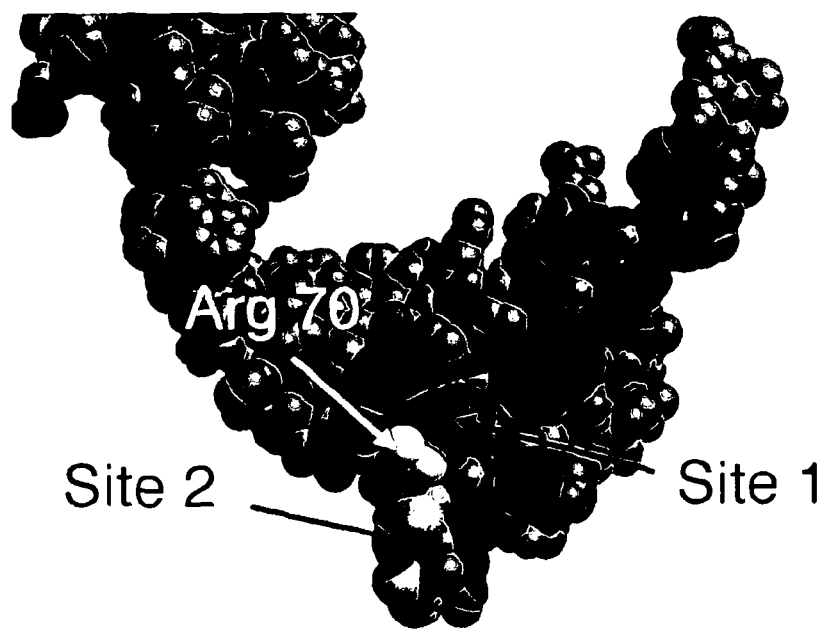
FIG. 12 illustrates the location of two "pockets", designated Site 1 (red) and Site 2 (blue), that surround the amino acids critical for Lym-1 binding (yellow) on the β-subunit of HLA-DR10. These two sites were targeted for ligand binding and used in the computational docking studies.

The program DOCK (UCSF) was used to perform a "virtual" screen of the Available Chemical Directory database of small molecules to identify the top ranked 1,000 molecules predicted to bind in the two unique pockets identified as Site 1 and Site 2 (FIG. 12). Details of the computational docking procedures are described in Example 2.

The top ranked 2,500 molecules were then visually inspected to select down to thirty-five molecules for experiment binding assays (Table 5). This final selection process was based on chemical properties including hydrophobic interactions, hydrogen bonding, and molecular size, and well as practical criteria including commercial availability and cost, ease of synthetic linkage, the overall structural diversity of the set of molecules.

TABLE 5

Ligands predicted to bind to Site 1 on the beta subunit of HLA-DR10 by computational docking

| No. | Compound |
|---|---|
| 1. | 7-Amino-4-chloromethylcoumarin, glycyl-1-proline amide, hydrochloride |
| 2. | 5-([4,6-Dichlorotriazin-2-yl]amino)-fluorescein hydrochloride |
| 3. | 2-[2-[3-Chloro-5-(trifluoromethyl)-2-pyridinyl]carbohydrazonoyl]benzene carboxylic acid |
| 4. | 4-[[2-(4-Cyano-3-phenyl-5-isoxazolyl)vinyl]amino]benzenecarboxylic acid |
| 5. | 4-[2-(2,4-Dichlorophenyl)hydrazino]-4-oxo-2-phenyl-2-butenoic acid |
| 6. | 3-(2-[[3-Chloro-5-(trifluoromethyl)-2-pyridinyl]oxy]anilino)-3-oxopropanoic acid |
| 7. | 3-[(4-Chlorobenzyl)thio]imidazo[1,5-a]pyridine-1-carboxylic acid |
| 8. | 2-[([1,1'-Biphenyl]-4-ylamino)carbonyl]benzoic acid |
| 9. | Bis[4-(3-aminophenoxy)phenyl]sulfone |
| 10. | 4,4'-Bis(4-aminophenoxy)biphenyl |
| 11. | 5(6)-Carboxytetramethylrhodamine n-succinimidyl ester |
| 12. | 1,4-Phenylenebis[[4-(4-aminophenoxy)phenyl]methanone] |
| 13. | H-Tyr(Br—Z)—OEt |
| 14. | '7-Amino-4-chloromethylcoumarin, 1-alanyl-l-proline amide, hydrochloride |
| 15. | '5-(N'-[2-aminoethyl]thioureidofluorescein) |
| 16. | Achatin I, Ammonium salt |
| 17. | Fmoc-Asp(OBzl)-OH |
| 18. | Fmoc-Bip-OH |
| 19. | Menai H535 |
| 20. | 2'-Methoxy-5'-methyl-3,4,5,6-tetrachlorophthalanilic acid |
| 21. | 4-Dimethylaminoazobenzene-4'-sulfonyl-l-valine |
| 22. | Bigchap |
| 23. | Arg-gly-asp-thr (SEQ ID NO: 25) |
| 24. | n-Allyl-2-[(1-benzyl-2-oxo-1,2-dihydro-3-pyridinyl)carbonyl]-1-hydrazinecarbothioamide |
| 25. | n'-Methoxy-n-[7-(4-phenoxyphenyl)[1,2,4]triazolo[1,5-a]pyrimidin-2-yl]iminoformamide |
| 26. | n-[[6-(4-Chlorophenoxy)-3-pyridyl]carbonyl]-n'-[3-(trifluoromethyl)phenyl]urea |
| 27. | n-[[6-(4-Chlorophenoxy)-3-pyridyl]carbonyl]-n'-(4-chlorophenyl)urea |
| 28. | n,n'-Diphenylbenzidine |
| 29. | Rcl s16, 963-3 |
| 30. | N,N'-bis-(4-amino-2-chloro-phenyl)-terephthalamide4-[[5-(trifluoromethyl)pyridin-2-yl]oxy]phenyl N-phenylcarbamate |
| 31. | Methidiumpropyl ethylenediame tetraacetic acid |
| 32. | N-(4-[[3-Chloro-5-(trifluoromethyl)-2-pyridinyl]methyl]phenyl)-4-iodobenzenecarboxamide |
| 33. | 2-(4-Chlorophenyl)-2-[6-[(4-chlorophenyl)sulfanyl]-3-pyridazinyl]acetamide |
| 34. | 6-Chloro-n4-(4-phenoxyphenyl)-2,4-pyrimidinediamine |
| 35. | 4-Amino-2-anilino-5-benzoyl-3-thiophenecarbonitrile |

This procedure was repeated for identification of thirty-five potential binders for Site 2. Table 6 lists those ligands predicted by molecular docking to bind to Site. 2.

TABLE 6

Ligands predicted to bind to Site 2 on the beta subunit of HLA-DR10 by computational docking 1. Leu-enkephalin
2. 4-[4-(4-Chlorobenzyl)piperazino]-3-nitrobenzenecarboxylic acid
3. Beta-casomorphin (1-2)
4. L-Aspartic acid, alpha-(4,5-dimethoxy-2-nitrobenzyl) ester, hydrochloride
5. Cefadroxil
6. 3,3',5-Triiodo-dl-thyronine
7. H-Glu(anilide)-OH
8. H-Trp-phe-OH
9. Glycylglycyl-D,L-phenylalanine
10. Thymopoietin II (33-36)
11. Thiophosphoric acid S-(3-(3-amino-propylamino)-propyl) ester, di-hydrate
12. Dynorphin A (13-17), Porcine
13. 1-Alanyl-l-alanyl-1-tryptophan
14. Asp-arg-val-tyr (SEQ ID NO: 26)
15. A-VI-5
16. Glu-thr-pro $NH_2$ (SEQ ID NO: 27)
17. (D-ala2)-Beta-casomorphin (1-5) (bovine)
18. Tyr-D-ala-gly-phe-D-met acetate salt (SEQ ID NO: 28)
19. Arg-gly-asp-thr (SEQ ID NO: 29)
20. N-Alpha,n-omega-di-cbz-1-arginine
21. Asp-lys acetate salt
22. (+)-Allo-octopine
23. Sodium 7-[(2-amino-2-phenylacetyl)amino]-3-methyl-8-oxo-5-thia-1-azabic cyclo[4.2.0]oct-2-ene-2-carboxylate
24. Val-ile-his-asn
25. 2-Amino-8-(diphenylphosphinyl)-octanoic acid
26. Glu-His-Pro $NH_2$ (SEQ ID NO: 30)
27. Bapaba
28. H-glu(lys)-OH
29. Bis-boc-l-arg
30. H-arg(mtr)-OH
31. 4-Aminomethyl-L-phenylalanine boc
32. H-met-met-OH
33. H-trp-ile-OH
34. N-alpha benzoyl-arginine-4-amino benzoic acid
35. (Thr46)-osteocalcin (45-49) (human)

As a result of the computational docking, 30 compounds from both the Site 1 and Site 2 lists were experimentally screened by NMR. Eleven compounds were found to bind to HLA-DR10, giving a successful hit rate of 37%. These ligands are listed in Table 7.

TABLE 7

NMR screened ligands that were found to bind to HLA-DR10. Ligands are separated by computationally predicted docking sites

| Site 1: | Site 2: |
| --- | --- |
| 5(6) carboxytetramethylrhodamine-n-succinimidyl ester | N-alpha benzoyl-arginine-4-amino benzoic acid |
| Methidiumpropyl EDTA | 5-leu-enkephalin (YAGFM) |
| Deoxycholic acid | N alpha N omega dicarbobenzoxyarginine |
| FMOC-aspartic acid(O-benzyl)-OH | Angiotensin II (DRVY) |
| 4-dimethylaminoazobenzene-4'-sulfonyl-L-valine | Bis-BOC-L-arginine |
| 4-[[5-(trifluoromethyl)pyridin-2-yl]oxy]phenyl N-phenylcarbamate | |

From Table 7, 5 synthetic high affinity ligands (SHALs) have been synthesized, containing different sets of the Site 1 and Site 2 ligands. Three of these molecules (FIG. 13A), all containing the ligand pairs deoxycholate and 5-leu-enkephalin, have been shown to bind to isolated HLA-DR10. None of these three SHALs bind to albumin or streptavidin. The first of the three to be tested more extensively, JP459B (FIG. 13B), has been determined to bind to HLA-DR10 with a Kd=23 nM using Surface Plasmon Resonance. Using Raji membrane extracts, this SHAL competed with Lym-1 for binding to HLA-DR10. Binding studies performed with live cells showed JP459B bound to Raji human lymphoma cells, but not normal DU145, LnCAP or 22RV cells (FIG. 17E-H). Experiments using frozen human lymphoma tissue sections also demonstrated JP459B binding to large cell lymphoma, exuberantly, but less to small cell lymphoma cells (FIG. 17A-D). Similar results were obtained with Lym-1 antibody. More extensive testing with normal and tumor tissue arrays is in progress.

In subsequent screenings additional ligands have been shown to bind to HLA-DR10. These are shown in Table 8.

TABLE 8

Additional ligands that bind to HLA-DR10.

| ligand ID | species |
| --- | --- |
| 11 | 3,3',5-Triiodo-dl-thyronine (Predicted Site 2) (TI) |
| 7 | 2-(4-Chlorophenyl)-2-[6-[(4-chlorophenyl)suflfanyl]-3-pyridazinyl] acetamide (12F) |
| 9 | 4-Amino-2-anilino-5-benzoyl-3-thiophenecarbonitrile (5K) |
| 8 | 6-Chloro-n4-(4-phenoxyphenyl)-2,4-pyrimidinediamine (7L) |
| 6 | N-(4-[[3-Chloro-5(trifluoromethyl)-2-pyridinyl]methyl]phenyl)-4-iodobenzenecarboxamide (6J) |

In addition 1,4-phenylenebis[[4-(4-aminophenoxy)phenyl]methanone] precipitated onto the target protein.

Example 2

Computational Methods for Use in the Creation of SHALS
A) Overview of the Roles and Methods of Molecular Simulations As described herein, molecular modeling can be used to initially identify ligands for use in the construction of SHALs and/or for the optimization of SHALs. At present there is no single molecular modeling methodology that can be used to model target molecules, screen for binding ligands, simulate binding of a polydentate SHAL and predict optimal SHAL structure. A number of well established modeling methods, however can be used to facilitate these tasks as described herein.

Starting at the highest level, the prediction of the tertiary structures target molecules (e.g., protein cancer markers) are typically predicted using highly empirical methods based on primary sequence homology to proteins with experimentally known structure. The accuracy of these so-called homology-based protein structure prediction methods depend on the availability of homologous protein structures and the expertise of the individual modeler. To identify small molecules (ligands) that specifically bind into protein pockets, computational "docking" can be employed as described herein. Docking uses a relatively simple empirical force field to describe the ligand-protein interaction and can therefore be used to rapidly screen 100,000's of possible ligands. To determine preferred macromolecular conformations and interactions, classical molecular dynamics can used, which models the molecules using empirical ball-and-spring force fields. Finally, for the precise prediction of small molecule structures and interactions, one can computationally solve the quantum mechanical equations describing the electrons and nuclei within the molecules. This so-called first principles approach can either be used to determine the structures and energies of static "snapshots" of the molecules or to simulate the atomic motions of the molecular systems. The former approach, is referred to as ab initio quantum chemistry while the latter approach is called first principles molecular dynamics (in contrast to classical molecular dynamics) and constitutes a nearly exact simulation of nature.

B) Homology-Based Protein Structure Predictions.

The basic concept of homology-based protein structure prediction relies on the observation that structural features of proteins are conserved during evolution to a much higher degree than their sequences, and therefore proteins related even by distant sequence similarity can be expected to have similar 3D structures (Chothia and Lesk (1986) *EMBO J.,* 5: 823-826). Thus, once a three-dimensional structure is determined for at least one representative of a protein family, models for other family members can be derived using the known structure as a template. Homology-based protein modeling consists of four major steps: finding known structures related to the protein sequence to be modeled, aligning the sequence with these structures, building a three-dimensional model, and assessing the model (Marti-Renom et al. (2000) *Annu Rev Biophys Biomol Struct.,* 29: 291-325).

Figure 15:
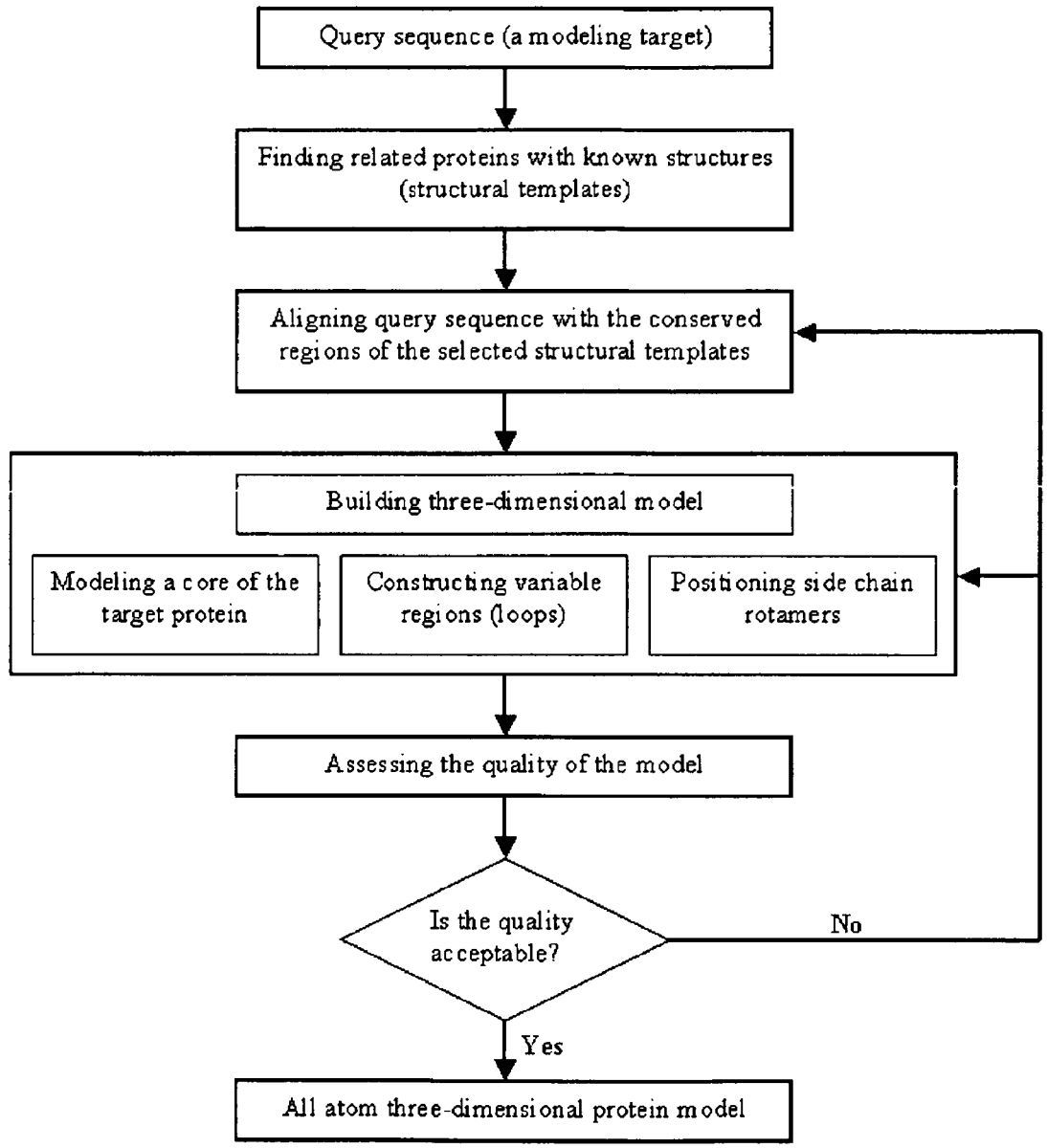
FIG. 15 illustrates a flowchart describing major steps in homology-based protein modeling.

Homology-based protein structure prediction (also referred to as comparative modeling) produces an all-atom model of a sequence based on its alignment with one or more related protein structures. Building of the three-dimensional model itself includes either sequential or simultaneous modeling of the core of the protein, loops and side chains. FIG. 15 illustrates a flowchart describing major steps in homology-based protein modeling.

The accuracy of a model, built using comparative modeling technique, usually is related to the percentage of sequence identity with the structure on which it is based. High-accuracy comparative models are based on more than 50% sequence identity to their templates. They tend to have about 1 Å root-mean-square (RMS) error for the main chain atoms. Such accuracy is comparable with medium resolution nuclear magnetic resonance (NMR) structure or low resolution X-ray structure. The errors in such cases are usually limited to mistakes in side chain rotamer assignment, small shifts or distortions in the core main chain regions, and occasionally larger errors in loops.

One general modeling approach will be similar to that successfully used earlier to model both high and low homology target proteins (Venclovas et al. (1999) *Proteins—Structure Function and Genetics,* 73-80). Since our modeling objects (e.g., cancer markers such as HLA-DR10) can have high sequence homology (>50% sequence identity) we can rely on pairwise sequence comparison of modeling target (query) with the proteins of known structures (from the Protein Data Bank (PDB)) to identify the closest structural templates. To do this, a sensitive Smith-Waterman pairwise sequence comparison algorithm (Smith and Waterman (1981) *J. Mol. Biol,* 147: 195-197) implemented in the SSEARCH program (Pearson (1991) *Genomics* 11: 635-650) can be used. At the high level of sequence homology structure alignment for the conserved structural regions can be used directly in model-building.

When a number of structural templates of comparable similarity are available one can use MODELLER, a comparative modeling program capable of automatically combining a number of template structures to better represent the structure of the query. Where critical regions are present in the target molecule, special care can be taken in assigning conformations to these regions. The candidate conformations for these regions can be produced by searching a database of homologous structures for the fragments of identical length that also satisfy the steric constraints for these regions. Both sequence similarity and structural context near the region can be taken into account in selecting the actual conformation. Side chains within the model can be positioned using a backbone-dependent rotamer library (Bower et al. (1997) *J. Mol. Biol.* 267: 1268-1282).

Assessment of the obtained models can be done using several techniques. One of these, ProsaII (Sippl (1993) *Proteins,* 17: 355-362; Aloy et al. (2000) *J Comput Aided Mol. Des.* 14: 83-92), which is used to detect errors in protein structures, creates an energy profile along the sequence of the protein. The regions that are assigned high energy values by ProsaII often serve as good indicators of errors in representing the structure of these particular regions. For the detailed checks of modeled structures, the structure verification module of the WHATIF program (Vriend (1990) *J. Mol. Graph.* 8: 52-56) can be used along with visual inspection. If these assessments of model quality identify any problems in the modeled structure, appropriate steps (such as loop assignment or side chain positioning) will be repeated in an iterative manner until an acceptable quality three-dimensional model is obtained.

Using these methods a computer model of the molecular structure of the HLA-DR 10 beta subunit containing the region shown to be critical for Lym-1 antibody binding to malignant B cells was developed and the structure was compared with the structure with other HLA-DR molecules (see Example 1, supra.). This model was used to develop HLA-DR10 specific SHALs as described herein.

C) Computational Docking

Computational methods such as docking have been used to speed up the process of drug discovery and inhibitor design by screening large numbers of molecules and predicting whether or not they bind into the active sites of target proteins (Desjarlais et al. (1990) *Proc. Natl. Acad. Sci. U.S.A.*, 87: 6644-6648; Mao et al. (1998) *Bioorganic and Medicinal Chem. Letts.*, 8: 2213-2218; Olson and Goodsell (1998) *Environmental Res.*, 8: 273-285; Rutenber et al. (1993) *J. Biol. Chem.*, 268: 15343-15346). These efforts have met with moderate success in the design of new drugs effective against HIV proteins critical for infection and transmission of the disease In certain embodiments, this approach is generally useful as a first step in the identification of ligands (binding moieties) that usually bind to the target molecule(s) in the micromolar range. Detailed protocols for docking methods using SPHGEN and DOCK have been described in the literature. For example, these methods have been used to identify ligands that bind to specific sites on the targeting domain of tetanus neurotoxin (Cosman et al. (2002) *Chem Res Toxicol* 15: 1218-1228; Lightstone et al. (2000) *Chem. Res. Toxicol.*, 13: 356-362).

The program DOCK 4.0 was used to computationally screen the Available Chemical Directory (~300,000) of small molecules to identify the top ranked 2,500 molecules predicted to bind to the identified Site 1 and Site 2 (FIG. 12).

Computational docking can be thought of as a three-step process: 1) site identification of the protein surface; 2) docking of ligands into the identified binding site; and 3) scoring and the ranking of the ligands (Halperin et al., (2002) *Proteins: Structure, Function, and Genetics*, 47: 409-443). For site identification, the solvent accessible surface of the target protein is generally calculated. Using the program SPHGEN, a utility in DOCK (Moustakas and Kuntz (2002). DOCK5.0 (San Francisco, UCSF)), concave pockets on the protein surface were identified by filling the pockets with different sized radii spheres. Essentially, this calculates the volume of the pocket. The surface of the protein may have anywhere from thirty to hundreds of pockets based on the size and shape of the protein. Once these pockets were identified, visual inspection of the pockets identified the binding site based on the size of the pocket and the available experimental evidence, such as known amino acids involved in binding or catalysis. The chosen binding pocket was then used in the subsequent docking procedure.

Figure 16:
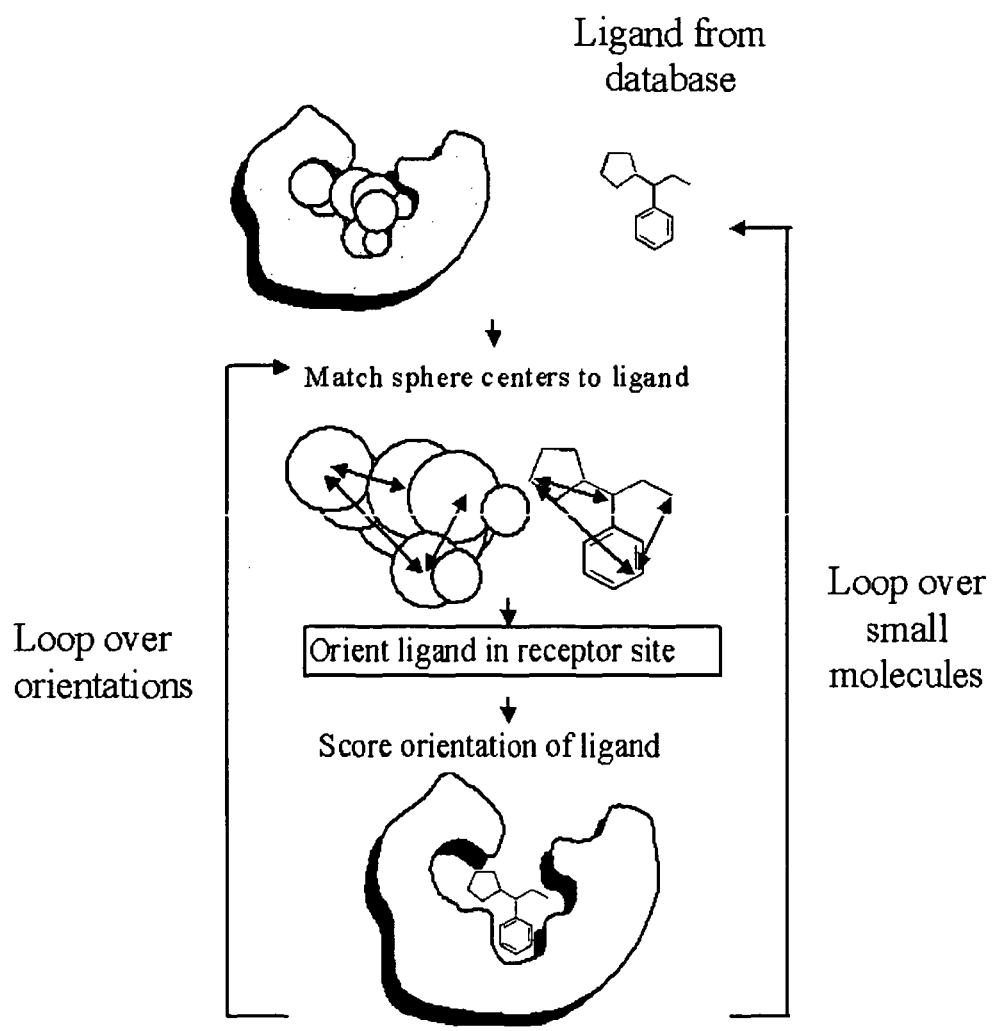
FIG. 16 illustrates a DOCK algorithm. (1) A "negative image" is generated by filling a pocket with spheres. (2) A candidate ligand is retrieved from a database. (3) Internal distances are matched between a subset of sphere centers and ligand atoms (usually three to eight centers are chosen). (4) The ligand is oriented into the active site. (5) The interaction for that orientation is evaluated by a scoring function; the process is repeated for new orientations—typically 10,000 orientations are generated per ligand. The top-scoring orientation is retained. The process is repeated for a new ligand in the database
Figure 17A:
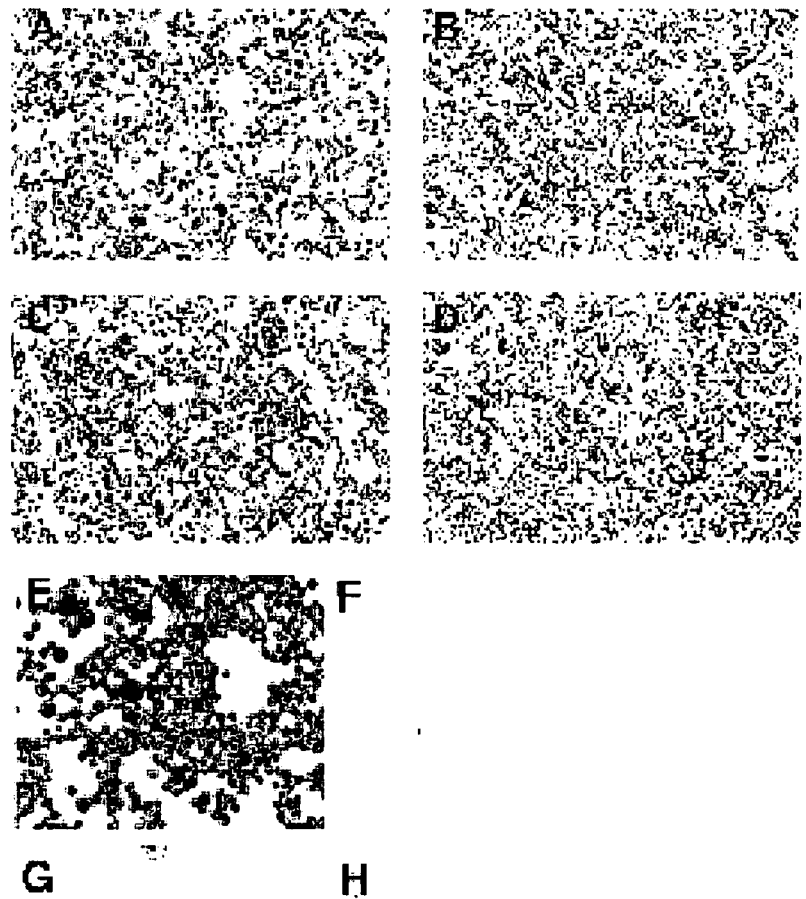
FIGS. 17A and 17B illustrate binding of SHAL JP459B to cells displaying HLA-DR10.
Figure 17B:
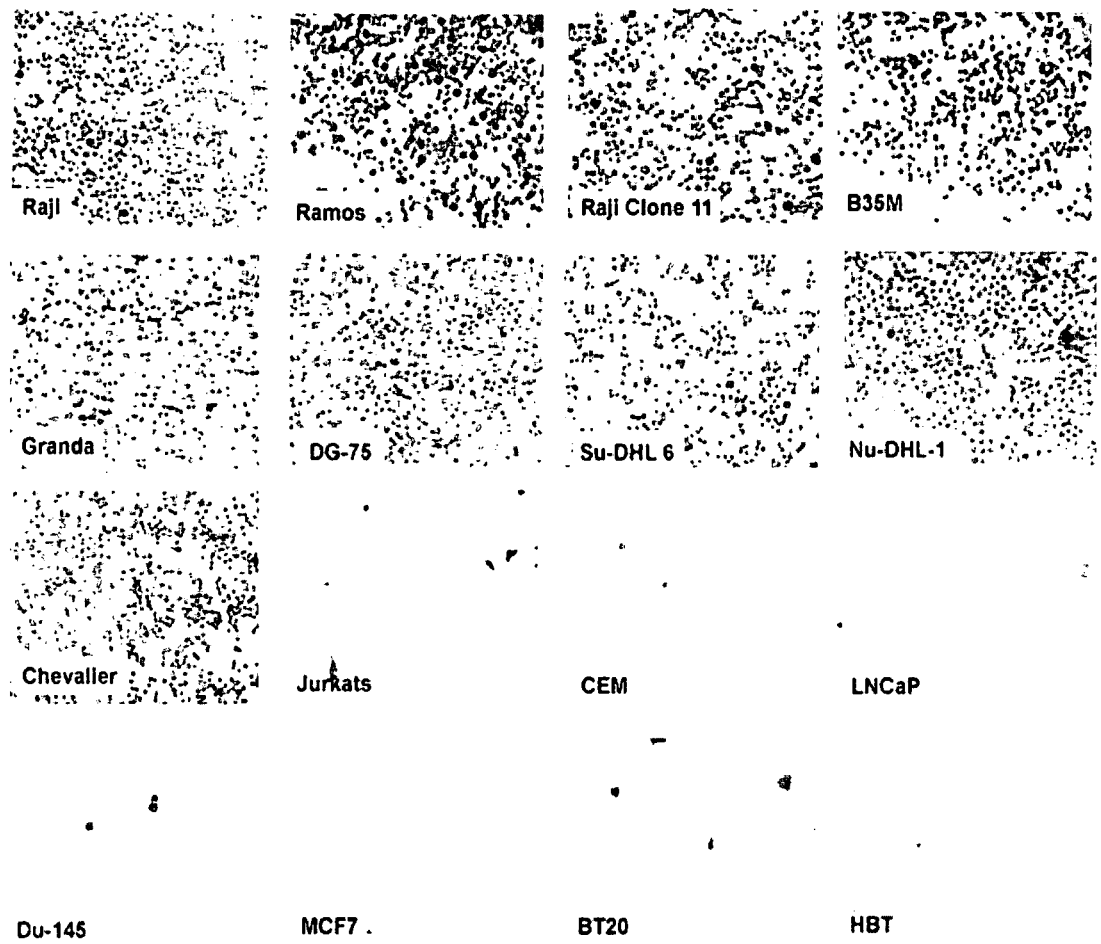
Figure 18:
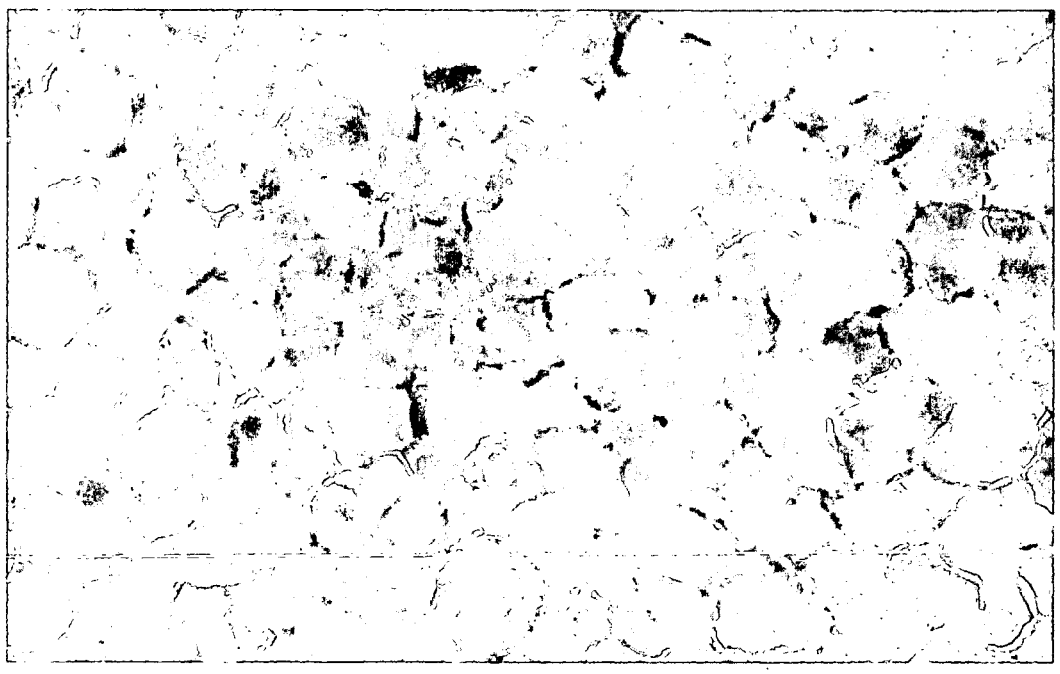
FIG. 18 shows a tissue section from NH lymphoma illustrating that JP459B staining of lymphoma cells is localized to the cell membrane.

Docking studies identify small molecules that might bind specifically to the chosen binding site on the protein. The DOCK 5.0 program screens a database of compounds on the computer and predicts which molecules will likely bind tightly to the binding site. This procedure is illustrated in FIG. 16 We used the Available Chemicals Directory (ACD) from MDL as our database of compounds to screen.

The database was prepared by prefiltering to remove soaps and dyes. After the partial charges for the compounds were calculated by using Gasteiger-Marsili charges (Gasteiger and Marsili (1978) *Tetrahedron Letts.*, 34: 3181-3184; Gasteiger and Marsili (1980) *Tetrahedron* 36: 3219-3288; Gasteiger and Marsili (1981) *Organic Magnetic Resonance* 15:353-360) in Sybyl, the database was divided by total compound charge, and compounds with formal charge $>\pm 3$ are filtered out. Also, compounds <10 and >80 heavy atoms (not hydrogens) were removed to focus on compounds within the size range for lead (preliminary) drug compounds. This prefiltering made the database more efficient and eliminated unnecessary calculations on compounds known to either never bind or bind indiscriminately. To simulate a flexible docking technique, 20 unique conformations were generated for each compound in the database. Each of these conformations was then rigidly docked into the binding site. Different orientations within the binding site were examined for each of the conformations of each of the ligands. All compounds were scored by energy minimization where the intermolecular van der Waals and electrostatic terms are derived from AMBER (Weiner (1984) *J. Am. Chem. Soc.*, 106: 765-784). Though the molecules are ranked based on the scores, the scoring function does not predict the binding affinities.

The top ranked 2,500 molecules were then visually inspected to select down to thirty-five molecules for experiment binding assays as described in Example 1. Ligands were selected and bidentate SHALs were constructed and tested as described in Example 1.

The binding of lead compounds to the target can be improved by several orders of magnitude by using multiple (2-3) compounds linked together. For the inhibitor to be effective, it needs to recognize specifically the target protein and bind with high affinity.

D) Quantum Chemical Calculations

A wide variety of chemical simulation methods have been developed, ranging from empirical ball-and-spring type molecular mechanics models to ab initio (first principles) quantum chemical methods that calculate approximate solutions to the exact quantum mechanical equations describing the electrons and nuclei. Typically, the choice of methods involves trade-offs between accuracy, size of the chemical system, and computational cost. These modeling methods can be broadly divided into molecular dynamics methods that simulate the time evolution of chemical processes and static methods that predict time-independent molecular properties such as the lowest energy configuration of a molecule or the energy of a chemical reaction. One can use all three molecular modeling methods described below: ab initio quantum chemistry, classical molecular dynamics and first principles molecular dynamics in the design and optimization of SHALs as described herein.

1. Ab Initio Quantum Chemistry (QM)

Ab initio quantum chemistry involves computing approximate solutions to the exact non-relativistic Schroedinger equation describing a molecular system (Jensen (1999) Introduction to Computational Chemistry, New York, John Wiley and Sons). In principle these methods can predict the properties of any chemical system to arbitrary accuracy, but in practice the computational cost limits the accuracy of these methods and the size of the molecular systems to which they can be applied. Nevertheless, ab initio quantum chemical calculations are routinely applied to calculate accurate structures and reaction energies for molecular systems including up to hundreds of atoms.

There is a hierarchy of different ab initio quantum chemical methods involving increasingly accurate mathematical descriptions of the electronic wave function—the mathematical description of the distribution of electrons around the nuclei of a molecule (Id.). Application of quantum chemistry typically requires the choice of both the description of the electron-electron interactions (level of theory) and the spatial flexibility of the electrons (basis set). A fairly new class of methods called Density Functional Theory (DFT) has been developed that includes empirical parameterizations of the electron-electron interactions, and often provides accuracy comparable to the earlier high-level quantum chemical methods (such as Coupled Cluster methods), but with a much lower computational cost. The DFT methods are usually denoted by the empirical electron-electron "functional" employed. Two widely used DFT functionals are the Becke 3-parameter hybrid exchange functional (Becke (1993) *J. Chem. Phys.* 98: 5648-5652) and the Lee-Yang-Parr gradient corrected electron correlation functional (Lee et al. (1988) *Chemical Physics* 123: 1-25). These have been widely demonstrated to yield accurate chemical structures and reaction energies for most molecules when used with sufficient basis sets (Jensen (1999) *Introduction to Computational Chemistry*, New York, John Wiley and Sons).

The quantum chemical simulations described herein are used to study chemical processes that occur in the immediate extracellular environment. The quantum chemical methods described above typically describe only an isolated (usually described as "gas-phase") molecule and therefore do not include the chemical environment, such as solvent molecules and counterions, which frequently is critical to the structure and energetics of biological molecules. Explicitly including the surrounding water molecules and counter ions is usually not computationally practical; however, several methods have been developed within the quantum chemistry approach for effectively including the effects of solvent interactions. Typically these methods model the solvent as a continuous medium that polarizes in response to the quantum chemically derived charges. Although there are many situations where explicit inclusion of the solvent is necessary, these so-called polarizable continuum models have proven reasonably accurate in predicting solvent-phase chemical properties including total solvation energies and acid constants (Schüürmann et al. (1998) *J. Physical Chemistry* A 102: 6706-6712; Tran and Colvin (2000) *J. Molecular Structure, Theochem* 532: 127-137).

The Langevin dipole method of Warshel is related to these polarizable continuum models, but includes a more realistic representation of the polar solvent. The Langevin dipole method models the solvent as a large set of polarizable dipoles on a fixed three-dimensional grid (Luzhkov and Warshel (1992) *J. Computational Chemistry* 13: 199-213). This approach has recently been parameterized for use with ab initio derived solute charges and shown to yield solvation energies for neutral and ionic molecules comparable or better than PCM methods described above (Florian and Warshel (1997a) *J Am Chem. Soc.,* 119: 5473-5474).

2. First principles Molecular Dynamics (FPMD)

By combining the forces determined directly from a QM method to drive the classical motion of all the atoms in a simulation, one can achieve the accuracy of quantum mechanics (QM) with the advantages of classical molecular dynamics. This approach became computationally feasible with the development of a new technique based on density functional theory (DFT) (Kohn Sham (1965) *Physical Review* 140: A1133) that treats electronic degrees of freedom at the same time as the nuclear equations of motion (Car and Parrinello (1985) *Physical Review Letters* 55: 2471-2474; Galli and Parrinello (1991) Pp. 283-304 In: *Computer Simulation in Materials Science*, The Netherlands, Kluwer Academic Publishers). Since the method employs QM theory to describe the entire system, it is often referred to as first principles molecular dynamics (FPMD). In the typical implementation of FPMD, only the chemically active valence electrons are explicitly described with an expansion in a plane-wave basis, while the chemically inert core electrons are represented by pseudopotentials (Galli and Pasquarello (1993) Pp. 261-313 In: *Computer Simulation in Chemical Physics*, D. J. Tildesley, ed. Dordrecht, Kluwer; Yin and Cohen (1982) *Physical Review B (Condensed Matter)* 25: 7403-7412). Because the pseudopotentials are transferable by design, this method does not require reparameterization when new systems are studied. In addition, the use of a plane wave basis set naturally lends itself to the application of periodic boundary conditions, so the method is well suited for modeling systems in the condensed phase. This method, combined with several other computational improvements (Gygi (1993) *Physical Review B* 48: 11692-11700; Hutter et al. (1994) *Computational Materials Science* 2: 244-248; Payne et al. (1992) *Rev. Modern Physics* 64: 1045-1097), has been instrumental in solving the problem of integrating QM and MD.

The first applications of FPMD simulations were limited to small systems such as silicon (Car and Parrinello (1985) *Physical Review Letters* 55: 2471-2474; Stich et al. (1989) *Physical Review Letters* 63: 2240-2243). As these methods have been continuously improved upon, and advanced computational resources have become available (such as the DOE teraflop scale supercomputers) it is now possible to investigate small biochemical systems containing several hundreds of atoms for picosecond timescales (Carloni and Alber (1998) Perspectives in *Drug Discovery and Design* 9/11: 169-179; Pantano et al. (2000) *J. Molecular Structure (Theochem)* 530: 177-181; Rovia and Parrinello (2000) *International Journal of Quantum Chemistry* 80: 1172-1180). For example, we have recently simulated the conformational dynamics of a small chemical model of the DNA backbone in solution. As the number of systems that have been investigated with this new approach increases, it is becoming clear that the increased computational expense is repaid in the form of extremely accurate structural and dynamical properties. In particular, such methods potentially allow for very accurate dynamical simulations of chemical phenomena including chelator-metal ion interactions and enzyme-catalyzed reactions.

E) Classical Molecular Dynamics (MD)

Classical molecular dynamics can be used to in identifying the exact orientation of the ligands in the in the binding sites of the target molecule(s) (e.g.HLA-DR 10 binding sites (Site 1 and Site 2)). This information can be used in designing the multivalent ligands to carry radioisotopes selectively to the target molecule and/or to cells displaying the target molecule.

In particular, this structural data helps identify which functional groups on the ligand(s) can be used to synthetically attach the linker. For all ligands that are experimentally verified to bind to the target, classical molecular dynamics can be performed on the ligand in the target binding sites to determine conformation and orientation of the ligand and the specific interactions mediating the binding specificity (e.g., hydrogen bonds, electrostatic and Van der Waals interactions). In certain embodiments, the molecular dynamics simulations will include the target and the ligands solvated in a periodic water box. For each ligand, 500 ps to several nanosecond simulations can be performed using multiple starting orientations.

An important component of the polydentate SHALs of this invention is the molecular linker between the individual ligands (binding moieties) comprising the SHAL. Typically this linker adopts an aqueous-phase conformation (or set of conformations) that holds the two (or more) ligands at appropriate distances to efficiently bind into their binding site on the target surface. To assist in designing this linker classical molecular dynamics can be performed on the linker molecular alone and the linker bound to specific ligand compounds.

The program CHARMM can be used to perform classical molecular dynamics simulations on various linkers. For example, simulations performed with PEG linkers can utilize a different number of PEG units (4, 6, and 8) in the molecules. The starting structures for all four simulations can have the molecules in a fully extended conformation. These extended molecules can be solvated in water boxes and sodium ions were added to each water box to neutralize the systems. These solvated systems were heated to e.g., to 300 K and allowed to equilibrate for 200 picoseconds. Typically simulations can be run at constant temperature (NVT ensemble) and electrostatic interactions treated by particle mesh Ewald (PME) summation.

Initially the two compounds to be linked can be visually examined together bound to the protein as determined by docking and molecular dynamics using computer graphics. For example, a polyethylene glycol (PEG) linker will be built using molecular drawing software (AMPAC) between the two compounds. This structure can then be simulated using classical molecular dynamics in a periodic water box, e.g., as described above for several nanoseconds. One can analyze the resulting data on the dynamical motions to measure the average ligand-ligand distance and relative ligand orientation. This data can be compared with the distance between the ligands and relative orientation on the target 10 surface to determine the optimal length for the linker.

Molecular dynamics simulations can also be used to investigate a number of other properties on the overall SHALs to optimize their therapeutic effectiveness. In particular molecular dynamics simulations can be used to investigate a number of modifications including the chemical structure of the linker itself, and the two ligands at each end. The goal of these simulations will be to identify likely effects of such modifications on target binding efficiency and specificity prior to expensive synthetic modifications.

Molecular dynamics methods use an empirically derived classical force field to simulate the motion of each atom in a chemical system. This methodology is highly developed for the simulation of nucleic acids, (Beveridge and McConnell (2000) Curr. *Opinion in Structural Biology* 10: 182-196) and proteins (Brooks et al. (1983) *J. Computational Chemistry* 4: 187-217; Cheatham and Brooks (1998) *Theoretical Chemistry Accounts* 99: 279-288; Doniach and Eastman (1999) *Curr. Opinion in Structural Biology* 9: 157-163). Typical published molecular dynamics simulations involve 10-100,000 atoms (including both the biomolecules being simulated and a surrounding shell of water and counter ions) which are simulated for multi-nanoseconds of time, with the largest published simulation being a 1 microsecond simulation of a small protein (Duan and Kollman (1998) *Science* 282: 740-744). The multinanosecond time scale is thought sufficient to capture structural relaxation and solvent reorganization, and is long enough in some cases to simulate transitions between different macromolecular conformations (Cheatham and Kollman (1996) *J. Mol. Biol.,* 259: 434-444; Yang and Pettitt (1996) *J. Physical Chemistry A* 100: 2564-2566).

A molecular dynamics simulation of polyethylene glycol (PEG) has recently been published that is relevant to the design of PEG linkers for SHALs. Heymann and Grubmuller used classical molecular dynamics to describe the conformational and elastic properties of individual PEG chains (Heymann and Grubmuller (1999) *Chemical Physics Letters* 307: 425-432; Young and Lovell (1992) Introduction to Polymeres, New York, Chapman and Hall). They simulated a PEG 18-mer (~1 kDalton molecular weight) in the aqueous phase (solvated by 1539 water molecules) and in the gas-phase (to approximate solvation in a non-polar solvent such as hexadecane). They found that in the gas-phase the PEG rapidly collapsed to a compact structure with no local structure, as measured by the degree to which the PEG had a helical local structure. In water, the PEG behaves very differently. It does show a reduction in the radius of gyration compared to the fully extended structure, but retains a marked degree of helicity and therefore some degree of stiffness. These simulations indicate that the local stiffening of the PEG structure is caused by water molecules that form hydrogen bond bridges between successive oxygens in the PEG chain. They further simulated the stretching of the PEG chain with a range of forces from 0 to 500 picoNewtons (this mimics experimental studies with Atomic Force Microscopes). They find good agreement in their predicted force versus extension curves with values recently measured in a single PEG molecule (Oesterhelt et al. (1999) *New Journal of Physics* 1: 6.1-6.11).

These results demonstrate that classical molecular dynamics simulations of PEG can accurately reproduce complex properties such as the force/extension curves and strongly supports the accuracy of the proposed PEGylated scaffold simulations. Although the PEGylated scaffold currently in use (13.6 kDalton molecular weight) is considerably larger than the PEG 18-mer simulated by Heymann and Grubmiller, it is well within reach of routine molecular dynamics simulations.

Molecular dynamics simulations can readily be performed with the CHARMM software package (Brooks et al. (1983) *J. Computational Chemistry* 4: 187-217) using the version 22 parameter set (MacKerell et al. (1998) *J. Physical Chemistry B* 102: 3586-3616). Analysis can be performed using the analysis tools distributed with CHARMM and VMD, a graphical molecular dynamics analysis tool (Humphrey et al. (1996) *J. Molecular Graphics* 14: 33-38).

The steps in a typical setup and simulation runs are as follows:

A. Preliminary Setup.

1. Calculation of partial charges for atom types not included in CHARMM force field. Model compounds containing the unparameterized atom types will be optimized at the Hartree-Fock level of theory using a 6-31G(d) basis set. Upon convergence, partial charges of each atom will be computed using Merz-Kollman charge fitting scheme (Besler et al. (1990) *J. Computational Chemistry* 11: 431-439). These charges can replace the default atomic charges.

2. Molecules to be Simulated:

a. Construction of Molecular Structures

The molecules to be simulated can be built using QUANTA and the atomic charges will be obtained as in step one above. The net charge of the whole compound can then be computed.

b. Solvation of the Molecular Structures:

The molecules and molecular complexes constructed in step 2a can be neutralized using $Na^+$ ions that are positioned using the SOLVATE program. The whole system can then be solvated in a box of water molecules and this simulation box can be subsequently adjusted to yield the appropriate density.

B. Running the Simulation:

1. Equilibration of the Molecule/Water/Counterion System:

a. Minimization: To remove residual strain remaining in the molecular structures from the construction phase, the solvated molecules from step 2b above can be minimized for 10,000 steps, of which the first 1,000 iterations are performed using steepest descent and the rest using adopted basis Newton-Raphson methods.

b. Equilibration: After minimization, The temperature can be ramped up from OK to 300K over 10 ps and held fixed at 300K thereafter. The system can be equilibrated for 200 ps at constant temperature. The long range forces are handled by particle mesh Ewald method Essmann et al. (1995) *J. Chemical Physics* 103: 8577-8593. The water molecules are TIP3P (Jorgensen et al. (1983) *J. Chemical Physics* 79: 926-935). An integration time step of 2 femtoseconds can be used, and the SHAKE algorithm can be employed to restraint all the motions of the hydrogen atoms (Reichert and Welch (2001) *Coordination Chemistry Reviews* 212: 111-131).

c. Production runs: For the production simulations, constant temperature molecular dynamics (using the NVT ensemble) can be used. The particle mesh Ewald method (Essmann et al. (1995) *J. Chemical Physics* 103: 8577-8593) can be used for the long range forces. During the dynamics runs, the complete set of atomic coordinates can be saved every 0.1 ps for subsequent analysis. For the preliminary simulations, the molecular dynamics simulations ran on our Compac Alpha computers at a speed corresponding to approximately 625 cpu hours (~4 weeks) per nanosecond, therefore, multinanosecond simulations of these systems will be routinely feasible on our large network of workstations.

Example 3

Synthesis and Testing of a Bi-Denatate Shal

Figure 14:
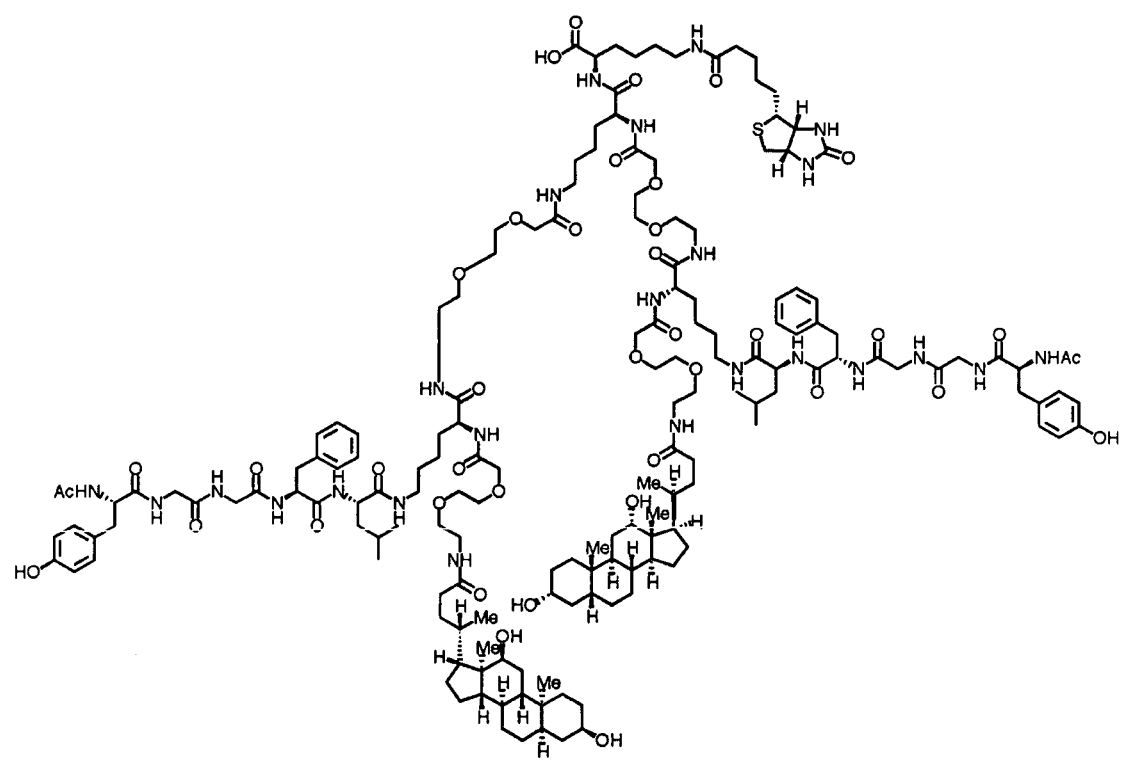
FIG. 14 illustrates the structure of a bivalent version of JP459B. Red is deoxycholate; Green is 5-leu-enkephalin; Blue is the lysine linker; and Black is the PEG linker and biotin.

The bivalent SHAL (LeacPLD)$_2$LPDo was synthesized, purified by HPLC and characterized by mass spectrometry. This SHAL has two JP459B bidentate ligands interconnected via a linker and a DOTA attached on the third arm (see, e.g., FIG. 14).

SHALs were designed around an orthogonally protected lysine residue to facilitate synthesis on solid phase resin. A commercially available Fmoc-protected amino acid-like mini-peg (2 CH$_2$O's) was used as a linker to incrementally increase the distance between the enkephalin and the deoxycholate moieties. Fmoc-biotinyl-lysine was used to introduce biotin into the SHALs for biacore experiments. All SHALs follow the same configuration: CO$_2$H:Biotin-lysine: lysine: (a lysine NH$_2$: 0, 1, 2 mini-peg linker, deoxycholate)(g lysine NH$_2$: LFGGY-NHAc). The bis-bidentate SHAL follows the convention: CO$_2$H:Biotin-lysine:lysine: [(a lysine NH$_2$: 0, 1, 2 mini-peg linker, deoxycholate)(g lysine NH$_2$: LFGGY-NHAc)]2- and therefore is unsymmetrical about the second lysine residue.

All chemicals used were purchased from Aldrich or Nova Biochem. SHALs were synthesized using standard Fmoc solid phase synthesis on chlorotritylchloride resin. Ligands were cleaved from the resin and the protecting groups removed using the appropriate reagents. Trifluoroacetic acid esters formed on the primary alcohols of deoxycholate during cleavage from the resin were removed by stirring in ammonium bicarbonate. SHALs were purified using reverse phase high performance liquid chromatography (HPLC).

Analytical HPLC was carried out at 1 mL/min on an Agilent 1100 machine (Waters Symmetry C18, 5 mm, 4.2×150 mm column) and preparative HPLC was carried out at 10 mL/min on a Waters preparative machine (Waters Symmetryprep C18, 7 mm, 19×300 mm column). SHALs were characterized using nuclear magnetic resonance (NMR) spectroscopy and electrospray mass spectrometry. 1H and $^{13}$C NMR spectra were recorded on a Bruker DRX 500 MHz spectrometer. Mass spectra were acquired on a Micromass Quattro Micro API mass spectrometer operating in positive ion mode.

Mass spectrometry of the (LeacPLD)$_2$LPDo showed that it does not contain any free DOTA. Free DOTA would not be expected to be present based on the process used to synthesize the SHAL. (LeacPLD)$_2$LPDo was synthesized by attaching each linker component or ligand onto a growing chain covalently attached to the surface of a resin. After each chemical reaction the resin was extensively washed to remove the unreacted products. DOTA was attached to the linker at the beginning of the synthesis. After the excess DOTA was washed away, multiple additional chemical reactions that were carried out on the resin to add the various linkers and ligands, and after each reaction the unreacted products were again washed away. By the time the synthesis of the SHAL was completed, the amount of free DOTA present in the sample was undetectably examination of the HPLC and mass spectrum. The DOTA link is extremely stable, so it does not come off the SHAL once it's been attached.

During radiochemistry, components that may be present in the early runoff peak that can have associated radioisotopic label include the buffer salt (ammonium bicarbonate), possibly a trace amount of trifluoroacetate removed from the SHAL hydroxyls during the final synthesis step, and excess EDTA and free and EDTA-complexed isotope that didn't bind to the DOTA. Dialysis may simply not be the preferred method for efficiently eliminating all this material. Reverse dialysis is one preferred method for purification. Alternatively, chelate (EDTA) scrubbing after radiochemistry can be performed using an EDTA bead column to remove radiometal that has not been DOTA chelated or is loosely attached in a non-specific manner.

To get the metal into the DOTA efficiently, adjusting the reaction mix to an adequate alkaline pH is also important. Since the SHAL as a molecule is quite different from an antibody-DOTA molecule, the method used to raise the pH on the SHAL-DOTA complex preferably also raises the pH sufficiently on the SHAL. One can easily get other metals in DOTA if they are present at any stage. These can be detected by checking the mass spectrum of the compound. We have looked at the spectrum from purified SHALs and see little or no other metal there.

Biotinylated deoxycholate-iodothyronine SHALs are synthesized in an analogous manner.

Figure 20:
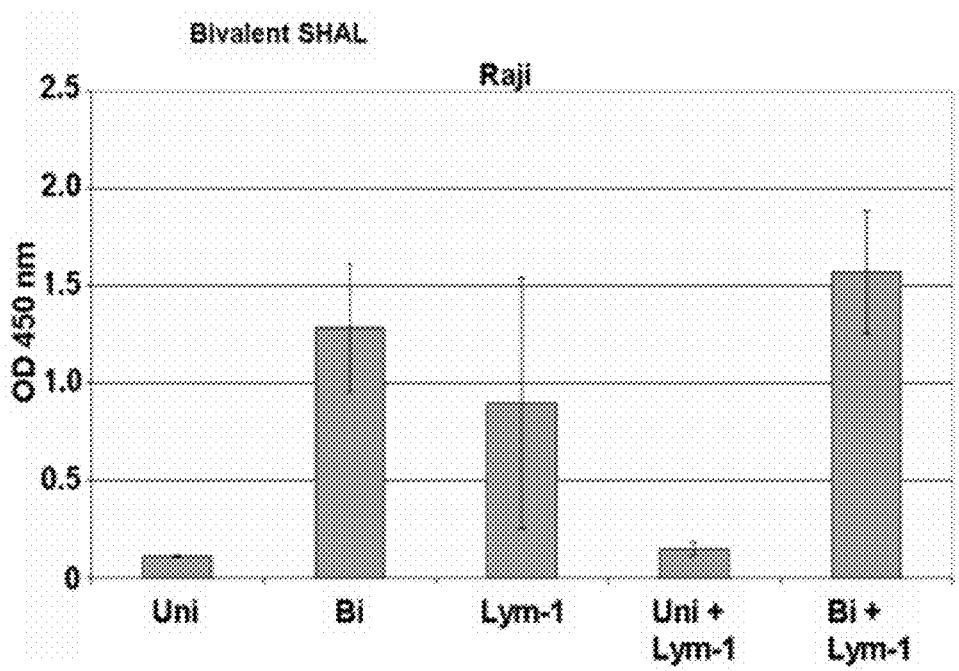
FIG. 20 illustrates the binding of univalent bidentate SHAL and bivalent bidentate SHAL 070804LeacPLDB to Raji cells in presence and absence of Lym-1 antibody.

ELISA assays showed that SHAL, LeacPLBD (the univalent bidentate SHAL), bind to and discriminate between cells containing HLA-DR10 and those that do not contain HLA-DR10 (see FIG. 20).

Figure 19:
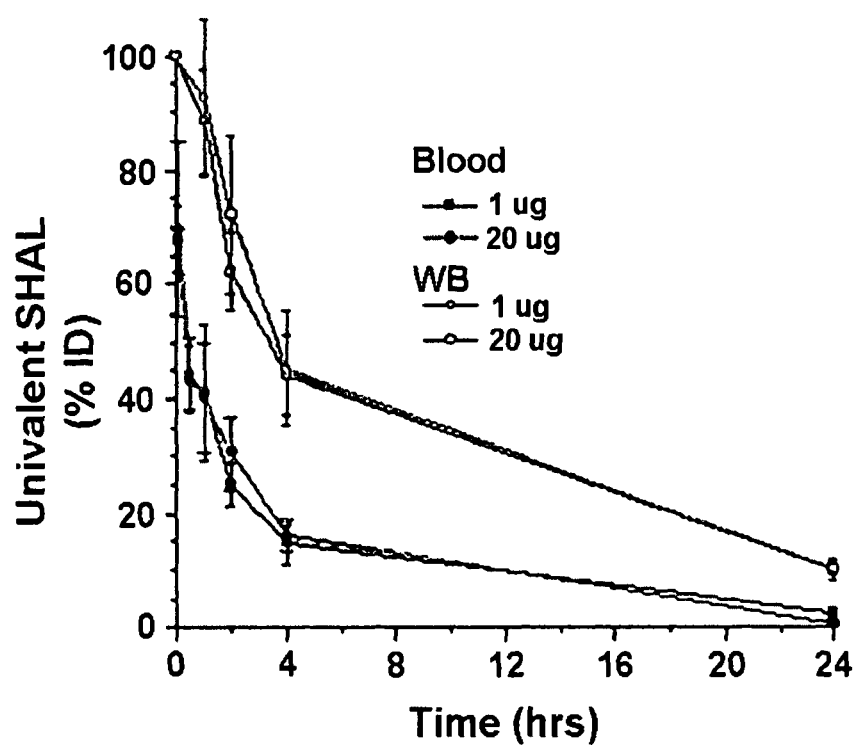
FIG. 19 illustrates $^{111}$In-DOTA [SHAL 070804(Leac-PLD)$_2$LPDo] biodistribution in Raji tumored mice.

Several pharmacokinetic, biodistribution and imaging studies were performed with consistent results. In certain embodiments, $^{111}$In-DOTA [SHAL 070804(LeacPLD)$_2$LPDo] biodistribution was determined in Raji tumored mice (see, e.g., FIG. 19A).

Example 4

Development of Synthetic High Affinity Ligands that Bind to a Structural Epitope on the Tumor Cell Receptor HLA-DR10

A number of cell surface protein receptors have been identified that distinguish malignant cancer cells from their normal counterparts. While several of these receptors have been shown to be more abundant on cancer cells (e.g., CD20, CD22), others have been confirmed to differ structurally (e.g., HLA-DR10, Muc-1) from the same or closely related receptors present on normal cells. This has led to the development of a variety of antibody-based, receptor-specific reagents conjugated to radioisotopes for use in radioimmunotherapy. Lym-1, an antibody developed to bind to a unique structural epitope on the abundant cell surface receptor HLA-DR10 found only on human lymphoma and normal B-cell lymphocytes, has been used with some success in the treatment of non Hodgkin's lymphoma. In an effort to develop smaller and more effective therapeutics for treating non Hodgkin's lymphoma, we have synthesized the first in a series of small (<3 kD) selective high affinity ligands (SHALs) that bind to this same HLA-DR10 structural epitope. A homology model for HLA-DR10 was created using four known crystal structures of related HLA-DR molecules. Two unique "pockets" located on the surface of the protein adjacent to key amino acids required for Lym-1 binding were identified, and computational docking techniques were used to prescreen a large library of small molecules to predict which compounds should bind to each site. A small number of these compounds were tested experimentally using NMR spectroscopy to confirm their binding to the isolated HLA-DR10 protein, and pairs of compounds binding to the two different "pockets" were linked together using solid phase synthetic chemistry to create a series of bidentate reagents with different length linkers. The SHAL exhibiting the highest affinity for isolated HLA-DR10 (~23 nM) has been shown to bind selectively to nine different cultured cell lines containing HLA-DR10 and to frozen and fixed tissue sections obtained from patients with small cell and large cell human lymphomas. A bivalent form of this SHAL was also synthesized and shown to further enhance cell binding.

Example 5

Hexa-Arginine Enhanced Uptake and Residualization of Selective High Affinity Ligands by Rah Lymphoma Cells Summary A variety of arginine-rich peptide sequences similar to those found in viral proteins have been conjugated to other molecules to facilitate their transport into the cytoplasm and nucleus of targeted cells. The selective high affinity ligand (SHAL) (DvLPBaPPP)$_2$LLDo, which was developed to bind only to cells expressing HLA-DR10, has been conjugated to one of these peptide transduction domains, hexa-arginine, to assess the impact of the peptide on SHAL uptake and internalization by Raji cells, a B-cell lymphoma.

An analog of the SHAL (DvLPBaPPP)$_2$LLDo containing a hexa-arginine peptide was created by adding six D-arginine residues sequentially to a lysine inserted in the SHAL's linker. SHAL binding, internalization and residualization by Raji cells expressing HLA-DR10 were examined using whole cell binding assays and confocal microscopy. Raji cells were observed to bind two fold more $^{111}$In-labeled hexa-arginine SHAL analog than Raji cells treated with the parent SHAL. Three fold more hexa-arginine SHAL remained associated with the Raji cells after washing, suggesting that the peptide also enhanced residualization of the $^{111}$In transported into cells. Confocal microscopy showed both SHALs localized in the cytoplasm of Raji cells, whereas a fraction of the hexa-arginine SHAL localized in the nucleus.

The incorporation of a hexa-D-arginine peptide into the linker of the SHAL (DvLPBaPPP)$_2$LLDo enhanced both the uptake and residualization of the SHAL analog by Raji cells. In contrast to the abundant cell surface binding observed with Lym-1 antibody, the majority of (DvLPBaPPP)$_2$LArg6AcLLDo and the parent SHAL were internalized. Some of the internalized hexa-arginine SHAL analog was also associated with the nucleus. These results demonstrate that several important SHAL properties, including uptake, internalization, retention and possibly intracellular distribution, can be enhanced or modified by conjugating the SHALs to a short polypeptide.

BACKGROUND

Several strategies have been used to selectively deliver toxic chemicals or radiation to cancer cells (DeNardo (2005) *Semin Oncol.*, 32:S27-35; Torchilin (2007) *AAPS J.*, 9:E128-147), for gene therapy (Jeong et al. (2005) *J Control Release* 107:562-570; Xia et al. (2007) *J Gene Med* 10:306-315) or as tools for transfecting cells (Shigeta K (2007) *J Control Release* 118:262-270) and silencing genes (Liu (2007) *Brief Funct Genomic Proteomic* 6:112-119). Some of the earliest approaches used to enhance the cellular uptake of therapeutics and other molecules (fluorescent dyes, enzymes, antibodies and other proteins) involved introducing the molecules into liposomes or micelles (Constantinides et al. (2008) *Adv Drug Deliv Rev* 60:757-767; Samad et al. (2007) *Curr Drug Deliv* 4:297-305). Such constructs have been shown to fuse with the cell's membrane, introducing the contents inside the cell or transferring the lipid-bound components into the cell's membrane. Another highly successful approach has been to develop antibodies that target cell-specific membrane proteins and to use these antibodies to deliver radionuclides or other cytotoxic molecules to the surface of a specific population of cells (Brumlik et al. (2008) *Expert Opin Drug Deliv* 5:87-103; DeNardo et al. (1998) *Cancer Biother Radiopharm* 13:239-254; Tolmachev et al. (2007) *Cancer Res.* 67:2773-2782). More recently, intracellular delivery has been accomplished by attaching the molecules to be transported to naturally occurring transmembrane "shuttles", peptides or proteins that readily pass through cellular membranes. One of the more successful shuttles is a nuclear localization signal peptide derived from the SV40 T antigen (Yoneda (1997) *J Biochem* 121:811-817). This sequence, other peptide sequences derived from the transduction domain of the HIV-1 protein Tat (Schwarze et al. (1999) *Science* 285:1569-1572; Torchilin et al. (2003) *Proc. Natl. Acad. Sci., USA*, 100:1972-1977), penetratin (Tseng et al. (2002) *Mol Pharmacol* 62:864-872), and intact proteins such as the herpes virus protein VP22 (Phelan et al. (1998) *Nat Biotechnol* 16:440-443) and anti-DNA antibodies (Avrameas et al. (1998) *Proc. Natl. Acad. Sci., USA*, 95:5601-5606) are currently being used to facilitate the transport of liposomes, viruses, enzymes, antibodies and a variety of other proteins into cells. Considerable success has also been achieved using synthetic cationic peptide transporters such as oligoarginine (Futaki (2005) *Adv Drug Deliv Rev* 57:547-558;

Han et al. (2001) *Mol Cells* 12:267-271; Kim et al. (2007) *Int J Pharm* 335:70-78; Tung and Weissleder (2003) *Adv Drug Deliv Rev* 55:281-294), lactosylated poly-L-lysine (Midoux et al. (1993) *Nucleic Acids Res* 21:871-878) and short peptide sequences selected from phage display libraries (Kamada et al. (2007) *Biol Pharm Bull* 2007, 30:218-223) that exhibit sequence similarities to know peptide shuttles.

Recently, several small molecule antibody mimics that show promise as targeting agents for cancer imaging or therapy have been synthesized [24-28]. In addition to exhibiting selectivities and affinities (nM to pM) similar to antibodies, these molecules have the potential to minimize some of the difficulties associated with the use of protein-based drug delivery systems. They retain the more desirable pharmacokinetic properties of small molecules, are less likely to be immunogenic, may prove stable enough for oral delivery, and the costs associated with producing the drug can be reduced significantly. The SHAL family of antibody mimics can also be easily modified to carry radioactive metals, a variety of tags that enable their use as imaging agents, and other small molecules (e.g. toxins or inhibitors). Another potentially useful modification includes alterations that facilitate uptake and internalization of the SHAL by the targeted cell, which would be expected to both increase tumor residence time and deliver the SHAL into an environment (the cytoplasm or nucleus) where it could cause additional damage.

Working with a SHAL developed previously for targeting HLA-DR10, an abundant cell surface receptor over-expressed on B-cell malignancies, we synthesized a peptide analog to the SHAL by conjugating it to hexa-arginine, a peptide that has been demonstrated previously to facilitate the transport of proteins and nucleic acids into cells. Binding studies conducted with the SHAL and its hexa-arginine analog in vitro using HLA-DR10 expressing Raji cells show that the hexa-arginine sequence changed the SHALs properties significantly, enhancing both SHAL internalization and radionuclide residualization.

Methods

SHAL Design.

The process used to create a homology model for HLA-DR10, identify unique binding cavities within the Lym-1 epitope, select ligands that bind in these cavities, and create the (DvLPBaPPP)$_2$LLDo SHAL has been reported previously (Balhorn et al. (2007) *Clin Cancer Res* 13:5621s-5628s). A process for producing a hexa-arginine peptide analog of this parent SHAL, (DvLPBaPPP)$_2$LArg$_6$AcLLDo, was developed by modifying the synthesis to include the incorporation of an additional lysine residue into the middle of the linker connecting the two SHAL monomers and attaching an arginine hexapeptide to the free amine on this lysine.

SHAL Synthesis.

The two dimeric SHALs (DvLPBaPPP)$_2$LLA and (DvLPBaPPP)$_2$LArg$_6$AcLLA were synthesized on chlorotrityl chloride resin using orthogonally protected lysine (L) residues and miniPEGs (P) to link the two small ligands Dv and Ba as previously described for (DvLPBaPPP)$_2$LLA (Balhorn et al. (2007) *Clin Cancer Res* 13:5621s-5628s; Hok et al. (2007) *Bioconjug Chem* 18:912-921). To produce the amine derivative of the hexa-arginine SHAL (DvLPBaPPP)$_2$LArg$_6$AcLLA, a second Dde-D-Lys(Fmoc)-OH lysine residue was inserted into the linker during SHAL synthesis by performing two sequential Dde-D-Lys(Fmoc)-OH coupling steps. At the alpha position of the third lysine, six consecutive arginine residues were inserted by reacting the resin with Fmoc-D-Arg(Pbf)-OH six times. The sixth Arg residue was protected with an acetate (Ac) by reacting with acetic anhydride in N,N diisopropyl-ethylamine (DIEA)/dimethylformamide (DMF). The guanidinium groups on all six arginine residues remain protected with trifluoroacetic acid (TFA)-sensitive 2,2,4,6,7-Pentamethyldihydrobenzofuran-5-sulfonyl (Pbf) protecting groups throughout the rest of the synthesis. The remainder of the synthesis was then completed as described previously for (DvLPBaPPP)$_2$LLA (Id.). Analytical HPLC and electrospray ionization mass spectrometry (ESI-MS) were performed to confirm the purity and identity of the (DvLPBaPPP)$_2$LLA and (DvLPBaPPP)$_2$LArg$_6$AcLLA free amine SHALs.

(DvLPBaPPP)$_2$LLA:

Starting with 50 mg (0.07 mmol) resin and 30 mg (0.07 mmol) Fmoc-D-Lys(Boc)-OH, 34 mg of (DvLPBaPPP)$_2$LLA (Rt=7.86 min, Waters Symmetry C18, 5 µm, 4.2×150 mm column, diode array detector with a linear gradient from 95% H$_2$O, 1% TFA to 80% acetonitrile (MeCN), 1% TFA over 12 min) was isolated as red solid after purification. ESI-MS: m/z calculated for C$_{150}$H$_{224}$N$_{34}$O$_{41}$S$_2$ (M+3H)$^{3+}$ 1075.60, found 1075.62; calculated for (M+4H)$^{4+}$ 806.95, found 806.93; calculated for (M+5H)$^{5+}$ 645.76, found 645.68; calculated for (M+6H)$^{6+}$ 538.30, found 538.21.

(DvLPBaPPP)$_2$LArg$_6$AcLLA:

81 mg of (DvLPBaPPP)$_2$LArg$_6$AcLLA (Rt=8.30 min) starting from 90 mg (0.12 mmol) resin and 154 mg (0.29 mmol) Fmoc-D-Lys(Boc)-OH was isolated as red solid after purification. ESI-MS: m/z calculated for C$_{194}$H$_{310}$N$_{60}$O$_{49}$S$_2$ (M+3H)$^{3+}$ 1444.71, found 1444.65; calculated for (M+4H)$^{4+}$ 1083.76, found 1083.78; calculated for (M+5H)$^{5+}$ 867.23, found 867.18; calculated for (M+6H)$^{6+}$ 722.86, found 722.78; calculated for (M+7H)$^{7+}$ 619.74, found 619.62.

Attachment of DOTA to SHALs.

The amine analog of the SHAL (DOTA-SHAL precursor with a free epsilon amine on the first lysine) was dissolved in 500 µl anhydrous DMF and 100 µl DIEA. The hexafluorophosphate (PF$_6$) salt of DOTA N-hydroxysuccinimide (NHS) ester (933.36 g/mol, 1-1.5 equivalents) was added to the mixture as a solid. The mixture was nutated for 15 min and the reaction was monitored by analytical HPLC. Upon completion the reaction solution was diluted with 300 µl H$_2$O and 300 µl MeCN (both containing 1% TFA) and HPLC purified using an 85% H$_2$O (0.1% TFA) to 70% MeCN (0.1% TFA) gradient run over 25 min. The resulting purified DOTA-SHALs were lyophilized and subsequently analyzed by analytical HPLC (Waters Symmetry C18, 5 µm, 4.2×150 mm column, diode array detector) using a linear gradient from 95% H$_2$O (1% TFA) to 80% MeCN (1% TFA) over 12 min) and characterized by ESI-MS.

(DvLPBaPPP)$_2$LLDo:

Reaction of the (DvLPBaPPP)$_2$LLA amine SHAL (6.0 mg, 1.86 µmol) with DOTA NHS ester (2.0 mg, 2.14 µmol) gave 100% (Rt=7.664 min) conversion by crude analytical HPLC and yielded (DvLPBaPPP)$_2$LLDo (8.0 mg, red solid) after purification. ESI-MS: m/z calculated for C$_{166}$H$_{250}$N$_{38}$O$_{48}$S$_2$ (M+2H)$^{2+}$ 1806.09, found 1806.22; calculated for (M+3H)$^{3+}$ 1204.40, found 1204.49; calculated for (M+4H)$^{4+}$ 903.55, found 903.61; calculated for (M+5H)$^{5+}$ 723.04, found 723.07; calculated for (M+6H)$^{6+}$ 602.70, found 602.64.

(DvLPBaPPP)$_2$LArg$_6$AcLLDo:

Reaction of (DvLPBaPPP)$_2$LArg$_6$AcLLA amine SHAL (15.0 mg, 3.46 mmol) with DOTA NHS ester (5.0 mg, 5.36 µmol) gave 100% (Rt=7.70 min) conversion by crude analytical HPLC and yielded (DvLPBaPPP)$_2$LArg$_6$AcLLDo (12.0 mg, red solid) after purification. ESI-MS: m/z calculated for $C_{210}H_{336}N_{64}O_{56}S_2$ $(M+3H)^{3+}$ 1573.51, found 1573.54; calculated for $(M+4H)^{4+}$ 1180.38, found 1180.43; calculated for $(M+5H)^{5+}$ 944.51, found 944.52; calculated for $(M+6H)^{6+}$ 787.26, found 787.26; calculated for $(M+7H)^{7+}$ 674.94, found 674.88; calculated for $(M+8H)^{8+}$ 590.69, found 590.58.

Radiochemistry.

As described previously (Id.), the DOTA-SHALs were labeled with carrier-free $^{111}$InCl$_3$ (MDS Nordion, Vancouver, Canada) using the following method (DeNardo et al. (2007) *J Nucl Med* 48:1338-1347). An aliquot of $^{111}$InCl$_3$ (15-20 µl) was added to a solution of DOTA-SHAL (25-50 µg) in 0.1 M NH$_4$OAc, pH 5.3 (50 µl); the final pH of the reaction mixture was adjusted to 6.5 by adding 4M NH$_4$OAc and the mixture was incubated for 1 h at 37° C., then 10-20 µl of 0.1 Methylenediaminetetraacetic acid (EDTA) was added to sequester excess, free $^{111}$In$^{3+}$. The radiolabeled product was purified using HPLC, followed by dialysis in phosphate-buffered saline (PBS) with a 1 kD cut off membrane. The purity of the $^{111}$In-labeled SHALs was determined by thin layer chromatography (TLC) (10% NH$_4$OAc-MeOH 1:1), HPLC and cellulose acetate electrophoresis (CAE). CAE resolved $^{111}$In-DOTA-SHALs and $^{111}$In-EDTA; radioactive peaks were observed at 2.3-3.0 cm and >6.5 cm, respectively. Similar results were observed in the TLC assay; $^{111}$In-DOTA-SHALs showed little migration from the point of application ($R_F$=0.25-0.3), whereas $^{111}$In-EDTA moved towards the solvent front ($R_F$=0.5). By HPLC, $^{111}$In-EDTA eluted at 2.5-3.0 ml and $^{111}$In-DOTA-SHALs at 9.5-10 ml. The $^{111}$In labeled SHALs were purified using RP-HPLC or a 1 kD dialysis membrane in PBS, and concentrated using a Savant Speedvac SC110 (Thermo Fisher Scientific, Inc, Waltham, Mass., USA). Final radiochemical purity was determined using C18-RP-TLC (EM Science, DC-Plastikfolien kieselgel 60 F254, Chemy Hill, N.J.), HPLC, and CAE. $^{111}$In-DOTA-SHAL product yields ranged from 70-90% and the purity of the product ranged from 90-95%. The final product was dissolved in 10% dimethylsulfoxide (DMSO) in PBS, and proved stable over 72 hours at room temperature.

SHAL Binding to Isolated HLA-DR10 Protein

Protein binding experiments were conducted using surface plasma resonance on a Biacore 3000 (Biacore, Piscataway, N.J.) at 25° C. A research grade streptavidin immobilized chip (SA chip, Biacore) was preconditioned and normalized according to the manufacturers instructions. Biotin labeled SHALs were dissolved in DMSO and diluted in 1.05×PBS (Biacore) to a final concentration of 1×PBS pH 7.4, 5% DMSO, to match the running buffer. These SHALs were injected over the flow cell to yield a surface density of 500-1000 RU (response units). Biotin (50 µM E-Z Link Amine-PEO2-Biotin, Pierce) was injected over all cells for 1 minute at 20 µl/min as a block to reduce non-specific binding. One flow cell was used as a reference cell and a different SHAL was immobilized on each of the three other cells.

Experiments measuring the binding of HLA-DR10 to the SHALs were carried out at a flow rate of 30 µl/minute in PBS pH7.4 running buffer using all 4 flow cells. HLA-DR10 isolated from Raji cells (Rose et al. (1996) *Cancer Immunol Immunother* 43:26-30) was diluted in running buffer to a final concentration ranging from 10 nM to 1 µM, and a series of concentrations were run randomly in triplicate. Protein was injected for 3 minutes, allowed to dissociate for 5 minutes followed by regeneration of the surface using a 1 minute injection of 0.1% sodium dodecylsulfate (SDS) followed by a washing step with a 2 minute injection of running buffer. The data, which were double referenced by subtracting the blank reference surface and an average of 5 blank injections, were processed using the program SCRUBBER (University of Utah).

Cell Binding Assay

Raji human Burkitt's lymphoma B-cells (American Type Culture Collection, Manassas, Va.) were maintained in RPMI-1640 media supplemented with 10% fetal bovine serum, 2 mM L-glutamine, 1 mM sodium pyruvate, 1% of a solution of nonessential amino acids (GIBCO #11140-050), and 100 units/ml of Penicillin G, 100 µg/ml Streptomycin, and 0.25 µg/ml of Amphotericin B at 37° C. in a humidified 5% CO$_2$ atmosphere. Jurkat's cells (American Type Culture Collection, Manassas, Va.), an acute leukemia T-cell line, were maintained in the same medium with the addition of 10 mM 4-(2-hydroxyethyl)-1-piperazineethanesulfonic acid (HEPES).

A series of experiments were conducted to quantify the uptake of the $^{111}$In-labeled parent SHAL (DvLPBaPPP)$_2$LLDo and its hexa-arginine analog (DvLPBaPPP)$_2$LArg$_6$AcLLDo by Raji cells, a cell line that has been previously shown to express the HLA-DR10 variant. The assays were conducted using aliquots containing 10$^6$ cells suspended in 150 µl of PBS with 5% bovine serum albumin (BSA). Aliquots of cells were treated with 0.1, 1, 5, 10 or 25 ng of $^{111}$In-labeled (DvLPBaPPP)$_2$LLDo or (DvLPBaPPP)$_2$LArg$_6$AcLLDo for one hour at both 4° C. and 22° C. The tubes containing the treated cells were centrifuged to separate the cell pellet from the supernatant and the two fractions were counted in a calibrated gamma well counter to determine the amount of bound and free SHAL. Half of the cell pellets were washed twice with PBS and incubated at 22° C. for 15 min before centrifuging them again. The pooled washes and washed cell pellets were subsequently counted in the gamma well counter to assess how much of the bound SHAL could be removed by washing.

3-D Confocal Microscopy

SHAL binding and internalization by Raji and Jurkat's cells was assessed using the method described previously by O'Donnell et al. (O'Donnell et al. (1998) *Prostate* 37:91-97). Experiments were conducted comparing the binding of (DvLPBaPPP)$_2$LLDo (the parent SHAL), its hexa-arginine analog (DvLPBaPPP)$_2$LArg$_6$AcLLDo, and chimeric Lym-1 (chLym-1) to Raji cells. All steps were performed at 20° C., unless indicated.

Four million Raji cells (>92% viability) in log phase growth were pelleted at 300×g, washed, and blocked for 30 min in 1 ml of 1% fraction V BSA in PBS, with constant rotation. Cells were then incubated 1 hr, at 1 million per 250 µl, with either 1% BSA in PBS or a biotinylated primary reagent: 10 nM chLym-1, 10 µM parent SHAL, or 10 µM hexa-arginine SHAL. After four washes (two in 1% BSA in PBS, two in PBS), 50 µl of the cell suspensions was applied to freshly poly-L-Lysine coated slides, and cells were allowed to adhere for 10 min in a humid chamber. Fixation and permeabilization were performed at −20° C. by using a 4 min exposure to methanol. Jurkat's cells were treated in the same manner as a control.

Slides were then washed twice in PBS and blocked in 10% fetaplex serum (Gemini Bioproducts, West Sacramento, Calif.) in PBS for 15 min and washed once in PBS. The detection reagent, Streptavidin AlexaFluor 610 (Invitrogen, Carlsbad, Calif.) was diluted 1/500 in diluent, 1000 was applied; a parafilm cover slip was layered over the solution to prevent evaporation. The slides were incubated in a humid chamber for 30 min., washed 5 times for 5 min each in PBS, and rinsed briefly in double distilled H2O. After the slides dried, cover slips were mounted with ProlongGold with 4',6-diamidino-2-phenylindole (DAPI, Invitrogen, Carlsbad, Calif.). The slides were viewed with an Olympus FV1000 laser scanning confocal microscope and data were collected as Z-scans at 160×, with focal sections being taken 1 μm apart through the cell.

Statistical Analysis

Data is reported as mean±SD. Statistical comparisons were based on the Wilcoxon rank sum test (Hollander and Wolfe (1973) *Nonparametric statistical methods*. New York: Wiley Publications), a procedure based on ranking the values of two test groups. Differences were considered statistically significant if p values were ≤0.05. The p-values were determined by the transformation $Z=TANH^{-1}r$ for the correlation coefficients (*CRC Handbook of Tables for Probabilities and Statistics*. 2nd edn. Boca Raton, Fla.: CRC Press; 1968).

Results

SHAL Design and Synthesis.

Figure 25A:
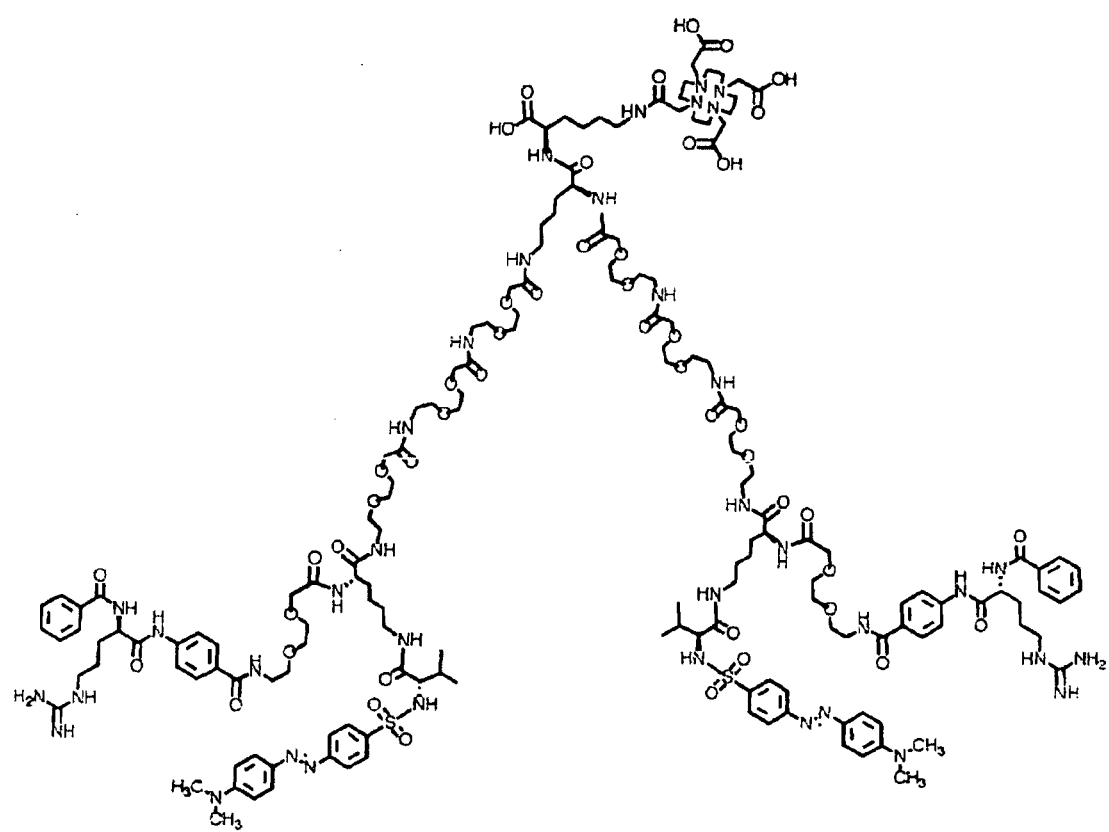
FIGS. 25A and 25B illustrate structures of the dimeric SHAL (DvLPBaPPP)$_2$LLDo (FIG. 25A) and the hexa-arginine analog (DvLPBaPPP)$_2$LArg$_6$AcLLDo (FIG. 25B).
Figure 25B:
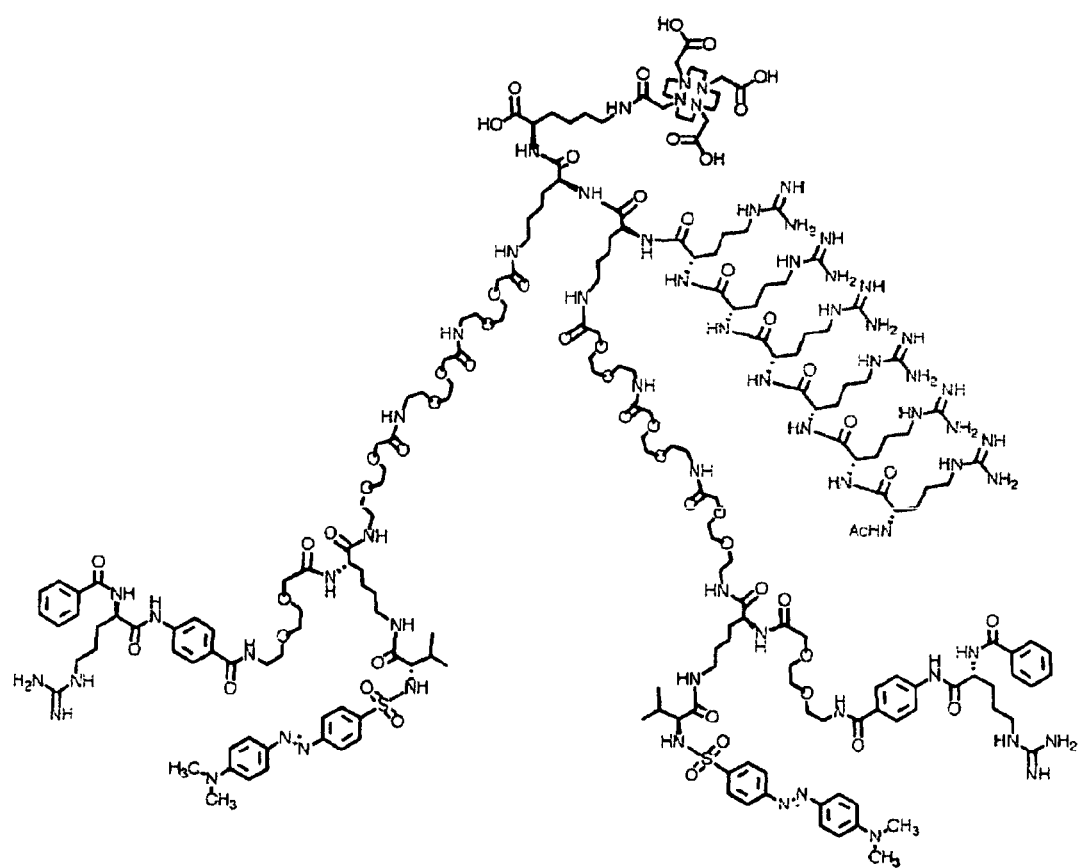

Two forms of the free amine SHAL, $(DvLPBaPPP)_2LLA$, and the hexa-arginine analog, $(DvLPBaPPP)_2LArg_6AcLLA$, were synthesized in multi-milligram amounts and purified by high performance liquid chromatography (HPLC). A biotin was attached to the ε-amino group of the terminal amine (A) on both $(DvLPBaPPP)_2LLA$ and $(DvLPBaPPP)_2LArg_6AcLLA$ to produce biotinylated forms for use in cell and protein binding experiments. 1,4,7,10-tetraazacyclododecane-1,4,7,10-triacetic acid (DOTA) was attached to both $(DvLPBaPPP)_2LLA$ and $(DvLPBaPPP)_2LArg_6AcLLA$ at the same site to enable the SHALs to be labeled with $^{111}$In. The DOTA SHAL $(DvLPBaPPP)_2LLDo$ (FIG. 25A) and the hexa-arginine SHAL analog $(DvLPBaPPP)_2LArg_6AcLLDo$ (FIG. 25B) were labeled with $^{111}$In at high efficiency (>90%) with specific activities ranging from 70-85 μCi/μg SHAL. Analyses of the resulting radiolabeled SHAL by HPLC and cellulose acetate electrophoresis (CAE) showed the purity of the product to be greater than 90%. D-isomers of arginine incorporated during the synthesis of the hexa-arginine sequence in $(DvLPBaPPP)_2LArg_6AcLLDo$ were used to minimize the proteolytic susceptibility of the peptide. While more detailed experiments need to be carried out to adequately assess the stability of the SHAL in vivo, data obtained from one preliminary CAE experiment showed no evidence of degradation when the hexa-D-arginine SHAL analog was incubated in human plasma at 37° C. for 24 hrs (data not shown).

SHAL Affinity for HLA-DR10 Protein.

Surface Plasmon resonance binding studies were conducted with both SHALs to estimate and compare the affinity of the two SHALs for isolated HLA-DR10 protein. In a series of kinetic experiments in which biotinylated versions of the SHALs were immobilized on the surface of a streptavidin chip, the parent SHAL $(DvLPBaPPP)_2LLDo$ was observed to bind to HLA-DR10 with a Kd~21 nM. A similar Kd, ~34 nM, was obtained for the hexa-arginine containing analog $(DvLPBaPPP)_2LArg_6A$ cLLDo.

Analysis of SHAL Uptake by Rah Cells Expressing HLA-DR10.

In vitro cell binding experiments were conducted using $^{111}$In-labeled parent SHAL and the hexa-arginine SHAL analog to quantify SHAL uptake and to evaluate the effect of adding the hexa-arginine tag. Uptake was assessed using Raji cells, a lymphoma cell line expressing HLA-DR10. Aliquots containing $10^6$ cells were incubated with increasing amounts of SHAL containing $^{111}$In labeled SHAL as a tracer, and cell-associated $^{111}$In was measured before and after washing the cell pellets.

Figure 26:
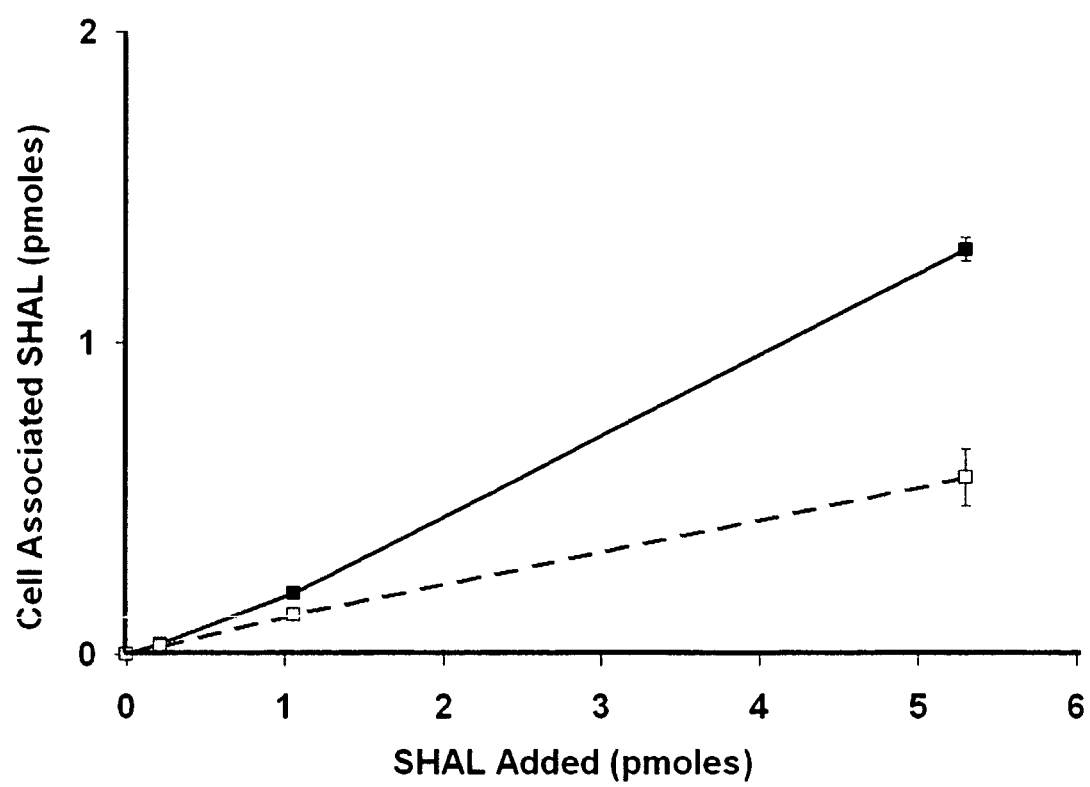
FIG. 26 illustrates binding of $^{111}$In radiolabeled SHAL (DvLPBaPPP)$_2$LLDo and its hexa-arginine analog (DvLPBaPPP)$_2$LArg$_6$AcLLDo to Raji cells. Total $^{111}$In-(DvLPBaPPP)$_2$LArg$_6$AcLLDo bound to Raji cells (unwashed), solid squares; total $^{111}$In-(DvLPBaPPP)$_2$LLDo bound to Raji cells (unwashed), open squares. Cell pellets containing $10^6$ cells were resuspended in 150 µl 5% BSA/PBS buffer containing 0-25 ng of $^{111}$In labeled SHAL and incubated at RT for 1 hour. The samples were centrifuged to separate the cells from the supernatant and both were counted in a calibrated gamma well counter to quantify bound and unbound SHAL. Error bars are included for each data point, but in the majority of the cases the error is smaller than the data point and the error bar is not visible.

Analyses of the unwashed cell pellets showed that both the parent SHAL and the hexa-arginine SHAL are bound by Raji cells. Cell associated SHAL increased linearly with increasing SHAL concentration in the media for both SHALs (FIG. 26), and the amount of bound SHAL showed no evidence of reaching saturation over the range of SHAL concentration tested. Raji cells treated with the hexa-arginine SHAL, in contrast to those treated with the parent SHAL, bound twice as much SHAL (Table 9). A larger proportion of the hexa-arginine SHAL (67%) was also retained by the cells after washing when compared to the parent SHAL (~46%), leading to a final hexa-arginine SHAL content three times that of its parent.

TABLE 9

Retention (residualization) of bound SHAL by Raji cells.

| SHAL | pmoles SHAL Bound/$10^6$ cells | | Percent SHAL Retained |
|---|---|---|---|
| | unwashed | Washed | |
| $(DvLPBaPPP)_2LLDo$ | 0.568 ± 0.091 | 0.263 ± 0.000 | 46 |
| $(DvLPBaPPP)_2LArg_6$-AcLLDo | 1.300 ± 0.038 | 0.876 ± 0.017 | 67 |

Figure 27:
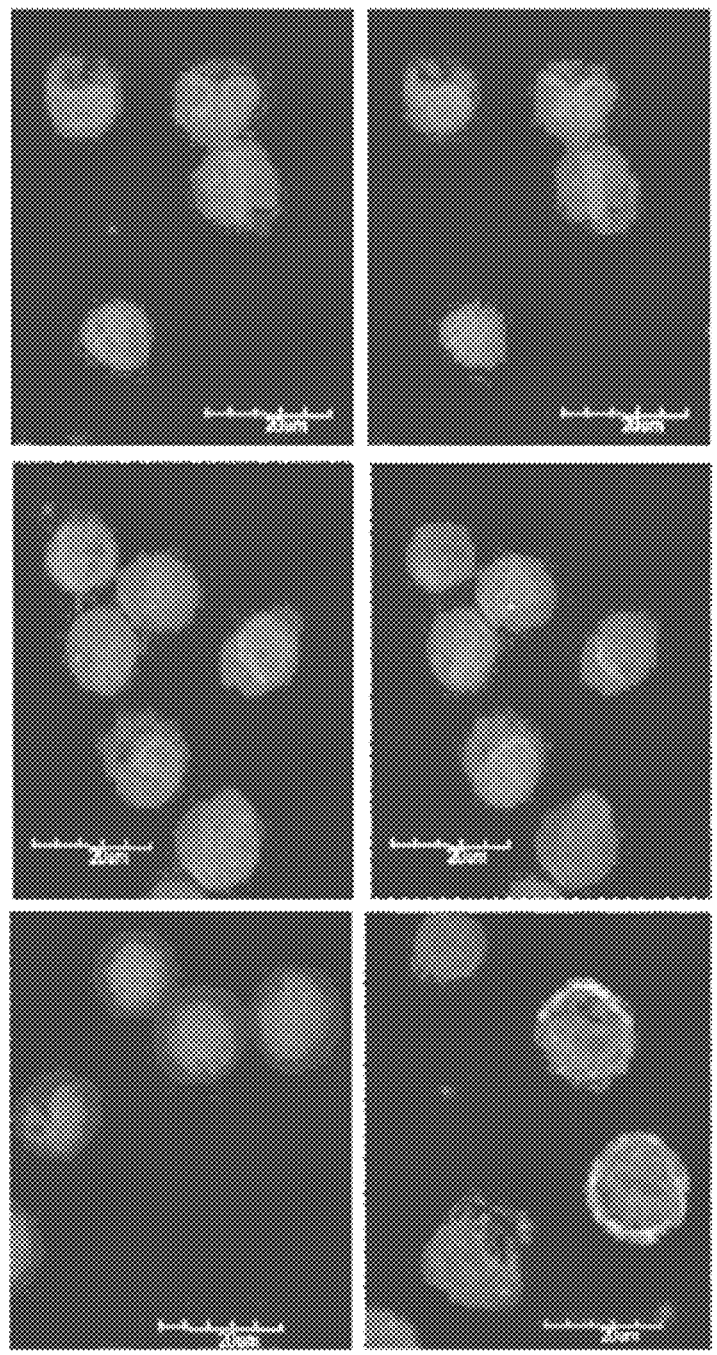
FIG. 27 shows fluorescent 3-D confocal microscopy of parent SHAL (DvLPBaPPP)$_2$LLDo (top row) binding to live Raji cells compared to the hexa-arginine analog (DvLPBaPPP)$_2$LArg$_6$AcLLDo (middle row). Two mid-cell focal planes within the Raji cells are shown (left to right). Jurkat's cells treated with (DvLPBaPPP)$_2$LArg$_6$AcLLDo (left panel, bottom row) show minimal SHAL uptake. Lym-1 (right panel, bottom row) exhibits primarily cell surface membrane binding to Raji cells. The parent SHAL shows intracellular binding, while the hexa-arginine analog demonstrates not only marked cytoplasmic binding but also intranuclear targeting. DAPI is used as the nuclear stain and AlexaFlor 610 demonstrates the location of SHAL in these merged sequential laser images.

Identical samples of cells used in experiments shown in FIG. 27 were incubated as described in above with 5.3 pmoles of $_{111}$In-labeled $(DvLPBaPPP)_2LLDo$ or $(DvLPBaPPP)_2LArg_6AcLLDo$ and then washed two times with BSA/buffer. The cell pellets were then counted to provide estimates of SHAL remaining bound after washing.

SHAL Localization by 3-D Confocal Microscopy.

Fluorescence images collected at focal planes near the center of Raji cells treated with biotinylated forms of the parent and hexa-arginine SHALs for only an hour confirmed that both SHALs were taken up by Raji cells (FIG. 27). In contrast to Lym-1 antibody, which binds to HLA-DR10 on the cell surface, the sectioned images taken from the center of the cells showed that both SHALs were localized inside Raji cells and distributed throughout the cytoplasm. Raji cells took up significantly more of the hexa-arginine SHAL than the parent SHAL, as evidenced by the more intense staining of the cytoplasm of cells treated with equivalent concentrations of the two SHALs. SHAL uptake was not observed in control Jurkat's cells (cells lacking HLA-DR10). A fraction of the hexa-arginine SHAL also appeared to be associated with the nucleus. Nuclear staining was not observed in cells treated with the parent SHAL.

Discussion

Numerous cell penetrating peptides (CPPs) derived from viral and other proteins that traverse cell and nuclear membranes have been employed as shuttles to improve the efficiency of transport of liposomes, exogenous proteins and nucleic acids, and other molecules into the cytoplasm and nuclei of cells (Schwarze et al. (1999) *Science* 285:1569-1572; Torchilin et al. (2003) *Proc. Natl. Acad. Sci., USA*, 100:1972-1977; Tseng et al. (2002) *Mol Pharmacol* 62:864-872; Phelan et al. (1998) *Nat Biotechnol* 16:440-443; Avrameas et al. (1998) *Proc. Natl. Acad. Sci., USA*, 95:5601-5606; Futaki (2005) *Adv Drug Deliv Rev* 57:547-558; Han et al. (2001) *Mol Cells* 12:267-271; Kim et al. (2007) *Int Pharm* 335:70-78; Tung and Weissleder (2003) *Adv Drug Deliv Rev* 55:281-294; Midoux et al. (1993) *Nucleic Acids Res* 21:871-878; Kamada et al. (2007) *Biol Pharm Bull* 2007, 30:218-223). Studies characterizing the efficiency of internalization of different CPP sequences, all of which have a high content of arginine residues (Futaki (2006) *Biopolymers* 84:241-249), have shown that arginine homopolymers containing as few as six arginine residues are highly effective in transporting small organic molecules (Kirschberg et al. (2003) *Org Lett* 5:3459-3462; Rothbard et al. (2000) *Nat*

Med 6:1253-1257) and large proteins into cells (Futaki et al. (2001) *J Biol Chem* 276:5836-5840).

In an effort to develop SHALs that are more efficiently internalized and residualized by the cells they target, we synthesized a hexa-arginine conjugate of (DvLPBaPPP)$_2$LLDo, a SHAL containing the two ligands dabsylvaline (Dv) and N-benzoyl-L-arginyl-4-amino benzoic acid (Ba) that had been shown previously to bind selectively to HLA-DR10 expressing cell lines (Balhorn et al. (2007) *Clin Cancer Res* 13:5621s-5628s). Hexa-arginine was chosen as the first shuttle sequence to be tested for its ability to facilitate the transport of SHALs into cells because it could be conjugated to a dimeric SHAL without changing its molecular mass significantly, thereby preserving the desirable properties of the SHAL as a small molecule therapeutic. Surface Plasmon resonance experiments comparing the binding of the SHAL and the hexa-arginine SHAL analog to purified HLA-DR10 protein showed that the addition of the hexa-arginine peptide to the dimeric SHAL did not interfere with SHAL binding to the protein.

3-D Confocal microscopy experiments revealed that both the parent SHAL and its hexa-arginine analog were taken up and internalized by HLA-DR10 expressing Raji cells. SHAL uptake was not observed in Jurkat's cells, a cell line lacking HLA-DR10. Optical sections taken through Raji cells showed that the binding of the SHALs was not confined to the cell surface, as is characteristic of Lym-1 antibody binding. Mid-plane sections taken from cells treated with the SHALs showed the SHAL-associated fluorescence to be distributed throughout the interior of the cells. In some images, areas of high SHAL concentration within the cytoplasm occasionally appeared to be associated with small organelle-like structures. The cytoplasm-associated fluorescence was significantly higher in Raji cells treated with the hexa-arginine SHAL analog, suggesting the addition of the hexa-arginine peptide enhanced cell uptake of the SHAL.

Experiments comparing the binding of $^{111}$In-labeled (Dv-LPBaPPP)$_2$LLDo and (DvLPBaPPP)$_2$LArg$_6$AcLLDo to live Raji cells confirmed that the hexa-arginine tag enhanced SHAL uptake. The presence of the tag also increased the amount of $^{111}$In-labeled SHAL that was retained by Raji cells. The amount of SHAL retained after washing did not reach saturation over the concentration range tested, suggesting that even higher concentrations of SHAL may be accumulated inside HLA-DR10 expressing cells than achieved in these experiments. At the highest concentration of hexa-arginine SHAL tested in the cell binding studies, the amount of residualized SHAL was equivalent to ~1.1×10$^6$ SHAL molecules per cell—the same number of HLA-DR10 molecules reported previously to be present on the surface of each Raji cell (Epstein et al. (1987) *Cancer Res* 47:830-840). These results, together with the confocal images showing the majority of the hexa-arginine SHAL is internalized, indicate that a significant fraction of the SHAL may be bound to the pool of HLA-DR10 known to be present inside the cell.

The observed enhancement in residualization of $^{111}$In-labeled hexa-arginine SHAL by Raji cells and the potential association of a fraction of the $^{111}$In-label with the nucleus are also important because radioisotope internalization and residualization have been shown to be highly advantageous for cancer therapy (Brouwers et al. (2003) *Clin Cancer Res* 9:3953S-3960S; Chen et al. (2006) *J Nucl Med* 47:827-836; Michel et al. (2002) *Clin Cancer Res* 8:2632-2639; Stein et al. (2995) *Clin Cancer Res* 11:2727-2734). Cancer therapeutics have been linked to a variety of radioisotopes that emit beta particles, alpha particles or Auger electrons. The range of beta emissions from isotopes routinely used in radioimmunotherapy, such as iodine-131, yttrium-90, and rhenium-188, extend for several millimeters, and therapeutics carrying these radionuclides create a "crossfire" (DeNardo (2005) *Semin Oncol.*, 32:S27-35; Bischof 92003) *Leuk Lymphoma* 44 Suppl 4:S29-36) or "bystander" (Boyd et al. (2006) *J Nucl Med* 47:1007-1015) effect destroying malignant cells to which the targeting agent is not directly bound. In this way, beta-emitters can potentially overcome resistance due to antigen-negative tumor cells. These characteristics make beta-particle therapy better suited for treating bulky tumors or large-volume disease. However, longer-ranged beta emissions can also destroy nearby normal cells.

The internalization of targeting agents such as the hexa-arginine SHAL (DvLPBaPPP)$_2$LArg$_6$AcLLDo can be exploited as a means of introducing Auger electron-emitting $^{111}$In into the cytoplasm and nucleus of cells where the Auger electrons have a very short, subcellular path length and high linear energy transfer (Bodei et al. (2003) *Cancer Biother Radiopharm* 18:861-877; Kassis (2003) *J Nucl Med* 44:1479-1481; McDevitt et al. (1998) *Eur J Nucl Med* 25:1341-1351). The radiation absorbed dose to the nucleus has been estimated to be 2-fold and 35-fold greater when $^{111}$In decays in the nucleus compared to when decay occurs in the cytoplasm or on the cell surface, respectively (Goddu et al. (1994) *J Nucl Med* 35:303-316; Hindorf et al. (2007) *Cancer Biother Radiopharm* 22:357-366). These properties render $^{111}$In and other Auger electron-emitters highly cytotoxic and damaging to DNA when they decay in close proximity to the cell nucleus (Costantini et al. (2007) *J Nucl Med* 48:1357-1368). By coupling Auger emitters to highly selective, residualizing targeting agents that accumulate to high concentrations inside tumor cells, a very powerful class of therapeutics may be developed that are more effective in treating many types of metastatic cancer.

Conclusions

The enhancement in hexa-arginine SHAL internalization by HLA-DR10 expressing lymphoma cells and the magnitude of the increase in SHAL residualization achieved by conjugating a hexa-arginine peptide to the SHAL are important because they show that small molecules such as SHALs can be designed to deliver radionuclides to malignant cells under conditions that lead to residualization of significant concentrations of radionuclide inside the cell. SHALs carrying Auger-emitting radionuclides may provide an alternative approach for increasing the therapeutic index achieved with SHALs beyond that attained by the accumulation of radionuclide-tagged targeting agents on the surface of the tumor cell. These results are also exciting because of the relevance of the SHAL-based approach to treating other forms of cancer. Internalizing SHALs targeting under-glycosylated MUC1, the androgen receptor and other tumor specific cell surface proteins that residualize the radioisotopes they carry could also be developed as small molecule therapeutics for a wide variety of other types of metastatic cancer.

Abbreviations used in this example.

Ac, acetate; Ba, N-benzoyl-L-arginyl-4-amino benzoic acid; Boc, tertiary butyloxycarbonyl; BSA, bovine serum albumin; CAE, cellulose acetate electrophoresis; CPP, cell penetrating peptide; DAPI, 4',6-diamidino-2-phenylindole; Dde, 1-(4,4-dimethyl-2,6-dixoxcyclohex-1-ylidene)ethyl; DIEA, N,N Diisopropyl-ethylamine; DMF, dimethylformamide; DMSO, dimethylsulfoxide; DOTA, 1,4,7,10-tetraazacyclododecane-1,4,7,10-tetraacetic acid; Dv, dabsylvaline; EDTA, ethylenediaminetetraacetic acid; ESI-MS, electrospray ionization mass spectrometry; Fmoc, fluorenylmethyloxy; HEPES, 4-(2-hydroxyethyl)-1-piperazineethanesulfonic acid; HPLC, high performance liquid chromatography; MeCN, acetonitrile; NHS, N-hydroxysuccinimide; Pbf, 2,2,4,6,7-Pentamethyldihydrobenzofuran-5-sulfonyl; PBS, phosphate buffered saline; PF6, hexafluorophosphate; RP-HPLC, reversed phase high performance liquid chromatography; SDS, sodium dodecylsulfate; SHAL, selective high affinity ligand; TFA, trifluoroacetic acid; TLC, thin layer chromatography.

Example 6

Molecular Specific and Cell Selective Cytotoxicity Induced by a Novel Synthetic HLA-DR Antibody Mimic for Lymphoma and Leukemia Summary.

Like rituximab, monoclonal antibodies reactive with human leukocyte antigen have potent antilymphoma activity. However, size limits their vascular and tissue penetration. To mimic monoclonal antibody binding, nanomolecules have been synthesized, shown specific for the β subunit of HLA-DR10, and selective for cells expressing this protein. Selective high affinity ligands (SHALs) containing the 3-(2-([3-chloro-5-trifluoromethyl)-2-pyridinyl] oxy)-anilino)-3-oxopropanoic acid (Ct) ligand residualized and had antilymphoma activity against expressing cells. Herein, we show the extraordinary potency in mice with human lymphoma xenografts of a tridentate SHAL containing this ligand. After titrating antilymphoma activity in cell culture, a randomized preclinical study of a tridentate SHAL containing the Ct ligand was conducted in mice with established and aggressive human lymphoma xenografts. Mice having HLA-DR10 expressing Raji B- or Jurkat's T-lymphoma xenografts were randomly assigned to receive either treatment with SHAL at a dose of 100 ng i.p. weekly for 3 consecutive weeks, or to be untreated. Primary end-points were cure, overall response rates and survival. Toxicity was also evaluated in these mice, and a USFDA general safety study was conducted in healthy Balb/c mice. In Raji cell culture, the threshold and $IC_{50}$ concentrations for cytotoxic activity were 0.7 and 2.5 nmol (pm/ml media), respectively. When compared to treated Jurkat's xenografts or untreated xenografts, Raji xenografts treated with the SHAL showed an 85% reduction in hazard of death (P=0.014; 95% confidence interval 32-95% reduction). There was no evidence for toxicity even after i.p. doses 2000 times greater than the treatment dose associated with cure of a majority of the mice with Raji xenografts. When compared with control groups, treatment selectively improved response rates and survival in mice with HLA-DR10 expressing human lymphoma xenografts at doses not associated with adverse events and readily achievable in patients.

Introduction

Cell surface proteins, such as CD20, CD22 and MHCII HLA-DR, have proven to be attractive targets for therapeutics for non-Hodgkin's lymphoma (NHL). One of these proteins, human leukocyte antigen (HLA) is upregulated on the surface of malignant B lymphocytes when compared to normal B lymphocytes. Moreover, intracellular HLA-DR protein is even more abundant. HLA-DR proteins serve as transmembrane and cytoplasmic signaling receptors and as peptide shuttles for the immune system (Leveilie et al. (2002) Ear. J. Immunol. 32: 2282-2289; Klemm et al. (1998) Annu. Rev. Immunol., 16: 569-592; Lane et al. (1990) J. Immunol., 144: 3684-3692). The monoclonal antibody (MAb), Lym-1, binds to a well-characterized epitope on the β subunit of HLA-DR and reacts with lymphoma tissue from about 90 and 50% of patients with B-cell lymphoma and leukemia, respectively (DeNardo et al. (1998) J. Clin. Oncol., 16: 3246-3256; Rose et al. 91996) Cancer Immunol. Immunother., 43: 26-30; Rose et al. (1999) Mol. Immunol., 36: 789-797). Although binding is restricted to the cell surface (Epstein et al. (1987) Cancer Res 47: 830-840), Lym-1 is highly active against malignant B cells in culture and in mice (DeNardo et al. (2005) Clin. Cancer Res., 11: 7075-7079; Tobin et al. (2007) Leuk. Lymphoma 48: 944-956, 2007; Zhang et al. (2007) Cancer Biother. Radiopharm, 22: 342-356).

To mimic MAb binding to HLA-DR10, while decreasing size, a series of selective high affinity ligands (SHALs)<5 kDa in size have been synthesized to bind in the Lym-1 epitopic region of the β subunit of HLA-DR protein based on in silico modeling and experimental studies. Bidentate versions of these novel nanomolecules showed many desired characteristics in vitro and in mice (Balhorn et al. (2007) Clin. Cancer Res., 13(Suppl. 18): S5621-S5628; DeNardo et al. (2007) J. Nucl. Med., 48: 1338-1347) but had no anti-lymphoma activity (West et al. (2006) Cancer Biother. Radiopharm., 21: 645-654). Strikingly, a tridentate SHAL containing the Ct ligand (3-(2-([3-chloro-5-trifluoromethyl)-2-pyridinyl]oxy)-anilino)-3-oxopropanionic acid) residualized inside and was cytotoxic for B-lymphoma cells in culture. Here, we titrate the cell selective antilymphoma activity of this SHAL, demonstrate its remarkable efficacy, selectivity and safety in mice with human lymphoma xenografts and show electron microscopic evidence for SHAL-induced autophagy.

Materials and Methods

Reagents and Cell Lines.

Murine (Peregrine Pharmaceuticals, Tustin, Calif.) and chimeric (A. Epstein, Los Angeles, Calif.) Lym-1, that bind to the β subunit of HLA-DR10 expressed on malignant B-cells (Epstein et al. (1987) Cancer Res 47: 830-840), and HLA-DR10 protein isolated from Raji Burkitt's B-cells using a Lym-1 affinity column, as described previously (Balhorn et al. (2007) Clin. Cancer Res. 13(Suppl. 18): S5621-S5628) were used as references. An HLA-DR10 expressing human B lymphoma cell line, Raji (American Type Culture Collection, Manassas, Va.), grown in RPMI-1640 with 10% fetal calf serum, supplemented with sodium pyruvate, non-essential amino acids and antibiotics (Gibco/Invitrogen, Carlsbad, Calif.), at 37° C. in a humidified, 5% $CO_2$ atmosphere and a non-expressing human T lymphoma cell line, Jurkat's (American Type Culture Collection, Manassas, Va.), grown as recommended by ATCC, were used for these experiments.

Drug Design and Chemistry.

Using homology modeling, HLA-DR amino acid residues critical for Lym-1 binding were mapped on a 3-D model of the HLA-DR10β subunit (Balhorn et al. (2007) Clin. Cancer Res., 13(Suppl. 18): S5621-S5628). Cavities within the Lym-1 epitopic surface of the protein were identified using SPHGEN (Kuntz et al. (1982) J. Mol. Biol. 161: 269-288; Desjarlais et al. (1988) J. Med. Chem., 31: 722-729). After computational ligand docking for each of the cavities, a combination of NMR spectroscopy, surface plasmon resonance (BIAcore 3000; Biacore, Piscataway, N.J.) and competitive binding experiments were used to confirm ligand binding to HLA-DR10 protein. Sets of ligands were then linked to create a SHAL, as described previously (Balhorn et al. (2007) Clin. Cancer Res., 13(Suppl. 18): S5621-S5628). Each SHAL was synthesized on chlorotritylchloride resin in a polyethylene column (Pierce Biotechnology, Inc.) using Fmoc solid phase chemistry to conjugate PEG monomer units and selected ligands through the alpha and epsilon amines of the N-terminal lysine. To synthesize the tridentate SHAL, a dabsylvaline (Dv) ligand was attached to the terminal amine of a PEG spacer conjugated to the alpha amine of the 2nd lysine residue and a 4-[4-(4-chlorobenzyl) piperazino]-3-nitrobenzenecarboxylic acid (Cb) ligand was attached to the terminal amine of a PEG conjugated to the alpha amine of the 3rd lysine. Lastly, the Ct ligand was also attached to the epsilon amine of the 3rd lysine (FIG. 28). Conversion to DOTA (or biotinylated) SHAL derivatives was accomplished, as described previously. The reaction was monitored by analytical high performance liquid chromatography (HPLC), and the DOTA (or biotinylated) derivatives were purified using reverse phase, high performance liquid chromatography (RP-HPLC). Analytic electrospray ionization-mass spectrometry (Agilent 1100 instrument, Waters Symmetry C18 column) was used to confirm the elemental and mass composition of the SHAL (molecular weight within 0.07% of the theoretical molecular weight). To examine SHAL binding to isolated or recombinant HLA-DR10 protein, surface plasmon resonance experiments were conducted, as previously described (Id.). SHAL binding was better than nanomolar and was blocked by Lym-1 addition.

Cytotoxicity Assay.

Raji cells harvested in log growth phase were centrifuged, resuspended in fresh media and counted in 10% trypan-blue dye to determine initial and subsequent viability, as previously described (West et al. (2006) *Cancer Biother. Radiopharm.*, 21: 645-654). When untreated, cells continued to multiply and nonviable cells, initially <5% of total cells, remained so over the course of the assays. To titrate cytotoxic activity, biotinylated tridentate SHAL at concentrations ranging between 0 and 7 nM (pm/ml media) was incubated with $0.5\times10_6$ cells/ml at 37° C. in a 5% $CO_2$, humidified atmosphere (NAPCO, Portland, Oreg.). After 1, 2 and 3 days, cells were resuspended in trypan blue dye and counted in a hemocytometer. The fractional viability and absolute number of viable and non-viable cells/ml were determined.

Efficacy and toxicity in mice.

Seven- to nine-week old female, athymic Balb/c nu/nu mice (Harlan Sprague Dawley, Inc., Frederick, Md.) were maintained according to University of California animal care guidelines under pathogen-free conditions and on a normal ad libitum diet. Raji or Jurkat's cells harvested in log phase and having >95% viability were implanted ($6\times10_6$ cells) subcutaneously in the lower abdomen 3-4 days after the mice were irradiated (400 cGy) to suppress xenograft rejection. When xenografts reached 20-500 $mm_3$ by caliper measurement, the mice were sorted by xenograft volume into 4 groups: SHAL-treated mice with Raji xenografts, SHAL-treated mice with Jurkat's xenografts, untreated mice with Raji xenografts or untreated mice with Jurkat's xenografts. Each mouse was injected with 100 µl of PBS or 100 ng DOTA-chelated tridentate SHAL i.p. on days 0, 7 and 14. Xenograft volume and survival were monitored for ≥84 days. The mice were also weighed 2-3 times each week for 4 weeks then weekly. Blood counts were measured prior to each SHAL or PBS dose and weekly for 4 weeks after the final dose using a Z Series Coulter Counter (Beckman Coulter Inc., Hialeah, Fla.) and a phase contrast microscope (Zeiss, Jena, Germany).

Xenograft volumes were calculated by the formula for hemiellipsoids (DeNardo et al. (1997) *Clin. Cancer Res.* 3:71-79). Responses were characterized as a cure, xenograft completely disappeared and did not regrow by 84 days, the formal censor day (>210 days to the present) complete remission (CR), xenograft disappeared for at least 7 days, but regrew, and partial remission (PR), xenograft volume decreased by at least 75% and remained stable for at least 7 days. All cures at 84 days in SHAL-treated mice persisted over a 210-day observation time for the mice. If a xenograft became >2000 mm3, the mouse was euthanized in accordance with University of California animal care guidelines and scored as a disease-related death.

Safety in Mice.

Each of 3 groups of 7 healthy Balb/c mice were given PBS, 20 or 200 µg of DOTA-chelated SHAL i.p., that is, 200 or 2,000 times the SHAL efficacy dose. Immediately prior to intervention, the mice were observed, weighed and blood counts (red, white and platelets) obtained, then the mice were observed daily, weighed 3 times each week and blood counts measured weekly for 4 weeks after intervention.

Electron Microscopy (EM).

Raji xenografts (53-132 $mm^3$) were harvested for EM from mice, untreated (control) and 2, 4 or 24 h after 100 ng of biotinylated SHAL. Xenografts were fixed, as described (18), using 4% paraformaldehyde in 0.1 M Sorenson's phosphate buffer, pH 7.35. After treating with 4% uranyl acetate in 70% ethanol for one hour and LR White acrylic resin overnight, polymerization was achieved in a microwave (Pelco 34700 BioWave, Pella Inc., Redding, Calif.). Ultra-thin sections (Leica Ultracut UCT, Leica, Vienna, Austria) were captured on gold grids, floated on Strepavidin-20 nm gold (BB International from Ted Pella Inc.) rinsed and stained with uranyl acetate and lead citrate before viewing using a Philips CM120 Biotwin Lens (FEI, Hillsboro, Oreg., made in Eindhoven, The Netherlands and Gatan MegaScan, model 794/20, digital camera (2K×2K), Pleasanton, Calif. Gatan BioScan, model 792, Pleasanton, Calif.).

Biostatistical Methods.

Initial analysis compared response rates by exact tests and survival times by log-rank tests for untreated Raji and Jurkat's mice and found no significant differences, so these groups were pooled for subsequent analysis. Response rates for treated Raji, treated Jurkat's and untreated mice were compared by $\chi^2$ and exact tests. Survival times were censored at 84 days for mice who had not died or been euthanized because of tumor growth before that time. Times were summarized descriptively by Kaplan-Meier curves and median survival and 95% confidence limits were obtained by the product-limit estimate. The two treated groups were compared to the untreated using a log-rank test for homogeneity across groups, followed by a proportional hazards model to estimate the effect of treatment compared to no treatment. Analyses were carried out using SAS/SAT® software (SAS Institute, Inc. SAS/STAT Version 9.0. 2004. Cary, N.C.: SAS Institute). All tests were two-sided at level 0.05.

Results

Cytotoxicity Assay.

Figure 29:
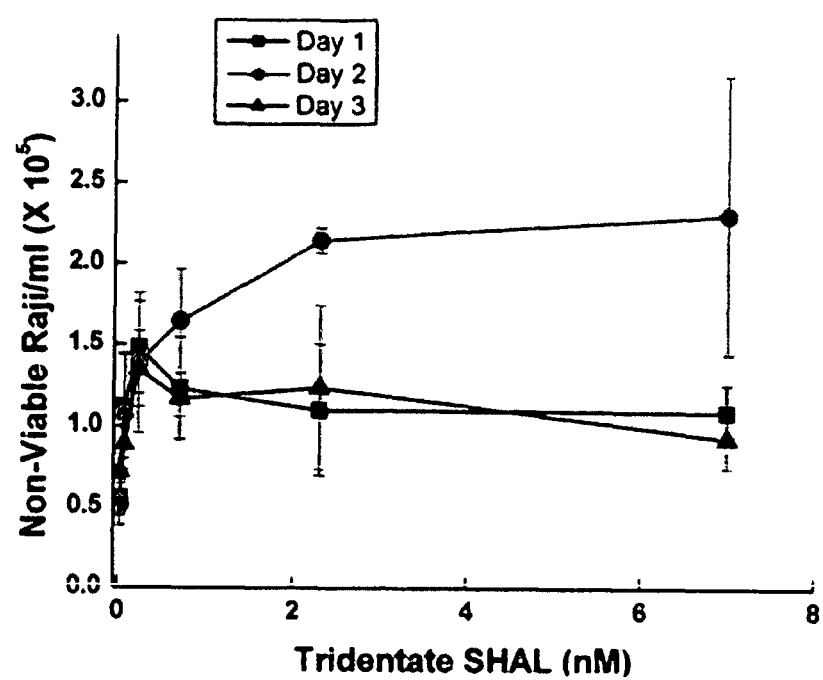
FIG. 29. Titration of SHAL cytotoxic activity in Raji human HLA-DR10 expressing lymphoma cells. Absolute number of non-viable cells observed 1, 2 or 3 days after addition of SHAL at concentrations shown. SHAL threshold and $IC_{50}$ concentrations were determined at 2 days to be 0.7 and 2.5 nM (pm/ml media), respectively (mean±SD).

When untreated, non-viable (dead) Raji cells remained <5% of the total cells over the 3 days of observation. Raji cells treated with SHAL (over a concentration range of 0-70 nM (pm/ml media)) showed more dead cells, both fractionally and absolutely, over the 3-day period when compared to the untreated controls. The maximum number of non-viable cells was observed on day 2 at SHAL concentrations between 2.3 and 7 nM, and the threshold and $IC_{50}$ SHAL cytotoxic concentrations were 0.7 and 2.5 nM (pm/ml media), respectively (FIG. 29).

Efficacy and Toxicity.

Figure 30:
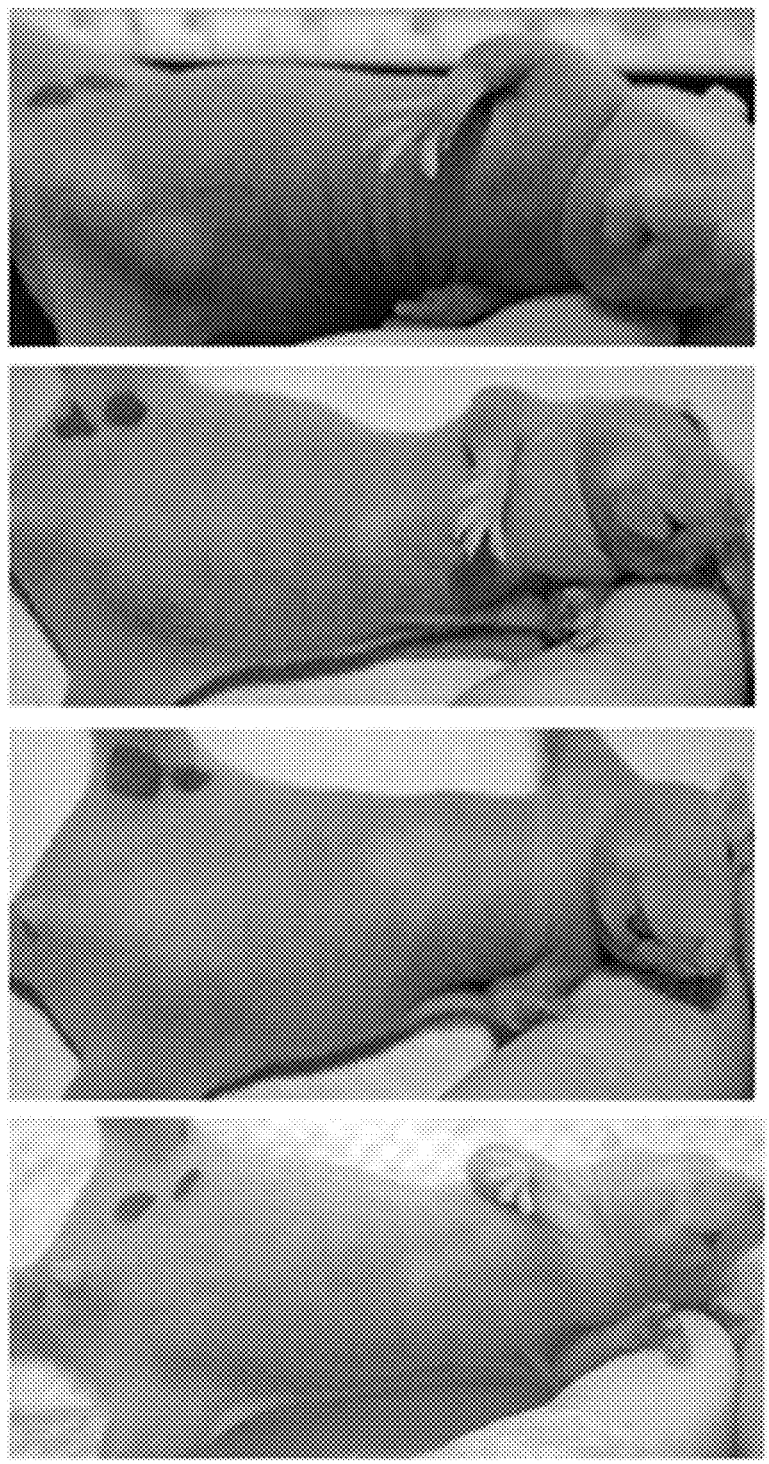
FIG. 30. Photographic evidence for cure in a mouse with a Raji xenograft; before SHAL treatment (upper), one week after the initial and a second 100 ng dose of SHAL i.p. By three weeks after the initial dose the xenograft had completely regressed and represented a cure that persisted over the period of observation of the mouse (>84 days; lower).
Figure 31:
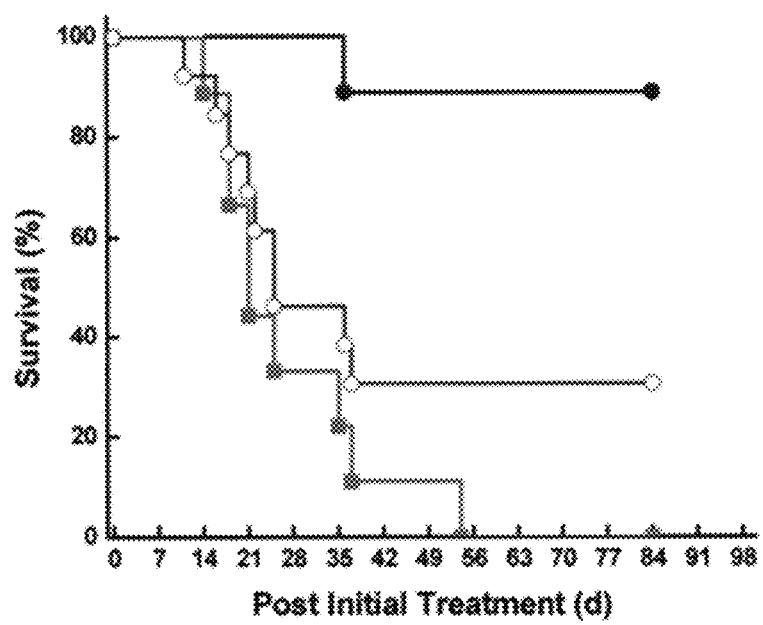
FIG. 31. Overall survival effect of SHAL in mice with established Raji or Jurkat's lymphoma xenografts. Mice with Raji or Jurkat's xenografts were treated with 100 ng SHAL i.p. once weekly for each of 3 consecutive weeks, or untreated. Mice with treated Raji xenografts (dark circle) had the longest survival while mice with treated Jurkat's xenografts (square) did not survive past 56 days. Two untreated mice (empty circle) with enlarging xenografts survived 84 days.

Regression in treated Raji xenografts typically began ~7 and reached complete remission ~30 days after initial SHAL treatment (FIG. 30). Although censored at 84 days, all cures in SHAL-treated Raji xenografts have persisted to the present, seemingly representing permanent cures. Because there were no significant differences in response and survival of untreated Raji and Jurkat's mice (P>0.08) they were combined for comparison to treated mice. Mice with Raji xenografts and treated with SHAL had a 69% cure rate and 77% overall response rate, significantly better than treated mice with Jurkat's xenografts (0%) and untreated mice (15% response) (P<0.001) (Table 10). The median survival times were 25 days for untreated mice and 21 days for treated mice with Jurkat's xenografts. The median survival time for treated mice with Raji xenografts was not estimable because almost all mice were alive at 84 days (FIG. 31). The proportional hazards model estimated that Raji mice had ~85% reduction in hazard of death compared to untreated and treated Jurkat's mice (P<0.001).

TABLE 10

Athymic mice with lymphoma xenografts, SHAL treated or untreated.

| Treatment Group | Mice | Response (%) Cure (%) | ORR (%)[a] |
|---|---|---|---|
| Raji | 13 | 69 | 77 |
| Jurkat's | 9 | 0 | 0 |
| Untreated | 13 | 15 | 15 |

[a]Overall response rate.

Safety in Mice.

All of the mice in the general safety study, including those given 2000 times the SHAL dose used in the efficacy trial, gained weight, showed stable blood counts and no adverse effects during 4 weeks of observation, thereby exceeding the requirements of the US FDA 'general safety' test guidelines.

Electron Microscopy.

Figure 32:
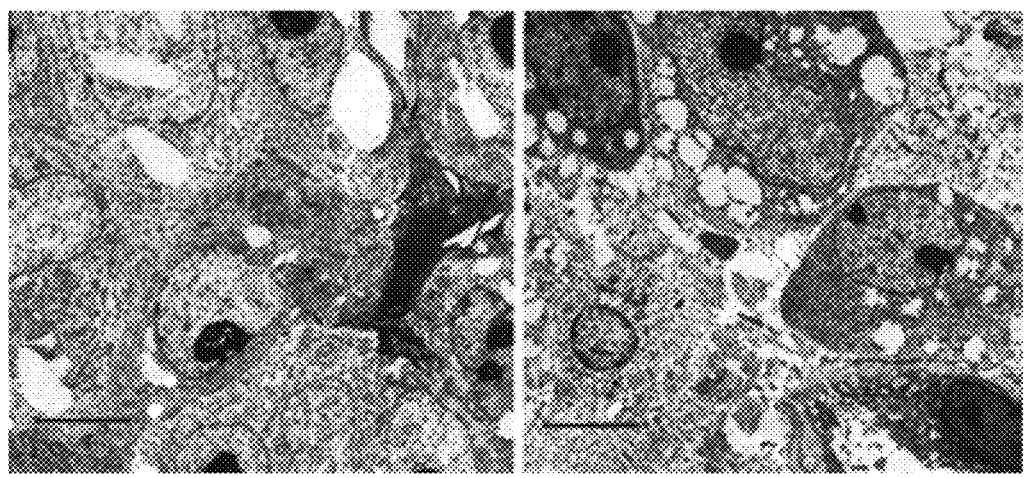
FIG. 32. Electron micrographs of Raji xenografts excised from an untreated mouse and a mouse 24 h after SHAL treatment. Cellular structures were normal for this aggressive xenograft, untreated (left), whereas cells in the SHAL-treated xenograft showed condensed and fragmented chromatin and loss of cytoplasmic structures consistent with autophagic death (right) (bar, 5 µm).

Raji xenograft EM from untreated mice showed healthy cells having well-defined cellular and nuclear membranes, and cytoplasmic organelles, including reticular endothelium, Golgi, and liposomes (FIG. 32). In contrast, Raji EM, harvested after SHAL treatment, were characterized by highly condensed nuclear chromatin and fragmented organelles, findings consistent with autophagicy (programmed) cell death.

Discussion

Proteins on the surface of malignant cells have been used to identify them and to serve as targets for therapy and imaging. The class II major histocompatibility, human leukocyte antigens (HLA) are abundant both on the surface and inside malignant B-lymphocytes (Epstein et al. (1987) Cancer Res 47: 830-840). These proteins are major signaling receptors for cell death (Levei et al. (2002) Eur. J. Immunol 32: 2282-2289; Lane et al. (1990) J. Immunol., 144: 3684-3692). Whereas intact MAbs recognize malignant cells selectively, size limits their blood clearance and tissue penetration. Based on predictions from in silico modeling and from empiric testing, small organic ligands have been selected to bind to sites within the Lym-1 MAb epitopic region of HLA-DR10. By covalently linking sets of these ligands together, SHALs have been generated to target B-cell derived lymphomas and leukemias Wok et al. (2007) Bioconjug. Chem., 18: 912-921). These novel nanomolecules mimic the affinity and selectivity of MAbs because of three-dimensional interactions made between multiple ligands in the SHAL and multiple sites located within the epitope of the target protein. SHALs are taken up rapidly by HLA-DR expressing xenografts and clear quickly from normal tissues (DeNardo et al. (2007) J. Nucl. Med., 48: 1338-1347) because the SHAL is ~50 times smaller than an immunoglobulin G molecule. Histochemical analyses has shown that SHALs bind to NHL tissues from patients and from mice (Balhorn et al. (2007) Clin. Cancer Res., 13(Suppl. 18): S5621-S5628). Previous studies have shown that the SHALs readily enter cells, but they do not leave cells that express HLA-DR10 and related HLA-DRs, behaving like a lobster and its trap.

These SHALs cross cell barriers efficiently, seemingly unaffected in HLA-DR10 expressing cells by cellular pumping mechanisms. SHALs containing a Ct (3-(2-([3-chloro-5-trifluoromethyl)-2-pyridinyl]oxy)-anilino)-3-oxopropanionic acid) ligand residualize inside and exhibit potent antilymphoma activity against live human HLA-DR10 expressing lymphoma cells (DeNardo et al. (2007) J. Nucl. Med., 48: 1338-1347). The present experiments demonstrate that the Ct ligand containing tridentate SHAL that has an $IC_{50}$ of 2.5 nM (pm/ml media) for HLA-DR10 expressing cells in culture also exhibits remarkable efficacy in mice with Raji xenografts. Permanent cures were achieved in 69% of these mice at a SHAL treatment dose 2000-fold less than the maximum dose tested and confirmed to be safe in healthy mice. The antilymphoma effect was only observed in mice with xenografts expressing HLA-DR10; Jurkat's xenografts were not affected by SHAL treatment. Because mice treated with 2000-fold more SHAL did not exhibit signs of adverse events, the SHAL seems to have an exceptional margin of safety as a potential therapeutic. It will be important in the future to conduct a dose response study with the tridentate SHAL in mice to ascertain whether or not the cure rate can be increased with a larger SHAL dose.

Electron micrographs of xenograft tissue from mice treated with the SHAL confirmed the SHAL's cytotoxicity to the Raji lymphoma cells. Extensive vacuolization and loss of cell structure suggest the possibility that SHAL binding to HLA-DR induced cell signaling that ultimately led to apoptosis and autophagic cell death. More extensive study will be required to confirm this hypothesis and identify the mechanism of action of the SHAL.

The results provide convincing evidence that SHALs have extraordinary potential as novel nanomolecules for targeting lymphoma and leukemia for molecular therapy. SHALs represent an attractive alternative to their biological counterparts, because these chemicals are ~50 times smaller, less expensive, easier to produce with consistency, stable and expected to have a long shelf-life and be effective when given orally. Furthermore, SHAL-based therapeutics can transport and residualize other agents near critical sites inside these malignant cells. The SHAL production platform is efficient, flexible, and permits rapid synthesis and modifications.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

SEQUENCE LISTING

<160> NUMBER OF SEQ ID NOS: 35

<210> SEQ ID NO 1
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Asp Tyr Lys Asp Asp Asp Asp Lys
1               5

<210> SEQ ID NO 2
<211> LENGTH: 20
<212> TYPE: PRT
<213> ORGANISM: Homo sapiens

<400> SEQUENCE: 2

Gly Val Thr Ser Ala Pro Asp Thr Arg Pro Ala Pro Gly Ser Thr Ala
1               5                   10                  15

Pro Pro Ala His
            20

<210> SEQ ID NO 3
<211> LENGTH: 237
<212> TYPE: PRT
<213> ORGANISM: Homo sapiens

<400> SEQUENCE: 3

Gly Asp Thr Arg Pro Arg Phe Leu Glu Glu Val Lys Phe Glu Cys His
1               5                   10                  15

Phe Phe Asn Gly Thr Glu Arg Val Arg Leu Leu Glu Arg Arg Val His
                20                  25                  30

Asn Gln Glu Glu Tyr Ala Arg Tyr Asp Ser Asp Val Gly Glu Tyr Arg
            35                  40                  45

Ala Val Thr Glu Leu Gly Arg Pro Asp Ala Glu Tyr Trp Asn Ser Gln
        50                  55                  60

Lys Asp Leu Leu Glu Arg Arg Ala Ala Val Asp Thr Tyr Cys Arg
65                  70                  75                  80

His Asn Tyr Gly Val Gly Glu Ser Phe Thr Val Gln Arg Arg Val Gln
                85                  90                  95

Pro Lys Val Thr Val Tyr Pro Ser Lys Thr Gln Pro Leu Gln His His
            100                 105                 110

Asn Leu Leu Val Cys Ser Val Asn Gly Phe Tyr Pro Gly Ser Ile Glu
        115                 120                 125

Val Arg Trp Phe Arg Asn Gly Gln Glu Glu Lys Thr Gly Val Val Ser
    130                 135                 140

Thr Gly Leu Ile Gln Asn Gly Asp Trp Thr Phe Gln Thr Leu Val Met
145                 150                 155                 160

Leu Glu Thr Val Pro Gln Ser Gly Glu Val Tyr Thr Cys Gln Val Glu
                165                 170                 175

His Pro Ser Val Met Ser Pro Leu Thr Val Glu Trp Arg Ala Arg Ser
            180                 185                 190

Glu Ser Ala Gln Ser Lys Met Leu Ser Gly Val Gly Gly Phe Val Leu
        195                 200                 205

Gly Leu Leu Val Leu Gly Ala Gly Leu Phe Ile Tyr Phe Arg Asn Gln
    210                 215                 220

```
Lys Gly His Ser Gly Leu Pro Pro Thr Gly Phe Leu Ser
225                 230                 235

<210> SEQ ID NO 4
<211> LENGTH: 197
<212> TYPE: PRT
<213> ORGANISM: Homo sapiens

<400> SEQUENCE: 4

Gly Asp Thr Arg Pro Arg Phe Leu Trp Gln Leu Lys Phe Glu Cys His
1               5                   10                  15

Phe Phe Asn Gly Thr Glu Arg Val Arg Leu Leu Glu Arg Cys Ile Tyr
            20                  25                  30

Asn Gln Glu Glu Ser Val Arg Phe Asp Ser Asp Val Gly Glu Tyr Arg
        35                  40                  45

Ala Val Thr Glu Leu Gly Arg Pro Asp Ala Glu Tyr Trp Asn Ser Gln
    50                  55                  60

Lys Asp Leu Leu Glu Gln Arg Arg Ala Ala Val Asp Thr Tyr Cys Arg
65                  70                  75                  80

His Asn Tyr Gly Val Gly Glu Ser Phe Thr Val Gln Arg Arg Val Glu
                85                  90                  95

Pro Lys Val Thr Val Tyr Pro Ser Lys Thr Gln Pro Leu Gln His His
            100                 105                 110

Asn Leu Leu Val Cys Ser Val Ser Gly Phe Tyr Pro Gly Ser Ile Glu
        115                 120                 125

Val Arg Trp Phe Arg Asn Gly Gln Glu Glu Lys Ala Gly Val Val Ser
    130                 135                 140

Thr Gly Leu Ile Gln Asn Gly Asp Trp Thr Phe Gln Thr Leu Val Met
145                 150                 155                 160

Leu Glu Thr Val Pro Arg Gly Glu Val Tyr Thr Cys Gln Val Glu His
                165                 170                 175

Pro Ser Val Thr Ser Pro Leu Thr Val Glu Trp Arg Ala Arg Ser Glu
            180                 185                 190

Ser Ala Gln Ser Lys
        195

<210> SEQ ID NO 5
<211> LENGTH: 191
<212> TYPE: PRT
<213> ORGANISM: Homo sapiens

<400> SEQUENCE: 5

Gly Asp Thr Arg Pro Arg Phe Leu Glu Gln Val Lys His Glu Cys His
1               5                   10                  15

Phe Phe Asn Gly Thr Glu Arg Val Arg Phe Leu Asp Arg Tyr Phe Tyr
            20                  25                  30

His Gln Glu Glu Tyr Val Arg Phe Asp Ser Asp Val Gly Glu Tyr Arg
        35                  40                  45

Ala Val Thr Glu Leu Gly Arg Pro Asp Ala Glu Tyr Trp Asn Ser Gln
    50                  55                  60

Lys Asp Leu Leu Glu Gln Lys Arg Ala Ala Val Asp Thr Tyr Cys Arg
65                  70                  75                  80

His Asn Tyr Gly Val Gly Glu Ser Phe Thr Val Gln Arg Arg Val Tyr
                85                  90                  95

Pro Lys Val Thr Val Tyr Pro Ala Lys Thr Gln Pro Leu Gln His His
            100                 105                 110
```

Asn Leu Leu Val Cys Ser Val Asn Gly Phe Tyr Pro Gly Ser Ile Glu
            115                 120                 125

Val Arg Trp Phe Arg Asn Gly Gln Glu Glu Lys Thr Gly Val Val Ser
        130                 135                 140

Thr Gly Leu Ile Gln Asn Gly Asp Trp Thr Phe Gln Thr Leu Val Met
145                 150                 155                 160

Leu Glu Thr Val Pro Arg Gly Glu Val Tyr Thr Cys Gln Val Glu His
                165                 170                 175

Pro Ser Val Thr Ser Pro Leu Thr Val Glu Trp Arg Ala Arg Ser
            180                 185                 190

<210> SEQ ID NO 6
<211> LENGTH: 190
<212> TYPE: PRT
<213> ORGANISM: Homo sapiens

<400> SEQUENCE: 6

Thr Arg Pro Arg Phe Leu Trp Gln Pro Lys Arg Glu Cys His Phe Phe
1               5                   10                  15

Asn Gly Thr Glu Arg Val Arg Phe Leu Asp Arg Tyr Phe Tyr Asn Gln
            20                  25                  30

Glu Glu Ser Val Arg Phe Asp Ser Asp Val Gly Glu Phe Arg Ala Val
        35                  40                  45

Thr Glu Leu Gly Arg Pro Asp Ala Glu Tyr Trp Asn Ser Gln Lys Asp
    50                  55                  60

Ile Leu Glu Gln Ala Arg Ala Ala Val Asp Thr Tyr Cys Arg His Asn
65                  70                  75                  80

Tyr Gly Val Val Glu Ser Phe Thr Val Gln Arg Arg Val Gln Pro Lys
                85                  90                  95

Val Thr Val Tyr Pro Ser Lys Thr Gln Pro Leu Gln His His Asn Leu
            100                 105                 110

Leu Val Cys Ser Val Ser Gly Phe Tyr Pro Gly Ser Ile Glu Val Arg
        115                 120                 125

Trp Phe Leu Asn Gly Gln Glu Glu Lys Ala Gly Asn Val Ser Thr Gly
    130                 135                 140

Leu Ile Gln Asn Gly Asp Trp Thr Phe Gln Thr Leu Val Met Leu Glu
145                 150                 155                 160

Thr Val Pro Arg Gly Glu Val Tyr Thr Cys Gln Val Glu His Pro Ser
                165                 170                 175

Val Thr Ser Pro Leu Thr Val Glu Trp Arg Ala Arg Ser Glu
            180                 185                 190

<210> SEQ ID NO 7
<211> LENGTH: 186
<212> TYPE: PRT
<213> ORGANISM: Homo sapiens

<400> SEQUENCE: 7

Pro Arg Phe Leu Glu Tyr Ser Thr Ser Glu Cys His Phe Phe Asn Gly
1               5                   10                  15

Thr Glu Arg Val Arg Tyr Leu Asp Arg Tyr Phe His Asn Gln Glu Glu
            20                  25                  30

Asn Val Arg Phe Asp Ser Asp Val Gly Glu Phe Arg Ala Val Thr Glu
        35                  40                  45

Leu Gly Arg Pro Asp Ala Glu Tyr Trp Asn Ser Gln Lys Asp Leu Leu
    50                  55                  60

```
Glu Gln Lys Arg Gly Arg Val Asp Asn Tyr Cys Arg His Asn Tyr Gly
 65                  70                  75                  80

Val Val Glu Ser Phe Thr Val Gln Arg Arg Val His Pro Lys Val Thr
                 85                  90                  95

Val Tyr Pro Ser Lys Thr Gln Pro Leu Gln His His Asn Leu Leu Val
                100                 105                 110

Cys Ser Val Ser Gly Phe Tyr Pro Gly Ser Ile Glu Val Arg Trp Phe
                115                 120                 125

Arg Asn Gly Gln Glu Glu Lys Thr Gly Val Val Ser Thr Gly Leu Ile
                130                 135                 140

His Asn Gly Asp Trp Thr Phe Gln Thr Leu Val Met Leu Glu Thr Val
145                 150                 155                 160

Pro Arg Gly Glu Val Tyr Thr Cys Gln Val Glu His Pro Ser Val Thr
                165                 170                 175

Ser Pro Leu Thr Val Glu Trp Arg Ala Arg
                180                 185

<210> SEQ ID NO 8
<211> LENGTH: 227
<212> TYPE: PRT
<213> ORGANISM: Homo sapiens

<400> SEQUENCE: 8

Arg Asp Ser Arg Gly Lys Lys Val Ile Thr Ala Phe Asn Glu Gly Leu
1               5                   10                  15

Lys Gly Gly Gly Gly Ser Leu Val Gly Gly Ser Gly Gly Gly Gly Gly
                20                  25                  30

Ser Arg Phe Trp Phe Leu Glu Tyr Cys Lys Ser Glu Cys His Phe Tyr
                35                  40                  45

Asn Gly Thr Gln Arg Val Arg Leu Ile Val Arg Tyr Phe Tyr Asn Leu
 50                  55                  60

Glu Glu Asn Leu Arg Phe Asp Ser Asp Val Gly Glu Phe Arg Ala Val
 65                  70                  75                  80

Thr Glu Leu Gly Arg Pro Asp Ala Glu Asn Trp Asn Ser Gln Pro Glu
                 85                  90                  95

Phe Leu Glu Gln Lys Arg Ala Glu Val Asp Thr Val Cys Arg His Asn
                100                 105                 110

Tyr Glu Ile Phe Asp Asn Phe Leu Val Pro Arg Arg Val Glu Pro Thr
                115                 120                 125

Val Thr Val Tyr Pro Thr Lys Thr Gln Pro Leu Lys His His Asn Leu
                130                 135                 140

Leu Val Cys Ser Val Ser Asp Phe Tyr Pro Gly Asn Ile Glu Val Arg
145                 150                 155                 160

Trp Phe Arg Asn Gly Lys Glu Glu Lys Thr Gly Ile Val Ser Thr Gly
                165                 170                 175

Leu Val Arg Asn Gly Asp Trp Thr Phe Gln Thr Leu Val Met Leu Glu
                180                 185                 190

Thr Val Pro Gln Gly Glu Val Tyr Thr Cys Gln Val Glu His Pro Ser
                195                 200                 205

Leu Thr Asp Pro Val Thr Val Glu Trp Lys Ala Gln Ser Thr Ser Ala
                210                 215                 220

Gln Asn Lys
225
```

```
<210> SEQ ID NO 9
<211> LENGTH: 18
<212> TYPE: PRT
<213> ORGANISM: Unknown
<220> FEATURE:
<223> OTHER INFORMATION: Description of Unknown: Illustrative
      transduction peptide

<400> SEQUENCE: 9

Ser Gly Glu His Thr Asn Gly Pro Ser Lys Thr Ser Val Arg Trp Val
1               5                   10                  15

Trp Asp

<210> SEQ ID NO 10
<211> LENGTH: 18
<212> TYPE: PRT
<213> ORGANISM: Unknown
<220> FEATURE:
<223> OTHER INFORMATION: Description of Unknown: Illustrative
      transduction peptide

<400> SEQUENCE: 10

Ser Met Thr Thr Met Glu Phe Gly His Ser Met Ile Thr Pro Tyr Lys
1               5                   10                  15

Ile Asp

<210> SEQ ID NO 11
<211> LENGTH: 18
<212> TYPE: PRT
<213> ORGANISM: Unknown
<220> FEATURE:
<223> OTHER INFORMATION: Description of Unknown: Illustrative
      transduction peptide

<400> SEQUENCE: 11

Gln Asp Gly Gly Thr Trp His Leu Val Ala Tyr Cys Ala Lys Ser His
1               5                   10                  15

Arg Tyr

<210> SEQ ID NO 12
<211> LENGTH: 18
<212> TYPE: PRT
<213> ORGANISM: Unknown
<220> FEATURE:
<223> OTHER INFORMATION: Description of Unknown: Illustrative
      transduction peptide

<400> SEQUENCE: 12

Met Ser Asp Pro Asn Met Asn Pro Gly Thr Leu Gly Ser Ser His Ile
1               5                   10                  15

Leu Trp

<210> SEQ ID NO 13
<211> LENGTH: 18
<212> TYPE: PRT
<213> ORGANISM: Unknown
<220> FEATURE:
<223> OTHER INFORMATION: Description of Unknown: Illustrative
      transduction peptide

<400> SEQUENCE: 13

Ser Pro Gly Asn Gln Ser Thr Gly Val Ile Gly Thr Pro Ser Phe Ser
1               5                   10                  15

Asn His
```

<210> SEQ ID NO 14
<211> LENGTH: 18
<212> TYPE: PRT
<213> ORGANISM: Unknown
<220> FEATURE:
<223> OTHER INFORMATION: Description of Unknown: Illustrative
      transduction peptide

<400> SEQUENCE: 14

Ser Ser Gly Ala Asn Tyr Phe Phe Asn Ala Ile Tyr Asp Phe Leu Ser
1               5                   10                  15

Asn Phe

<210> SEQ ID NO 15
<211> LENGTH: 18
<212> TYPE: PRT
<213> ORGANISM: Unknown
<220> FEATURE:
<223> OTHER INFORMATION: Description of Unknown: Illustrative
      transduction peptide

<400> SEQUENCE: 15

Gly Thr Ser Arg Ala Asn Ser Tyr Asp Asn Leu Leu Ser Glu Thr Leu
1               5                   10                  15

Thr Gln

<210> SEQ ID NO 16
<211> LENGTH: 13
<212> TYPE: PRT
<213> ORGANISM: Human Immunodeficiency virus

<400> SEQUENCE: 16

Gly Arg Lys Lys Arg Arg Gln Arg Arg Arg Pro Pro Gln
1               5                   10

<210> SEQ ID NO 17
<211> LENGTH: 16
<212> TYPE: PRT
<213> ORGANISM: Drosophila sp.

<400> SEQUENCE: 17

Arg Gln Ile Lys Ile Trp Phe Gln Asn Arg Arg Met Lys Trp Lys Lys
1               5                   10                  15

<210> SEQ ID NO 18
<211> LENGTH: 17
<212> TYPE: PRT
<213> ORGANISM: Herpes simplex virus

<400> SEQUENCE: 18

Asn Ala Lys Thr Arg Arg His Glu Arg Arg Arg Lys Leu Ala Ile Glu
1               5                   10                  15

Arg

<210> SEQ ID NO 19
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Arg Arg Arg Arg Arg Arg
1               5

```
1               5

<210> SEQ ID NO 20
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Gly Gly Gly Gly Ser
1               5

<210> SEQ ID NO 21
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Arg Glu Asp Leu Lys
1               5

<210> SEQ ID NO 22
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Arg Glu Asp Leu
1

<210> SEQ ID NO 23
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Arg Asp Glu Leu
1

<210> SEQ ID NO 24
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 24

Lys Asp Glu Leu
1

<210> SEQ ID NO 25
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Arg Gly Asp Thr
1

<210> SEQ ID NO 26
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Asp Arg Val Tyr
1

<210> SEQ ID NO 27
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: D-Ala
<220> FEATURE:
<221> NAME/KEY: MOD_RES
<222> LOCATION: (5)..(5)
<223> OTHER INFORMATION: D-Met

<400> SEQUENCE: 27

Tyr Ala Gly Phe Met
1               5

<210> SEQ ID NO 28
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Arg Gly Asp Thr
1

<210> SEQ ID NO 29
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 29

Val Ile His Asn
1

<210> SEQ ID NO 30
<211> LENGTH: 56
<212> TYPE: PRT
<213> ORGANISM: Homo sapiens

<400> SEQUENCE: 30

Pro Asp Thr Arg Pro Ala Pro Gly Ser Thr Ala Pro Pro Ala His Gly
1               5                   10                  15

Val Thr Ser Ala Pro Asp Thr Arg Pro Ala Pro Gly Ser Thr Ala Pro
            20                  25                  30

Pro Ala His Gly Val Thr Ser Ala Pro Asp Thr Arg Pro Ala Pro Gly
        35                  40                  45

Ser Thr Ala Pro Pro Ala His Gly
    50                  55

<210> SEQ ID NO 31
<211> LENGTH: 4
<212> TYPE: PRT
<213> ORGANISM: Artificial Sequence
<220> FEATURE:
<223> OTHER INFORMATION: Description of Artificial Sequence: Synthetic
      4xHis tag

<400> SEQUENCE: 31

His His His His
1

<210> SEQ ID NO 32
<211> LENGTH: 5
<212> TYPE: PRT
<213> ORGANISM: Artificial Sequence
<220> FEATURE:
<223> OTHER INFORMATION: Description of Artificial Sequence: Synthetic
      5xHis tag

<400> SEQUENCE: 32

His His His His His
1               5

<210> SEQ ID NO 33
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 33

His His His His His His
1               5

<210> SEQ ID NO 34
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
```

What is claimed is:

1. A selective high affinity ligand (SHAL) that specifically binds to a cancer cell expressing HLA-DR10, wherein said SHAL comprises the structure:

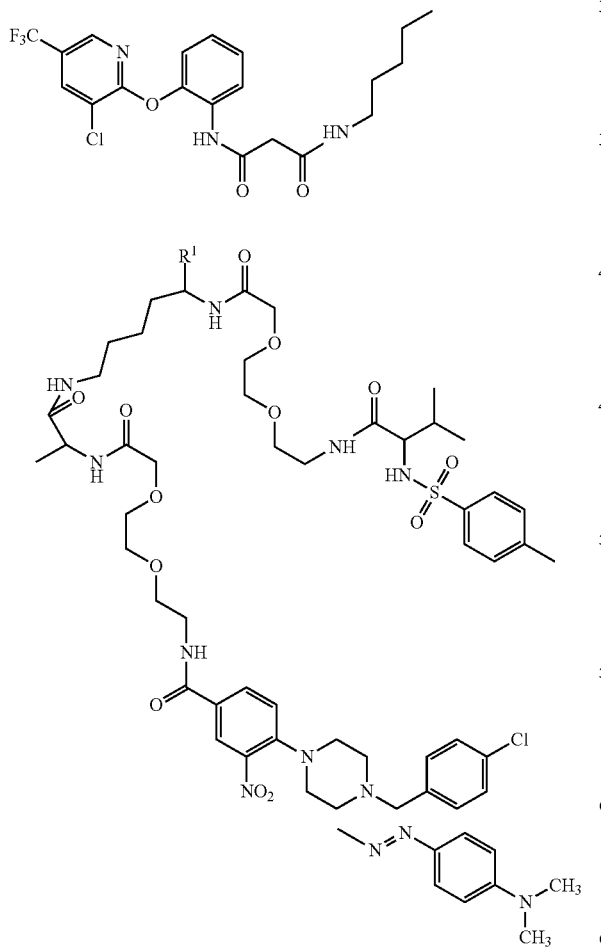

wherein $R^1$ is selected from the group consisting of COOH, a linker, an effector, and a linker attached to an effector, wherein:

when $R^1$ is a linker, the linker is polyethylene glycol, biotin, or lysine; and when $R^1$ is an effector, the effector is selected from avidin, biotin, and a cytotoxin selected from the group of a Diphtheria toxin, a *Pseudomonas* exotoxin, a ricin, an abrin, and a thymidine kinase, a chelate comprising (a) a metal isotope selected from the group of $^{99}$Tc, $^{203}$Pb, $^{67}$Ga, $^{68}$Ga, $^{72}$As, $^{111}$In, $^{113m}$In, $^{97}$Ru, $^{62}$Cu, $^{64}$Cu, $^{52}$Fe, $^{52m}$Mn, $^{51}$Cr, $^{186}$Re, $^{188}$Re, $^{77}$As, $^{90}$Y, $^{67}$Cu, $^{169}$Er, $^{121}$Sn, $^{127}$Te, $^{142}$Pr, $^{143}$Pr, $^{198}$Au, $^{199}$Au, $^{161}$Tb, $^{109}$Pd, $^{165}$Dy, $^{149}$Pm, $^{151}$Pm, $^{153}$Sm, $^{157}$Gd, $^{159}$Gd, $^{166}$Ho, $^{172}$Tm, $^{169}$Yb, $^{175}$Yb, $^{177}$Lu, $^{105}$Rh, and $^{111}$Ag, (b) bismuth 213, or (c) DOTA, 4[[5-(Trifluoromethyl)pyridin-2-yl]oxy]phenyl]N-phenylcarbamate, (R)-2-[4-(5-chloro-3-fluoro-2-pyridyloxy)phenoxy]propionic acid, 2-(((3-chloro-5(trifluoromethyl)pyridin-2-yloxy)phenoxy)methyl)acrylates, 2-(((3-chloro-5(trifluoromethyl)pyridin-2-yloxy)phenyl)methyl)acrylates, 2-(((3-chloro-5(trifluoromethyl)pyridin-2-yloxy)phenyl) methyl)acrylonitriles, 3-(3-chloro-4-{[5-(trifluoromethyl)-2-pyridinyl]oxy}anilino)-3-oxopropanoic acid, Sethoxydim, Clethodim, 5-(Tetradecyloxy)-2-furoic acid, 2-[(2,6-Dichlorophenyl)amino]benzeneacetic acid, 2-[4-(4-Chlorophenoxy)phenoxy]propanoic acid, (RS)-2-{4-[3-chloro-5-(trifluoromethyl)-2-pyridinyl]oxy]phenoxy}propanoic acid, (RS)-2-[4-(6-chloro-1,3-benzoxazol-2-yloxy) phenoxy]propanoic acid, (RS)-2-[4-(2,4-dichlorophenoxy)phenoxy]propanoic acid, (RS)-2-{4-[5-(trifluoromethyl)-2-pyridyloxy]phenoxy}propanoic acid, (RS)-2-[4-(6-chloroquinoxalin-2-yloxy)phenoxy]propanoic acid, and (RS)-2-[4-(α,α,α-trifluoro-p-tolyloxy)phenoxy]propanoic acid.

2. The SHAL of claim 1, wherein said SHAL comprises the structure:

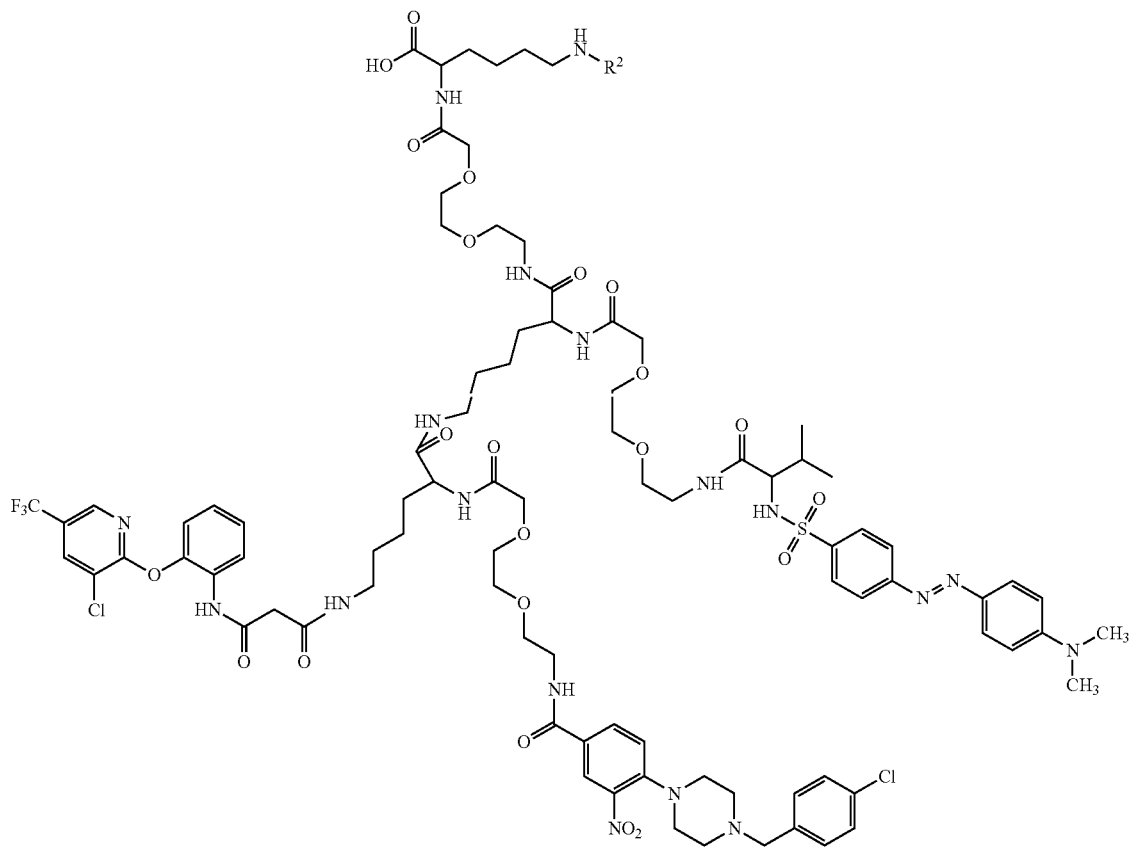

wherein $R^2$ is selected from the group consisting of COOH, a linker, an effector, and a linker attached to an effector, wherein:

when $R^2$ is a linker, the linker is polyethylene glycol, biotin, or lysine; and when $R^1$ is an effector, the effector is selected from avidin, biotin, and a cytotoxin selected from the group of a Diphtheria toxin, a *Pseudomonas* exotoxin, a ricin, an abrin, and a thymidine kinase, a chelate comprising (a) a metal isotope selected from the group of $^{99}$Tc, $^{203}$Pb, $^{67}$Ga, $^{68}$Ga, $^{72}$As, $^{111}$In, $^{113m}$In, $^{97}$Ru, $^{62}$Cu, $^{64}$Cu, $^{52}$Fe, $^{52m}$Mn, $^{51}$Cr, $^{186}$Re, $^{188}$Re, $^{77}$As, $^{90}$Y, $^{67}$Cu, $^{169}$Er, $^{121}$Sn, $^{127}$Te, $^{142}$Pr, $^{143}$Pr, $^{198}$Au, $^{199}$Au, $^{161}$Tb, $^{109}$Pd, $^{165}$Dy, $^{149}$Pm, $^{151}$Pm, $^{153}$Sm, $^{157}$Gd, $^{159}$Gd, $^{166}$Ho, $^{172}$Tm, $^{169}$Yb, $^{175}$Yb, $^{177}$Lu, $^{105}$Rh, and $^{111}$Ag, (b) bismuth 213, or (c) DOTA, 4[[5-(Trifluoromethyl)pyridin-2-yl]oxy]phenyl]N-phenylcarbamate, (R)-2-[4-(5-chloro-3-fluoro-2-pyridyloxy)phenoxy]propionic acid, 2-(((3-chloro-5(trifluoromethyl)pyridin-2-yloxy)phenoxy)methyl)acrylates, 2-(((3-chloro-5(trifluoromethyl)pyridin-2-yloxy)phenyl)methyl)acrylates, 2-(((3-chloro-5(trifluoromethyl)pyridin-2-yloxy)phenyl)methyl)acrylonitriles, 3-(3-chloro-4-{[5-(trifluoromethyl)-2-pyridinyl]oxy}anilino)-3-oxopropanoic acid, Sethoxydim, Clethodim, 5-(Tetradecyloxy)-2-furoic acid, 2-[(2,6-Dichlorophenyl)amino]benzeneacetic acid, 2-[4-(4-Chlorophenoxy)phenoxy]propanoic acid, (RS)-2-{4-[3-chloro-5-(trifluoromethyl)-2-pyridinyl]oxy]phenoxy}propanoic acid, (RS)-2-[4-(6-chloro-1,3-benzoxazol-2-yloxy)phenoxy]propanoic acid, (RS)-2-[4-(2,4-dichlorophenoxy)phenoxy]propanoic acid, (RS)-2-{4-[5-(trifluoromethyl)-2-pyridyloxy]phenoxy}propanoic acid, (RS)-2-[4-(6-chloroquinoxalin-2-yloxy)phenoxy]propanoic acid, and (RS)-2-[4-(α,α,α-trifluoro-p-tolyloxy)phenoxy]propanoic acid.

3. The SHAL according to claim 1 or 2, wherein said SHAL is polyvalent or polyspecific.

4. The SHAL of claim 1 or 2, wherein the SHAL has antilymphoma activity.

5. The SHAL of any one of claim 1 or 2, wherein said linker is polyethylene glycol (PEG) or lysine.

6. The SHAL according to claim 1 or 2, wherein the effector is DOTA or biotin.

7. A method of inhibiting the growth or proliferation of a cancer cell that expresses an HLA-DR10 marker, said method comprising: contacting said cancer with a selective high-affinity polydentate ligand (SHAL) according to claim 1 or 2.

8. A method of detecting a cancer cell, said method comprising:
    contacting said cancer cell with a chimeric molecule comprising an SHAL according to claim 1 or 2 attached to a detectable label; and
    detecting the presence or absence of said detectable label.

9. The method of claim 8, wherein said detectable label is selected from the group consisting of a gamma-emitter, a positron-emitter, an x-ray emitter, an alpha emitter, and a fluorescence-emitter.

10. A method of detecting a cancer cell, said method comprising:
    contacting a cancer cell with a SHAL according to claim 1 or 2 attached to an epitope tag;

contacting said chimeric molecule with a chelate comprising a detectable moiety whereby said chelate binds to said epitope tag thereby associating said detectable moiety with said chelate; and detecting said detectable moiety.

11. The method of claim 10, wherein said detectable moiety comprises (i) a radionuclide, (ii) a detectable moiety selected from the group consisting of a gamma-emitter, a positron-emitter, an alpha emitter, an x-ray emitter and a fluorescence-emitter or (iii) a metal isotope selected from the group consisting of $^{99}$Tc, $^{203}$Pb, $^{67}$Ga, $^{68}$Ga, $^{72}$As, $^{111}$In, $^{113m}$In, $^{97}$Ru, $^{62}$Cu, $^{641}$Cu, $^{52}$Fe, $^{52m}$Mn, $^{51}$Cr, $^{186}$Re, $^{188}$Re, $^{77}$As, $^{90}$Y, $^{67}$Cu, $^{169}$Er, $^{121}$Sn, $^{127}$Te, $^{142}$Pr, $^{143}$Pr, $^{198}$Au, $^{199}$Au, $^{161}$Tb, $^{109}$Pd, $^{165}$Dy, $^{149}$Pm, $^{151}$Pm, $^{153}$Sm, $^{157}$Gd, $^{159}$Gd, $^{166}$Ho, $^{172}$Tm, $^{169}$Yb, $^{175}$Yb, $^{177}$Lu, $^{105}$Rh, and $^{111}$Ag and said detecting comprises external imaging or internal imaging.

* * * * *

UNITED STATES PATENT AND TRADEMARK OFFICE
CERTIFICATE OF CORRECTION

PATENT NO. : 9,884,070 B2  
APPLICATION NO. : 12/988801  
DATED : February 6, 2018  
INVENTOR(S) : Sally J. Denardo, Gerald L. Denardo and Rodney L. Balhorn Page 1 of 1

It is certified that error appears in the above-identified patent and that said Letters Patent is hereby corrected as shown below:

In the Claims

In Column 111, Claim 1, please replace the structure:

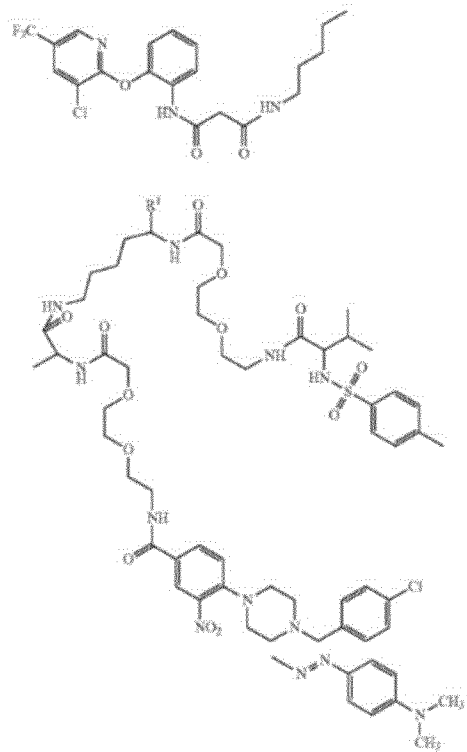

, with the structure:

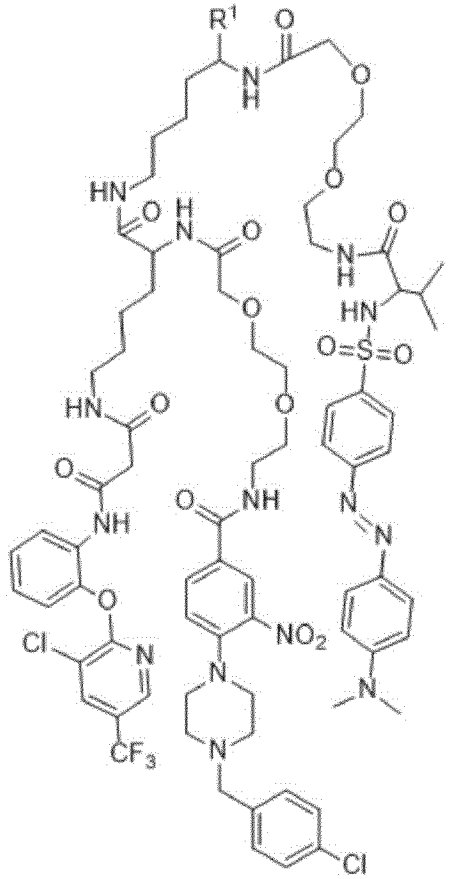

.

Signed and Sealed this  
Twelfth Day of February, 2019

Andrei Iancu  
*Director of the United States Patent and Trademark Office*